(12) United States Patent
Ward

(10) Patent No.: US 8,883,501 B2
(45) Date of Patent: Nov. 11, 2014

(54) METHOD FOR RETARDING THE DIFFERENTIATION OF PLURIPOTENT CELLS

(75) Inventor: Christopher Michael Ward, Manchester (GB)

(73) Assignee: The University of Manchester, Manchester (GB)

( * ) Notice: Subject to any disclaimer, the term of this patent is extended or adjusted under 35 U.S.C. 154(b) by 1007 days.

(21) Appl. No.: 12/184,907

(22) Filed: Aug. 1, 2008

(65) Prior Publication Data
US 2009/0155222 A1 Jun. 18, 2009

Related U.S. Application Data

(63) Continuation of application No. PCT/GB2007/000356, filed on Feb. 2, 2007.

(30) Foreign Application Priority Data

Feb. 2, 2006 (GB) .................................. 0602063.0

(51) Int. Cl.
| | | |
|---|---|---|
| *C12N 5/06* | (2006.01) | |
| *C12N 5/00* | (2006.01) | |
| *C12N 15/113* | (2010.01) | |
| *C12N 5/0735* | (2010.01) | |

(52) U.S. Cl.
CPC .......... *C12N 5/0606* (2013.01); *C12N 15/1138* (2013.01); *C12N 2310/14* (2013.01); *C12N 2501/58* (2013.01); *C12N 2310/111* (2013.01)
USPC .......................................... 435/377; 435/325

(58) Field of Classification Search
USPC ................................................ 435/377, 325
See application file for complete search history.

(56) References Cited

FOREIGN PATENT DOCUMENTS

| | | | |
|---|---|---|---|
| EP | 1 109 021 A1 | 6/2001 | |
| EP | 1 734 112 A1 | 12/2006 | |
| WO | WO 00/24916 A1 | 5/2000 | |
| WO | WO 01/75109 A3 | 10/2001 | |
| WO | WO 02/34880 A3 | 5/2002 | |
| WO | WO 03/087305 | 12/2003 | |

OTHER PUBLICATIONS

Muller et al. Immunity 6:257-264, 1997.*
Sylvester et al. Arch Surg. 139:93-99, 2004.*
Vrtovec and Scott. Nature Biotechnology 26(4):393-395, 2008.*
Dang, S.M. et al, Controlled, scalable embryonic stem cell differentiation culture, Stem Cells, 2004, pp. 275-282, vol. 22, Alphamed Press, Dayton, OH, U.S.
Fok, E.Y.L. et al, Shear-controlled single-step mouse embryonic stem cell expansion and embryoid body-based differentiation, Stem Cells 2005, pp. 1333-1342, vol. 23, Alphamed Press, Dayton, U.S.
Nagaoka, M. et al, E-Cadherin-coated Plates Maintain Pluripotent ES Cells without Colony Formation, Dec. 2006, vol. 1, pps, PLoS ONE, PLoS ONE is an international, peer-reviewed, open-access, online publication.
Sandra Guaita, Isabel Puig, Clara Franci, Marta Garrido, David Dominguez, Eduard Batlle, Elena Sancho, Shoukat Dedhar, Antonio Garcia De Herreros and Joseph Baulida, "Snail Induction of Epithelial to Mesenchymal Transition in Tumor Cells is Accompanied by MUC1 Repression adn ZEB1 Expression," The Journal of Biological Chemistry, Vkol. 277, No. 42, Octoer 18, pp. 39209-39216, 2002.
Michelle D. Hines, Hong C. Jin, Margaret J. Wheelock and Pamela J. Jensen, "Inhibition of Cadherin Function Differentially Affects Markers of Terminal Differentiation in Cultured Human Keratinocytes," Journal of Cell Science 1-2, 4569-4579 (1999).
Ruey-Long Hong, Yeong-Shiau Pu, Jan-Show Chu, Wei-Jei Lee, Yao-Chang Chen, Cheng-Wen Wu, "Correlation of Expression CD44 Isoforma and E-cadherin With Differentation in Human Urothelial Cell Lines and Transitional Cell Carcinoma," Cancer Letters 89 (1995) 81-87.
A. Miyoshi, Y. Kitajima, K. Sumi, K. Sato, A. Hagiwara, Y. Koga and K. Miyazaki, "Snail and SIPI Increase Cancer Invasion by Upregulating MMP Famiily in Hepatocellular Carcinoma Cells," British journal of Cancer (2004) 90, 1265-1273.
Ina Posert, David Dominguez, Antonio Garcia E Herreros, Alina Varnal, Reinherd Buettner and Anja K. Bosserhoff, "Loss of E-cadherin Expression in Melanoma Cells Involves Up-regulation of the Transcriptional Repressor Snail," The Journal of Biol Chem, 276, 27, 24661-2466 2001.
David Sarrio, Belen Perez-Mies, David Hardisson, Gema Moreno-Bueno, Asuncion Suarez, Amparo Cano, Jorge Martin-Perez, Carlos Gamallo and Jose Palacios, "Cystoplasmic Localization of p120ctn and E-cadherin Loss Characterize Lobular Breast Carcinoma From Preinvasive to Metastatic Lesions," Oncogene 2004 23, 3272-83.
J. Shih, M. Tsai, T. Chang, Y. Chang, A. Yuan, C. Yu, S. Lin, G. Liou, M. Lee, J. Chen, T. Hong S. Yang, J. Su, Y. Lee and P. Yang, "Transcription Repressor Slug Promotes Carcinoma Invasion and Predicts Outcome of Patients with Lung Adenocarcinoma," Clin Cancer Res 2005, 11 (22) 8070-8078.
International Search Report, PCT/GB2007/000356, mailed Aug. 3, 2007.
Patents Act 1977: Search Report Under Section 17, GB0602063.0, May 24, 2006.

* cited by examiner

*Primary Examiner* — Marcia S Noble
(74) *Attorney, Agent, or Firm* — Faegre Baker Daniels LLP

(57) ABSTRACT

There is provided a method of retarding differentiation of a biological cell, the method comprising culturing the cell in the presence of an inhibitor of E-cadherin activity. The method is particularly advantageous in retarding the differentiation of stem or progenitor cells, and allows suspension culture of such cells in a manner that enables large scale expansion of cell populations. There is also provided a stem or progenitor cell comprising a construct encoding an inhibitor of E-cadherin activity; and a cell culture medium, for use in the retardation of biological cell differentiation, comprising an inhibitor of E-cadherin activity.

21 Claims, 63 Drawing Sheets

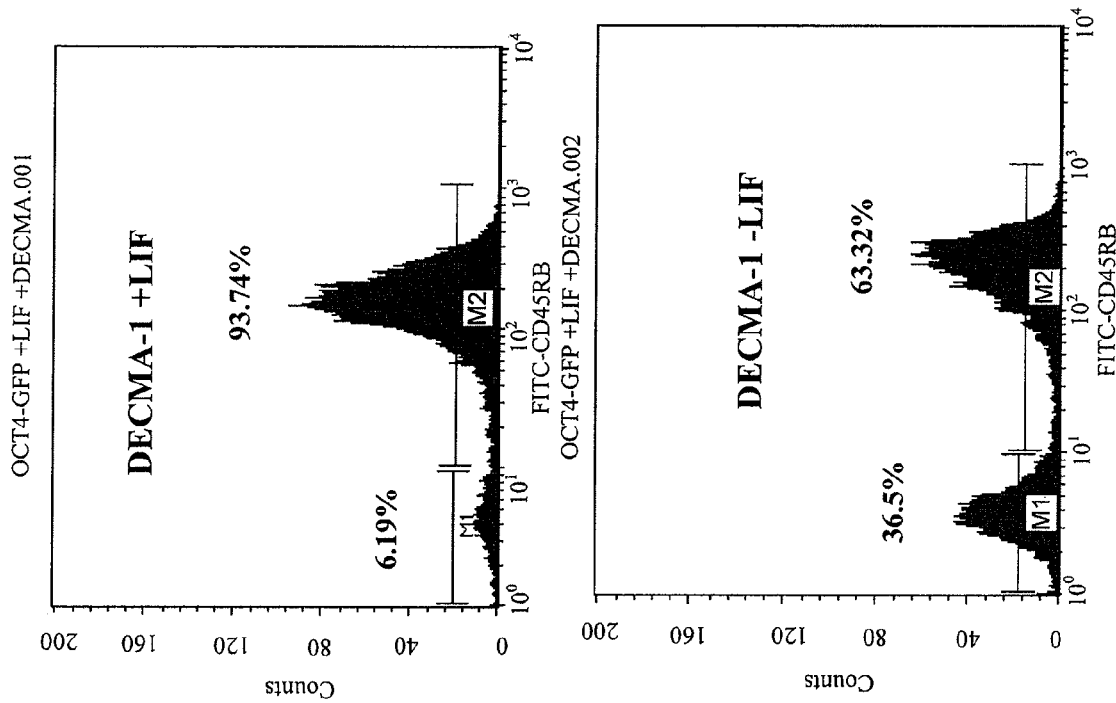
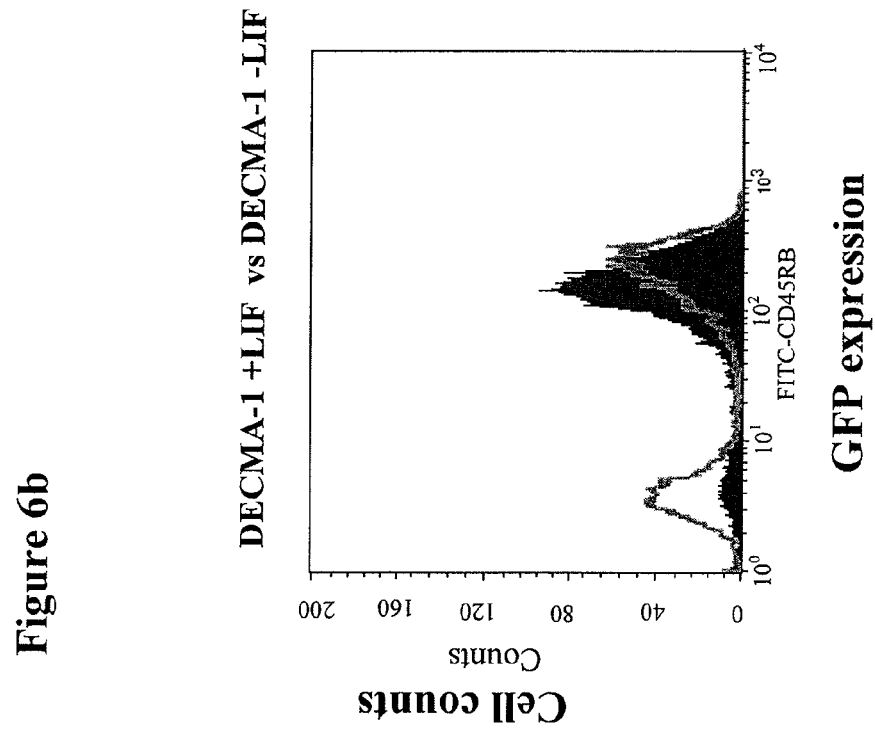
Figure 6b

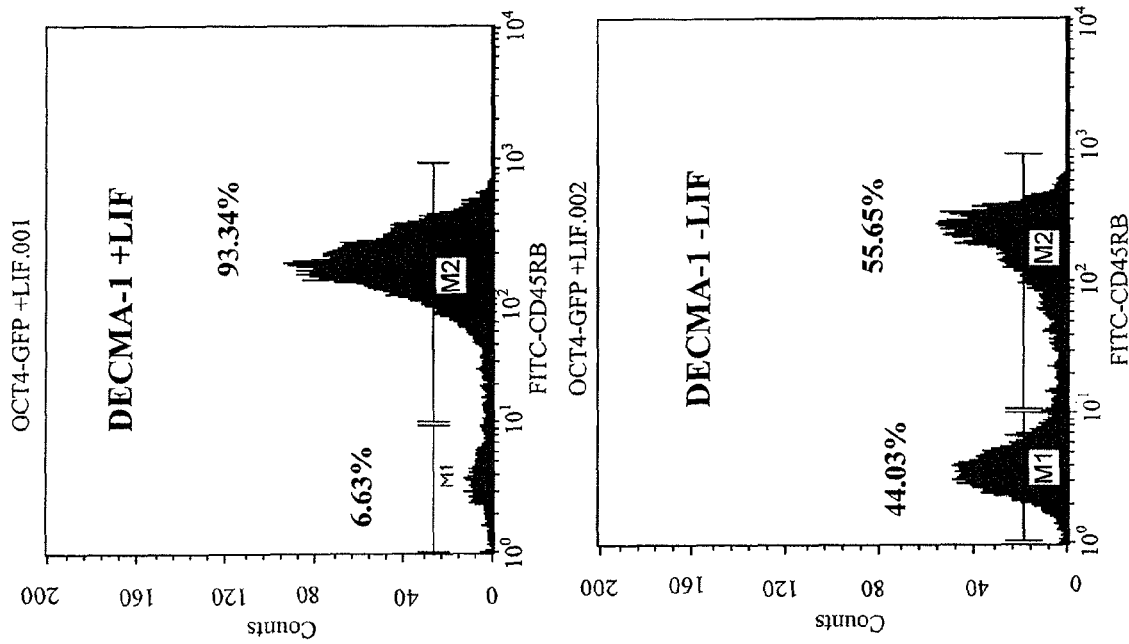
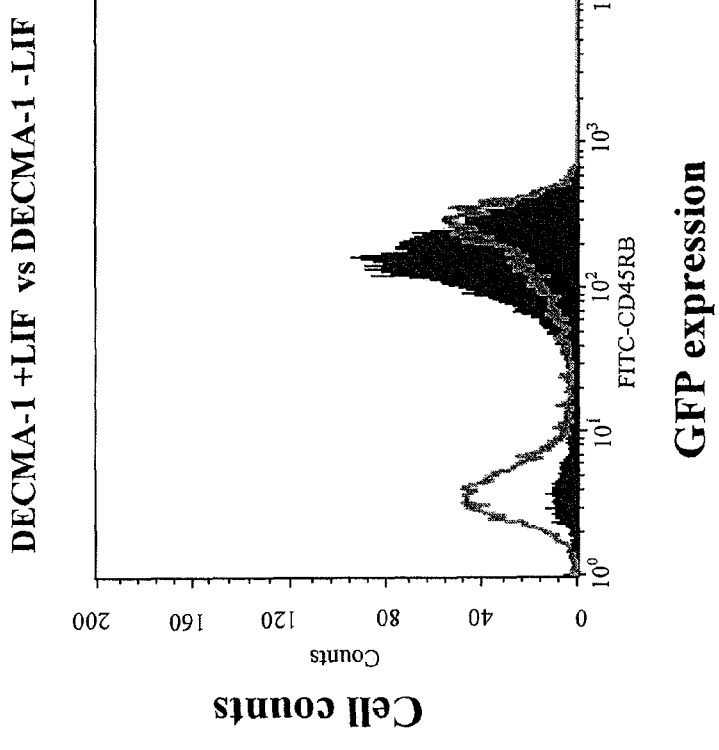
Figure 6c

Figure 7A

Human E-cadherin sequences

Sequence ID No. 1 DNA sequence – NCBI NM_004360

```
   1 agtggcgtcg gaactgcaaa gcacctgtga gcttgcggaa gtcagttcag actccagccc
  61 gctccagccc ggcccgaccc gaccgcaccc ggcgcctgcc ctcgctcggc gtccccggcc
 121 agccatgggc ccttggagcc gcagcctctc ggcgctgctg ctgctgctgc aggtctcctc
 181 ttggctctgc caggagccgg agccctgcca ccctggcttt gacgccgaga gctacacgtt
 241 cacggtgccc cggcgccacc tggagagagg ccgcgtcctg ggcagagtga attttgaaga
 301 ttgcaccggt cgacaaagga cagcctattt ttccctcgac acccgattca aagtgggcac
 361 agatggtgtg attacagtca aaaggcctct acggtttcat aacccacaga tccatttctt
 421 ggtctacgcc tgggactcca cctacagaaa gttttccacc aaagtcacgc tgaatacagt
 481 ggggcaccac caccgccccc cgccccatca ggcctccgtt tctggaatcc aagcagaatt
 541 gctcacattt cccaactcct ctcctggcct cagaagacag aagagagact gggttattcc
 601 tcccatcagc tgcccagaaa atgaaaaagg cccatttcct aaaaacctgg ttcagatcaa
 661 atccaacaaa gacaaagaag gcaaggtttt ctacagcatc actggccaag gagctgacac
 721 acccctgtt ggtgtcttta ttattgaaag agaaacagga tggctgaagg tgacagagcc
 781 tctggataga gaacgcattg ccacatacac tctcttctct cacgctgtgt catccaacgg
 841 gaatgcagtt gaggatccaa tggagatttt gatcacggta accgatcaga atgacaacaa
 901 gcccgaattc acccaggagg tctttaaggg gtctgtcatg gaaggtgctc ttccaggaac
 961 ctctgtgatg gaggtcacag ccacagacgc ggacgatgat gtgaacacct acaatgccgc
1021 catcgcttac accatcctca gccaagatcc tgagctccct gacaaaaata tgttcaccat
1081 taacaggaac acaggagtca tcagtgtggt caccactggg ctggaccgag agagtttccc
1141 tacgtatacc ctggtggttc aagctgctga ccttcaaggt gaggggttaa gcacaacagc
1201 aacagctgtg atcacagtca ctgacaccaa cgataatcct ccgatcttca atccccaccac
1261 gtacaagggt caggtgcctg agaacgaggc taacgtcgta atcaccacac tgaaagtgac
1321 tgatgctgat gcccccaata cccagcgtg ggaggctgta tacaccatat tgaatgatga
1381 tggtggacaa tttgtcgtca ccacaaatcc agtgaacaac gatggcattt tgaaaacagc
1441 aaagggcttg gattttgagg ccaagcagca gtacattcta cacgtagcag tgacgaatgt
1501 ggtaccttt gaggtctctc tcaccacctc cacagccacc gtcaccgtgg atgtgctgga
1561 tgtgaatgaa gcccccatct ttgtgcctcc tgaaaagaga gtggaagtgt ccgaggactt
1621 tggcgtgggc caggaaatca tcctacac tgcccaggag ccagacacat ttatggaaca
1681 gaaaataaca tatcggattt ggagagacac tgccaactgg ctggagatta atccggacac
```

Figure 7B

```
     1741 tggtgccatt tccactcggg ctgagctgga cagggaggat tttgagcacg
tgaagaacag
     1801 cacgtacaca gccctaatca tagctacaga caatggttct ccagttgcta
ctggaacagg
     1861 gacacttctg ctgatcctgt ctgatgtgaa tgacaacgcc cccataccag
aacctcgaac
     1921 tatattcttc tgtgagagga atccaaagcc tcaggtcata aacatcattg
atgcagacct
     1981 tcctcccaat acatctccct tcacagcaga actaacacac ggggcgagtg
ccaactggac
     2041 cattcagtac aacgacccaa cccaagaatc tatcattttg aagccaaaga
tggccttaga
     2101 ggtgggtgac tacaaaatca atctcaagct catggataac cagaataaag
accaagtgac
     2161 caccttagag gtcagcgtgt gtgactgtga aggggccgcc ggcgtctgta
ggaaggcaca
     2221 gcctgtcgaa gcaggattgc aaattcctgc cattctgggg attcttggag
gaattcttgc
     2281 tttgctaatt ctgattctgc tgctcttgct gtttcttcgg aggagagcgg
tggtcaaaga
     2341 gcccttactg cccccagagg atgacacccg ggacaacgtt tattactatg
atgaagaagg
     2401 aggcggagaa gaggaccagg actttgactt gagccagctg cacaggggcc
tggacgctcg
     2461 gcctgaagtg actcgtaacg acgttgcacc aacccctcat agtgtccccc
ggtatcttcc
     2521 ccgccctgcc aatcccgatg aaattggaaa ttttattgat gaaaatctga
aagcggctga
     2581 tactgaccec acagcccegc cttatgattc tctgctcgtg tttgactatg
aaggaagcgg
     2641 ttccgaagct gctagtctga gctccctgaa ctcctcagag tcagacaaag
accaggacta
     2701 tgactacttg aacgaatggg gcaatcgctt caagaagctg gctgacatgt
acggaggcgg
     2761 cgaggacgac tagggactc gagagaggcg ggccccagac ccatgtgctg
ggaaatgcag
     2821 aaatcacgtt gctggtggtt tttcagctcc cttcccttga gatgagtttc
tggggaaaaa
     2881 aaagagactg gttagtgatg cagttagtat agctttatac tctctccact
ttatagctct
     2941 aataagtttg tgttagaaaa gtttcgactt atttcttaaa gctttttttt
ttttcccatc
     3001 actctttaca tggtggtgat gtccaaaaga tacccaaatt ttaatattcc
agaagaacaa
     3061 ctttagcatc agaaggttca cccagcacct tgcagatttt cttaaggaat
tttgtctcac
     3121 ttttaaaaag aaggggagaa gtcagctact ctagttctgt tgttttgtgt
ataatttt
     3181 ttaaaaaaaa tttgtgtgct tctgctcatt actacactgg tgtgtccctc
tgccttttt
     3241 tttttttta agacagggtc tcattctatc ggccaggctg gagtgcagtg
gtgcaatcac
     3301 agctcactgc agccttgtcc tcccaggctc aagctatcct tgcacctcag
cctcccaagt
     3361 agctgggacc acaggcatgc accactacgc atgactaatt ttttaaatat
ttgagacggg
     3421 gtctccctgt gttacccagg ctggtctcaa actcctgggc tcaagtgatc
ctcccatctt
     3481 ggcctcccag agtattggga ttacagacat gagccactgc acctgcccag
ctccccaact
```

Figure 7C

```
      3541 ccctgccatt ttttaagaga cagtttcgct ccatcgccca ggcctgggat
gcagtgatgt
      3601 gatcatagct cactgtaacc tcaaactctg gggctcaagc agttctccca
ccagcctcct
      3661 ttttattttt ttgtacagat ggggtcttgc tatgttgccc aagctggtct
taaactcctg
      3721 gcctcaagca atccttctgc cttggcccc  caaagtgctg ggattgtggg
catgagctgc
      3781 tgtgcccagc ctccatgttt taatatcaac tctcactcct gaattcagtt
gctttgccca
      3841 agataggagt tctctgatgc agaaattatt gggctctttt agggtaagaa
gtttgtgtct
      3901 ttgtctggcc acatcttgac taggtattgt ctactctgaa gacctttaat
ggcttccctc
      3961 tttcatctcc tgagtatgta acttgcaatg ggcagctatc cagtgacttg
ttctgagtaa
      4021 gtgtgttcat taatgtttat ttagctctga agcaagagtg atatactcca
ggacttagaa
      4081 tagtgcctaa agtgctgcag ccaaagacag agcggaacta tgaaaagtgg
gcttggagat
      4141 ggcaggagag cttgtcattg agcctggcaa tttagcaaac tgatgctgag
gatgattgag
      4201 gtgggtctac ctcatctctg aaaattctgg aaggaatgga ggagtctcaa
catgtgtttc
      4261 tgacacaaga tccgtggttt gtactcaaag cccagaatcc ccaagtgcct
gcttttgatg
      4321 atgtctacag aaaatgctgg ctgagctgaa cacatttgcc caattccagg
tgtgcacaga
      4381 aaaccgagaa tattcaaaat tccaattttt ttcttaggag caagaagaaa
atgtggccct
      4441 aaaggggggtt agttgagggg taggggtag  tgaggatctt gatttggatc
tctttttatt
      4501 taaatgtgaa tttcaacttt tgacaatcaa agaaaagact tttgttgaaa
tagctttact
      4561 gtttctcaag tgttttggag aaaaaaatca accctgcaat cacttttgg
aattgtcttg
      4621 attttcggc  agttcaagct atatcgaata tagttctgtg tagagaatgt
cactgtagtt
      4681 ttgagtgtat acatgtgtgg gtgctgataa ttgtgtattt tctttggggg
tggaaaagga
      4741 aaacaattca agctgagaaa agtattctca aagatgcatt tttataaatt
ttattaaaca
      4801 attttgttaa accataaaaa aaaaaaa
```

Sequence ID No. 2 Protein sequence – NCBI AAY68225 mgpwsrslsa llllqvssw lcqepepchp gfdaesytft vprrhlergr vlgrvnfedc
     61 tgrqrtayfs ldtrfkvgtd gvitvkrplr fhnpqihflv yawdstyrkf
stkvtlntvg
    121 hhhrppphqa svsgiqaell tfpnsspglr rqkrdwvipp iscpenekgp
fpknlvqiks
    181 nkdkegkvfy sitgqgadtp pvgvfiiere tgwlkvtepl dreriatytl
fshavssngn
    241 avedpmeili tvtdqndnkp eftqevfkgs vmegalpgts vmevtatdad
ddvntynaai
    301 aytilsqdpe lpdknmftin rntgvisvvt tgldresfpt ytlvvqaadl
qgeglsttat
    361 avitvtdtnd nppifnptty kgqvpenean vvittlkvtd adapntpawe
avytilnddg

Figure 7D

```
    421 gqfvvttnpv nndgilktak gldfeakqqy ilhvavtnvv pfevslttst
atvtvdvldv
    481 neapifvppe krvevsedfg vgqeitsyta qepdtfmeqk ityriwrdta
nwleinpdtg
    541 aistraeldr edfehvknst ytaliiatdn gspvatgtgt lllilsdvnd
napipeprti
    601 ffcernpkpq viniidadlp pntspftael thgasanwti qyndptqesi
ilkpkmalev
    661 gdykinlklm dnqnkdqvtt levsvcdceg aagvcrkaqp veaglqipai
lgilggilal
    721 lililllllf lrrravvkep llppeddtrd nvyyydeegg geedqdfdls
qlhrgldarp
    781 evtrndvapt lmsvprylpr panpdeignf idenlkaadt dptappydsl
lvfdyegsgs
    841 eaaslsslns sesdkdqdyd ylnewgnrfk kladmyggge dd
```

Figure 8A     Mouse E-cadherin

Sequence ID No. 3 DNA sequence - from NCBI BC098501

```
  agccgcggcg cactactgag ttcccaagaa cttctgctag actcctgccc ggcctaaccc
61 ggccctgccc gaccgcaccc gagctcagtg tttgctcggc gtctgccggg tccgccatgg
121 gagcccggtg ccgcagcttt tccgcgctcc tgctcctgct gcaggtctcc tcatggcttt
181 gccaggagct ggagcctgag tcctgcagtc ccggcttcag ttccgaggtc tacaccttcc
241 cggtgccgga gaggcacctg gagagaggcc atgtcctggg cagagtgaga tttgaaggat
301 gcaccggccg gccaaggaca gccttctttt cggaagactc ccgattcaaa gtggcgacag
361 acggcaccat cacagtgaag cggcatctaa agctccacaa gctggagacc agtttcctcg
421 tccgcgcccg ggactccagt catagggagc tgtctaccaa agtgacgctg aagtccatgg
481 ggcaccacca tcaccggcac caccaccgcg accctgcctc tgaatccaac ccagagctgc
541 tcatgtttcc cagcgtgtac ccaggtctca gaagacagaa acgagactgg gtcatccctc
601 ccatcagctg ccccgaaaat gaaaagggtg aattcccaaa gaacctggtt cagatcaaat
661 ccaacaggga caaagaaaca aaggttttct acagcatcac cggccaagga ctgacaaac
721 cccccgttgg cgttttcatc attgagaggg agacaggctg gctgaaagtg acacagcctc
781 tggatagaga agccattgcc aagtacatcc tctattctca tgccgtgtca tcaaatgggg
841 aagcggtgga ggatcccatg gagatagtga tcacagtgac agatcagaat gacaacaggc
901 cagagtttac ccaggaggtg tttgagggat ccgttgcaga aggcgctgtt ccaggaacct
961 ccgtgatgaa ggtctcagcc accgatgcag acgatgacgt caacacctac aacgctgcca
1021 tgcctacac catcgtcagc caggatcctg agctgcctca caaaacatg ttcactgtca
1081 atagggacac cgggggtcatc agtgtgctca cctctgggct ggaccgagag agttaccctat
1141 catacactct ggtggttcag gctgctgacc ttcaaggcga aggcttgagc acaacagcca
1201 aggctgtgat cactgtcaag gatattaatg acaacgctcc tgtcttcaac ccgagcacgt
1261 atcagggtca agtgcctgag aatgaggtca atgcccggat cgccacactc aaagtgaccg
1321 atgatgatgc cccaacact ccggcgtgga aagctgtgta caccgtagtc aacgatcctg
1381 accagcagtt cgttgtcgtc acagacccca cgaccaatga tggcattttg aaaacagcca
1441 agggcttgga ttttgaggcc aagcagcaat acatccttca tgtgagagtg gagaacgagg
1501 aaccctttga ggggtctctt gtcccttcca cagccactgt cactgtggac gtggtagacg
1561 tgaatgaagc cccatcttt atgcctgcgg agaggagagt cgaagtgccc gaagactttg
1621 gtgtgggtca ggaaatcaca tcttataccg ctcgagagcc ggacacgttc atggatcaga
```

Figure 8B

```
   1681 agatcacgta tcggatttgg agggacactg ccaactggct ggagattaac
ccagagactg
   1741 gtgccatttt cacgcgcgct gagatggaca gagaagacgc tgagcatgtg
aagaacagca
   1801 catatgtagc tctcatcatc gccacagatg atggttcacc cattgccact
ggcacgggca
   1861 ctcttctcct ggtcctgtta gacgtcaatg ataacgctcc catcccagaa
cctcgaaaca
   1921 tgcagttctg ccagaggaac ccacagcctc atatcatcac catcttggat
ccagaccttc
   1981 cccccaacac gtcccccttt actgctgagc taacccatgg ggccagcgtc
aactggacca
   2041 ttgagtataa tgacgcagct caagaatctc tcattttgca accaagaaag
gacttagaga
   2101 ttggcgaata caaaatccat ctcaagctcg cggataacca gaacaaagac
caggtgacca
   2161 cgttggacgt ccatgtgtgt gactgtgaag ggacggtcaa caactgcatg
aaggcgggaa
   2221 tcgtggcagc aggattgcaa gttcctgcca tcctcggaat ccttggaggg
atcctcgccc
   2281 tgctgattct gatcctgctg ctcctactgt ttctacggag gagaacggtg
gtcaaagagc
   2341 ccctgctgcc accagatgat gatacccggg acaatgtgta ttactatgat
gaagaaggag
   2401 gtggagaaga agaccaggac tttgatttga gccagctgca caggggcctg
gatgcccgac
   2461 cggaagtgac tcgaaatgat gtggctccca ccctcatgag cgtgccccag
tatcgtcccc
   2521 gtcctgccaa tcctgatgaa attggaaact tcatcgatga aaacctgaag
gcagccgaca
   2581 gcgaccccac ggcaccccct tacgactctc tgttggtgtt cgattacgag
ggcagtggtt
   2641 ctgaagccgc tagcctgagc tcactgaact cctctgagtc ggatcaggac
caggactacg
   2701 attatctgaa cgagtggggc aaccgattca agaagctggc ggacatgtac
ggcggtggcg
   2761 aggacgacta ggggactagc aagtctcccc cgtgtggcac catgggagat
gcagaataat
   2821 tatatcagtg gtctttcagc tccttccctg agtgtgtaga agagagactg
atctgagaag
   2881 tgtgcagatt gcatagtggt ctcattctcc ttactggact gtctgtgtta
ggatggtttt
   2941 cactgattgt tgaaatcttt ttttattttt tattttttaca gtgctgagat
ataaactgtg
   3001 cctttttttg tttgtttgtt tctgtttttg ttcttttgag cagaacaaaa
aaaagggacc
   3061 actatgcatg ctgcacacgt ctcagattct taggtacaca cctgattctt
aggtgcatgc
   3121 catagtggga tatgttgctt tgatcagaac ctgcagggag gttttcgggc
accacttaag
   3181 tttcttggcg tttctttcaa accgttctct aagatgcatt tttatgaatt
ttattaaaga
   3241 gttttgttaa aaaaaaaaaa aaaaaaaaaa aaaaaaaaaa aaaaaaaaa
aaaaaaaaaa
   3301 aaaaaaaaaa aaaa
```

Figure 8C

Sequence ID No. 4 Protein sequence – from NCBI NP_033994.

```
mgarcrsfsa llllqvssw lcqelepesc spgfssevyt fpvperhler ghvlgrvrfe
gctgrprtaf fsedsrfkva tdgtitvkrh lklhkletsf lvrardsshr elstkvtlks
mghhhhrhhh rdpasesnpe llmfpsvypg lrrqkrdwvi ppiscpenek gefpknlvqi
ksnrdketkv fysitgqgad kppvgvfiie retgwlkvtq pldreaiaky ilyshavssn
geavedpmei vitvtdqndn rpeftqpvfe gfvaegavpg tsvmkvsatd adddvntyna
aiaytivsqd pelphknmft vnrdtgvisv ltsgldresy ptytlvvqaa dlqgeglstt
akavitvkdi ndnapvfnps tyqgqvpene vnariatlkv tdddapntpa wkavytvvnd
pdqqfvvvtd pttndgilkt akgldfeakq qyilhvrven eepfegslvp statvtvdvv
dvneapifmp aerrvevped fgvgqeitsy tarepdtfmd qkityriwrd tanwleinpe
tgaiftraem dredaehvkn styvaliiat ddgspiatgt gtlllvlldv ndnapipepr
nmqfcqrnpq phiitildpd lppntspfta elthgasvnw tieyndaaqe slilqprkdl
eigeykihlk ladnqnkdqv ttldvhvcdc egtvnncmka givaaglqvp ailgilggil
allililll lflrrrtvvk epllppdddt rdnvyyydee gggeedqdfd lsqlhrglda
rpevtrndva ptlmsvpqyr prpanpdeig nfidenlkaa dsdptappyd sllvfdyegs
gseaaslssl nssesdqdqd ydylnewgnr fkkladmygg gedd
```

Figure 9A

Rat E-cadherin sequences

Sequence ID No. 5  DNA sequence – NCBI NM_031334
```
   1 ctggtgtggg agccgcggcg cactactgag ttctcaagaa cttctgctag acttcagccc
  61 ggcctaaccc ggctctgccc gaccgcaccc gagctcagtg tttgctcggc gtttgcccgg
 121 ccagccatgg gagcccggtg ccgcagcttc tccgcgctcc tgctcctgct gcaggtctcc
 181 tcgtggcttt gtcagcagcc ggagtcggag tctgactcct gccgtcccgg cttcagttcc
 241 gaggtctaca ccttcctggt gccggagagg cacctggaga gaggccacat cctgggcaga
 301 gtgaaatttg aaggatgcac cggccgtcca aggacagcct tcttttctga agactcccga
 361 ttcaaagtgt ctacagatgg cgtcatcaca gtcaaacggc atctaaagct tcacaagctg
 421 gagaccagtt ttctcgtcca tgcctgggac tccagttaca ggaagctttc taccaaagtg
 481 acactgaagt ccctgggcca ccaccaccac cggcatcacc acagagaccc tgtctctgaa
 541 tccaacccag agctgctcac gtttcccagc tttcaccagg gtctgagaag acagaaacga
 601 gactgggtca tccctcccat caactgcccg gaaaatcaaa agggcgaatt ccccagcga
 661 ctggttcaga tcaaatccaa cagggacaaa gagacaacgg ttttctacag catcaccggc
 721 ccaggagctg acaaaccccc tgttggcgtt ttcatcattg agagggagac aggctggctg
 781 aaagtgacgc agcctctgga cagagaagcc attgacaagt accttctcta ctctcatgct
 841 gtgtcatcaa atgggggaagc cgtggaggat cccatggaga tagtggtcac agtcacagat
 901 cagaatgaca acaggccaga gtttatccag gaggtctttg agggatctgt tgcagaaggc
 961 gctcttccag gaacctccgt gatgcaggtc tcagccactg atgcagacga tgacataaac
1021 acctacaatg ctgccatcgc ctacaccatc ctcagccaag atcctgagct gcctcacaaa
1081 aacatgttca ctgtcaaccg ggacactggg gtcatcagtg tggtcacctc cggactggac
1141 cgagagagtt accctacata tactctggtg gttcaggctg ccgaccttca aggcgaaggc
1201 ctaagcacaa cagcaaaagc tgtgatcact gtcaaggata ttaatgacaa cgctcccatc
1261 ttcaacccaa gcacgtacca gggtcaagtg cttgagaatg aggtcggtgc ccgtattgcc
1321 acactcaagg tgactgatga tgatgccccc aacactccag cgtggaatgc tgtgtacacc
1381 gtagtcaatg atcctgatca tcagttcact gtcatcacag acccccaagac caacgagggc
1441 attctgaaaa cagccaaggg cttggatttt gaggccaagc agcagtacat tctgcacgtg
1501 acagtggaaa atgaggagcc ctttgagggg tctcttgtcc cttccacagc cactgtcacc
1561 gtggatgtgg tagacgtgaa tgaagcccccc attttttgtgc ctgcggagaa gagagtcgag
1621 gtgcctgagg actttggtgt gggtctggag atcgcatctt cacactgcgcg agagccagac
1681 acattcatgg aacagaagat cacgtatcgg atttggaggg acactgccaa ttggctggag
```

Figure 9B

```
1741 attaacccag agactggggt catttccact cgggctgaga tggacagaga
agattcggag
1801 catgtgaaga acagcacgta tacagctctc atcattgcca cagatgatgg
ttcacccatt
1861 gccactggca cagggactct tctcctggtc ctgtcagacg tcaacgacaa
tgctcccatc
1921 ccagaacctc gaaatatgca gttctgccag agaaacccga agcccatgt
catcaccatc
1981 ttggatccag accttcccc aaacacatcc cccttcactg cagagctcac
ccatggggcc
2041 agcgtcaact ggaccattga gtacaatgac gcagaacaag aatctctcat
tttgcaacca
2101 agaaaggact tagagattgg cgaatacaaa atcaatctca agctctcgga
taaccagaat
2161 aaagaccagg tgaccacgtt ggaggtccac gtgtgtgact gtgaagggac
cgtcaacaac
2221 tgcatgaagg cgatctccct ggaagcagga ttacaagttc ccgccatcct
tggaatcctg
2281 ggagggatcc tggccctcct gattctgatc ctcctgctcc tactgtttct
acggaggaga
2341 acggtggtca aagagccctt gctgccacca gatgacgata cccgggacaa
tgtgtattac
2401 tatgatgaag agggaggtgg agaagaagac caggactttg atttgagcca
gctgcacagg
2461 ggccttgatg ccagaccgga agtgattcga aatgatgtgg ctcccaccct
catgagcatg
2521 ccccagtatc gtccccgtcc agccaatcct gatgaaatcg ggaacttcat
cgatgaaaac
2581 ctgaaggcag cggacagtga ccccacagcg ccccttacg actctctgtt
ggtgtttgac
2641 tatgagggga gtggttctga agctgcctcc ctgagctcgc tgaactcctc
tgagtcagat
2701 caggaccagg actacgatta tctgaacgaa tggggcaacc ggttcaagaa
gctggccgat
2761 atgtatggtg gcggcgaaga agactagaga gtcgttcctg tgtggcacca
tgggagatgc
2821 agaatcatga tgtcagtggt ctttcagctc cttccctgac tttgtagaag
agagactgat
2881 ctgagaagta tgcagattgc atactggtcc cactctacct accagtctgt
ctgtgttagg
2941 agggttttca ctggttgttg gaatcttttt ctaaaatgtt tttgttttta
cagtgctgtg
3001 atgtgatgaa ctgtaccctc tttttgtttt tgttttgagc tatgttctgc
tccggacaca
3061 cagcccccaa gccttcacc cctcactaat tttttacat tgtatacttt
cactcaatta
3121 ccatgtttat gttctgtatt ctaatagcca ctaagttcct gaattctgtt
gcctggccca
3181 ggtgctattc tgtgacacag tagtgcctgg gccctttat ggtaagagac
aggtttcttg
3241 gtgtgggtgc aactgagctg gatagtgtat gtttcaaaca cctttcctgt
gttctctccc
3301 cacctccaga gtgtctttac ttattcagct gtgtgtttgg ggcagaacaa
aaaaataatg
3361 ggaccactat gcaagctgcg aagattctaa ggtgcacacc tgattcttag
gcagatgcca
3421 tagtgagata tgttgctttg gttctctatc caatgctgtg accgggacct
gcagcgaggt
3481 tttcggacac cgtggtttct tgcgtttctt tcaaaccagc agtaaaaaat
ggttttttct
```

Figure 9C

```
    3541 gagagagact ggagtgccac caccaaagat agaggagaga agccaagctt
ggggacagca
    3601 agcatgccag tgaacctgac cactgtcatg agtcatgtgg gtggccacat
gtccgtgaac
    3661 ctggccagtt ggcacactga tggtgagggt acaaggaggc tagacctcgt
cccacaaaat
    3721 ttctggaaga attagggttg tctcagccaa tgtttcctag ctggaatcct
gtccatgtat
    3781 gtgttcctga agcccaggaa atacacccct ctagtgcctg cttttgatgg
tagttataga
    3841 aaagaccggc tgatttggac ctgagttgcc caatcttaag tacaaataga
aaactgagac
    3901 tatgctgggt gtgttggtgc acgcctttaa tcccggcact cgggaggcag
agacagtctc
    3961 agatctctct gagttcaagg tcagcctggt atagtaagtg aattccagga
cagccagggc
    4021 tacacagaaa ctctgtcttg gaaaaccaaa aagaaaact gagaatatta
gagattgtgc
    4081 attttctcag aaagcaggaa gaaaacacca ctctgatggg aaaagggagg
caaggcccett
    4141 gagacttttc attgaaattg ctgtactcac ataattttgg aagcaaatga
tgactgcaat
    4201 caactgtgag aactgttggt ttctctgtag tttaattgtc taatgttgat
agcgtgccct
    4261 ttgtatgtag tttgagtgta tatgtgtgtg ggtgctgata attttgtatt
ttgtggggag
    4321 tggaaaaggc aagcaatcgg aactgttctc taagatgcat ttttatgaat
tttattaaag
    4381 agttttgtta aactgt
```

Sequence ID No. 6 Protein sequence – NCBI NP_112624

```
  1 mgarcrsfsa llllqvssw lcqqpesesd scrpgfssev ytflvperhl erghilgrvk
 61 fegctgrprt affsedsrfk vstdgvitvk rhlklhklet sflvhawdss
yrklstkvtl
121 kslghhhhrh hhrdpvsesn pelltfpsfh qglrrqkrdw vippincpen
qkgefpqrlv
181 qiksnrdket tvfysitgpg adkppvgvfi ieretgwlkv tqpldreaid
kyllyshavs
241 sngeavedpm eivvtvtdqn dnrpefiqev fegsvaegal pgtsvmqvsa
tdadddinty
301 naaiaytils qdpelphknm ftvnrdtgvi svvtsgldre syptytlvvq
aadlqgegls
361 ttakavitvk dindnapifn pstyqgqvle nevgariatl kvtdddapnt
pawnavytvv
421 ndpdhqftvi tdpktnegil ktakgldfea kqqyilhvtv eneepfegsl
vpstatvtvd
481 vvdvneapif vpaekrvevp edfgvgleia sytarepdtf meqkityriw
rdtanwlein
541 petgvistra emdredsehv knstytalii atddgspiat gtgtlllvls
dvndnapipe
601 prnmqfcqrn pkphvitild pdlppntspf taelthgasv nwtieyndae
qeslilqprk
661 dleigeykin lklsdnqnkd qvttlevhvc dcegtvnncm kaisleaglq
vpailgilgg
721 ilallilill llflrrrtv vkepllppdd dtrdnvyyyd eegggeedqd
fdlsqlhrgl
781 darpevirnd vaptlmsmpq yrprpanpde ignfidenlk aadsdptapp
ydsllvfdye
841 gsgseaasls slnssesdqd qdydylnewg nrfkkladmy gggeed
```

Figure 10A

Canine E-cadherin sequences

Sequence ID No. 7 DNA sequence (predicted) – NCBI XM_536807

```
   1 atggccttgt ttgggatcaa ggctgcccgc ttccatgtgg aggggtgcag ccgcagccaa
  61 tcagcggcgc gggggcggg gcctcgcggc tcacctggcg gccggacgcg gccccgctca
 121 gtggcgtcgg gcgctgcggg cacctgtgat tcgcggaagt cctgccgcct cgcgccgcct
 181 cgcgccgcct cgcgccgcct cgcgcccggc tctcgacccc cgcccgccat gggccctcgg
 241 tacggcggcg ccccgcgct cctgctcccg ctgctgctgc tgctgcaggt ctcatcgggg
 301 ctctgccaag agccggagcc ctgccgccct ggctttggcg ctgacagcta cacgttcacc
 361 gtgccccggc gacacttgga gagaggccgt gtcctgggca gggtgagttt tgaaggatgc
 421 accggtctac ctaggacagc ctatgtttct gatgacaccc gattcaaagt gggcacagat
 481 ggtgtgatta cagtcaagcg gcctctacaa cttcataaac cagagataag ttttcttgtc
 541 catgcctggg actccagccg caggaagctc tccaccagag ttaggctgaa ggcagcgacg
 601 caccaccacc accaccatca tgatgctccc tctaaaaccc agacagaggt gctcacattt
 661 cccagttccc agcatggact cagaagacag aagagagact gggttatccc tcctatcagc
 721 tgcccggaaa acgagaaagg cccatttcct aaaaacctgg ttcagatcaa gtctaacagg
 781 gacaaagaaa tcaaggtttt ctacagcatc actggccaag gagctgacgc acctcctgtt
 841 ggtgtgttta ttattgaaag agaaacagga tggctgaagg tgactgagcc tctggataga
 901 gaacaaattg ctaagtacat tctctactct catgccgtat cttctaatgg gaatgcggtt
 961 gaagacccaa tggagatcgt gatcacggtg acagatcaga atgacaacaa gcccgagttc
1021 accaggcag tcttccaagg atctgtcacg gaaggtgccc ttccaggcac ctctgtgatg
1081 caggtgacag ccacagatgc ggatgatgat gtgaatacct acaacgctgc catcgcttac
1141 agcatcctca cacaagaccc cctcctgcct agcagcatga tgttcactat caacaaggac
1201 acaggagtca tcagcgtgct caccactggg ctggaccgag agggtgtccc catgtacacc
1261 ttggtggttc aggctgctga cctgcaaggc gaaggcttaa ctacaactgc aacagctgtg
1321 atcacagtca ctgacatcaa tgataacccc ccatcttca acccaaccac gtaccaggga
1381 cgggtgcctg agaacaaggc taacgtcgaa atcgctgtac tcaaagtgac ggatgctgat
1441 gtccccgata cccggcctg gagggctgtg tacaccatat tgaacaataa caatgatcaa
1501 tttgttgtca ccacagaccc agtaactaac gacggcattt tgaaaacaac taagggcttg
1561 gattttgagg acaagcagca gtatgtcttg tacgtgactg tggtgaacgt gaccccgttt
1621 gaggtcatcc tctccacctc cacagccact gtcactgtgg acgtggaaga tgtgaatgaa
```

Figure 10B

```
    1681 gcccccatct tcatcccttg cccaaaggta gtgtcaatcc ctgaagactt
tggtgtgggc
    1741 caggaaatca catcctacac cgccgaggat ccagatacat atatggaaca
gaggataacg
    1801 tatcggattt ggagggatgc tgccggttgg ctggaggtta atccagaatc
tggtgccatt
    1861 ttcactcggg ctgagctgga cagagaggat tttgagcacg tgaagaatag
cacgtatgaa
    1921 gccctcatta tagccattga caacggttct ccagttgcta ctggaacggg
aactcttcta
    1981 ctggtcctct ctgatgtgaa tgacaatggc cccattccag aacctcgaaa
tatggacttc
    2041 tgccagaaaa acccacagcc tcatgtcatc aacatcattg atccagatct
tcccccaac
    2101 acatctccct tcacagcaga actaacacac ggcgcaagtg tcaactggac
catcgagtac
    2161 aatgacccag gtgggaattg gactcgtgaa tctctaatt tgaagccaaa
gaaaacttta
    2221 gagttgggtg actacaaaat aaatctcaag ctcacagata accagaacaa
ggaccaggtg
    2281 accaccctag atgtgtttgt gtgcgactgc gaaggtgtcg tcaacagctg
caagaggacg
    2341 gcgccttacg ccgaagcagg cttgcaggtt cctgccatct tgggcattct
cggaggaatc
    2401 ctcgctctac taatcctgat tctgctgctt ctgctatttg ttcggaggag
aagggtggtc
    2461 aaagagccct tacttcccc agaagatgac acccgggaca atgtttatta
ctatgatgaa
    2521 gaaggaggtg gagaggagga tcaggacttt gacttgagcc agttgcacag
gggcctggat
    2581 gctcggcctg aagtgactcg caatgatgtg gccccaaccc tcctgagtgt
gccccagtat
    2641 cggccccgcc ctgccaatcc tgatgaaatt ggaaacttta ttgatgaaaa
cctgaaggca
    2701 gcggacactg accctactgc tcctccttat gactctctgc tcgtgtttga
ctatgaagga
    2761 agcggttctg aagctgctag tctgagctcc ttgaactcct cagagtcaga
ccaagaccag
    2821 gactatgact acctgaatga atggggcaat cgcttcaaga agctggcgga
catgtatgga
    2881 ggtggcgagg acgactag
```

DNA sequence (promoter region) – NCBI AF330163  Seq Id No. 58

```
  1 ccgcccgccg caggtgcagc cgcagccaat cagcggcgcg gggggcgggg cctcgcggct
 61 cacctggcgg ccggacgcgg ccccgctcag t
```

DNA sequence (partial coding sequence) – NCBI AF330162  Seq Id No. 8

```
  1 agtggcgtcg ggcgctgcgg gcacctgtga ttcgcggaag tcctgccgcc tcgcgccgcc
 61 tcgcgccgg ctctcgaccc ccgccgcca tgggccctcg gtacggcggc
gccccgcgc
121 tcctgctccc gctgctgctg ctgctgcagg tctcatcggg gctctgccaa
gagccggagc
181 cctgccgccc tggctttggc gctgacagct acacgttcac cgtgcccgg
cgacacttgg
```

Figure 10C

```
    241 agagaggccg tgtcctgggc agggtgagtt ttgaaggatg caccggtcta
cctaggacag
    301 cctatgtttc tgatgacacc cgattcaaag tgggcacaga tggtgtgatt
acagtcaagc
    361 ggcctctaca acttcataaa ccagagataa gttttcttgt ccatgcctgg
gactccagcc
    421 gcaggaagct ctccaccaga gttaggctga aggcagcgac gcaccaccac
caccaccatc
    481 atgatgctcc ctctaaaacc cagacagagg tgctcacatt tcccagttcc
cagcatggac
    541 tcagaagaca gaagagagac tgggttatcc ctcctatcag ctgcccggaa
aacgagaaag
    601 gcccatttcc taa
```

Sequence ID No. 8 Protein sequence (incomplete)– NCBI AAL09464                Seq ID No. 59

```
  1 mgpryggapa lllplllllq vssglcqepe pcrpgfgads ytftvprrhl ergrvlgrvs
 61 fegctglprt ayvsddtrfk vgtdgvitvk rplqlhkpei sflvhawdss
rrklstrvrl
121 kaathhhhhh hdapsktqte vltfpssqhg lrrqkrdwvi ppiscpenek gpfp
```

Figure 11A

Bovine E-cadherin sequences

Sequence ID No. 9 DNA sequence – NCBI AY508164

```
atgggcccctt ggagccgcag cctctctgcg ctctgctgct gctgcaggtg taatccgtgg
     61 ctctgccggg agccggagcc ctgcattcct ggctttggtg ctgagagtta cacgttcacc
    121 gtgccccggc ggaacttgga gagagggcga gtcctaggca gagtgagttt tgaaggatgt
    181 gctggcctac caaggacagt ctatgtttct gatgacaccc gattcaaagt gcacacagat
    241 ggcgtgctta cagtcagacg acctgtacac cttcatcgtc cagagctaag ttttcttgtc
    301 catgcctggg actccaccca caggaagctc tccaccaaag tgacactgga ggtatcagcg
    361 caccaccacc accaccacag tcatcatgac tctccctctg gaacccagac agaagtgctc
    421 acatttcctg gcccccacca tggtctcagg agacagaaga gagactgggt tattcctcct
    481 atcagctgcc cagaaaatga aaaggccca tttcctaagt cgctggtcca gatcaaatct
    541 aacaaggaga agaaaccca gttttctac agcatcactg ccaacgagc tgatacaccc
    601 cctgtcggtg tttttattat tgaaagagaa acaggatggt taaaagtgac acagcctctg
    661 gatagagaac agattgccaa gtacattctc ttctctcatg ccgtgtcttc aaatggacaa
    721 gccattgaag agcctatgga gattgtgatc accgtgaccg accagaatga caacaagccc
    781 cagttcaccc aggaggtctt caaggcgtct gccctggaag gcgctcttcc aggaacctct
    841 gtgatgcagg tcacggccac agatatagat gacgaggtga acacctacac cgctgccatc
    901 ggttacacaa tcccagccca agatcccatg ctgccgcaca caaaaatgtt caccatcaac
    961 aaggaaacag gcgtcatcag tgtgctcacc accgggctgg accgtgagag ttttcccaca
   1021 tacaccctga tggtccaagc agcagacctt aacggcgaag gcttgagcac aactgcaacg
   1081 gccgtgatca cagtcttgga caccaatgat aatgctccca gattcaaccc aaccacgtac
   1141 gtggggtcgg tgcctgagaa cgaggctaat gtggccatca ccacactcac agtgactgat
   1201 gccgacgacc ccaacacccc ggcatgggag gctgtttaca cagtattaaa tgataacgag
   1261 aagcaattta tcgtcgtcac agacccagtc accaatgaag gcactctgaa aacagctaag
   1321 ggcttggatt ttgaggccaa gcagcagtac atcctgtacg tggcagtgac aaatgtggcc
   1381 ccctttgaag tcactctccc cacttccaca gccaccgtca ctgtggatgt gatagatgtg
   1441 aatgaagccc ccatctttgt gcctcctcaa aagagagtgg aagtgcccga ggactttggc
   1501 gtgggcctgg agatcacatc ctatactgcc cgggagccag acacatttat ggaacagaag
   1561 atcacgtatc ggatttggag ggacactgcc aactggctgg agattaatcc agaaacgggt
   1621 gccatttcca ctcgggctga gttggacaga gaggatgtcg atcatgtgaa gaacagcacg
   1681 tacacggccc tcattatagc cactgacaat ggttctccac ctgccactgg gacaggcacc
```

Figure 11B

```
     1741 ctgctcttgt tcctcgatga tgtgaatgac aatggccccg taccagaacc
ccggaccatg
     1801 gacttctgcc agaggaatcc tgagcctcat atcatcaaca tcaatgatcc
tgatctccct
     1861 ccgaacacct cccccttttac agcagaactg acacatgggg cgagtgtcaa
ttggaccatt
     1921 gagtacaatg accaagaacg tgagtctctg attttgaagc caaagaaaac
cttagagctg
     1981 ggtgaccaca aaatcaatct caagctcata gacaaccaga acaaagacca
ggtgaccaca
     2041 cttgatgtgc acgtgtgtga ctgtgatggg atcgtcagca actgcaggaa
ggcacggcct
     2101 gctgaagcag gattgcaagt tcccgccatc ctggggatcc ttggaggcat
ccttgctttt
     2161 ctgatcctta ttttgctgct tctgctactt gttcggagga gaagggtggt
caaagagccc
     2221 ttactgcccc cagaagatga cacccgggac aatgtgtatt actatgatga
agaaggaggt
     2281 ggagaagaag atcaggactt tgacttgagc cagttacata ggggcctgga
tgctcggcct
     2341 gaagtgactc gcaatgacgt ggcaccaacc ctcatgagtg tgccccagta
ccgaccccgc
     2401 cctgccaatc ctgatgaaat tggaaacttt attgatgaaa acctgaaggc
agctgatagt
     2461 gaccccactg cccacccta tgactctctg ctggtgtttg attatgaagg
aagtggttcc
     2521 gaagctgcta ctctgagctc cctgaactcc tcagagtcag accaagacca
ggactatgac
     2581 tacctgaatg aatggggcaa tcgcttcaag aagctggcgg acatgtatgg
aggcggcgag
     2641 gacgactag
```

Figure 11C

Sequence ID No. 10 Protein sequence – NCBI NP_001002763

```
mgpwsrslsa lcccrcnpw lcrepepcip gfgaesytft vprrnlergr vlgrvsfegc
     61 aglprtvyvs ddtrfkvhtd gvltvrrpvh lhrpelsflv hawdsthrkl stkvtlevsa
    121 hhhhhhshhd spsgtqtevl tfpgphhglr rqkrdwvipp iscpenekgp fpkslvqiks
    181 nkeketqvfy sitgqradtp pvgvfiiere tgwlkvtqpl dreqiakyil fshavssngq
    241 aieepmeivi tvtdqndnkp qftqevfkas alegalpgts vmqvtatdid devntytaai
    301 gytipaqdpm lphnkmftin ketgvisvlt tgldresfpt ytlmvqaadl ngeglsttat
    361 avitvldtnd naprfnptty vgsvpenean vaittltvtd addpntpawe avytvlndne
    421 kqfivvtdpv tnegtlktak gldfeakqqy ilyvavtnva pfevtlptst atvtvdvidv
    481 neapifvppq krvevpedfg vgleitsyta repdtfmeqk ityriwrdta nwleinpetg
    541 aistraeldr edvdhvknst ytaliiatdn gsppatgtgt lllflddvnd ngpvpeprtm
    601 dfcqrnpeph iinindpdlp pntspftael thgasvnwti eyndqeresl ilkpkktlel
    661 gdhkinlkli dnqnkdqvtt ldvhvcdcdg ivsncrkarp aeaglqvpai lgilggilaf
    721 lilillllll vrrrrvvkep llppeddtrd nvyyydeegg geedqdfdls qlhrgldarp
    781 evtrndvapt lmsvpqyrpr panpdeignf idenlkaads dptappydsl lvfdyegsgs
    841 eaatlsslns sesdqdqdyd ylnewgnrfk kladmyggge dd
```

Figure 12

Sequence ID No. 11 – amino acid sequence of CAD-HAV domain of E-cadherin

HAV

Figure 13A

Sequence ID No. 12 Slug - Human 1 mprsflvkkh fnaskkpnys eldthtviis pylyesysmp vipqpeilss gayspitvwt
61 taapfhaqlp nglsplsgys sslgrvsppp psdtsskdhs gsespisdee erlqsklsdp
121 haieaekfqc nlcnktystf sglakhkqlh cdaqsrksfs ckycdkeyvs lgalkmhirt
181 htlpcvckic gkafsrpwll qghirthtge kpfscphcnr afadrsnlra hlqthsdvkk
241 yqckncsktf srmsllhkhe esgccvah Sequence ID No. 13 Slug – Mouse 1 mprsflvkkh fnaskkpnys eldthtviis pylyesypip vipkpeilts gayspitvwt
61 ssaaplhspl psglspltgy ssslgrvspp psdtsskdh sgsespisde eerlqpklsd
121 phaieaekfq cnlcnktyst fsglakhkql hcdaqsrksf sckycdkeyv slgalkmhir
181 thtlpcvcki cgkafsrpwl lqghirthtg ekpfscphcn rafadrsnlr ahlqthsdvk
241 kyqckncskt fsrmsllhkh eesgccvah Sequence ID No. 14 Snail – Human 1 mprsflvrkp sdpnrkpnys elqdsnpeft fqqpydqahl laaipppeil nptaslpmll
61 wdsvlapqaq piawaslrlq esprvaelts lsdedsgkgs qppsppspap ssfsstsvss
121 leaeayaafp glgqvpkqla qlseakdlqa rkafnckycn keylslgalk mhirshtlpc
181 vcgtcgkafs rpwllqghvr thtgekpfsc phcsrafadr snlrahlqth sdvkkyqcqa
241 cartfsrmsl lhkhqesgcs gcpr Sequence ID No. 15 Snail – Mouse 1 mprsflvrkp sdprrkpnys elqdacveft fqqpydqahl laaipppevl npaaslptll
61 wdsllvpqvr pvawatlplr espkavelts lsdedsgkss qppsppspap ssfsstsass
121 leaeafiafp glgqlpkqla rlsvakdpqs rkifnckycn keylslgalk mhirshtlpc
181 vcttcgkafs rpwllqghvr thtgekpfsc shcnrafadr snlrahlqth sdvkryqcqa
241 cartfsrmsl lhkhqesgcs ggpr Sequence ID No. 16 SIP1 – Human 1 mkqpimadgp rckrrkqanp rrknvvnydn vvdtgsetde edklhiaedd gianpldqet
61 spasvpnhes sphvsqallp reeeedeire ggvehpwhnn eilqasvdgp eemkedydtm
121 gpeatiqtai nngtvknanc tsdfeeyfak rkleerdgha vsieeylqrs dtaiiypeap
181 eelsrlgtpe angqeendlp pgtpdafaql ltcpycdrgy krltslkehi kyrhekneen
241 fscplcsytf ayrtqlerhm vthkpgtdqh qmltqgagnr kfkctecgka fkykhhlkeh

Figure 13B

```
301 lrihsgekpy ecpnckkrfs hsgsysshis skkciglisv ngrmrnnikt gsspnsvsss
361 ptnsaitqlr nklengkpls mseqtgllki ktepldfndy kvlmathgfs gtspfmnggl
421 gatsplgvhp saqspmqhlg vgmeaplIgf ptmnsnlsev qkvlqivdnt vsrqkmdcka
481 eeisklkgyh mkdpcsqpee qgvtspnipp vglpvvshng atksiidytl ekvneakacl
541 qslttdsrrq lsnlkkeklr tlidlvtddk mienhnlstp fscqfckesf pgpiplhqhe
601 rylckmneei kavlqpheni vpnkagvfvd nkalllssvl sekgmtspin pykdhmsvlk
661 ayyamnmepn sdellkisia vglpqefvke wfeqrkvyqy snsrspsler sskplapnsn
721 pptkdsllpr spvkpmdsit spsiaelhns vtncdpplrl tkpshftnik pvekldhsrs
781 ntpsplnlss tssknshsss ytpnsfssee lqaepldlsl pkqmkepksi iatknktkas
841 sisldhnsvs sssensdepl nltfikkefs nsnnldnkst npvfsmnpfs akplytalpp
901 qsafppatfm ppvqtsipgl rpypgldqms flphmaytyp tgaatfadmq qrrkyqrkqg
961 fqgelldgaq dymsglddmt dsdsclsrkk ikktesgmya cdlcdktfqk ssslIrhkye
1021 htgkrphqcq ickkafkhkh hliehsrlhs gekpyqcdkc gkrfshsgsy sqhmnhrysy
1081 ckreaeerea aerearekgh leptellmnr aylqsitpqg ysdseeresm prdgesekeh
1141 ekegedgygk lgrqdgdeef eeeeeesenk smdtdpetir deeetgdhsm ddssedgkme
1201 tksdheednm edgm
```

Sequence ID No. 17 SIP1 – Mouse

```
1 mkqpimadgp rckrrkqanp rrknvvnydn vvdagsetde edklhiaedd slanpldqdt
61 spasmpnhes sphmsqgllp reeeeeelre svvehswhsg eilqasvagp eemkedydam
121 gpeatiqtti nngtvknanc tsdfeeyfak rkleerdgha vsieeylqrs dtaiiypeap
181 eelsrlgtpe angqeendlp pgtpdafaql ltcpycdrgy krltslkehi kyrhekneen
241 fscplcsytf ayrtqlerhm vthkpgldqh qmltqgagnr kfkctecgka fkykhhlkeh
301 lrihsgekpy ecpnckkrfs hsgsysshis skkciglisv ngrmrnnikt gsspnsvsss
361 ptnsaitqlr nklengkpls mseqtgllki ktepldfndy kvlmathgfs gsspfmnggl
421 gatsplgvhp saqspmqhlg vgmeaplIgf ptmnsnlsev qkvlqivdnt vsrqkmdckt
481 edisklkgyh mkdpcsqpee qgvtspnipp vglpvvshng atksiidytl ekvneakacl
541 qslttdsrrq lsnlkkeklr tlidlvtddk mienhsistp fscqfckesf pgpiplhqhe
601 rylckmneei kavlqpheni vpnkagvfvd nkalllssvl sekgltspin pykdhmsvlk
661 ayyamnmepn sdellkisia vglpqefvke wfeqrkvyqy snsrspsler tskplapnsn
721 pttkdsllpr spvkpmdsit spsiaelhns vtscdpplrl tksshftnik avdkldhsrs
781 ntpsplnlss tssknshsss ytpnsfssee lqaepldlsl pkqmrepkgi iatknktkat
841 sinldhnsvs sssensdepl nltfikkefs nsnnldnksn npvfgmnpfs akplytplpp
901 qsafppatfm ppvqtsipgl rpypgldqms flphmaytyp tgaatfadmq qrrkyqrkqg
961 fqgdlldgaq dymsglddmt dsdsclsrkk ikktesgmya cdlcdktfqk ssslIrhkye
1021 htgkrphqcq ickkafkhkh hliehsrlhs gekpyqcdkc gkrfshsgsy sqhmnhrysy
1081 ckreaeerea aerearekgh lgptellmnr aylqsitpqg ysdseeresm prdgesekeh
```

Figure 13C 1141 ekegeegygk lrrrdgdeee eeeeeesenk smdtdpetir deeetgdhsm ddssedgkme
1201 tksdhcednm edgmg Sequence ID No. 18 E2A – Human – Amino acid sequence
MNQPQRMAPVGTDKELSDLLDFSMMFPLPVTNGKGRPASLAGAQ

FGGSGLEDRPSSGSWGSGDQSSSSFDPSRTFSEGTHFTESHSSLSSSTFLGPGLGGKS

GERGAYASFGRDAGVGGLTQAGFLSGELALNSPGPLSPSGMKGTSQYYPSYSGSSRRR

AADGSLDTQPKKVRKVPPGLPSSVYPPSSGEDYGRDATAYPSAKTPSSTYPAPFYVAD

GSLHPSAELWSPPGQAGFGPMLGGGSSPLPLPPGSGPVGSSGSSSTFGGLHQHERMGY

QLHGAEVNGGLPSASSFSSAPGATYGGVSSHTPPVSGADSLLGSRGTTAGSSGDALGK

ALASIYSPDHSSNNFSSSPSTPVGSPQGLAGTSQWPRAGAPGALSPSYDGGLHGLQSK

IEDHLDEAIHVLRSHAVGTAGDMHTLLPGHGALASGFTGPMSLGGRHAGLVGGSHPED

GLAGSTSLMHNHAALPSQPGTLPDLSRPPDSYSGLGRAGATAAASEIKREEKEDEENT

SAADHSEEEKKELKAPRARTSPDEDEDDLLPPEQKAEREKERRVANNARERLRVRDIN

EAFKELGRMCQLHLNSEKPQTKLLILHQAVSVILNLEQQVRERNLNPKAACLKRREEE
KVSGVVGDPQMVLSAPHPGLSEAHNPAGHM

Sequence ID No. 19 E2A – human – DNA encoding sequence
1 gcctgaggtg cccgccctgg ccccaggaga atgaaccagc cgcagaggat ggcgcctgtg
61 ggcacagaca aggagctcag tgacctcctg gacttcagca tgatgttccc gctgcctgtc
121 accaacggga agggccggcc cgcctccctg gcggggcgc agttcggagg ttcaggtctt
181 gaggaccggc ccagctcagg ctcctggggc agcggcgacc agagcagctc ctcctttgac
241 cccagccgga ccttcagcga gggcacccac ttcactgagt cgcacagcag cctctcttca
301 tccacattcc tgggaccggg actcggaggc aagagcgggg agcggggcgc ctatgcctcc
361 ttcggggagag acgcaggcgt gggcggcctg actcaggctg gcttcctgtc aggcgagctg
421 gccctcaaca gccccggggcc cctgtcccct tcgggcatga aggggacctc ccagtactac

Figure 13D

```
 481 ccctcctact ccggcagctc ccggcggaga gcggcagacg gcagcctaga cacgcagccc
 541 aagaaggtcc ggaaggtccc gccgggtctt ccatcctcgg tgtacccacc cagctcaggt
 601 gaggactacg gcagggatgc caccgcctac ccgtccgcca agaccccag cagcacctat
 661 cccgccccct tctacgtggc agatggcagc ctgcacccct cagccgagct ctggagtccc
 721 ccgggccagg cgggcttcgg gcccatgctg ggtgggggct catccccgct gccctccg
 781 cccggtagcg gcccggtggg cagcagtgga agcagcagca cgtttggtgg cctgcaccag
 841 cacgagcgta tgggctacca gctgcatgga gcagaggtga acggtgggct cccatctgca
 901 tcctccttct cctcagcccc cggagccacg tacggcggcg tctccagcca cacgccgcct
 961 gtcagcgggg ccgacagcct cctgggctcc cgagggacca cagctggcag ctccggggat
1021 gccctcggca aagcactggc ctcgatctac tccccggatc actcaagcaa taacttctcg
1081 tccagcccct ctaccccgt gggctccccc cagggcctgg caggaacgtc acagtggcct
1141 cgagcaggag ccccggtgc cttatcgccc agctacgacg ggggtctcca cggcctgcag
1201 agtaagatag aagaccacct ggacgaggcc atccacgtgc tccgcagcca cgccgtgggc
1261 acagccggcg acatgcacac gctgctgcct ggccacgggg cgctggcctc aggtttcacc
1321 ggccccatgt cgctgggtgg gcggcacgca ggcctggttg gaggcagcca cccgaggac
1381 ggcctcgcag gcagcaccag cctcatgcac aaccacgcgg ccctccccag ccagccaggc
1441 accctccctg acctgtctcg gcctcccgac tcctacagtg ggctagggcg agcaggtgcc
1501 acggcggccg ccagcgagat caagcgggag gagaaggagg acgaggagaa cacgtcagcg
1561 gctgaccact cggaggagga gaagaaggag ctgaaggccc ccgggcccg gaccagccca
1621 gacgaggacg aggacgacct tctccccca gagcagaagg ccgagcggga gaaggagcgc
1681 cgggtggcca ataacgcccg ggagcggctg cgggtccgtg acatcaacga ggcctttaag
1741 gagctggggc gcatgtgcca actgcaccctc aacagcgaga gccccagac caaactgctc
1801 atcctgcacc aggctgtctc ggtcatcctg aacttggagc agcaagtgcg agagcggaac
1861 ctgaatccca agcagcctg tttgaaacgg cgagaagagg aaaaggtgtc aggtgtggtt
1921 ggagaccccc agatggtgct ttcagctccc cacccaggcc tgagcgaagc ccacaacccc
1981 gccgggcaca tgtgaaaggt atgcctccgt gggacgagcc acccgctttc agccctgtgc
2041 tctggcccca gaagccggac tcgagacccc gggcttcatc cacatccaca cctcacacac
2101 ctgttgtcag catcgagcca acaccaacct gacaaggttc ggagtgatgg gggcggccaa
2161 ggtgacactg ggtccaggag ctccctgggg ccctggccta ccactcactg gcctcgctcc
2221 ccctgtcccc gaatctcagc caccgtgtca ctctgtgacc tgtcccatgg atcctgaaac
2281 tgcatcttgg ccctgttgcc tgggctgaca ggagcatttt ttttttcc agtaaacaaa
2341 acctgaaagc aagcaacaaa acatacactt tgtcagagaa gaaaaaaatg ccttaactat
2401 aaaaagcgga gaaatggaaa catatcactc aaggggatg ctgtggaaac ctggcttatt
2461 cttctaaagc caccagcaaa ttgtgcctaa gcgaaatatt ttttttaagg aaaataaaaa
2521 cattagttac aagatttttt ttttcttaag gtagatgaaa attagcaagg atgctgcctt
2581 tggtctctgg tttttttaag cttttttttgc atatgttttg taagcaacaa attttttttgt
2641 ataaaagtcc cgtgtctctc gctatttctg ctgctgttcc tagactgagc attgcatttc
```

Figure 13E

```
2701 ttgatcaacc agatgattaa acgttgtatt aaaaagaccc cgtgtaaacc tgagcccccc
2761 ccgtcccccc ccccggaagc cactgcacac agacagacgg ggacaggcgg cgggtctttt
2821 gtttttttga tgttgggggt tctcttggtt ttgtcatgtg gaaagtgatg cgtgggcgtt
2881 ccctgatgaa ggcaccttgg ggcttccctg ccgcatcctc tcccctcagg aagggggactg
2941 acctgggctt gggggaaggg acgtcagcaa ggtggctctg accctcccag gtgactctgc
3001 caagcagctg tggccccagc ggtaccctac acaacgccct ccccaggccc ccctaagctg
3061 ctctcccttg gaacctgcac agctctctga aatggggcat tttgttggga ccagtgaccc
3121 ctggcatggg gaccacaccc tggagcccgg tgctggggac ctcctggaca ccctgtcctt
3181 cactccttgc cccagggacc caggctcatg ctctgaactc tggctgagag gagtctgctc
3241 aggagccagc acaggacacc ccccacccca ccccaccatg tccccattac accagagggc
3301 catcgtgacg tagacaggat gccaggggcc tgaccagcct ccccaatgct ggggagcatc
3361 cctggcctgg ggccacacct gctgccctcc ctctgtgtgg tccaagggca agagtggctg
3421 gagccggggg actgtgctgg tctgagcccc acgaaggcct tgggctgtgg ctccgaccct
3481 gctgcagaac cagcagggtg tcccctcggg cccatctgtg tccatgtcc cagcacccag
3541 gcctctctcc aggtctcctt ttctggtctt ttgccatgag ggtaaccagc tcttcccagc
3601 tggctgggac tgtcttgggt ttaaaactgc aagtctccta ccctgggatc ccatccagtt
3661 ccacacgaac tagggcagtg gtcactgtgg cacccaggtg tgggcctggc tagctggggg
3721 ccttcatgtg cccttcatgc ccctccctgc attgaggcct tgtggacccc tgggctggct
3781 gtgttcatcc ccgctgcagg tcgggcgtct ccccccgtgc cactcctgag actccaccgt
3841 taccccccagg agatcctgga ctgcctgact cccctcccca gactggcttg ggagcctggg
3901 ccccatggta gatgcaaggg aaacctcaag gccagctcaa tgcctggtat ctgcccccag
3961 tccaggccag gcggagggga ggggctgtcc ggctgcctct ccttctcgg tggcttcccc
4021 tgcgccctgg gagtttgatc tcttaaggga acttgcctct ccctcttgtt ttgctcctgc
4081 cctgccccta ggtctgggtg gcagtggccc catagcctct ggaactgtgc gttctgcata
4141 gaattcaaac gagattcacc cagcgcgagg aggaagaaac agcagttcct gggaaccaca
4201 attatggggg gtgggggtg tgatctgagt gcctcaagat ggttttcaaa aaattttttt
4261 taaagaaaat aattgtatac gtgtcaacac agctggctgg atgattggga ctttaaaacg
4321 accctctttc aggtggattc agagacctgt cctgtatata acagcactgt agcaataaac
4381 gtgacatttt ataaag
```

Sequence ID No. 20 E2A – Mouse – Amino acid sequence
MMNQSQRMAPVGSDKELSDLLDFSMMFPLPVANGKSRPASLGGT

QFAGSGLEDRPSSGSWGSSDQNSSSFDPSRTYSEGAHFSDSHSSLPPSTFLGAGLGGK

GSERNAYATFGRDTSVGTLSQAGFLPGELSLSSPGPLSPSGIKSSSQYYPSFPSNPRR

Figure 13F

RAADGGLDTQPKKVRKVPPGLPSSVYPPSSGDSYSRDAAAYPSAKTPSSAYPSPFYVA

DGSLHPSAELWSTPSQVGFGPMLGDGSSPLPLAPGSSSVGSGTFGGLQQQDRMGYQLH

GSEVNGSLPAVSSFSAAPGTYSGTSGHTPPVSGAAAESLLGTRGTTASSSGDALGKAL

ASIYSPDHSSNNFSPSPSTPVGSPQGLPGTSQWPRAGAPSALSPNYDAGLHGLSKMED

RLDEAIHVLRSHAVGTASDLHGLLPGHGALTTSFTGPMSLGGRHAGLVGGSHPEEGLT

SGASLLHNHASLPSQPSSLPDLSQRPPDSYSGLGRAGTTAGASEIKREEKEDEEIASV

ADAEEDKKDLKVPRTRTSSTDEVLSLEEKDLRDRERRMANNARERVRVRDINEAFREL

GRMCQLHLKSDKAQTKLLILQQAVQVILGLEQQVRERNLNPKAACLKRREEEKVSGVV
　　　　　GDPQLPLSAAHPGLGEAHNPAGHL

Sequence ID No. 21 E2A – Mouse – DNA encoding sequence

```
   1 gcgccggcgg ctgcgggcgt agcgggccac cgcgggccac cgccgcgcgc cgccgcctct
  61 gctacagtcc cttcccgcgg ggcctgctct gagagaagct cgagagagac caggcgacgc
 121 gaacgcgagt ggggaggagg aaggacgcgc gaccccgagc cctgcgcgct cccgccgccc
 181 acgcgcgacc ctcggggacg cgccgccac ccttttgtcc ccggggtccc cgagggcggt
 241 gggcagcagg gagccccggt gcaccggtg catgccccg cccagcaggg ctgtctctag
 301 acctggggga cgcacccag ttccaacacc tgctgtcctg ggtggatgat gaaccagtct
 361 cagagaatgg caccgtggg ctctgacaag gaactgagtg acctcctgga cttcagcatg
 421 atgttccgc tacctgtggc caatgggaag agccggcccg cctccctcgg gggaacccag
 481 tttgcaggct caggactgga ggaccgaccc agctcaggct cctggggcag cagtgaccag
 541 aacagttctt cctttgaccc tagccggaca tacagcgaag gtgcccactt cagtgactcc
 601 cacagcagcc tgccgccttc cacgttccta ggagctgggc ttggaggcaa gggcagtgag
 661 cggaatgcct atgccaccttt tgggagagac accagtgttg gcaccttgag tcaggctggc
 721 ttcctgccag gtgagctgag cctcagcagt cccgggccac tgtccccatc gggcatcaag
 781 agcagctccc agtattaccc ctcattcccc agcaaccctc gtcggagagc tcagatggt
 841 ggcctggata ctcagccgaa gaaggtccgg aaggttccgc ctggtctccc ttcctcggtg
 901 tatccgccca gctcaggtga cagctacagc agggatgctg cagcctaccc ctccgccaag
 961 acccccagca gcgcttaccc ctcccccttc tacgtggcag atggcagcct gcacccatca
1021 gctgagctct ggagtacgcc tagccaggtg ggctttgggc ccatgctagg tgacggctct
```

Figure 13G

```
1081 tcccctctgc cccttgcacc gggcagcagc tccgtgggca gtggtacctt tggggcctc
1141 cagcagcagg atcgcatggg ctaccagctg catggatctg aggttaatgg ctcgctccca
1201 gctgtatcca gcttttcggc tgcccctggc acttacagtg ggacttccgg ccacacgccc
1261 cctgtgagtg gggccgcagc tgaaagcctc ctaggcaccc gagggactac agccagcagc
1321 tcaggggatg cccttgggaa ggcactggcc tcgatctact ccccggatca ctccagcaat
1381 aatttctcac ctagccctc aacgcctgtg ggttcacccc agggcctgcc agggacatca
1441 cagtggcccc gggcaggagc gcccagtgcc ttatccccca actacgatgc aggtctccat
1501 ggcctgagca agatggagga ccgcttggac gaggccatcc atgtcctgcg aagccacgct
1561 gttggcaccg ctagcgatct ccatgggctt ttgcctggcc atgcgcact gaccacgagc
1621 ttcaccggcc ccatgtcact gggcggggcgg catgccggcc tggtcggggg aagccatcct
1681 gaggagggcc tcacaagtgg ggccagtctt ttgcataacc atgccagcct ccccagccag
1741 cccagttccc tccctgacct ctcacagaga cctcccgact cctatagtgg actcggggag
1801 gcaggcacaa cagcgggtgc cagcgagatc aagcgggagg agaaagagga tgaggaaatc
1861 gcatcagtag ccgacgccga agaggacaag aaggacctga aggtcccacg cacgcgcacc
1921 agcagtacag atgaggtgct gtccctggag gagaaggacc tgagggaccg ggagaggcgt
1981 atggccaata acgctcggga gcgggtgcgc gtgcgggaca ttaacgaggc cttccgggag
2041 ctgggccgca tgtgccagct gcacctcaag tcggataagg cgcagaccaa gctgctcatc
2101 ctgcagcagg cggtgcaggt catcctgggc ctggagcagc aggtgcgaga acgcaacctg
2161 aaccccaaag cagcctgctt gaagcggagg gaggaggaga aggtgtctgg cgtggtcggg
2221 gacccacagc tgcccctgtc agccgcccac ccgggcctgg gtgaggccca caacccagcc
2281 gggcacctgt gagccgtcac agcttcttcg ttggaccagg gaccaccata tctctgcccg
2341 gggtgcatca ggacggttct ggatgagaca ggtctccatc gaagcatgag cagagagagg
2401 gctctgggga cacttcaggg cctggggagg gtggcactga acagctccct gcttggcccc
2461 agtgaccaag cagaaaagtt cctccctctc ggttaaccag aactggaaac aaagcagcat
2521 gctcccttt caaaaaggaa agaaagatgc cttaactatg taagacggaa gagtcggacc
2581 gtgccctggc agggcggcct gggactggct tctacttcag agccaccagc acatcgtgcc
2641 taagcatttt tcgttttttt aaaggagaat aaaggaacat tagttttcag attttttttt
2701 taaatgtaga caaaagttag caagaacgag gccttccgtg tctttttttt ttcccttagc
2761 ttttttttcc gtatgttttg taagcaacaa atttttgtat aaaagtctca tgtctgtttc
2821 tgtttctaga aaaaaaaaaa aaaaaaaaaa aaaaaatatt taaaaaaaaa aaaaaaaaaa
2881 aaaaaaaaaa aaaaaaaa
```

Figure 14A

5 x human E-cadherin in pRNAtin-H1.2neo
DQ090940 Homo sapiens cadherin 1, type 1, E-cadherin (epithelial) (CDH1) gene, complete cds.

Sequence ID No. 22. siRNA insert 1: 76 bp. start at 2258

```
BamH I                                                          Hind III
GGATCCCGTATTACGACCTTTCTTGGCATTGATATCCGTGCCAAGAAAGTTCGTAAATATTTTTTCCAAAAGCTT          2258-2278
     ^| Antisense       | Loop  |  Sense        | Termination Signal
```

Sequence ID No. 23. siRNA insert 2: 76 bp. start at 339

```
BamH I                                                          Hind III
GGATCCCGTTTCTTGAGCCATAAATGCTCTTGATATCCGGAGCATTTATGGCTCAAGAAATTTTTTCCAAAAGCTT         339-359
     ^| Antisense       | Loop  |  Sense        | Termination Signal
```

Sequence ID No. 24. siRNA insert 3: 76 bp. start at 478

```
BamH I                                                          Hind III
GGATCCCGTTAGTGAGTCAGCAAATTGATTGATATCCGATCAATTTGCTGACTCACTAATTTTTTCCAAAAGCTT          478-498
     ^| Antisense       | Loop  |  Sense        | Termination Signal
```

Sequence ID No. 25. siRNA insert 4: 76 bp. start at 986

```
BamH I                                                          Hind III
GGATCCCGTGTGAGCCATGAGCCACTGAGTTGATATCCGCTCAGTGGCTCATGGCTCACATTTTTTCCAAAAGCTT         986-1006
     ^| Antisense       | Loop  |  Sense        | Termination Signal
```

Sequence ID No. 26. siRNA insert 5: 76 bp. start at 2976

```
BamH I                                                          Hind III
GGATCCCGCATAGTCAACAACCAGGCAGGTTGATATCCGCCTGCCTGGTTGTTGTTGACTATGTTTTTTCCAAAAGCTT      2976-2996
     ^| Antisense       | Loop  |  Sense        | Termination Signal
```

Figure 14B

3 x mouse E-cadherin in pRNAtin-H1.2neo
BC098501 Mus musculus cadherin 1, mRNA (cDNA clone MGC:107495 IMAGE:30023851), complete cds.

Sequence ID No. 27. siRNA insert 1: 76 bp. start at 2126
BamH I                                                                                      Hind III
GGATCCCGTTGTTCTGGTTATCCGGAGCTTGATATCCGGCTCCGGATAACCAGAACAATTTTTCCAAAAGCTT
  ^| Antisense          | Loop         | Sense                | Termination Signal Sequence ID No. 28. siRNA insert 2: 76 bp. start at 1385
BamH I                                                                                      Hind III
GGATCCCGTCTGTGACGACAACGAACTGCTTGATATCCGGCAGTTCGTTGTCGTCACAGATTTTTCCAAAAGCTT
  ^| Antisense          | Loop         | Sense                | Termination Signal Sequence ID No. 29. siRNA insert 3: 76 bp. start at 369
BamH I                                                                                      Hind III
GGATCCCGTAGAATGCCGCTTCACTGTGATTTGATTTGATATCCGATCACAGTGAAGCGGCATCTATTTTTCCAAAAGCTT
  ^| Antisense          | Loop         | Sense                | Termination Signal

Figure 15A

Sequence ID No. 30 Human E-cadherin mRNA  NM_004360

1 agtggcgtcg gaactgcaaa gcacctgtga gcttgcggaa gtcagttcag actccagccc
      61 gctccagccc ggcccgaccc gaccgcaccc ggcgcctgcc ctcgctcggc gtcccggcc
      121 agccatgggc ccttggagcc gcagcctctc ggcgctgctg ctgctgctgc aggtctcctc
      181 ttggctctgc caggagccgg agccctgcca ccctggcttt gacgccgaga gctacacgtt
      241 cacggtgccc cggcgccacc tggagagagg ccgcgtcctg ggcagagtga attttgaaga
      301 ttgcaccggt cgacaaagga cagcctattt tcccctcgac acccgattca aagtgggcac
      361 agatggtgtg attacagtca aaaggcctct acggtttcat aacccacaga tccatttctt
      421 ggtctacgcc tgggactcca cctacagaaa gttttccacc aaagtcacgc tgaatacagt
      481 ggggcaccac caccgccccc cgccccatca ggcctccgtt tctggaatcc aagcagaatt
      541 gctcacattt cccaactcct ctcctggcct cagaagacag aagagagact gggttattcc
      601 tcccatcagc tgcccagaaa atgaaaaagg cccatttcct aaaaacctgg ttcagatcaa
      661 atccaacaaa gacaaagaag gcaaggtttt ctacagcatc actggccaag gagctgacac
      721 acccctgtt ggtgtcttta ttattgaaag agaaacagga tggctgaagg tgacagagcc
      781 tctggataga gaacgcattg ccacatacac tctcttctct cacgctgtgt catccaacgg
      841 gaatgcagtt gaggatccaa tggagatttt gatcacggta accgatcaga atgacaacaa
      901 gcccgaattc acccaggagg tctttaaggg gtctgtcatg gaaggtgctc ttccaggaac
      961 ctctgtgatg gaggtcacag ccacagacgc ggacgatgat gtgaacacct acaatgccgc
      1021 catcgcttac accatcctca gccaagatcc tgagctccct gacaaaaata tgttcaccat
      1081 taacaggaac acaggagtca tcagtgtggt caccactggg ctggaccgag agagtttccc
      1141 tacgtatacc ctggtggttc aagctgctga ccttcaaggt gaggggttaa gcacaacagc
      1201 aacagctgtg atcacagtca ctgacaccaa cgataatcct ccgatcttca atccccaccac
      1261 gtacaagggt caggtgcctg agaacgaggc taacgtcgta atcaccacac tgaaagtgac
      1321 tgatgctgat gccccaata cccagcgtg ggaggctgta tacaccatat tgaatgatga
      1381 tggtggacaa tttgtcgtca ccacaaatcc agtgaacaac gatggcattt tgaaaacagc
      1441 aaagggcttg gattttgagg ccaagcagca gtacattcta cacgtagcag tgacgaatgt
      1501 ggtaccttt gaggtctctc tcaccacctc cacagccacc gtcaccgtgg atgtgctgga
      1561 tgtgaatgaa gcccccatct ttgtgcctcc tgaaaagaga gtggaagtgt ccgaggactt
      1621 tggcgtgggc caggaaatca catcctacac tgcccaggag ccagacacat ttatggaaca

Figure 15B

```
     1681 gaaaataaca tatcggattt ggagagacac tgccaactgg ctggagatta
atccggacac
     1741 tggtgccatt tccactcggg ctgagctgga caggaggat tttgagcacg
tgaagaacag
     1801 cacgtacaca gccctaatca tagctacaga caatggttct ccagttgcta
ctggaacagg
     1861 gacacttctg ctgatcctgt ctgatgtgaa tgacaacgcc cccataccag
aacctcgaac
     1921 tatattcttc tgtgagagga atccaaagcc tcaggtcata aacatcattg
atgcagacct
     1981 tcctcccaat acatctccct tcacagcaga actaacacac ggggcgagtg
ccaactggac
     2041 cattcagtac aacgacccaa cccaagaatc tatcattttg aagccaaaga
tggccttaga
     2101 ggtgggtgac tacaaaatca atctcaagct catggataac cagaataaag
accaagtgac
     2161 caccttagag gtcagcgtgt gtgactgtga agggggccgcc ggcgtctgta
ggaaggcaca
     2221 gcctgtcgaa gcaggattgc aaattcctgc cattctgggg attcttggag
gaattcttgc
     2281 tttgctaatt ctgattctgc tgctcttgct gtttcttcgg aggagagcgg
tggtcaaaga
     2341 gcccttactg cccccagagg atgacacccg gacaacgtt tattactatg
atgaagaagg
     2401 aggcggagaa gaggaccagg actttgactt gagccagctg cacaggggcc
tggacgctcg
     2461 gcctgaagtg actcgtaacg acgttgcacc aaccctcatg agtgtccccc
ggtatcttcc
     2521 ccgccctgcc aatcccgatg aaattggaaa ttttattgat gaaaatctga
aagcggctga
     2581 tactgacccc acagcccgc cttatgattc tctgctcgtg tttgactatg
aaggaagcgg
     2641 ttccgaagct gctagtctga gctccctgaa ctcctcagag tcagacaaag
accaggacta
     2701 tgactacttg aacgaatggg gcaatcgctt caagaagctg gctgacatgt
acggaggcgg
     2761 cgaggacgac tagggactc gagagaggcg ggccccagac ccatgtgctg
ggaaatgcag
     2821 aaatcacgtt gctggtggtt tttcagctcc cttcccttga gatgagtttc
tggggaaaaa
     2881 aaagagactg gttagtgatg cagttagtat agctttatac tctctccact
ttatagctct
     2941 aataagtttg tgttagaaaa gtttcgactt atttcttaaa gcttttttt
ttttcccatc
     3001 actctttaca tggtggtgat gtccaaaaga tacccaaatt ttaatattcc
agaagaacaa
     3061 ctttagcatc agaaggttca cccagcacct tgcagatttt cttaaggaat
tttgtctcac
     3121 ttttaaaaag aaggggagaa gtcagctact ctagttctgt tgttttgtgt
ataaatttt
     3181 ttaaaaaaaa tttgtgtgct tctgctcatt actacactgg tgtgtccctc
tgccttttt
     3241 ttttttttta agacagggtc tcattctatc ggccaggctg gagtgcagtg
gtgcaatcac
     3301 agctcactgc agccttgtcc tcccaggctc aagctatcct tgcacctcag
cctcccaagt
     3361 agctgggacc acaggcatgc accactacgc atgactaatt ttttaaatat
ttgagacggg
     3421 gtctccctgt gttacccagg ctggtctcaa actcctgggc tcaagtgatc
ctcccatctt
```

Figure 15C

```
     3481 ggcctcccag agtattggga ttacagacat gagccactgc acctgcccag
ctccccaact
     3541 ccctgccatt ttttaagaga cagtttcgct ccatcgccca ggcctgggat
gcagtgatgt
     3601 gatcatagct cactgtaacc tcaaactctg gggctcaagc agttctccca
ccagcctcct
     3661 ttttattttt ttgtacagat ggggtcttgc tatgttgccc aagctggtct
taaactcctg
     3721 gcctcaagca atccttctgc cttggccccc caaagtgctg ggattgtggg
catgagctgc
     3781 tgtgcccagc ctccatgttt taatatcaac tctcactcct gaattcagtt
gctttgccca
     3841 agataggagt tctctgatgc agaaattatt gggctctttt agggtaagaa
gtttgtgtct
     3901 ttgtctggcc acatcttgac taggtattgt ctactctgaa gacctttaat
ggcttccctc
     3961 tttcatctcc tgagtatgta acttgcaatg ggcagctatc cagtgacttg
ttctgagtaa
     4021 gtgtgttcat taatgtttat ttagctctga agcaagagtg atatactcca
ggacttagaa
     4081 tagtgcctaa agtgctgcag ccaaagacag agcggaacta tgaaaagtgg
gcttggagat
     4141 ggcaggagag cttgtcattg agcctggcaa tttagcaaac tgatgctgag
gatgattgag
     4201 gtgggtctac ctcatctctg aaaattctgg aaggaatgga ggagtctcaa
catgtgtttc
     4261 tgacacaaga tccgtggttt gtactcaaag cccagaatcc ccaagtgcct
gcttttgatg
     4321 atgtctacag aaaatgctgg ctgagctgaa cacatttgcc caattccagg
tgtgcacaga
     4381 aaaccgagaa tattcaaaat tccaattttt ttcttaggag caagaagaaa
atgtggccct
     4441 aaaggggggtt agttgagggg taggggggtag tgaggatctt gatttggatc
tctttttatt
     4501 taaatgtgaa tttcaactttt tgacaatcaa agaaaagact tttgttgaaa
tagctttact
     4561 gtttctcaag tgttttggag aaaaaaatca accctgcaat cacttttttgg
aattgtcttg
     4621 attttttcggc agttcaagct atatcgaata tagttctgtg tagagaatgt
cactgtagtt
     4681 ttgagtgtat acatgtgtgg gtgctgataa ttgtgtattt tctttgggggg
tggaaaagga
     4741 aaacaattca agctgagaaa agtattctca aagatgcatt tttataaatt
ttattaaaca
     4801 attttgttaa accataaaaa aaaaaaaa
```

Figure 16A

Sequence ID No. 31 Mouse E-cadherin mRNA BC098501

```
   1 agccgcggcg cactactgag ttcccaagaa cttctgctag actcctgccc ggcctaaccc
  61 ggccctgccc gaccgcaccc gagctcagtg tttgctcggc gtctgccggg tccgccatgg
 121 gagcccggtg ccgcagcttt tccgcgctcc tgctcctgct gcaggtctcc tcatggcttt
 181 gccaggagct ggagcctgag tcctgcagtc ccggcttcag ttccgaggtc tacacctttc
 241 cggtgccgga gaggcacctg gagagaggcc atgtcctggg cagagtgaga tttgaaggat
 301 gcaccggccg gccaaggaca gccttctttt cggaagactc ccgattcaaa gtggcgacag
 361 acggcaccat cacagtgaag cggcatctaa agctccacaa gctggagacc agtttcctcg
 421 tccgcgcccg ggactccagt catagggagc tgtctaccaa agtgacgctg aagtccatgg
 481 ggcaccacca tcaccggcac caccaccgcg accctgcctc tgaatccaac ccagagctgc
 541 tcatgtttcc cagcgtgtac ccaggtctca gaagacagaa acgagactgg gtcatccctc
 601 ccatcagctg ccccgaaaat gaaaagggtg aattcccaaa gaacctggtt cagatcaaat
 661 ccaacaggga caaagaaaca aaggttttct acagcatcac cggccaagga gctgacaaac
 721 cccccgttgg cgttttcatc attgagaggg agacaggctg gctgaaagtg acacagcctc
 781 tggatagaga agccattgcc aagtacatcc tctattctca tgccgtgtca tcaaatgggg
 841 aagcggtgga ggatcccatg gagatagtga tcacagtgac agatcagaat gacaacaggc
 901 cagagtttac ccaggaggtg tttgagggat ccgttgcaga aggcgctgtt ccaggaacct
 961 ccgtgatgaa ggtctcagcc accgatgcag acgatgacgt caacacctac aacgctgcca
1021 tcgcctacac catcgtcagc caggatcctg agctgcctca caaaacatg ttcactgtca
1081 atagggacac cggggtcatc agtgtgctca ctctgggct ggaccgagag agttaccccta
1141 catacactct ggtggttcag gctgctgacc ttcaaggcga aggcttgagc acaacagcca
1201 aggctgtgat cactgtcaag gatattaatg acaacgctcc tgtcttcaac ccgagcacgt
1261 atcagggtca agtgcctgag aatgaggtca tgcccggat cgccacactc aaagtgaccg
1321 atgatgatgc ccccaacact ccggcgtgga aagctgtgta caccgtagtc aacgatcctg
1381 accagcagtt cgttgtcgtc acagacccca cgaccaatga tggcattttg aaaacagcca
1441 agggcttgga ttttgaggcc aagcagcaat acatccttca tgtgagagtg gagaacgagg
1501 aaccctttga ggggtctctt gtccttcca cagccactgt cactgtggac gtggtagacg
1561 tgaatgaagc ccccatcttt atgcctgcgg agaggagagt cgaagtgccc gaagactttg
1621 gtgtgggtca ggaaatcaca tcttataccg ctcgagagcc ggacacgttc atggatcaga
```

Figure 16B

```
   1681 agatcacgta tcggatttgg agggacactg ccaactggct ggagattaac
ccagagactg
   1741 gtgccatttt cacgcgcgct gagatggaca gagaagacgc tgagcatgtg
aagaacagca
   1801 catatgtagc tctcatcatc gccacagatg atggttcacc cattgccact
ggcacgggca
   1861 ctcttctcct ggtcctgtta gacgtcaatg ataacgctcc catcccagaa
cctcgaaaca
   1921 tgcagttctg ccagaggaac ccacagcctc atatcatcac catcttggat
ccagaccttc
   1981 cccccaacac gtcccccttt actgctgagc taacccatgg ggccagcgtc
aactggacca
   2041 ttgagtataa tgacgcagct caagaatctc tcattttgca accaagaaag
gacttagaga
   2101 ttggcgaata caaaatccat ctcaagctcg cggataacca gaacaaagac
caggtgacca
   2161 cgttggacgt ccatgtgtgt gactgtgaag ggacggtcaa caactgcatg
aaggcgggaa
   2221 tcgtggcagc aggattgcaa gttcctgcca tcctcggaat ccttggaggg
atcctcgccc
   2281 tgctgattct gatcctgctg ctcctactgt ttctacggag gagaacggtg
gtcaaagagc
   2341 ccctgctgcc accagatgat gatacccggg acaatgtgta ttactatgat
gaagaaggag
   2401 gtggagaaga agaccaggac tttgatttga gccagctgca caggggcctg
gatgcccgac
   2461 cggaagtgac tcgaaatgat gtggctccca ccctcatgag cgtgccccag
tatcgtcccc
   2521 gtcctgccaa tcctgatgaa attggaaact tcatcgatga aaacctgaag
gcagccgaca
   2581 gcgacccacc ggcacccccct tacgactctc tgttggtgtt cgattacgag
ggcagtggtt
   2641 ctgaagccgc tagcctgagc tcactgaact cctctgagtc ggatcaggac
caggactacg
   2701 attatctgaa cgagtggggc aaccgattca agaagctggc ggacatgtac
ggcggtggcg
   2761 aggacgacta ggggactagc aagtctcccc cgtgtggcac catgggagat
gcagaataat
   2821 tatatcagtg gtctttcagc tccttccctg agtgtgtaga agagagactg
atctgagaag
   2881 tgtgcagatt gcatagtggt ctcattctcc ttactggact gtctgtgtta
ggatggtttt
   2941 cactgattgt tgaaatcttt ttttattttt tatttttaca gtgctgagat
ataaactgtg
   3001 ccttttttg tttgtttgtt tctgtttttg ttcttttgag cagaacaaaa
aaaagggacc
   3061 actatgcatg ctgcacacgt ctcagattct taggtacaca cctgattctt
aggtgcatgc
   3121 catagtggga tatgttgctt tgatcagaac ctgcagggag gttttcgggc
accacttaag
   3181 tttcttggcg tttctttcaa accgttctct aagatgcatt tttatgaatt
ttattaaaga
   3241 gttttgttaa aaaaaaaaaa aaaaaaaaaa aaaaaaaaaa aaaaaaaaaa
aaaaaaaaaa
   3301 aaaaaaaaaa aaaa
```

METHOD FOR RETARDING THE DIFFERENTIATION OF PLURIPOTENT CELLS

PRIORITY CLAIM

This application is a continuation application of International Application PCT/GB2007/000356, filed Feb. 2, 2007, which claims priority to GB 0602063.0, filed Feb. 2, 2006, each of which are hereby incorporated by reference in their entirety.

FIELD OF THE INVENTION

Some embodiments relates to materials and methods for cultivating biological cells, such that the cells do not differentiate prematurely and/or for using various cells.

BACKGROUND

The present invention provides a method of retarding the differentiation of a biological cell. The biological cell may preferably comprise a stem or progenitor cell. The invention further provides cell culture media that may be used to retard differentiation of cultured cells, biological cells comprising constructs useful in the retardation of cell differentiation, and methods for the therapeutic manipulation of biological cells.

The production, maintenance and use of stem and progenitor cells is currently the subject of much scientific interest and research. Stem and progenitor cells constitute a highly valuable system for studying aspects of development and have the potential to revolutionise the treatment of injury and disease as the basis of cellular therapies.

The therapeutic use of stem cells offers a powerful new therapeutic approach as compared to existing drug-based therapies. This new approach may have applications in degenerative illnesses (e.g. Alzheimer), cardiovascular diseases, cancer and diseases of the nervous system (e.g. Multiple sclerosis). Many such diseases are currently untreatable.

Disease management is currently achieved through the use of disease modifying drugs, often whose activities the body often poorly tolerates. In addition, these drugs are limited in their ability to control only the symptoms of a disease and are unable to offer cures. Poor disease coverage coupled with the failings in current drug based therapies is driving the quest for new disease management methods and treatments.

The most promising development towards such goals is in the development of regenerative tissue engineering stem cell based therapies. In fact, the potential of stem cells as therapeutic cures is well known; with over 10,000 individuals undergoing successful bone marrow stem cell transplantations yearly in the UK.

Estimations currently predict an explosion in the stem cell market, reaching a value in the region of $10 billion by 2010.

The therapeutic use of stem cells relies on the ability of these cells to give rise to multiple tissue types. Accordingly such cells are able to generate replacement tissue in subjects to which they are administered.

Stem cells such as human embryonic stem (hES) cells are widely believed to have the capability to revolutionize disease therapeutics with the potential of meeting many of the unmet medical needs. Embryonic stem cells are unique in their ability to develop and differentiate into all the cells and tissues of the body. As such, they are a potential source of replacement cells and tissues for organ repair in chronic diseases. The unique characteristics that commend embryonic stem cells to therapeutic use are:

i) They are unspecialised cells capable of proliferation and self-renewal.
ii) Under specific physiological conditions they can be induced to become cells with specific functions, such as beating cells of the heart.

Current protocols for the culture and growth of stem cells (such as from stem cells from mouse and human sources) requires the involvement of skilled technicians, as well as the use of specialized cell culture media intended to maximise the yield of pluripotent or multipotent cells within such cultures.

However, current techniques for the culture of stem or progenitor cells are subject to spontaneous differentiation of the cultured cells which gives rise to the development of various differentiated cell types. Such spontaneous differentiation severely decreases the yield of pluripotent or multipotent cells over extended passages, a decrease that is particularly notable in human cell cultures. If cells to be used for therapy undergo uncontrolled differentiation during culture the number of possible lineages into which they may develop, and hence their ultimate therapeutic potential, is reduced. Therefore, for ES cells to realise their potential in cellular therapy applications it is essential that increased yields of pluripotent cells are achievable using cost-effective medium, absence of animal products (such as serum) and minimum technical requirements.

Stem cells offer the promise of treatment, and possibly, the cure of a broad array of human diseases, benefiting patients, family members, physicians and society in general.

Current approaches to maintaining the undifferentiated phenotype of ES cells are focused on the identification of exogenous and endogenous factors able to maintain the pluripotent state (the ability of the cells to differentiate into all cell types). For example, addition of leukemia inhibitory factor (LIF) to mouse ES cells can promote the undifferentiated growth of these cells. However, even LIF, the "gold standard" factor for undifferentiated mouse ES cell culture, cannot maintain homogeneous undifferentiated ES cell populations. Neither can it prevent spontaneous differentiation of the cells in suspension culture, a technique essential for obtaining sufficient quantities of pluripotent cells to allow transfer of ES cell therapies into the clinic.

The market readiness of stem cell therapy awaits the development of technologies capable of imparting control and direction on hES cell growth.

Current methods for the derivation and maintenance of stem cells such as embryonic stem cells are technically demanding and inefficient, with a success rate generally less than 30%.

Current laboratory methods used to maintain cultures of proliferative hES cells are also unable to produce such cells fast enough to respond to increasing demand. Current methods rely on recapitulation of the cell-cell and cell-matrix environment and are limited to production in inefficient monolayer culture.

To date pluripotent hES cells have proven difficult to expand in vitro and significant spontaneous differentiation occurs under current "optimal" growth conditions. Leukemia inhibitory factor (LIF) is the current "gold standard" for undifferentiated mouse ES cell culture. However LIF cannot maintain homogeneous ES cell populations, neither can it prevent spontaneous differentiation of the cells.

The growth factor fibroblast growth factor 2 (FGF-2) is also commonly used as a supplement in the culture of human stem cells, such as human embryonic stem cells. This growth factor helps human stem cells to remain undifferentiated and capable of proliferation in culture.

Currently, hES cells are generally grown in direct contact with mouse feeder cells or in media pre-conditioned by nutrient components derived from such cells. Such cells carry the risk of passing microbes and infectious agents to the recipient. As such the FDA has stated that it will demand extensive testing and long term follow up studies on therapies using such technologies. Mechanisms aimed at removing such dangers have thus far focused on the use of expensive growth factor supplements.

To date, none of the prior art techniques have been consistently successful enough to allow their widespread clinical use in biological cell-based therapies. There therefore remains a need to develop improved methods for preparing biological cells for therapeutic use, and improved methods of therapy utilizing biological cells.

Furthermore, it will also be appreciated in the light of the above that there exists a need to develop new or improved cell culture methods, conditions and media capable of promoting biological cell growth without maturation and/or differentiation. Such new or improved cell culture resources may be of use not only in the therapeutic adaptation of stem and/or progenitor cells, but also in the culture of biological cells (and particularly stem and/or progenitor cells) for research and/or development purposes. Although it is desirable to be able to culture such cells (for example to allow expansion of cell numbers without maturation or differentiation) there is a general lack of suitable resources available to the skilled person in the prior art.

SUMMARY

In a first aspect of the present invention there is provided a method of retarding differentiation of a biological cell, the method comprising culturing the cell in the presence of an inhibitor of E-cadherin activity.

In a second aspect of the invention there is provided the use of an inhibitor of E-cadherin activity to maintain undifferentiated biological cells in culture.

In a third aspect the present invention also provides the use of an inhibitor of E-cadherin activity in the manufacture of a culture medium for retarding the differentiation of biological cells.

In a fourth aspect the invention provides a cell culture medium suitable for the retardation of biological cell differentiation, the cell culture medium comprising an inhibitor of E-cadherin activity.

The present invention is based upon the inventors' new and surprising finding that the inhibition of E-cadherin activity is able to retard the differentiation of biological cells. The cadherins are a family of integral membrane proteins which are involved in calcium-dependent cell adhesion. E-cadherin is so called because of its association with the epithelium. Cadherins comprise an extracellular domain of approximately 600 amino acid residues, a transmembrane domain, and an intracellular domain of 150 amino acid residues. The extracellular domain comprises four repeated sequences that are believed to be associated with calcium ion binding. The gene encoding E-cadherin is known as cdh1.

The amino acid sequence of human E-cadherin is shown in Sequence ID No. 2, and the sequence of DNA encoding this protein is shown in Sequence ID No. 1. The amino acid sequence of murine E-cadherin is shown in Sequence ID No. 4, and the sequence of DNA encoding this protein shown in Sequence ID No. 3. The amino acid sequence of rat E-cadherin is shown in Sequence ID No. 6 (with the sequence of DNA encoding this protein shown in Sequence ID No. 5), and the amino acid sequences of canine and bovine E-cadherin are shown in Sequence ID No. 8 and Sequence ID No. 10 respectively (with the sequences of DNA molecules encoding these proteins shown in Sequence ID Nos. 7 and 9 respectively).

It is known that E-cadherin molecules may bind one another by an extracellular domain designated "CAD-HAV". The CAD-HAV domain of human E-cadherin is represented by amino acid residues 233 to 235 of Sequence ID No. 2, and is shown in Sequence ID No. 11. The CAD-HAV domain may represent a preferred region through which activity of E-cadherin activity may be inhibited, as considered further below.

Another region that may be targeted in the inhibition of E-cadherin activity is the area around the tryptophan residue found at position 156 (Trp156) of Sequence ID No. 2. This residue has been shown to be crucial in the dimerisation of E-cadherin EC1 domain (Laur et al., *Archives of Biochemistry and Biophysics,* 2002: 400; 141-147). Suitable inhibitors of E-cadherin activity targeting this domain may include antibodies capable of binding to epitopes incorporating Trp156, as well as fragments or derivatives of E-cadherin comprising this residue (for example soluble fragments incorporating Trp156).

It will be appreciated that the differentiation of a wide range of biological cell types may be retarded. However, this activity is particularly pronounced in the case of progenitor and stem cells, given the undifferentiated nature of such cells, and so stem and progenitor cells constitute preferred biological cells in the context of the present invention. As set out in the introduction, the development of techniques by which differentiation of stem or progenitor cells in culture may be avoided or retarded is much needed in association with the use of such cells for therapeutic or research purposes. Without wishing to be bound by any hypothesis, the inventors believe that inhibitors of E-cadherin activity function with a dual role, both as survival factors for cultured cells, and also as agents capable of preventing cell differentiation and maturation during culture.

For the purposes of the present invention stem cells are taken to comprise nullipotent, totipotent or pluripotent cells, and progenitor cells (or precursor cells) to comprise multipotent cells. Totipotent cells are those cells capable of giving rise to all extraembryonic, embryonic and adult cells of the embryo. Accordingly it can be seen that totipotent cells may ultimately give rise any type of differentiated cell found in an embryo or adult. By comparison, pluripotent cells are cells capable of giving rise to some extraembryonic and all embryonic and adult cells. Thus it can be seen that pluripotent cells are able to give rise to a more limited range of cell types than are totipotent cells. Nullipotent cells are those that will not undergo differentiation without the action of an exogenous cue to differentiation. Multipotent cells are cells able to give rise to diverse cell types in response to appropriate environmental cues (such as action of soluble growth factors or the substrate on which the cell, or its progeny, is located), but are more restricted in their potential lineage formation than are pluripotent, nullipotent or totipotent cells.

One suitable source of pluripotent stem cells that may be used in accordance with the present invention is those derived from the inner cell mass/epiblast (or other cells, such as blastomeres) of pre-implantation embryos. Such embryonic stem (ES) cells are readily obtainable and are capable of giving rise to all possible embryonic and adult cell lineages. Accordingly ES cells represent preferred cells for use in the invention.

The skilled person will appreciate that, although the methods and media of the invention are suitable for use with stem cells of all types and derived from all species (including human cells such as human embryonic stem cells), it may be preferred for the purposes of the present invention that any stem cell is other than a human embryonic stem cell.

Although they do not wish to be bound by any hypothesis, the inventors believe that the beneficial effects observed on culturing biological cells in the presence of inhibitors of E-cadherin activity arise as a result of the inhibitor's action as a survival factor, an extracellular signal required in order to induce a cell to divide, and without which a cell may undergo apoptosis. Accordingly, in a further aspect the present invention also provides the use of an inhibitor of E-cadherin activity as a survival factor for biological cells.

The action of inhibitors of E-cadherin activity as survival factors that are able to prevent cell differentiation and maturation is of great value in the culture of stem and progenitor cells, since it has previously been difficult to induce such cells to divide without inducing their maturation and differentiation at the same time. It will be appreciated that the use of inhibitors of E-cadherin activity in the culture of biological cells, such as stem or progenitor cells, has use in both therapeutic and non-therapeutic applications. Clearly, the ability to retard differentiation of biological cells (such as stem and progenitor cells) in culture has utility in cell culture undertaken for a wide range of non-therapeutic purposes, including (but not limited to) research and development uses. Therapeutic applications making use of the newly identified anti-differentiation properties of inhibitors of E-cadherin activity are considered elsewhere in the specification.

Conventional prior art techniques for promoting the expansion of stem or progenitor cell populations ex vivo rely on the use of "cocktails" of multiple cytokines. The cytokines are typically provided either as part of, or in addition to, serum supplementation. Commercially available media intended for use in the expansion of stem cell populations include factors such as leukemia inhibitory factor (LIF), interleukin-3 and interleukin-11 (IL-3 and IL-11), stem cell factor, FGF-2 and Flt-3 ligand. In such an embodiment the inventors believe that inhibitors of E-cadherin activity may serve to enhance the cultured cells' proliferation in response to the activity of the supplementing cytokines (i.e. the inhibitors of E-cadherin activity may be used to augment proliferation in response to known cytokine supplementation regimes). The inventors have found that the use in cell culture of inhibitors of E-cadherin activity in combination with one or more of the factors listed above is beneficial in that it allows greater expansion of cell populations than may be achieved using the prior art techniques.

The inventors have found that supplementation with inhibitors of E-cadherin activity allows stem cells populations to be expanded in culture using simpler cytokine cocktails than have previously been utilised. Such relatively simpler cytokine cocktails may be expected to provide reduced differentiation stimuli to cells so cultured. Of particular benefit is the combination of inhibitors of E-cadherin activity with LIF, which may be provided in combination with other factors, but is preferably provided alone.

Although the use of the factors listed above is of use in the ex vivo expansion of biological cells such as stem or progenitor cells, it is not without certain drawbacks. The presence of such cytokines, while helping to promote cell division, causes maturation and differentiation of the cultured cells. This maturation is outside the control of the practitioner, and may represent a major disadvantage, since it decreases the number of different cell lineages to which the cells may ultimately give rise and may prevent controlled differentiation of the cells into preferred cell types.

In contrast to prior art techniques, the inventors have found that supplementation of cell culture medium with an inhibitor of E-cadherin activity promotes cell survival without differentiation. This effect has been observed in all cell types investigated thus far. Inhibitors of E-cadherin activity may be used to retard cell differentiation, and/or promote cell survival, even in the absence of other growth factor supplements. For example, the inventors have found that inhibitors of E-cadherin activity may be used in accordance with the invention in order to retard cell differentiation, and/or promote cell survival, in the absence of LIF. Alternatively or additionally, inhibitors of E-cadherin activity may be used in accordance with the invention in order to retard cell differentiation, and/or promote cell survival, in the absence of FGF-2.

Multipotent or nullipotent cells cultured in the presence of inhibitors of E-cadherin activity are particularly useful in both therapeutic and non-therapeutic applications since they retain their capability to give rise to a wide range of cell types (i.e. retain their multipotent or nullipotent characteristics). In accordance with this finding it will be appreciated that in preferred embodiments of the invention biological cells may be cultured in the presence of inhibitors of E-cadherin activity whilst in media that are devoid of other cytokines or serum. In the context of use of inhibitors of E-cadherin activity in serum or cytokine free conditions a major function of the inhibitor may be to provide a survival signal for the cultured cells.

Accordingly, in a further aspect, the present invention also provides a cell culture medium, for use in the retardation of biological cell differentiation, comprising an inhibitor of E-cadherin activity, wherein the medium is serum free. The invention also encompasses inhibitors of E-cadherin activity that are formulated for use as a supplement for a serum free culture medium. The use of serum-free media as described herein is particularly advantageous in the context of the inhibition of differentiation of cells intended for therapeutic applications, since this reduces the risk of contamination by agents (such as infectious or otherwise deleterious agents) that may be present in serum. It will be appreciated that synthetic media and artificial serum may be used without the risk of potential contamination with animal agents that may occur via use of "natural" serum. Serum free media in accordance with the invention may advantageously also be free of supplements such as LIF and/or FGF-2.

In an additional and notable advantage over the prior art, the inventors have found that culture of stem or progenitor cells in the presence of inhibitors of E-cadherin activity allows the three-dimensional liquid culture ("suspension culture") of such cells. It will be appreciated that culture in accordance with this embodiment of the invention may preferably be undertaken using fermenters. In a preferred application, culture in accordance with this embodiment of the invention may utilise a stirred bioreactor system in which the cultured cells are either free-floating in the medium or grown on an inert surface (e.g. glass beads). Optimised conditions for the growth of cells cultured in accordance with this aspect of the invention, including preferred rates of propeller rotation, preferred oxygen tension and suitable culture media for use, may be derived by the practitioner using normal culture optimisation techniques.

The inventors have found that, in the event it is wished that cell culture in accordance with the invention be suspension culture, E-cadherin activity should preferably be inhibited totally (or substantially totally). Total (or substantially total) inhibition of E-cadherin activity helps to prevent the generation of cell to cell interactions between cultured cells. Such interactions may otherwise contribute to formation of embryoid bodies in which cultured cells may differentiate.

In the case that it is wished that cell culture in accordance with the invention be effected on a substrate, partial or total inhibition may be used. Indeed it may be preferred that partial inhibition (either by use of an inhibitor that is unable to totally inhibit E-cadherin activity, or by use of an amount of an inhibitor that is not sufficient to totally inhibit E-cadherin activity) is used, since this may advantageously allow cells cultured in this manner to retain functional cell to cell interactions. Suitable substrates may include solid substrates (such as conventional tissue plastics) or suitable gels. It may be preferred that an inhibitor of E-cadherin activity be incorporated in a cell culture substrate. Suitable inhibitors of E-cadherin activity that may be incorporated in such a cell culture substrate include peptide inhibitors (such as those incorporating the CAD-HAV domain or Trp156) or their derivatives, or antibodies such as DECMA-1 or SHE78.7. Means by which such inhibitors may be incorporated in cell culture substrates in such a way that they are able to inhibit E-cadherin activity of cultured cells will be apparent to those of skin in the art. Cell culture substrates in accordance with this aspect of the invention may be provided in the form of tissue culture dishes or flasks, or as beads for use in suspension culture.

Except for where the context requires otherwise, references to "cell culture in accordance with the invention" should be taken to encompass cell culture techniques making use of the methods or uses of the invention; and/or cell culture techniques making use of cells of the invention; and/or cell culture techniques making using of cell culture media of the invention.

Inhibitors of E-cadherin activity suitable for use in accordance with the preceding aspects of the invention may be selected from the entire range of inhibitors described within the present specification. It will be appreciated that the preceding aspects of the invention may employ a single inhibitor of E-cadherin activity, or they may employ a combination of two or more inhibitors of E-cadherin activity.

For the purposes of the present invention an inhibitor of E-cadherin activity may be any substance, compound or molecule capable of decreasing, blocking or otherwise abrogating the biological activity of E-cadherin. It will be appreciated that in the present context the "biological activity" of E-cadherin referred to above is the capacity of E-cadherin to contribute to the differentiation of biological cells.

An example of an inhibitor of E-cadherin activity suitable for use in accordance with the present invention may comprise E-cadherin neutralising antibodies. Suitable neutralising antibodies are those that, when bound to an epitope present on E-cadherin, prevent E-cadherin's contribution to cell differentiation.

For example, the anti-E-cadherin antibody DECMA-1 (available from Sigma, Dorset, UK under the catalogue number U3254) may be used as an inhibitor of E-cadherin activity suitable for use in accordance with the invention. Alternatively, a preferred inhibitor of E-cadherin activity may be an antibody other than DECMA-1. One example of a further E-cadherin neutralising antibody that may be used in accordance with the present invention is SHE78-7 (also referred to as SHE78.7), which is commercially available from Zymed Labs, Inc., S. San Francisco, Calif. (Cat. No. 13-5700). DECMA-1 antibody was raised against mouse embryonal carcinoma cell line PCC4 Aza RI and SHE78.7 was raised against human placenta, therefore. In the light of this, it will be appreciated that DECMA-1 may be more effective at inhibition of E-cadherin activity in mouse (including mouse stem cells such as mouse embryonic stem cells) and SHE78.7 more effective for inhibition of E-cadherin activity in human cells (including human stem cells such as human embryonic stem cells).

In particular, it may be preferred that SHE78.7 be used as an inhibitor of E-cadherin activity when it is wished to inhibit E-cadherin activity associated with human cells. The inventors have found that DECMA-1 be used as a preferred inhibitor of E-cadherin activity when it is wished to inhibit E-cadherin activity associated with murine cells.

Antibodies suitable for use as inhibitors of E-cadherin activity in accordance with the present invention include monoclonal activity-neutralizing antibodies and polyclonal activity-neutralizing antibodies, as well as fragments of such antibodies that retain the neutralizing activity. Suitable examples of fragments that may be used include, but are not limited to, Fab or F(ab')hd 2, and Fv fragments.

Methods suitable for the generation and/or identification of antibodies capable of binding specifically to a target such as E-cadherin are well known to those skilled in the art. In general suitable antibodies may be generated by the use of isolated E-cadherin as an immunogen. E-cadherin may be administered to a mammalian organism, such as a rat, rabbit or mouse and antibodies elicited as part of the immune response. Suitable immunogens may include the full-length E-cadherin or an antigenic peptide fragment thereof (such as a preferred epitope associated with E-cadherin's biological function). Monoclonal antibodies capable of neutralizing E-cadherin activity can be produced by hybridomas, immortalized cell lines capable of secreting a specific monoclonal antibody. Suitable immortalized cell lines can be created in vitro by fusing two different cell types, usually lymphocytes, one of which is a tumour cell.

However, not withstanding the above, it may be preferred that the inhibitors to be used are inhibitors other than neutralising antibodies. In particular, it may be preferred that inhibitors for use in accordance with these aspects of the invention are other than the antibody DECMA-1 or SHE78.7. Examples of suitable inhibitors of E-cadherin activity that may be used in accordance with the invention are considered further below. Further examples of suitable inhibitors of E-cadherin activity that may be used in accordance with the present invention may comprise proteins (or protein derivatives) able to bind to E-cadherin and thereby prevent its biological activity. Such proteins or derivatives include naturally occurring proteins able to inhibit E-cadherin activity, as well as derivatives based on such naturally occurring proteins, and novel proteins or derivatives possessing suitable activity.

For example, it is well known that E-cadherin binds to other E-cadherin molecules via the most terminal CAD extracellular domain (CAD-HAV). Similarly, it has been shown that tryptophan residue Trp156 is linked to dimerisation of E-cadherin. Accordingly, suitable inhibitors of E-cadherin activity for use in accordance with the present invention may include protein or other binding molecules capable of binding the CAD-HAV sequence (Sequence ID No. 6) or a sequence incorporating residue Trp156. Preferred inhibitors of E-cadherin activity may comprise the CAD-HAV sequence, and a particularly preferred example of a suitable inhibitor of E-cadherin activity consists of the CAD-HAV sequence. Preferred inhibitors may comprise soluble E-cadherin fragments incorporating CAD-HAV and/or Trp156. Alternatively suitable protein or other binding molecules for use as inhibitors of E-cadherin activity in accordance with the present invention may be based on modified forms of the CAD-HAV sequence, or a sequence incorporating Trp156. Such modified forms may include derivatives that are modified in order to increase their biological activity, increase their resistance to protein degradation, increase their half-life, or otherwise increase their availability.

Suitable peptide inhibitors comprising the CAD-HAV sequence or Trp156 may comprise three or more contiguous amino acids from the sequence of E-cadherin shown in Sequence ID No. 2, or may comprise five, ten, twenty or more contiguous amino acid residues from Sequence ID No. 2 including the CAD-HAV sequence or Trp156.

Peptide inhibitors (such as those comprising the CAD-HAV sequence and/or sequences incorporating Trp156) may constitute preferred inhibitors of E-cadherin activity for use in accordance with the invention. Other suitable inhibitors of E-cadherin activity may be derived from such peptide inhibitors. Derivatives of this sort, such as peptoid derivatives, may have greater resistance to degradation, and may thus have improved shelf-lives compared to the peptides from which they are derived.

Suitable inhibitors of E-cadherin activity may also be conjugated with polyvalent/monovalent synthetic polymers, thereby increasing avidity of the inhibitors to their target protein. For example, in one preferred embodiment multiple forms of inhibitors suitable for use in accordance with the invention may be conjugated to a single polymer. Alternatively or additionally a suitable inhibitor may be conjugated to a suitable polymer in combination with one or more other factors required to maintaining pluripotency (e.g. suitable oligosaccharides).

Inhibitors of E-cadherin activity suitable for use in accordance with the invention may alternatively, or additionally, be capable of binding to the membrane proximal region of E-cadherin.

Further inhibitors of E-cadherin activity suitable for use in accordance with the present invention include the $\alpha_E\beta_7$ integrin, which is a naturally occurring binding partner of E-cadherin. Other suitable inhibitors may include E-cadherin-binding fragments of $\alpha_E\beta_7$ integrin, or derivatives of this integrin or its fragments. Suitable fragments may be selected in the light of the disclosure of Shiraishi et al, (J Immunol. 2005 Jul. 15; 175(2):1014-21).

Small molecule inhibitors of E-cadherin may represent preferred inhibitors for use in accordance with the present invention.

In a preferred embodiment of the invention cells may be induced to over-express naturally occurring inhibitors of E-cadherin activity. It may be preferred that such over expression of naturally occurring inhibitors by a cultured cell is achieved transiently (for instance such that expression occurs only during ex vivo culture and ceases on administration of cells to the subject requiring therapy, or such that expression occurs only during ex vivo expansion of cell populations and ceases in order to allow differentiation of the expanded population into cells having a desired phenotype). One example of such a naturally occurring inhibitor of E-cadherin activity is "Slug" (which is also known as "Snai2" and "snail homolog 2"). The amino acid sequence of the human form of Slug (NCBI reference number NP_003059) is shown in Sequence ID No. 12, and the amino acid sequence of the mouse form of Slug (NCBI reference number NP_035545) is shown in Sequence ID No. 13.

Another example of a suitable naturally occurring inhibitor of E-cadherin activity is "Snail". The amino acid sequence of the human form of Snail (NCBI reference number NP_005976) is shown in Sequence ID No. 14, and the amino acid sequence of the murine form of snail (NCBI reference number NP_035557) is shown in Sequence ID No. 15.

A further naturally occurring inhibitor of E-cadherin activity suitable for use in accordance with the present invention comprises SMAD interacting protein 1 "SIP1". The amino acid sequence of the human form of SIP1 (NCBI reference number BAB40819) is shown in Sequence ID No. 16, and the amino acid sequence of the mouse form of SIP1 (NCBI reference number AAD56590) is shown in Sequence ID No. 17.

E2A comprises a further naturally occurring inhibitor of E-cadherin activity suitable for use in accordance with the present invention. The human form of E2A is also known as "Homo sapiens transcription factor 3", "E2A immunoglobulin enhancer binding factors E12/E47" and "TCF3". The human form of E2A has been given NCBI reference number NM_003200. The amino acid sequence of human E2A is shown in Sequence ID No. 18, and DNA encoding the human form of E2A is shown in Sequence ID No. 19. The murine form of E2A is also known as "Mus musculus transcription factor E2a" and has NCBI reference number BC006860. The amino acid sequence of murine E2A is shown in Sequence ID No. 20, and the sequence of DNA encoding the murine form of E2A is shown in Sequence ID No. 21.

It will be appreciated that the naturally occurring inhibitors of E-cadherin described above merely represent examples of the range of naturally occurring inhibitors that may be used in accordance with the invention. These (and other) inhibitors may be used singly or in combination with other inhibitors (including combinations of naturally occurring and artificial inhibitors).

The inventors believe that Snail, Slug, SIP1 and E2A inhibiting E-cadherin expression by methylation/hypermethylation of the E-cadherin promoter, thus preventing or reducing gene transcription. Accordingly, agents capable of causing methylation or hypermethylation of the E-cadherin promoter represent preferred inhibitors of E-cadherin suitable for use in accordance with all aspects of the present invention. It will be appreciated that once such agents have caused methylation or hypermethylation of the E-cadherin promoter they need no longer be provided to cells the differentiation of which it is wished to retard.

Aptamers comprise a further example of preferred inhibitors of E-cadherin activity suitable for use in accordance with the present invention. Aptamers are nucleic acid molecules that that assume a specific, sequence-dependent shape and bind to specific target ligands based on a lock-and-key fit between the aptamer and ligand. Accordingly suitable aptamers may be designed to interact with E-cadherin protein or with nucleic acids encoding E-cadherin. Typically, aptamers may comprise either single- or double-stranded DNA molecules (ssDNA or dsDNA) or single-stranded RNA molecules (ssRNA).

As indicated above, aptamers may be used to bind (and thereby inhibit) E-cadherin protein and/or nucleic acids encoding E-cadherin protein. ssDNA aptamers may be preferred for use in the investigation of nucleic acids encoding E-cadherin. Suitable aptamers may be selected from random sequence pools, from which specific aptamers may be identified which have suitably high affinity for E-cadherin protein or nucleic acid targets. Methods for the production and selection of aptamers having desired specificity are well known to those skilled in the art, and include the SELEX (systematic evolution of ligands by exponential enrichment) process. Briefly, large libraries of oligonucleotides are produced, allowing the isolation of large amounts of functional nucleic acids by an iterative process of in vitro selection and subsequent amplification through polymerase chain reaction.

The use of aptamers as inhibitors of E-cadherin activity in accordance with the present invention may be advantageous, since aptamers have relatively stable shelf lives. This may be particularly preferred in association with cell culture media of the invention Preferably aptamers suitable for use in accordance with the invention may be stabilized by chemical modifications (for example 2'—$NH_2$ and 2'-F modifications).

Although the inventors do not wish to be bound by any hypothesis, it is believed that certain inhibitors, such as the antibody DECMA-1 mentioned above, achieve their effect through the internalisation of E-cadherin. Such internalised protein cannot achieve its normal biological function, and so biological activity is thereby inhibited. Accordingly agents capable of causing the internalisation of E-cadherin represent preferred inhibitors for use in accordance with the invention.

The preceding examples have concentrated primarily on inhibitors able to prevent biological activity that may otherwise be associated with E-cadherin that has already been expressed. It will be appreciated that other suitable inhibitors may include agents capable of preventing the expression of E-cadherin. Such inhibitors may prevent or reduce transcription of the E-cadherin gene, or may prevent or reduce translation of E-cadherin gene transcripts.

Examples of such inhibitors capable of preventing the expression of E-cadherin include aptamers (as considered above), antisense oligonucleotides and ribozymes. Suitable inhibitors will also encompass agents that can disrupt the E-cadherin gene.

The skilled person will realise that many of the inhibitors of E-cadherin activity described in the present specification, and particularly protein or nucleic acid agents as described herein, are suitable for cellular production (using the mechanism of gene transcription and expression). The skilled person will recognise that preferably such agents may be produced by the cells differentiation of which is to be retarded. Accordingly, in a further aspect, the invention also provides a biological cell comprising a construct encoding an inhibitor of E-cadherin activity. Such a biological cell is preferably a stem or progenitor cell, since these cells, which exhibit little or no differentiation, may advantageously be grown in culture to produce expanded populations of such stem or progenitor cells. Populations of this type may be beneficially used in therapeutic or non-therapeutic applications. It may be preferred that a biological cell in accordance with this aspect of the invention is one in which the construct is transiently incorporated, or in which the construct is transiently expressed. The inhibitor of E-cadherin activity encoded by the construct may preferably comprise a siRNA molecule, such as those set out in Sequence ID Nos. 22 to 29.

In a still further aspect of the invention, there is provided a method of retarding differentiation of a biological cell, the method comprising:
i) introducing a construct encoding an inhibitor of E-cadherin activity into a biological cell the differentiation of which is to be retarded; and
ii) expressing the construct such that differentiation of the cell is retarded.

Suitable constructs for use in accordance with the invention may be designed with reference to the nature of the inhibitor of E-cadherin that it is desired to use. Illustrative examples are described further below.

Suitable constructs may be extra-genomic, or may be incorporated into the biological cell's genomic DNA. In the case of constructs integrated into the DNA of a biological cell it may be a preferred feature that at least part of the construct encoding the RNAi product may be flanked by sequences (such as lox P sites) allowing the functional excision of the construct (i.e. allowing sufficient of the construct to be excised that the construct is substantially unable to further inhibit E-cadherin activity). For instance, in the case that the sequence is flanked by lox P sites excision may be effected using the site specific DNA recombinase Cre. The use of sequences allowing excision of constructs encoding inhibitors of E-cadherin activity may be preferred in situations where it is wished to transiently express the inhibitor before resuming E-cadherin activity in the cells ("return of function"). Examples of such situations include those in which it is wished to expand undifferentiated populations of cells, such as stem or progenitor cells, ex vivo before effecting the controlled differentiation of the expanded cell population into cells having a desired phenotype (or phenotypes). The differentiated cells may, for example, be used therapeutically or experimentally once either expression of the inhibitory construct has ceased or the desired differentiation has taken place.

Expression of constructs may be constitutive, in the event that it is desired to inhibit cell differentiation permanently, or to retard cell differentiation for protracted periods of time. Alternatively, it may more often be preferred that expression of the construct be inducible in accordance with the requirements of the practitioner. Appropriate techniques by which the expression of constructs encoding inhibitors of E-cadherin activity may be induced as required will be well known to those skilled in the art, and include the use of vectors inducible by agents such as tetracycline.

In a preferred embodiment a construct encoding an inhibitor of E-cadherin activity may comprise a construct encoding an RNA interference (RNAi) product capable of inhibiting E-cadherin activity.

Preferably an RNAi inhibitor of E-cadherin activity may comprise a so-called "hairpin loop" RNAi inhibitor. Such inhibitors are preferred in situations in which long-term inhibition of E-cadherin activity is required. Indeed, use of hairpin loop RNAi inhibitors may be able to effect total long-term inhibition of E-cadherin activity (referred to as "knocked down" gene activity) without the need to remove the naturally occurring E-cadherin gene.

Particularly preferred constructs for use in accordance with the invention may be based upon pRNAtin-H1.2neo/hygro tetracycline inducible vectors that are commercially available from Genscript Corporation. However, any RNAi vector may suffice, whether a plasmid or virus.

Preferred RNAi constructs which may be used to inhibit E-cadherin activity in accordance with the present invention are illustrated in Sequence ID No. 22 to Sequence ID No. 29. These sequences have been designed to achieve optimal inhibition of mRNA encoding E-cadherin, and thereby optimal inhibition of E-cadherin activity. However, it may be preferred that two or more of the RNAi constructs illustrated in Sequence ID No. 22 to Sequence ID No. 29 be used in combination to bring about a desired inhibition of E-cadherin activity (and thereby retardation of cell differentiation). As will be appreciated, such combinations should preferably be selected with reference to the species in which the desired inhibition is to be effected, so that to retard differentiation of human cells it may be preferred to combine constructs selected from the group comprising Sequence ID No. 22 to Sequence ID No. 26, whereas in the case of murine cells it may be preferred to combine constructs selected from the group comprising Sequence ID No. 27 to Sequence ID No. 29.

The genetic stability of cells into which constructs encoding inhibitors of E-cadherin activity have been introduced may be investigated using known techniques such as karyotype analysis. By way of example, a protocol suitable for effecting karyotype analysis in a manner suitable to investigate genetic stability of cells is described in the accompanying Experimental Protocols section.

Ribozymes complementary to mRNA encoding E-cadherin represent a further suitable class of inhibitors of E-cadherin activity that may be used in accordance with the present invention. Sequences encoding ribozymes are also eminently suitable for incorporation in constructs of the types described above. It is well recognised that RNA molecules comprising the well-categorised catalytic centre of ribozymes in combination with sequences complementary to an mRNA of interest may be used to cleave the selected mRNA and thereby prevent its translation to protein. Suitable oligonucleotides comprising the ribozyme catalytic centre in combination with sequences complementary to mRNA encoding E-cadherin (human form shown in Sequence ID No. 30 and murine form shown in Sequence ID No. 31) may thus be used as the template for generation of E-cadherin neutralising ribozymes.

It will be appreciated that a nucleic acid encoding an inhibitor of E-cadherin activity may be delivered to a biological cell as part of a vector of the type outlined above. Preferred vectors may additionally comprise selection elements allowing selection of those cells into which the vectors have been successfully introduced. Preferred methods for the introduction of vectors into cells may include uptake through electroporation.

The skilled person will recognise that a suitable nucleic acid encoding an inhibitor of E-cadherin activity may be introduced into a cell without the nucleic acid being incorporated in a vector. For instance, a nucleic acid encoding an inhibitor of E-cadherin activity may be incorporated within a liposome or virus particle. Alternatively a "naked" DNA molecule encoding such an inhibitor may be inserted into a biological cell by a suitable means, e.g. direct endocytotic uptake.

A nucleic acid encoding an inhibitor of E-cadherin may be transferred to the biological cells by transfection, infection, electroporation, microinjection, cell fusion, protoplast fusion or ballistic bombardment. For example, transfer may be by ballistic transfection with coated gold particles, liposomes containing the exogenous gene, and means of providing direct DNA uptake (e.g. endocytosis).

Electroporation (for example using the methodology made commercially available by Amaxa) may represent a preferred method by which vectors encoding inhibitors such as RNAi inhibitors (for example of the types described above) may be introduced into cells in which the vectors are to be expressed. It will be appreciated that the cells into which such vectors are introduced and expressed may preferably be cells that are to have their differentiation retarded in accordance with the invention.

The suitability of a putative inhibitor of F-cadherin activity for use in accordance with the present invention may be readily investigated by the skilled person using well-known techniques. A preferred technique that may be used to determine or assess the ability of a substance to inhibit E-cadherin activity is described in the Experimental results section. By way of example, a suitable technique capable of determining or assessing whether or not a test substance has E-cadherin inhibiting activity that makes it suitable for use in accordance with the invention may involve culturing cells in the presence of the test substance and LIF (or FGF-2 for human), and assessing the ability of cells so cultured to divide once LIF (or FGF-2 for human) is removed from the culture conditions. Such a technique makes use of cell counts to assess the efficacy of the test substance. Alternatively (or additionally) suitable techniques for the determination or assessment of E-cadherin inhibition by a test substance may compare the morphology of cells cultured in the presence or absence of the test compound, suitable inhibitory activity being indicated by a loss of cell-cell contact in ES, or suitable epithelial cell line, cultured in the presence of the test substance.

Alternative techniques that may be used to investigate suitable inhibitors of E-cadherin activity will be apparent to the skilled person.

Preferably an inhibitor of E-cadherin activity suitable for use in accordance with the present invention may be able to achieve at least 50% reduction in E-cadherin activity as assessed using the techniques described above. More preferably a suitable inhibitor of E-cadherin activity may be able to achieve at least 60%, 70% or 80% reduction. Even more preferably a suitable inhibitor may be able to achieve at least 85%, 90% or 95% reduction in E-cadherin activity. A most preferred inhibitor of E-cadherin activity may be able to totally prevent E-cadherin's biological activity (i.e. 100% reduction of E-cadherin activity as measured using the above techniques).

Accordingly it will be recognised that a preferred inhibitor of E-cadherin activity suitable for use in accordance with the present invention may be able to achieve at least 50% reduction in E-cadherin activity. A more preferred inhibitor of E-cadherin activity may be able to achieve at least 60%, 70% or 80% reduction. An even more preferred inhibitor may be able to achieve at least 85%, 90% or 95% reduction in E-cadherin activity, and a most preferred inhibitor of E-cadherin activity may be able to totally prevent E-cadherin's biological activity (i.e. 100% reduction of E-cadherin activity as measured using the above techniques).

Optimisation of the amount of an inhibitor of E-cadherin activity that may be required in order to bring about a desired level of retardation of cell differentiation may be achieved using techniques well known to the person skilled in the art. Suitable techniques may be applicable to both externally administered inhibitors and constructs encoding suitable inhibitors, and may include dose response studies using cultured cells. Optimisation may be undertaken with reference to the efficacy of the inhibitor of E-cadherin activity assessed using the criteria and methods set out above.

For example, using the methods described in the accompanying protocols and Experimental Results sections, the inventors have identified that it is not necessary to completely inhibit E-cadherin activity in order to culture human stem cells in accordance with the invention. Partial inhibition of E-cadherin activity may, in fact, be preferable to total inhibition in the event that it is wished to culture human stem cells in monolayers. However, these studies reported elsewhere in the specification have also identified that total inhibition of E-cadherin activity is optimal for suspension culture of human stem cells.

By retardation of differentiation of a biological cell is meant the prevention of expression of markers associated with differentiation and/or the loss of totipotent, multipotent, nullipotent, or pluripotent capabilities. For example, a pluripotent cell may be expected to express the stem cell markers Oct-4 and Nanog. As pluripotent cells undergo differentiation expression of Oct-4 and/or Nanog will decrease (even to the extent that such markers are no longer expressed), whilst expression of markers such as transthyretin (an endoderm marker), Sox-1 (a neuroectoderm marker), brachyury (a mesoderm marker) and/or zeta globin (a further mesoderm marker) may increase (depending on the differentiating cell types formed). PCR analysis represents a suitable method by which the absence or presence of transcripts for these may be investigated, and so by which retardation of differentiation may be assessed.

The use of inhibitors of E-cadherin activity to inhibit differentiation of stem and progenitor cells has specific utility in the culture of such cells from animal species that are normally difficult to culture. The rat constitutes an example of such a species. By improving the viability of cultured stem and progenitor cells derived from such "difficult" species (which in addition to rat include cats and dogs, as well as the African clawed frog *Xenopus laevis*) it is consequently possible to utilise the cultured cells in the preparation of transgenic animals. The generation of transgenic animals is a standard laboratory procedure in respect of species such as mice, but has, until now, been impossible in respect of species such as rat, cat, dog or *Xenopus*.

In producing transgenic animals in this manner, fertilised zygotes may be isolated from a subject animal and E-cadherin activity inhibited in the cells of the inner cell mass of the embryo, thereby retarding the differentiation of these cells. The time at which inhibitors of E-cadherin are administered should be selected in order to allow proper formation of the inner cell mass (an activity known to require function of E-cadherin), without allowing further differentiation of the cells. Suitable timings may be developed with reference to published studies which further describe the times at which E-cadherin activity required for inner cell mass formation takes place. Embryos prepared as described above may then be cultured in vitro to isolate the ES cells and inhibition of E-cadherin stopped (either by ending the administration or expression of inhibitors) when differentiation is required. It is the recognition that inhibitors of E-cadherin activity may be used to retard cellular differentiation that provides the inventive contribution to the production of transgenic animals in accordance with this aspect of the invention. The techniques that may be used for embryonic culture are (in so far as they do not relate to the inhibition of E-cadherin activity) not inventive themselves, and may be based on those known to the skilled person. For example, suitable references that may be used when selecting protocols for embryo culture include (but are not limited to) Thomson et al, *Science*. 1998 Nov. 6; 282(5391):1145-7 (Human); Thomson et al, *Proc Natl Acad Sci USA*. 1995 Aug. 15; 92(17):7844-8 (Primate); Buehr et al *Biol Reprod*. 2003 January; 68(1):222-9 (Rat); Dattena et al, *Mol Reprod Dev*. 2006 January; 73(1):31-9 (Sheep); Brook and Gardner, *Proc Natl Acad Sci USA*. 1997 May 27, 94(11): 5709-12 (Mouse).

The finding that inhibitors of E-cadherin activity may be used to retard differentiation of biological cells and act as a survival factor for stem and progenitor cells lends itself to a further aspect of the present invention, which is the use of an inhibitor of E-cadherin activity in the isolation of embryonic stem (ES) cells. A major application of this is in the isolation of rat ES cells for use in genetic models of human disease. To date, a rat ES cell has not been isolated and maintained in vitro, and, to date, knockout/knockin technologies that have proven very useful in mouse cannot be performed in rat. The present invention provides a means by which rat ES cells may be isolated (using the methods described above), these cells used according to known procedures to create a knockout ES cell line, and E-cadherin inhibition then ceased or reversed to allow the formation of a rat with a specific genotype, in the same way that is presently done for transgenic mice.

The action of inhibitors of E-cadherin activity as survival factors that are able to prevent cell differentiation and maturation, readily lends itself to the culture of cells that are to be adapted for use in therapeutic applications, since cells cultured in the presence of E-cadherin inhibitors retain the greatest possible therapeutic effectiveness.

According to a further aspect of the present invention there is provided a method of preparing a biological cell for therapeutic use, the method comprising the consecutive or concurrent steps of:
  i) culturing the biological cell in the presence of an inhibitor of E-cadherin activity; and
  ii) adapting the biological cell for therapeutic use.

According to a still further aspect of the present invention there is provided a method of therapy, the method comprising the consecutive or concurrent steps of:
  i) obtaining a biological cell;
  ii) culturing the biological cell in the presence of an inhibitor of E-cadherin activity; and
  iii) adapting the biological cell for therapeutic use
and further comprising administering the adapted biological cell to a subject in need of such therapy.

Biological cells prepared or adapted for therapeutic use in accordance with the preceding aspects of the invention may preferably be stem or progenitor cells.

Stem cell therapy represents a therapeutic method by which degenerative diseases (such as those caused by premature death or malfunction of cell types that the body is unable to replace) may be treated. It is hoped that addition of stem cells to a patient may help and promote the development of functional cells and/or tissues to replace those lost, thereby restoring normal healthy activity. Stem cells provided to a patient may be able to undergo differentiation under the control of suitable stimuli (either naturally occurring or artificially induced) and thereby replace or augment damaged, dysfunctional or diseased tissues. Ultimately it may be possible to regenerate new functional tissues ex vivo which may then be administered to subjects requiring therapy.

The adaptation of biological cells for use in stem cell therapy may typically involve ex vivo expansion of stem cell or progenitor cell numbers in order to produce an increased stem cell population, the cells of which are suitable for administration to a subject requiring such therapy. In order to have therapeutic effectiveness, cells to be used in stem cell therapy (which may either be true stem cells or certain types of progenitor cells) must retain their ability to differentiate into multiple cell lineages when administered to a subject. Currently the application of stem cell therapy is limited by the lack of suitable methods by which stem cells may be propagated without undergoing differentiation and maturation.

Cells cultured in the presence of inhibitors of E-cadherin activity are useful in methods of stem cell therapy since they promote stem cell survival in culture, and hence aid the expansion of stem cell numbers, but do not induce differentiation of the cultured cells. Suspension culture in accordance with the invention may be particularly advantageous in expansion of stem cell numbers. The inventors have found that suspension culture in accordance with the invention is able to achieve a 268,000,000 fold expansion of total stem cell numbers.

It is believed that stem cell therapy may have wide applications across a broad range of diseases. For example stem cell therapy may be used in the treatment of blood disorders (such as leukemia and sickle-cell anaemia), diseases of the brain and nervous systems (such as Parkinson's disease and Alzheimer's disease), musculo-skeletal disorders (such as muscular dystrophy, arthritis and osteoporosis), liver diseases (such as cirrhosis and hepatitis), spinal injuries, heart disease and diabetes.

Stem cell therapy may also be used to replace damaged tissue lost as a result of injury, trauma or cytotoxic insult. For example, such therapies may be used in neurodegenerative conditions, where central nervous system (CNS)-derived stem cells may be utilised to replace or augment damaged somatic cells, such as those located in the brain or spinal cord. Stem cells may be used therapeutically in contexts in which the circulatory system has been injured, such as ischemic tissue damage after vascular occlusion. In such contexts suitable stems cells may be administered to cause formation of new blood vessels, or to replace other damaged tissues. Expanded populations of stem cells may also be utilised in conditions in which the liver has been damaged, in order to induce regeneration of the injured tissue.

It will be appreciated that biological cells cultured, prepared and/or adapted in accordance with the invention are also suitable for use in the preparation and manufacture of medicaments. Therefore according to a still further aspect of the invention there is provided the use of a biological cell, cultured in the presence of an inhibitor of E-cadherin activity and adapted for therapeutic use, as a medicament. Medicaments in accordance with this aspect of the invention are suitable for use in the treatment of the diseases, disorders and injuries considered above.

Medicaments in accordance with the invention may be formulated according to protocols well known in the art. Suitable formulations may be determined based on the preferred route by which the medicament is to be administered. Preferably medicaments according to the invention may be prepared in forms suitable for administration by inhalation, by injection, or by implantation.

Preferably formulations for inhalation may preferably comprise biological cells provided in a suitable liquid carrier. Such a liquid carrier is preferably non-immunogenic, and may comprise a saline solution, cell culture medium, or distilled water. Formulations for injection may be as described above, or may also be provided in the form of a gel, which may preferably be capable of resolution by the body of the subject treated. Formulations suitable for implantation may take the forms described for injection or inhalation, and may also comprise biological cells provided in a scaffold or matrix capable of providing a foundation for new tissue development.

In both methods of therapy according to the present invention, and in the use of medicaments according to the invention, a therapeutically effective amount of biological cells (such as those adapted for therapeutic use) should be administered to the subject requiring therapy. A "therapeutically effective amount" in the context of the present invention is considered to be any amount of suitable biological cells (such as therapeutically adapted cells) which, when administered to a subject suffering from a disease against which the biological cells are effective, causes reduction, remission, or regression of the disease. A "subject" may be a human being, or any other animal, particularly a domestic or agricultural mammal.

In a further aspect, the invention provides A method of isolating biological cells deficient in E-cadherin, the method comprising:
i) culturing the cells in the absence of LIF and/or FGF-2;
ii) allowing biological cells that express E-cadherin to die or differentiate; and maintaining the cultured cells until biological cells deficient in E-cadherin proliferate.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIGS. 7A, B, C, and D shows Sequence ID No. 1 and Sequence ID No. 2;

FIGS. 8A, B and C shows Sequence ID No. 3 and Sequence ID No. 4;

FIGS. 9A, B and C shows Sequence ID No. 5 and Sequence ID No. 6;

FIGS. 10A, B, and C which shows respectively, Sequence ID No. 7; Sequence ID No. 58; and Sequence ID Nos. 8 and 59;

FIG. 11 shows Sequence ID No. 9 and Sequence ID No. 10;

FIG. 12 shows Sequence ID No. 11;

FIGS. 13A, B, C, D, E, F, and G shows Sequence ID No. 12 to Sequence ID No. 21;

FIGS. 14A and B shows Sequence ID No. 22 to Sequence ID No. 29;

FIGS. 15A, B and C shows Sequence ID No. 30;

FIGS. 16A and B shows Sequence ID No. 31;

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

EXPERIMENTAL RESULTS

The inventor has found that mouse ES cell lacking the Cdh1 (E-cadherin) gene exhibit decreased spontaneous differentiation in the presence of LIF and show similar properties when cultured in the absence of LIF. This is a new and surprising finding, and has led to the development of a valuable method by which the culture and manipulation of homogeneous populations of pluripotent stem cells may be affected.

The inventors have cultured E-cadherin null (Ecad−/−) ES cells in the laboratory for upwards of 42 passages in the absence of LIF and have found that these cultured cells maintain expression of the pluripotent transcript markers Oct-4 and Nanog and expression of OCT-4 protein. This pattern of expression clearly identifies that cells cultured such that E-cadherin activity is not present are able to maintain an undifferentiated phenotype. Furthermore, the division of such cells is not altered compared to Ecad−/− ES cells grown in the presence of LIF, illustrating that inhibition of E-cadherin activity does not adversely affect the ability of cells so cultured to divide. In comparison, wild type ES cells cultured in the same conditions (absence of LIF) lose pluripotency through differentiation and fail to divide at passage numbers 6-8 (when cultured under identical conditions to E-cadherin null ES cells).

1. Loss of E-Cadherin Gene from Mouse ES Cells Allows the Continuous Culture of Undifferentiated Cells in the Absence LIF Wild type (wt) mouse ES cells can be maintained in an undifferentiated (pluripotent) state in the absence of an embryonic fibroblast feeder layer by culture in the presence of LIF and foetal bovine serum. Upon removal of LIF from wt ES cells they differentiate to various lineages and lose expression of the pluripotent marker OCT-4.

The inventors have illustrated that removal of E-cadherin activity enables stem cells to be cultured without undergoing differentiation, even when LIF is removed from the culture conditions.

E-Cadherin Null (Ecad−/−) ES Cells Maintain OCT-4 Protein Expression in the Absence of LIF.

In this study Ecad−/− and wt D3 ES cells were cultured in the presence or absence of LIF for 12 days in a gelatin-treated 6-well plate. The prior art would suggest that stem cells cultured in the absence of LIF would undergo differentiation or apoptosis, since these outcomes represent a common response of cultured stem cells to the stress of LIF removal. The results of this study are shown in FIG. 1.

Figure 1A:
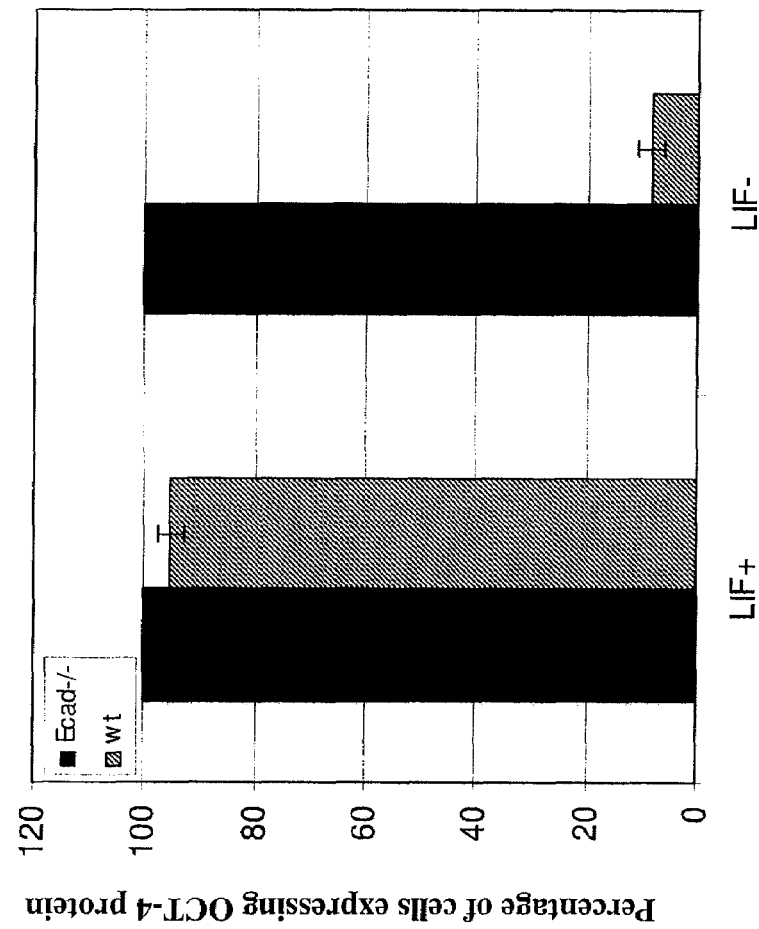
FIG. 1A shows a bar chart illustrating the percentage of wild type and E-cadherin knockout cells expressing the stem cell marker protein OCT-4.

FIG. 1A shows a bar chart illustrating the percentage of cells expressing the stem cell marker protein OCT-4. OCT-4 expression in both wild-type and E-cad−/− cells is shown, and comparison is made between cell populations cultured in the presence and absence of LIF. OCT-4 protein expression was determined using immunofluorescence and quantified by counting the number of OCT-4 positive and negative cells in 5 fields of view. Error bars show the SD.

Surprisingly the inventors found that Ecad−/− ES cells expressed the pluripotent marker OCT-4 in >99% of the cultured cell population, irrespective of LIF supplementation. Furthermore, Ecad−/− cells cultured in the absence of LIF maintained a phenotype identical to cells cultured in the presence of LIF, and apoptosis did not appear to be increased in cells cultured in the absence of LIF compared to those cultured in LIF. In contrast, wild type ES cells cultured under identical conditions exhibited 95.2% (±2.3) OCT-4 positive cells in the presence of LIF but only 8.3% (±4.2) OCT-4 positive cells in the absence of LIF.

The results clearly indicate that cultured stem cells in which E-cadherin activity is inhibited are able to maintain a pluripotent phenotype, and this indicates that differentiation among the cultured cells is retarded.

Figure 1B:
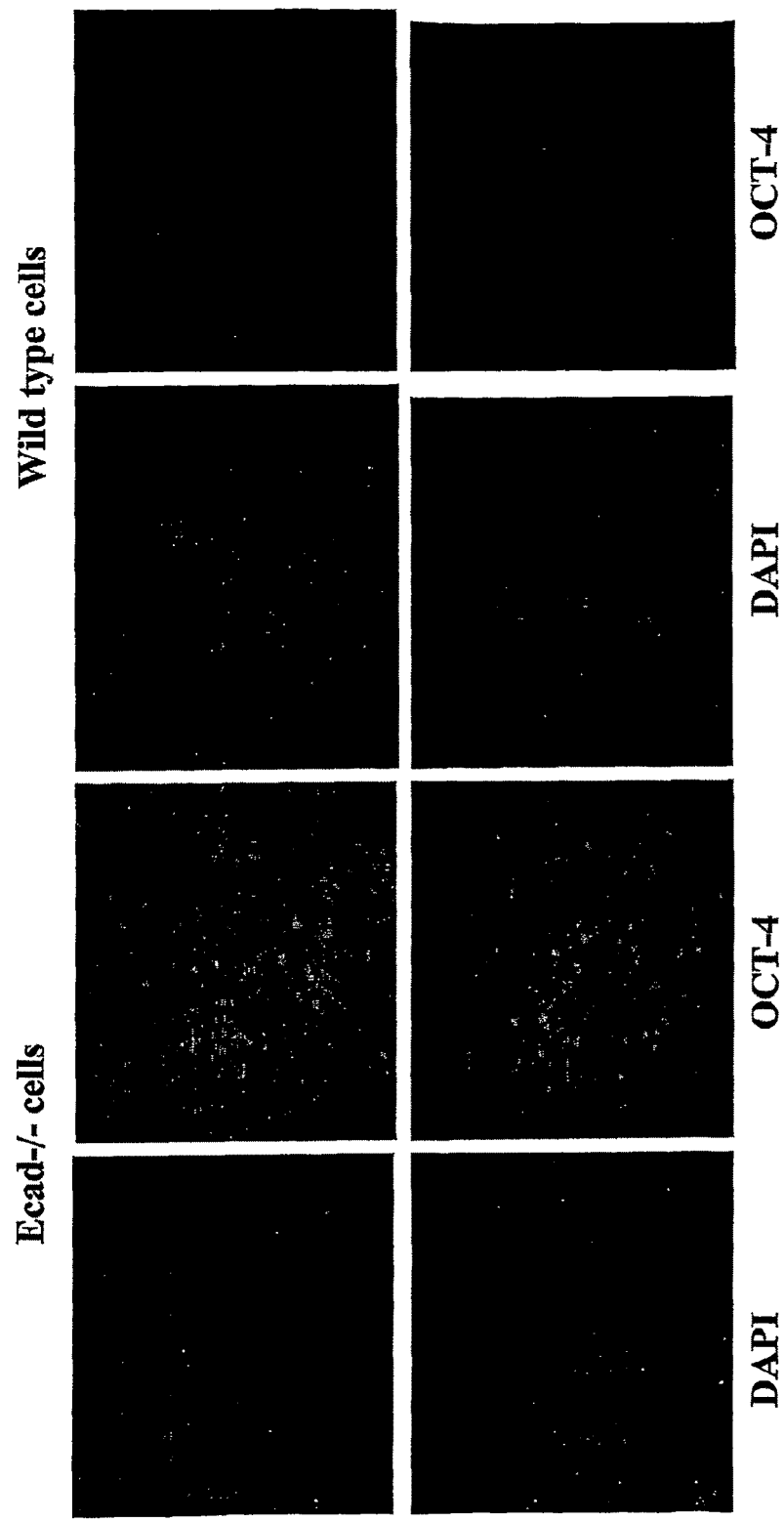
FIG. 1B shows immunofluorescence detection of OCT-4 protein in wild type and Ecad–/– cells.

FIG. 1B shows immunofluorescence detection of OCT-4 protein and DAPI (cell nucleus) in Ecad−/− and wt ES cells cultured for 12 days in the absence of LIF. The images compare expression of the pluripotent marker in populations of cells that have been cultured for 12 days in the absence of LIF. It can be seen that OCT-4 protein levels were significantly decreased in wild-type cells compared to Ecad−/− ES cells.

Figure 2:
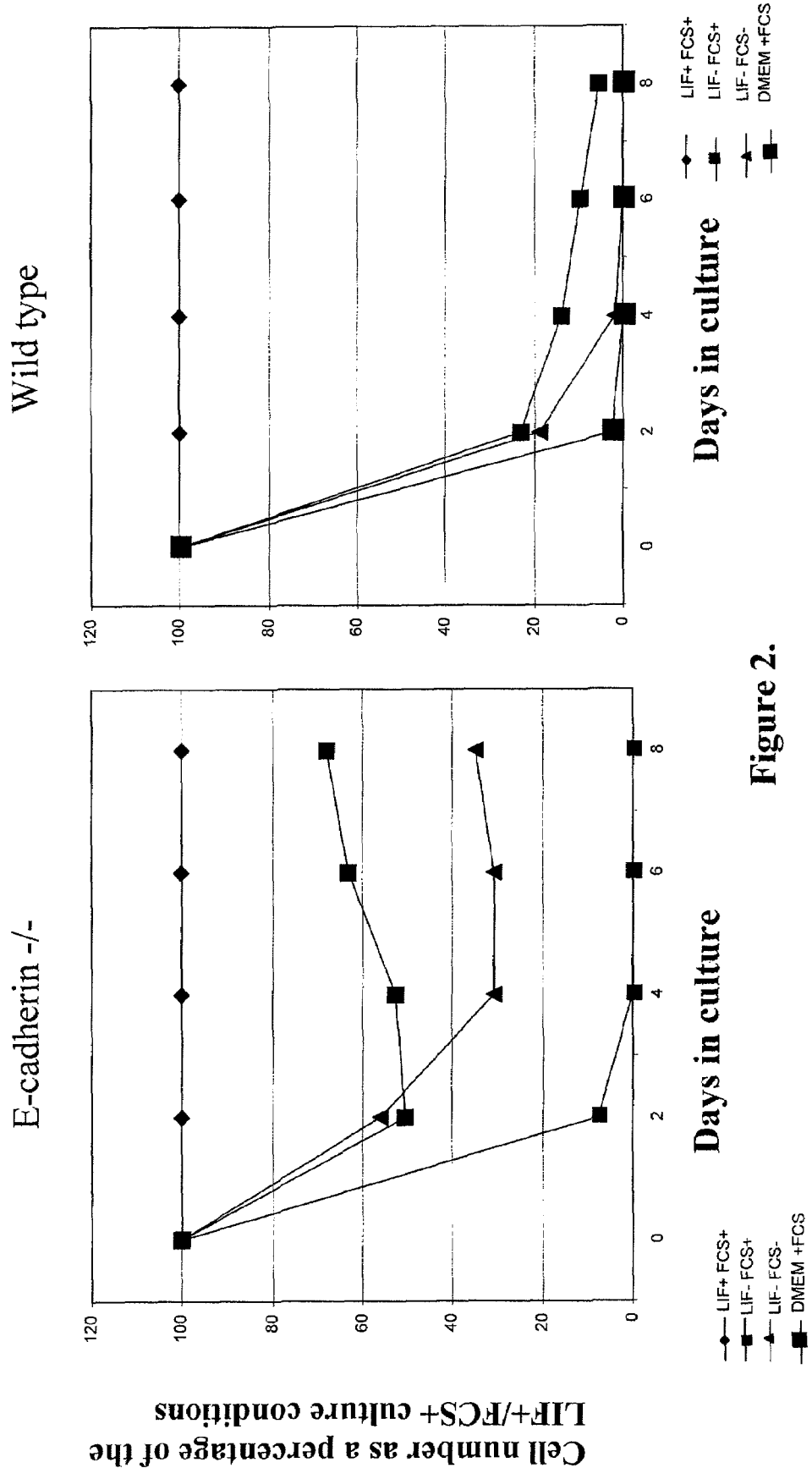
FIG. 2 shows the results of cell counts of populations of wild-type and Ecad–/– cells grown under various culture conditions.

FIG. 2 shows the results of cell counts of populations of wild-type and Ecad−/− cells cultured in various culture medium in the presence or absence of LIF over 6 days. Ecad−/− and wt D3 ES cells were cultured in a gelatin-treated 6-well plate in the presence or absence of LIF in ES cell medium containing either serum (FCS+) or synthetic serum (FCS−). In addition, the cells were cultured in DMEM +FCS/+L-glutamine. Cell numbers are shown as a percentage of the cell numbers obtained in optimal ES cell medium (FCS+/LIF+). Cell number was assessed at each passage by trypan blue exclusion method. As can be seen, Ecad−/− ES cells cultured in the absence of LIF with serum (LIF− FCS+) exhibit crisis for two days following removal of LIF. However, these cells recover to exhibit doubling times similar to cells cultured in the presence of LIF (LIF+ FCS+) and express OCT-4 in >99% of the cell population. It will be appreciated that such crisis events are common upon transfer of ES cells to different culture media (Chambers et al, 2003 Cell. 2003 May 30; 113(5):643-55), and that this crisis in no way detracts from the utility of the invention, illustrated by the subsequent recovery of the cells.

In contrast, wt ES cells exhibit decreased cell numbers, and these populations of cells do not recover over time (when cultured under identical conditions to E-cadherin null ES cells). Furthermore, such cells lack OCT-4 expression in the majority of the cell population indicating that the cultured cells have differentiated and thereby lost their pluripotent phenotype.

FIG. 2 also shows the results of cell counts of Ecad−/− and wild-type ES cell populations cultured in synthetic serum in the absence of LIF (LIF− FCS−). Under these conditions Ecad−/− ES cells exhibited crisis and subsequent increase in cell numbers (as found during culture in the presence of serum) whereas the wild-type ES cells were dead by day 6.

This study indicates that cells in which E-cadherin activity is inhibited (illustrated by Ecad−/− ES cells) do not differentiate in the absence of LIF and, by definition, are nullipotent. In an extension of this study Ecad−/− ES cells have now been cultured for 42 passages (approximately 90 days) in the absence of LIF and maintain OCT-4 protein expression in >99% of the cells.

The inventors believe that the inhibition of E-cadherin activity during cell culture provides a simple system allowing culture of ES cells in non-specialised medium without the need for experienced technicians. Furthermore, such culture may allow three-dimensional liquid culture of stem cells in fermenters, thereby markedly increasing the number of undifferentiated stem cells that may be produced. In summary, inhibition of E-cadherin activity in ES cells is an efficient method of inhibiting spontaneous differentiation and apoptosis of these cells while maintaining a homogeneous population of nullipotent cells.

2. Investigation of Transcript Expression in Ecad−/− Cells Cultured in the Presence or Absence of LIF E-cad−/−, Ecad+/− and wild type ES cells were cultured for 12 passages in a gelatin-treated 6-well plate in serum-containing medium in either the presence or absence of LIF. RNA representative of gene expression in the cultured cells was extracted and cDNA formed according to known protocols. Transcripts for pluripotent and differentiated markers were assessed by RT-PCR RNA was extracted and cDNA formed as described in the materials and methods. PCR was performed for 35 cycles (Ecad−/−) or 45 cycles (wt and Ecad+/−).

Figure 3:
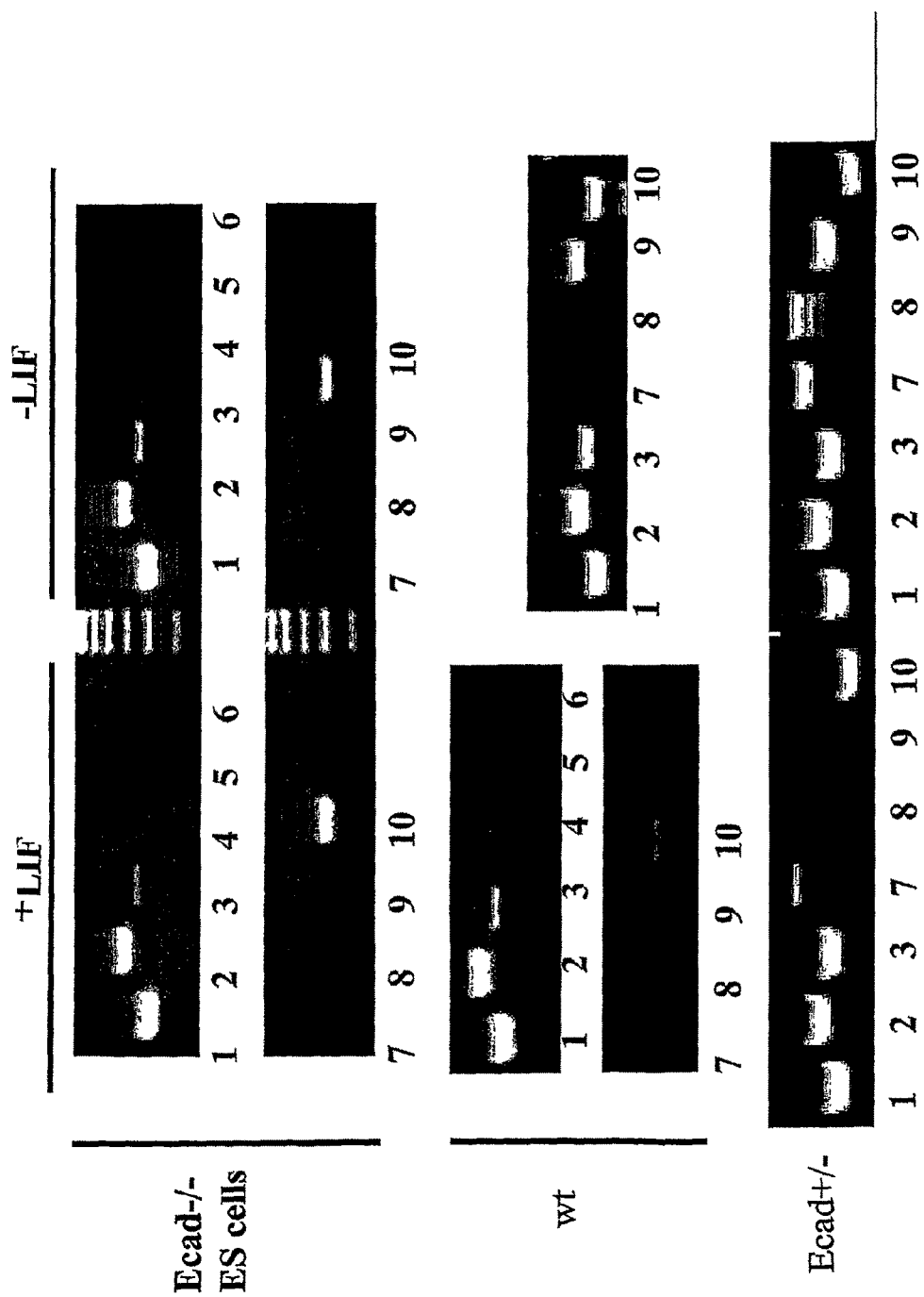
FIG. 3 shows expression of transcripts of a number of markers by wild type cells, Ecad–/– cells and Ecad+/– cells.

The results of this study are shown in FIG. 3. As can be seen, Ecad−/− ES cells cultured in the presence of LIF express the pluripotent markers Oct-4 and Nanog and the neuroectoderm marker NF68k. Of the transcript markers assessed, Ecad−/− cells exhibited the same expression profile as wild type D3 ES cells when grown in the presence of LIF. Detection of the neuroectoderm marker NF68k is consistent with published data (Ward et al, 2004 Exp Cell Res. February 15; 293(2):229-38), and is consistent with the maintenance of a pluripotent phenotype. The mesodermal marker brachyury is also consistently detected in Ecad+/− cells cultured in the presence of LIF, and not in Ecad−/− cells. This pattern of brachury expression is in contrast to patterns of expression that have been reported in the prior art.

Ecad−/− ES cells cultured for 17 passages (approximately 34 days) in the absence of LIF do not exhibit an altered transcript expression profile compared to Ecad−/− ES cells cultured in the presence of LIF (results indicated "−LIF"). For example, cells cultured in the absence of LIF maintain expression of the pluripotent markers Oct-4 and Nanog and the neuroectoderm marker NF68k.

When wild-type cells or Ecad+/− cells (i.e. cells in which E-cadherin activity is not inhibited) are cultured in the absence of LIF, no cells remain at passage 17 (they fail to maintain sufficient cell numbers between passages 6-8). The results indicate that this is due to the differentiation of the cells leading to significant cell death and increasing cell cycle times.

In order to assess the transcript expression in differentiating wild-type and Ecad+/− ES cells the inventors assessed transcript marker expression after removal of LIF for 12 days. Results of this study are also shown in FIG. 3 (in which 1 is b tubulin; 2 is oct4; 3 is nanog; 4 is fgf; 5 is bmp2; 6 is bmp4; 7 is TBra; 8 is zg; 9 is TTR; and 10 is NF68). In wild-type ES cells cultured in the absence of LIF for 12 days upregulation of the transcripts for the endodermal marker transthyretin and maintenance of the neuroectoderm marker NF68k was noted, and this change in transcription indicates the differentiation of the cells. After 12 days in the absence of LIF, Ecad+/− ES cells exhibit upregulation of transcripts encoding brachyury (mesoderm), ζ-globin (mesoderm) and transthyretin (endodermal), as well as maintenance of NF68k expression (neuroectoderm). Detection of Oct-4 and Nanog in differentiating cultures reflects the heterogeneity of the population and is consistent with published data (Ward et al, 2003, 2004).

The results of this study demonstrate that cells in which E-cadherin activity is inhibited (such as Ecad−/− ES cells) may be cultured and passaged in the absence of LIF without differentiation, and cells so cultured maintain a transcript expression profile consistent with an undifferentiated ES cell phenotype.

3. Overgrowth of Ecad−/− ES Cells Induces Differentiation to the Three Primary Germ Layers.

Figure 4:
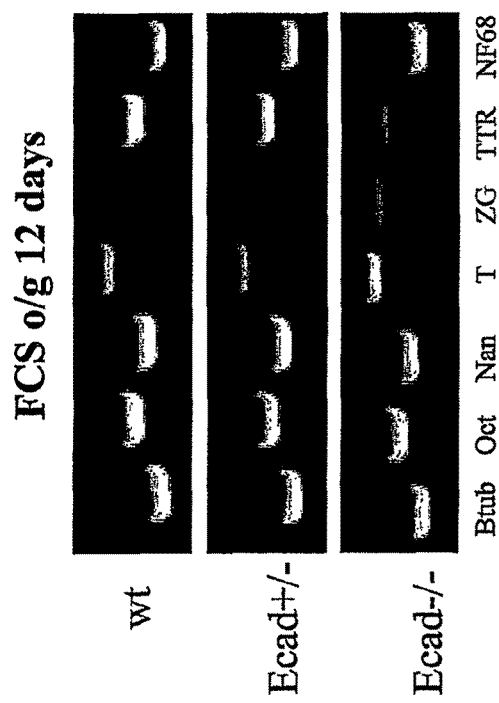
FIG. 4 shows expression of transcripts from sample cells induced to differentiate by overgrowing in culture.

Wild-type, Ecad+/− and Ecad−/− ES cells were plated out in a well of a 6-well culture plate in the presence of LIF and the medium replaced daily for 12 days without passaging of the cells. Overgrowth of ES cells is a very efficient method of inducing differentiation, since it induces toxic stress (such as oxygen tension etc.) that leads to the differentiation of the cultured cells. Results of this study are shown in FIG. 4. Ecad−/−, Ecad+/− and wt ES cells were cultured in a gelatin-treated 6-well plate in the presence of LIF and the medium replaced daily for 12 days without passaging of the cells. RNA was extracted and cDNA formed as described in the materials and methods. PCR was performed for 35 cycles Ecad−/− ES cells cultured under the conditions referred to above exhibited upregulation of transcripts for brachyury (mesoderm), ζ-globin (mesoderm) and transthyretin (endodermal) as well as maintenance of NF68k transcript expression (neuroectoderm). This demonstrates that at least a proportion of the cells within the Ecad−/− ES cell population were differentiating into the three primary germ layers. Wild-type cells exhibited a similar transcript profile to Ecad−/− ES cells, whereas Ecad+/− lacked expression of ζ-globin transcripts (probably reflecting the transient expression nature of this transcript during ES cell differentiation; Ward et al, 2004).

The skilled person will appreciate that the results of this study indicate that, in cultured cells in which E-cadherin activity is inhibited, differentiation of the cells is retarded to give rise to a phenotype that is effectively pluripotent rather than nullipotent. This in turn clearly indicates the suitability of inhibition of E-cadherin activity to inhibit stem cell differentiation while preserving the full range of therapeutic lineages that may be produced on subsequent differentiation of the stem cell in question.

Embryonic stem cells entirely lacking E-cadherin are unlikely to be able to form epithelium (as they have no E-cadherin) and should therefore be considered to be multipotent, rather than pluripotent, but, as shown elsewhere in the Experimental Results, stem cells in which E-cadherin activity is only transiently inhibited regain the ability to differentiate and form cell types representative of all tissues, on cessation of E-cadherin inhibition.

4. Ecad−/− ES Cells Divide Faster than wt ES Cells

Figure 5:
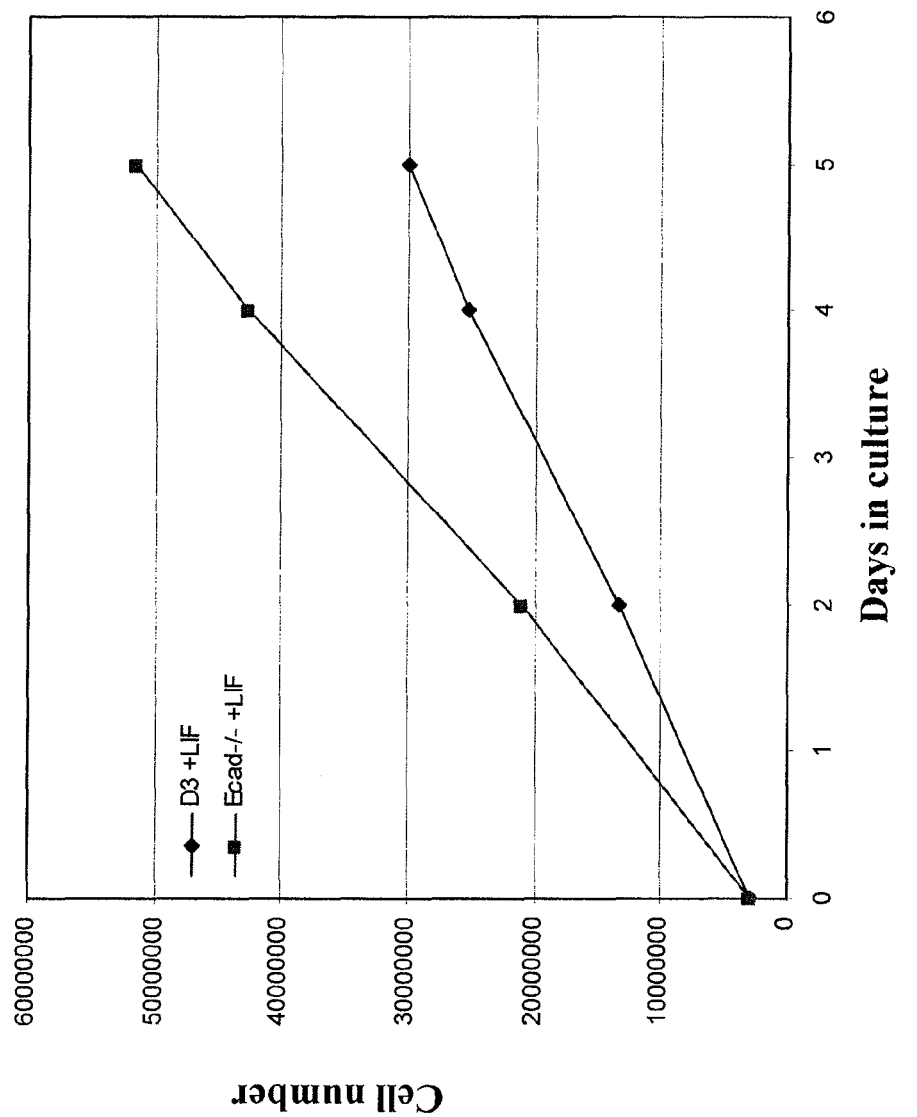
FIG. 5 shows changes in cell numbers of wild type D3 and Ecad–/– ES cells cultured in the presence of LIF and assessed at each passage FIGS. 6A, B, C, D and E the results of studies investigating the effect on cell numbers of culture in the presence of an E-cadherin function neutralising antibody, with or without LIF.

Wild type D3 and Ecad−/− ES cells were cultured in wells of a gelatin-treated 6-well plate ($3 \times 10^6$ cells/well) in the presence of LIF and cell numbers assessed at each passage. The results of this study are shown in FIG. 5.

Cells were passaged at days 2, 4 and 5, and cell numbers calculated at each passage. On average, Ecad−/− ES cells exhibited 1.67-fold increased cell numbers compared to wild-type ES cells (designated D3 in FIG. 5). E-cadherin null (Ecad−/−) ES cells exhibit increased cell numbers compared to wild-type (wt) D3 ES cells over 5 days in culture. Ecad−/− and wt D3 ES cells were plated at 3,000,000 cells/well in a gelatin-treated 6-well plate and cultured in the presence of LIF for 5 days. Cells were passaged as described in the materials and methods and viable cell numbers assessed using trypan blue exclusion. Repetition of this experiment on three separate occasions has shown that a similar trend of increased proliferation of cells in which E-cadherin activity is inhibited is consistently demonstrated (data not shown).

The results of this study illustrate that inhibition of E-cadherin activity represents a powerful means by which cell proliferation may be promoted. This indicates that inhibitors of E-cadherin activity may be used to expand biological cell populations in vitro, while retarding differentiation of the proliferating cultured cells.

Figure 6A:
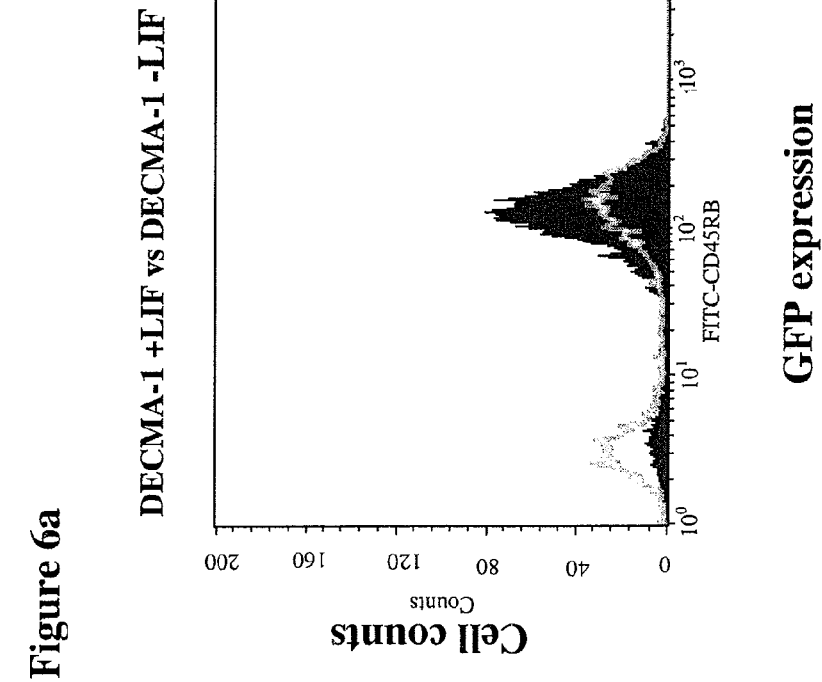
Figure 6D:
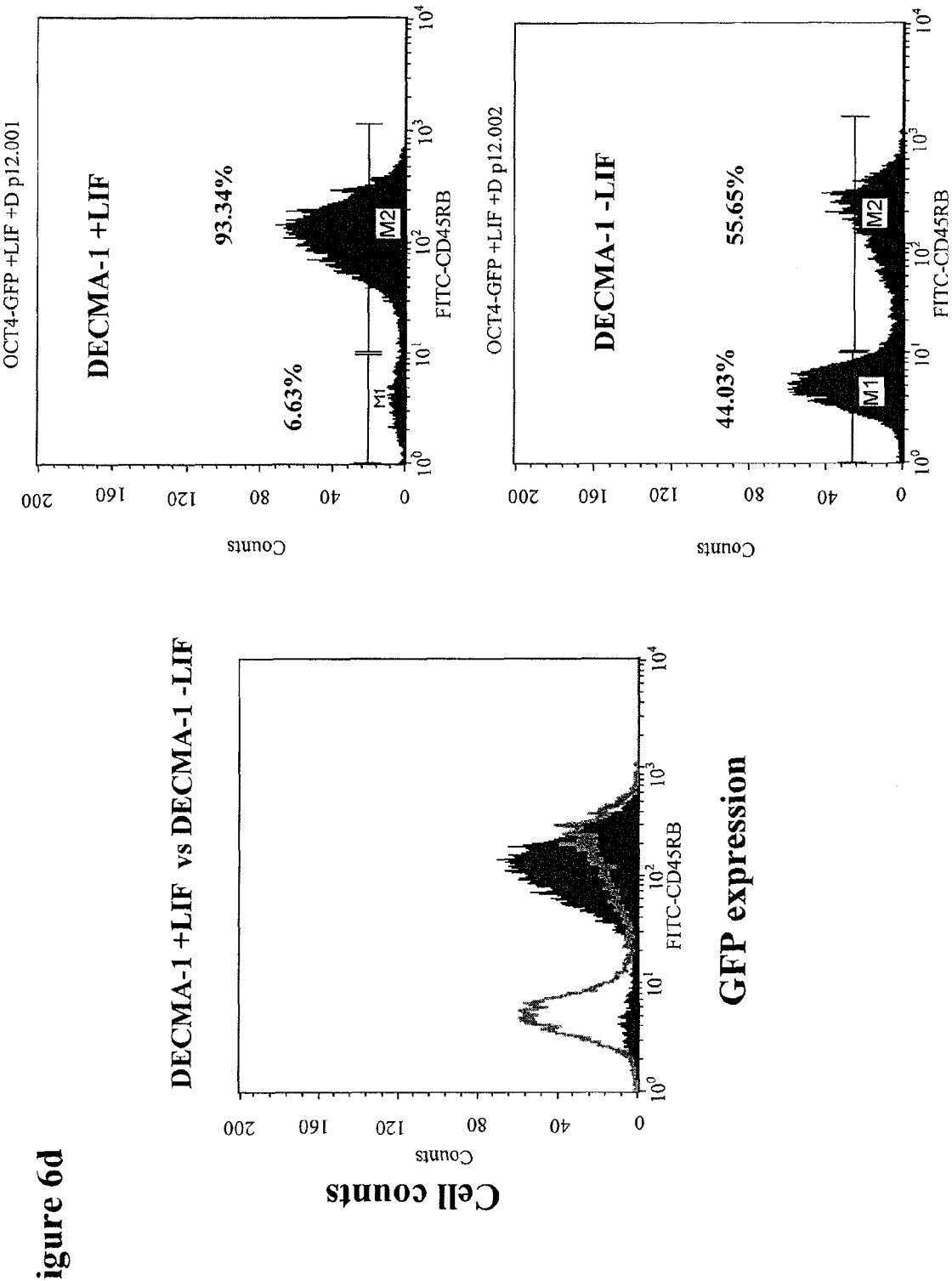

5. DECMA-1 Treatment of Oct4-GFP ES Cells in the Absence of LIF Delays Differentiation The inventors have investigated whether inhibition of the activity of cell surface E-cadherin protein is able to prevent differentiation of ES cells in culture. To do so, the inventors cultured biological cells from a number of cell lines in the presence of the neutralising antibody DECMA-1 (Sigma, Dorset, UK; Cat. No. U3254), an inhibitor of E-cadherin activity. OCT4-GFP ES cells were cultured in either DECMA-1 or control antibody in the presence or absence of LIF for 12 passages and assessed for GFP (Oct-4) expression by fluorescent flow cytometry. (FIG. 6A) At passage 8 all control cells cultured in the absence of LIF were dead. Right hand profiles show the proportion of DECMA-1 treated OCT4-GFP ES cells that are undifferentiated (GFP+; shifted to the right) or differentiated (GFP−; shifted to the left) cells in the +LIF (top) and −LIF (bottom) cell populations. Left hand FACS profile shows an overlay of the +LIF and −LIF cell populations show in the right hand profiles. (FIG. 6B) DECMA-1 treated cells at passage 10; profiles as described above. (FIG. 6C) DECMA-1 treated cells at passage 11, profiles as described above. (FIG. 6D) DECMA-1 treated cells at passage 12; profiles as described above. (FIG. 6E) Total cell numbers accumulating over 12 passages in OCT4-GFP ES cells treated with DECMA-1 and cultured in the presence or absence of LIF.

DECMA-1 appears to induce the internalisation of cell surface E-cadherin protein, thereby inhibiting the normal biological function of the molecule. The concentrations of the neutralising antibody required to induce a phenotype similar to that observed in Ecad−/− ES cells was dependent on the ES cell line investigated. For example, MESC ES cells required 2.9 μg/ml of antibody, D3 required 5.8 μg/ml and E14TG2a required 11.6 μg/ml DECMA-1 to induce loss of cell-cell contacts. An anti-tenascin antibody (Sigma; Cat. No. T3413) was used as a control antibody.

To study the effect of DECMA-1 on ES cell pluripotency/differentiation (i.e. the ability of the inhibitor of E-cadherin activity to induce cellular proliferation without differentiation) the inventors utilised E14TG2a ES cells expressing GFP under the regulatory elements of Oct-4 (Oct4-GFP ES cells). Loss or retention of pluripotency was assessed using fluorescent flow cytometry. The results of this study are shown in FIG. 6.

11.6 μg/ml of DECMA-1 or control antibody was added to the cells in a six well plate and the cells cultured for 12 passages in the presence or absence of LIF (fresh antibody was added at each passage). Addition of either DECMA-1 or control Ab to Oct4-GFP ES cells cultured in the presence of LIF for 12 passages did not affect Oct-4 expression, as defined by GFP expression.

At passage 8 (results shown in FIG. 6A) Oct4-GFP ES cells cultured in the absence of LIF in the presence of control Ab were unable to maintain cell proliferation (when cultured under identical conditions to nAb (DECMA-1)-treated ES cells) whereas Oct4-GFP ES cells cultured in the presence of LIF and the inhibitor of E-cadherin activity DECMA-1 exhibited 93.45% GFP-positive cells and Oct4-GFP ES cells cultured in the absence of LIF and presence of DECMA-1 exhibited 62.21% GFP-positive cells.

At passage 10 (results shown in FIG. 6B) Oct4-GFP ES cells cultured in the presence of LIF and DECMA-1 exhibited 93.74% GFP-positive cells and Oct4-GFP ES cells cultured in the absence of LIF and presence of DECMA-1 exhibited 63.32% GFP-positive cells (a slight increase on passage 8).

At passage 11 (results shown in FIG. 6C), Oct4-GFP ES cells cultured in the presence of LIF and DECMA-1 exhibited 93.34% GFP-positive cells and Oct4-GFP ES cells cultured in the absence of LIF and presence of DECMA-1 exhibited 55.65% GFP-positive cells.

At passage 12 (results shown in FIG. 6D), Oct4-GFP ES cells cultured in the presence of LIF and DECMA-1 exhibited 93.34% GFP-positive cells and Oct4-GFP ES cells cultured in the absence of LIF and presence of DECMA-1 exhibited 55.65% GFP-positive cells (no change from passage 1). These results clearly show that addition of the E-cadherin neutralising antibody DECMA-1 to Oct4-GFP ES cells can delay differentiation in the absence of LIF compared to control Ab treated cells.

Figure 6E:
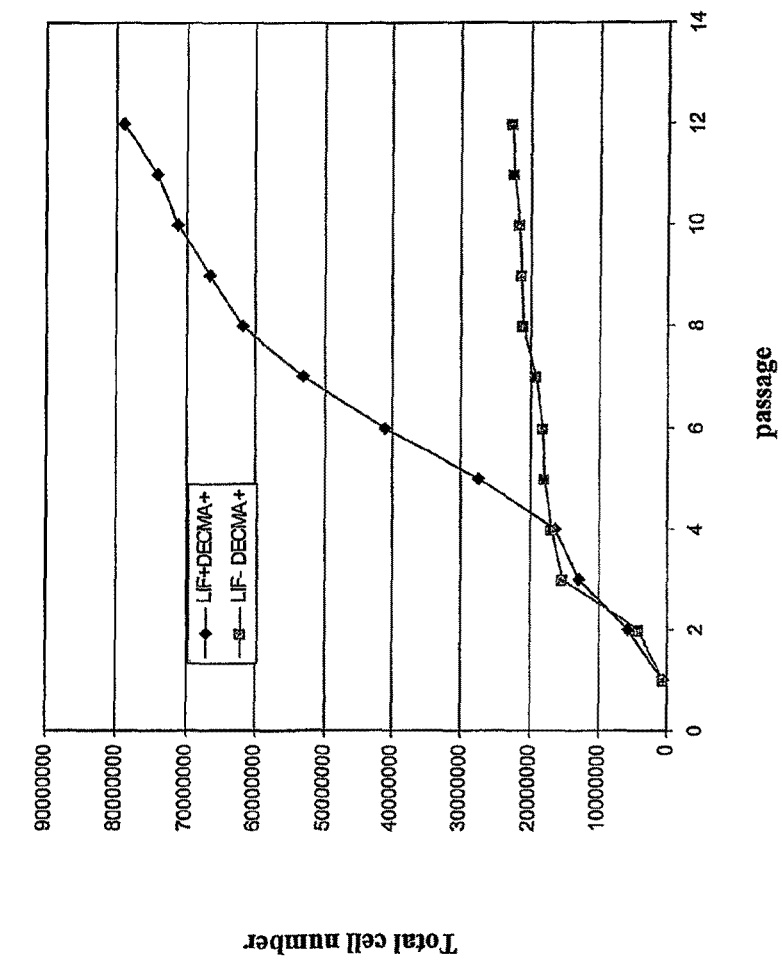

However, the total cell numbers obtained from the Oct4-GFP cells+DECMA-1 in the absence of LIF were somewhat reduced compared to cells cultured in the presence of LIF (as shown in FIG. 6E), although the inventors believe that this decrease may be overcome on optimisation of the dosage of the inhibitor of E-cadherin activity employed.

6. Inhibition of E-Cadherin Activity by Transient Expression of RNAi.

Vectors (pRNATin-H1.2 from Genscript) encoding the RNAi of Sequence ID No. 22 to Sequence ID No. 26 are introduced into human embryonic stem cells by means of electroporation using the Amaxa protocol. Vectors (pRNA-Tin-H1.2 from Genscript) encoding the RNAi of Sequence ID No. 27 to Sequence ID No. 29 is introduced into murine embryonic stem cells by means of the same protocol.

Vectors encoding suitable inhibitors of E-cadherin activity may preferably also comprise selection elements allowing selection of cells into which the vectors have been successfully introduced. Examples of such selection elements are well known to those skilled in the art and include antibiotic resistance genes. For example, it may be preferred that vectors encoding inhibitors of E-cadherin activity also comprise selection elements comprising a neomycin resistance gene. In accordance with this example, cells into which the vectors have been successfully introduced (for instance by means of electroporation) may be identified by virtue of their resistance to the antibiotic neomycin, this resistance being conferred by the neomycin resistance elements incorporated in the vectors encoding the RNAi inhibitors.

7. Assessment of E-Cadherin "Knockdown".

7.1 In Human Stem Cells.

Human stem cells transfected with vectors encoding inhibitors of E-cadherin activity as described elsewhere in the specification may be further investigated in order to confirm that E-cadherin activity in the cells is functionally inhibited. Such inhibition may be brought about through combined activity of one or more RNAi inhibitor (for example those encoded by Sequence ID No. 22 to Sequence ID No. 26). Functional inhibition of E-cadherin activity may be brought about by either partial inhibition or total inhibition of E-cadherin, so long as sufficient inhibition of E-cadherin activity occurs to give rise to the beneficial effects of retarding biological cell differentiation. Such functional inhibition of E-cadherin activity may be termed E-cadherin "knockdown".

The knockdown effectiveness of the individual RNAi inhibitors encoded by Sequence ID No. 22 to Sequence ID No. 26 may be investigated through the introduction of vectors encoding individual inhibitors selected from this group into human cells such as stem cells. Preferably each inhibitor may be individually tested, and combinations of individual inhibitors may also be investigated in order to identify whether such combinations are able to give rise to additive (or synergistic) inhibitory effects that may be of particular benefit in accordance with the present invention. It will be appreciated that when investigating the effects of vectors in this manner the vectors may be introduced into human cells by means of Amaxa electroporation, as described elsewhere.

7.2 In Murine Stem Cells.

Murine stem cells may be transfected (as described above with reference to human cells) and studied to confirm that E-cadherin activity in the cells is inhibited, either partially or entirely, through the combined activity of the RNAi inhibitors. Such inhibition of E-cadherin activity may be termed E-cadherin "knockdown"

The knockdown effectiveness of the individual RNAi inhibitors may be investigated through the introduction of vectors encoding individual inhibitors selected from Sequence ID No. 27 to Sequence ID No. 29 into murine stem cells. Each inhibitor is individually tested. Vectors may be introduced by means of Amaxa electroporation, as before.

8. Generation of Human and Murine Cell Lines in which E-Cadherin Knockdown has Been Efficiently Achieved.

Clonal populations may be derived by culture of cells in which E-cadherin knockdown has been efficiently achieved (for instance by means of the methods described above). Such clonal populations may be generated by methods such as ring cloning, and then expanded to generate cell lines in which E-cadherin activity is functionally inhibited through the action of RNAi inhibitors.

9. Evaluation of Reversible RNA Inhibition of E-Cadherin in hES Cells as a Tool for Inhibition of Differentiation.

The use of transient RNAi inhibition (for example using RNAi inhibitors as considered elsewhere encoded for by vectors such as Genscript pRNATin-H10.2) to block cellular differentiation may be investigated by visualisation of gross cellular morphology and by monitoring the expression of pluripotent markers (investigation of both marker proteins and mRNA encoding such proteins). Previous evaluation of this technology by repression of Oct-4 in mES cells has demonstrated its utility.

A preferred protocol by which transient expression of inhibitors of E-cadherin activity may be assessed will use Amaxa electroporation to allow incorporation of vectors encoding the RNAi inhibitors of Sequence ID No. 22 to Sequence ID No. 26. The study will initially investigate the effects achieved using combinations of RNAi inhibitors (including the introduction of all vectors into experimental cells by electroporation) to confirm E-cadherin knockdown and identify preferred inhibitor combinations. Thereafter, individual vectors encoding specific RNAi inhibitors will be assessed individually to identify preferred inhibitors suitable for use to bring about E-cadherin knockdown. As described previously, vectors used in this investigation will include a neomycin resistance gene, and cells into which the vectors have been successfully introduced (either singly or in combination) will be isolated by virtue of their neomycin resistance. Clonal populations of cells in which E-cadherin activity is inhibited will be isolated and used to derive efficient E-cadherin knockdown cell lines.

Genetic stability of the cells into which vectors encoding RNAi inhibitors have been introduced will be analysed by karyotype analysis in accordance with the protocols set out elsewhere in the specification.

10. Reversal of E-Cadherin Repression in Mouse and Human ES Cells.

It will clearly be appreciated that inhibition of E-cadherin activity allows differentiation of biological cells to be inhibited or retarded. Subsequent reversal of this inhibition (a reversal herein designated EcadR) allows the differentiation of biological cells to resume thereby giving rise to useful differentiated cell types.

Inhibition of E-cadherin activity in human and mouse ES cells (achieved using either RNAi inhibitors or function neutralising antibodies, although it will be appreciated that any suitable method of inhibition may be used) will be reversed. The ability of cells in which EcadR has been effected to differentiate into cells of the primary germ layers may then be assessed by RT-PCR and immunofluorescent analysis of various lineage markers. The ability of EcadR cells to differentiate into various cell lineages may additionally or alternatively be investigated via overgrowth of such cells (as described elsewhere in the specification) followed by suitable analysis to investigate whether markers of differentiation are expressed.

In vivo confirmation of the ability of the EcadR cells to differentiate and give rise to the three germ layers will be achieved by sub-cutaneous injection of the cells into Severe Combined Immunodeficiency Disease (SCID) mice. Tissue sections derived from the sites where EcadR cells have grown will then be processed for histology and the differentiation of the cells assessed. Such assessment may be carried out using standard histological analysis of suitably stained sections (for example stained with haemotoxylin and eosin) from the cell growths.

Mouse EcadR cells constitutively expressing β-galactosidase (ROSA26 cell line) will be injected into pre-implantation mouse blastocysts and their incorporation into the embryo assessed at E9.5 by β-galactosidase expression in embryo sections. These experiments will confirm that inhibition of E-cadherin and subsequent reversal of the inhibition does not affect the pluripotency of the ES cells.

11. To Determine Whether Inhibition of E-Cadherin in Mouse Embryos Increases the Efficiency of ES Cell Derivation.

Current techniques for the derivation of ES cell lines from mouse embryos are only 30% efficient. The inventors believe that efficiency of ES derivation may be improved using the methods of the invention. Therefore studies will be undertaken to determine whether E-cadherin repression in mouse embryos improves the derivation of ES cell lines. Briefly, E-cadherin expression will be inhibited in delayed implantation mouse embryos using either double stranded oligonucleotide RNAi or neutralising Abs (although it will be appreciated that alternative strategies may be used) and isolation efficiency of ES cell lines in which E-cadherin activity is inhibited compared to that achieved using control embryos.

12. Cell surface SSEA-1 Expression in Wild Type D3 (wt) and E-Cadherin Null (Ecad−/−) ES Cells Overgrown for 12 days.

Wild type (wt) or E-cadherin null (Ecad−/−) embryonic stem cells were cultured in a gelatin-treated 6-well plate in the presence of LIF. Culture medium was replaced daily for 12 days without passaging of the cells. Cells were trypsinised and assessed for expression of the primitive cell marker stage specific embryonic antigen-1 (SSEA-1) using a phycoerythrin-conjugated antibody recognising SSEA-1. Cell fluorescence was analysed using a Becton Dickinson FACS caliber. Viable cells were gated using forward and side scatter.

Figure 17:
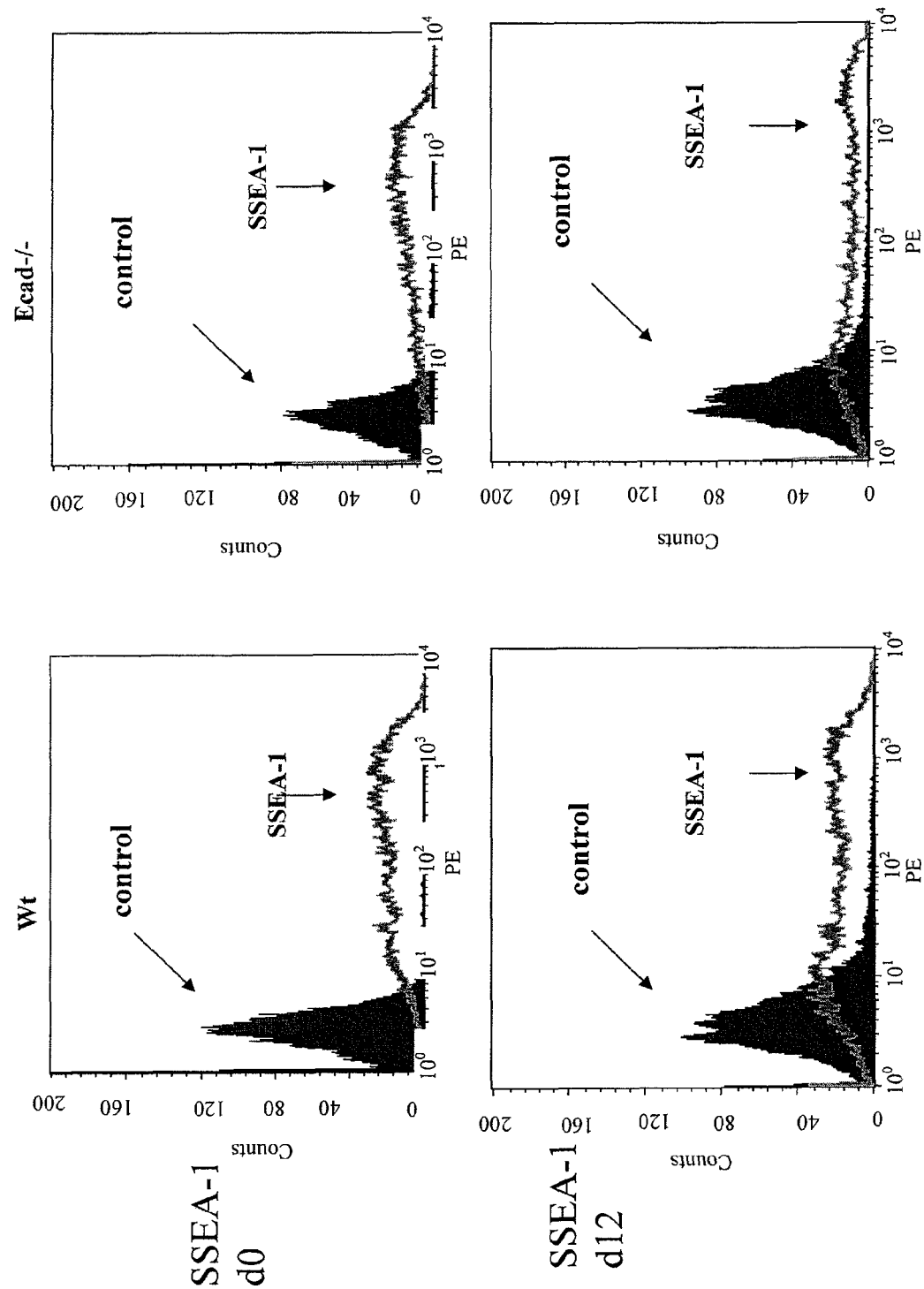
FIG. 17 shows the results described in the study set out under heading 12 of the Experimental Results section.

Data generated from representative of cells from this population are shown in FIG. 17. The level of SSEA-1 expression by wild type and E-cadherin null cells is comparable at both day 0 and day 12. This indicates that, although the differentiation of cells in which E-cadherin activity is inhibited (such as E-cadherin null ES cells) is retarded, such cells are able to differentiate when induced to overgrow. The data shown in FIG. 17 corroborate the results of RT-PCR shown in FIG. 4.

13. E-Cadherin Null ES Cells Remain Undifferentiated in Suspension Culture.

Wild type (wt) or E-cadherin null (Ecad−/−) ES cells were cultured for 30 days in suspension by plating $10^6$ cells (in 10 mls of medium lacking LIF) in a plastic bacteriological Petri dish. Culture medium was changed every day. Cells were passaged when required (usually every 2 days for E-cadherin null ES cells) by transfer of 2.5 mls of cell suspension into 7.5 mls of fresh medium.

Figure 18:
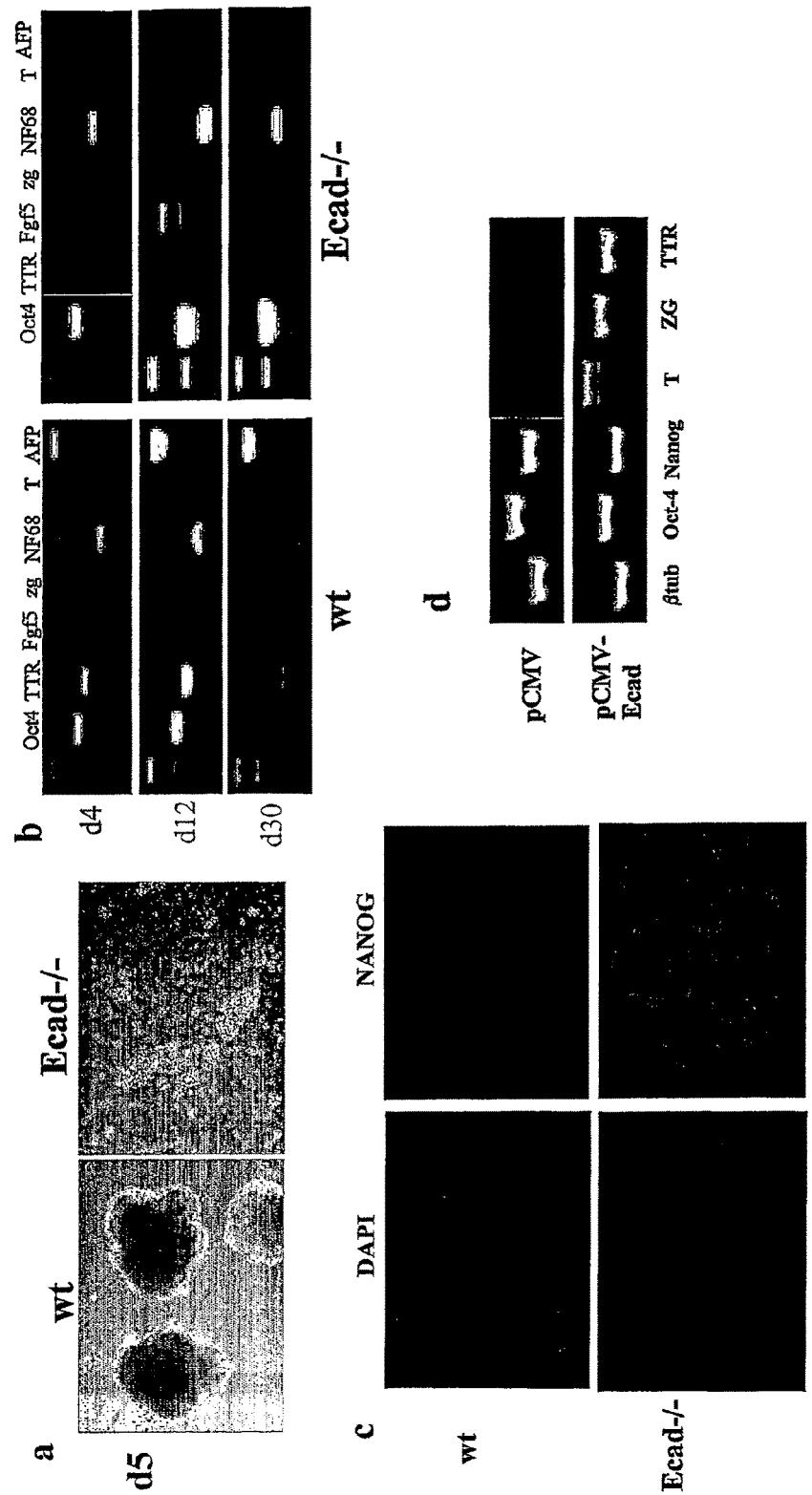
FIG. 18 shows the results described in the study set out under heading 13 of the Experimental Results section.

Cells cultured in this manner were investigated in a number of ways, and the results of these investigations are shown in FIG. 18.

Panel A of FIG. 18 shows phase contrast microscopy images comparing cultures of wild type and E-cadherin null cells at day 5 in suspension culture. It can be seen that E-cadherin null ES cell suspensions lack adhesion as compared to wild-type ES cells, since the E-cadherin null cells do not form embryoid bodies characteristic of the wild-type ES cells.

Panel B of FIG. 18 shows the results of analysis of the RNA content of cultured wild type and E-cadherin null cells. RNA was collected from the cell suspensions at day 4, 12 and 30 and assessed for Oct-4, transthyretin (TTR), fibroblast growth factor-5 (fgf-5), zeta-globin (zg), brachyury (T), neurofilament-68 (NF68) and alpha-foetal protein (AFP) transcripts using RT-PCR. Note that E-cadherin null ES cells fail to express the endoderm markers TTR and AFP and retain Oct-4 expression over 30 days. Detection of Fgf-5 transcripts suggest that a proportion of the E-cadherin null ES cells are of a primitive ectoderm (pluripotent) cell type, equivalent to the epiblast stage of the early embryo.

Panel C of FIG. 18 compares labelling for NANOG protein in wild type and E-cadherin null cells. After 30 days in the absence of LIF, cell suspensions of the type described above were cultured in gelatin-treated 6 well plates in the presence of LIF for 2 passages and assessed for NANOG protein expression using fluorescent microscopy. It can be seen that E-cadherin null ES cells maintain expression of nuclear NANOG, while wild type cells cultured in this manner did not exhibit any NANOG positive cells.

The results shown in panels B and C of FIG. 18 clearly illustrated that biological cells in which E-cadherin activity is inhibited do not differentiate in suspension culture. Furthermore, ES cells in which E-cadherin activity is inhibited maintain expression of the pluripotent nuclear Nanog protein. The expression of FGF-5 transcripts by these cells indicates that they may be representative of pluripotent primitive ectoderm cells.

The results shown in panel D of FIG. 18 investigate the RNA content of E-cadherin null cells cultured in suspension and then subject to forced expression of E-cadherin. E-cadherin null cells were cultured for 30 days in suspension in the absence of LIF and transfected with either a control vector (pCMV) or a vector expressing full length E-cadherin cDNA. The cells were then cultured for 3 days in the absence of LIF in gelatin treated tissue culture plates and assessed for expression of pluripotency-associated transcripts (Oct-4 and Nanog) and differentiation-associated transcripts brachury (T), zeta-globin (zg) and transthyretin (TTR). Both populations of cells expressed the pluripotency-associated transcripts, but only those cells transfected with full length E-cadherin cDNA expressed the differentiation markers.

These results illustrate that retardation of differentiation that occurs on inhibition of E-cadherin activity can be reversed when such inhibition ceases (in this case by forced expression of full length E-cadherin cDNA). This indicates that suspension culture of cells, such as ES cells, may be carried out while E-cadherin activity is inhibited in order to derive an expanded population of undifferentiated pluripotent cells, and that differentiation of these cells may then be induced by cessation or reversal of E-cadherin inhibition.

14. Addition of E-Cadherin Inhibitor DECMA-1 Antibody to Wild-Type ES Cells Delays their Differentiation in Suspension Culture.

Wild-type MESC ES cells (approx. $10^6$ cells in 10 mls of medium) were cultured for 10 days in the presence of either control antibody (cAb) or the E-cadherin inhibitor DECMA-1 antibody (nAb) (30 µl total antibody) in suspension in the absence of LIF in a plastic bacteriological Petri dish. Culture medium was changed every day. Cells were passaged when required (usually every 2 days for nAb treated ES cells) by transfer of 2.5 mls of cell suspension into 7.5 mls of fresh medium containing the appropriate antibody concentration.

Figure 19:
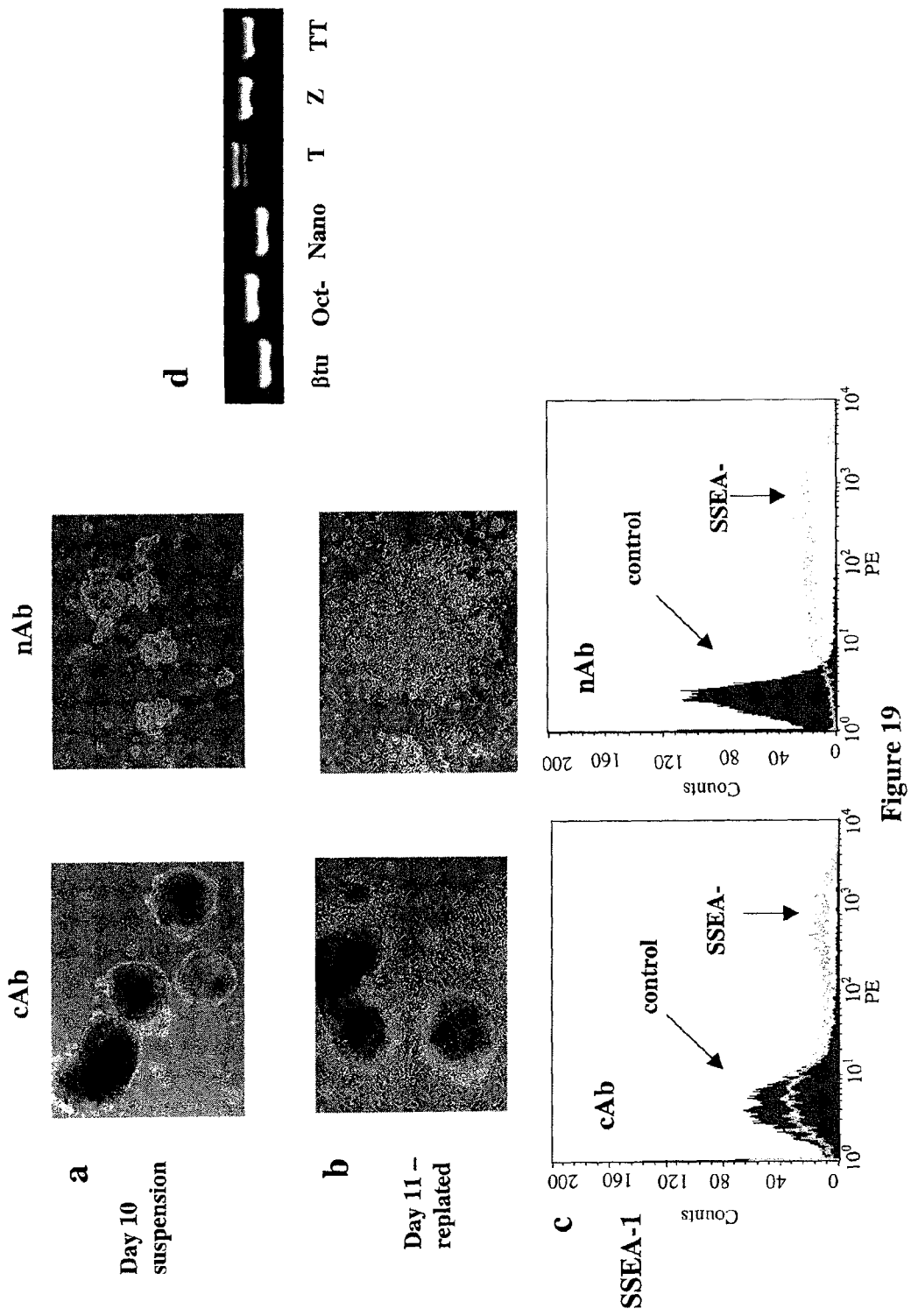
FIGS. 19A, B, C and D shows the results described in the study set out under heading 14 of the Experimental Results section.

Panel A of FIG. 19 compares phase contrast micrographs of cells cultured in suspension for 10 days in either cAb or nAb. It can be seen that cAb treated cultures include embryoid bodies, indicative of adhesions between the cultured cells, whereas the incidences of adhesion between nAb treated cell is much reduced.

Panel B of FIG. 19 compares phase contrast micrographs of cAb and nAb treated cells cultured as above, and then plated onto gelatin-treated tissue culture plates in the presence of LIF for 1 passage. Assessment of colony morphology illustrates that nAb treated cells exhibited ES cell like colony morphology but that cAb treated cells do not, cAb and nAb cells were plated onto gelatin-treated tissue culture plates in the presence of LIF for 2 passages and assessed for SSEA-1 expression using fluorescent flow cytometry as described above. The results of this study are shown in panel C of FIG. 19. These results show that nAb treated populations contained higher levels of SSEA-1 expressing cells than did their cAb treated counterparts. This indicates that cells cultured in the presence of the E-cadherin inhibitor DECMA-1 retain a less differentiated state than cells cultured in the presence of a control antibody.

nAb treated cells cultured as described in the preceding paragraph were further cultured in the absence of LIF and nAb for 3 days in gelatin treated tissue culture plates and assessed for expression of the pluripotent transcripts (Oct-4 and Nanog) and the differentiation-associated transcripts brachury (T), zeta-globin (zg) and transthyretin (TTR). The results of this assessment are shown in panel D of FIG. 19. These clearly indicate that, although nAb treated cells cultured in this manner can be induced to express markers of differentiation, they also retain pluripotency-associated transcripts.

15. Investigation of Transcript Expression in E-Cadherin Null (Ecad−/−) Cells Transfected with Full Length E-Cadherin cDNA and Wild Type (wt) D3 ES Cells Cultured in FCS–LIF for 3 Days.

Figure 20:
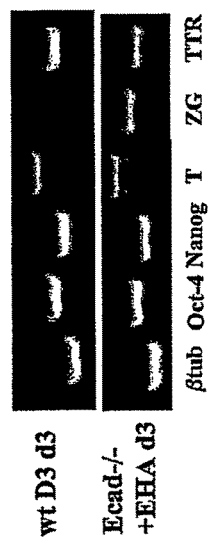
FIG. 20 shows the results described in the study set out under heading 15 of the Experimental Results section.

E-cadherin null cells were transfected with a vector expressing full length E-cadherin cDNA (EHA) and cultured for 3 days in the absence of LIF in gelatin treated tissue culture plates. RT-PCR was used to assess the expression of the pluripotent transcripts (Oct-4 and Nanog) and the differentiation-associated transcripts brachury (T), zeta-globin (zg) and transthyretin (TTR). The results of this assessment are shown in FIG. 20. Here it can be seen that when E-cadherin null cells are transfected with full length E-cadherin cDNA they express markers indicative of differentiation. Wild-type D3 ES cells represent a positive control. These results demonstrate that when inhibition of E-cadherin activity is ceased (in this case through forced expression of full length E-cadherin cDNA in E-cadherin−/− ES cells) cells are able to undergo differentiation.

16. RNAi Inhibition of E-Cadherin Activity in Wild-Type MESC ES Cells Results in Inhibition of Cell Surface E-Cadherin and Allows Culture of the Cells, and Retardation of Differentiation, in the Absence of LIF.

Figure 21:
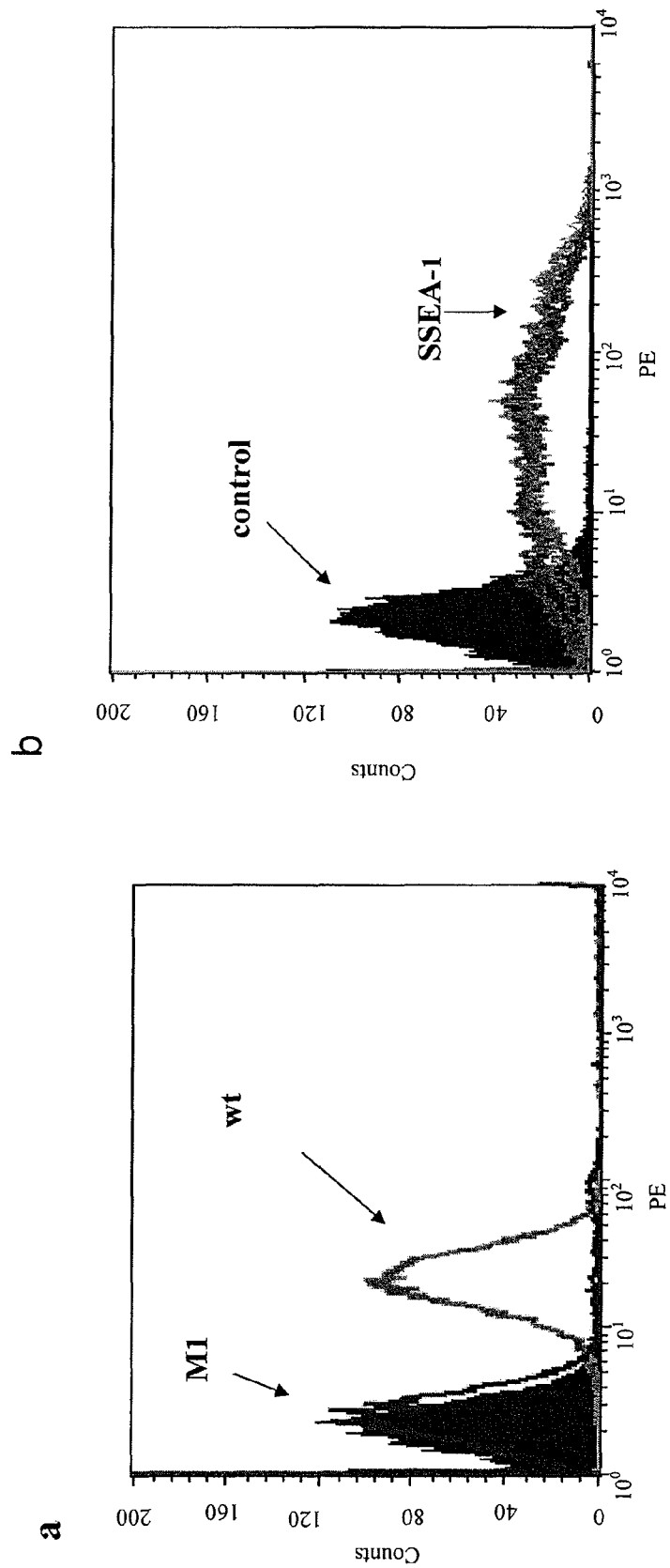
FIG. 21 shows the results described in the study set out under heading 16 of the Experimental Results section.

MESC20 ES cells were transfected with hairpin loop RNAi constructs as described in the experimental protocols. The cells' expression of E-cadherin and of the primitive cell marker SSEA-1 were investigated using fluorescence flow cytometry. The results of this investigation are shown in FIG. 21.

E-cadherin expressed by wild-type (wt) and RNAi treated MESC20 ES cells (clone M1) was labelled using the E-cadherin neutralising antibody DECMA-1, and labelling analysed by flow cytometry. The results are shown in panel A of FIG. 21, in which it can be seen that the labelling in M1 cells corresponds almost exactly to control values, while wild type cells exhibit far greater labelling. This indicates that E-cadherin was absent from almost the entire population of M1. This demonstrates that RNAi treatment represents a suitable means by which E-cadherin activity can be inhibited in cells such as stem cells.

MESC20 clone M1 ES cells (prepared as above) were cultured for 5 passages in the absence of LIF. SSEA-1 expression was then determined by fluorescent flow cytometry. The results are shown in panel B of FIG. 21, and show that that SSEA-1 expression was not decreased following removal of LIF. These results clearly indicate that inhibition of E-cadherin activity can retard cell differentiation (as evidenced by the high expression of the primitive cell marker SSEA-1) even in the absence of LIF.

17. RNAi Inhibition of E-Cadherin Activity in Wild Type MESC ES Cells Allows Suspension Culture for 30 Days in the Absence of Differentiation.

Wild type (wt) MESC or MESC ES cells transfected with E-cadherin RNAi cells (clone M1 as described above) were cultured for 30 days in suspension by plating $10^6$ cells in 10 mls of medium lacking LIF in a plastic bacteriological Petri dish. The culture medium was changed every day. Cells were passaged when required (usually every 2 days for E-cadherin RNAi ES cells) by transfer of 2.5 mls of cell suspension into 7.5 mls of fresh medium.

Culture in this manner was able to achieve a 268,000,000 fold expansion of total cell numbers.

Figure 22:
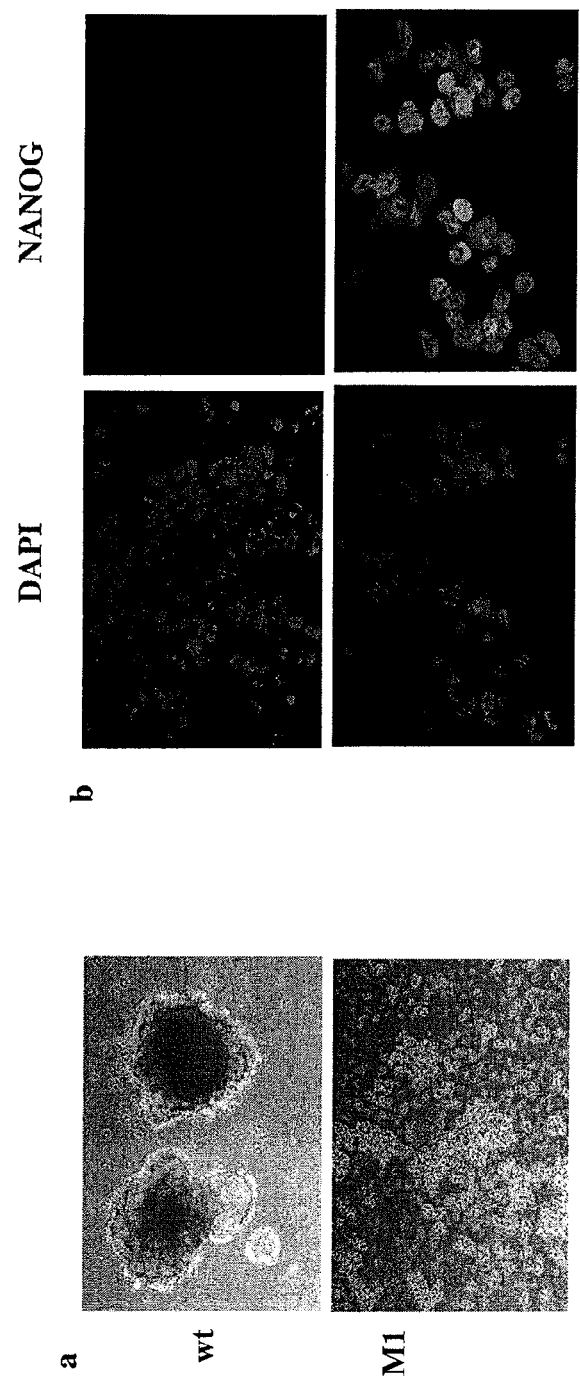
FIGS. 22A, B, C and D shows the results described in the study set out under heading 17 of the Experimental Results section.
Figure 22:
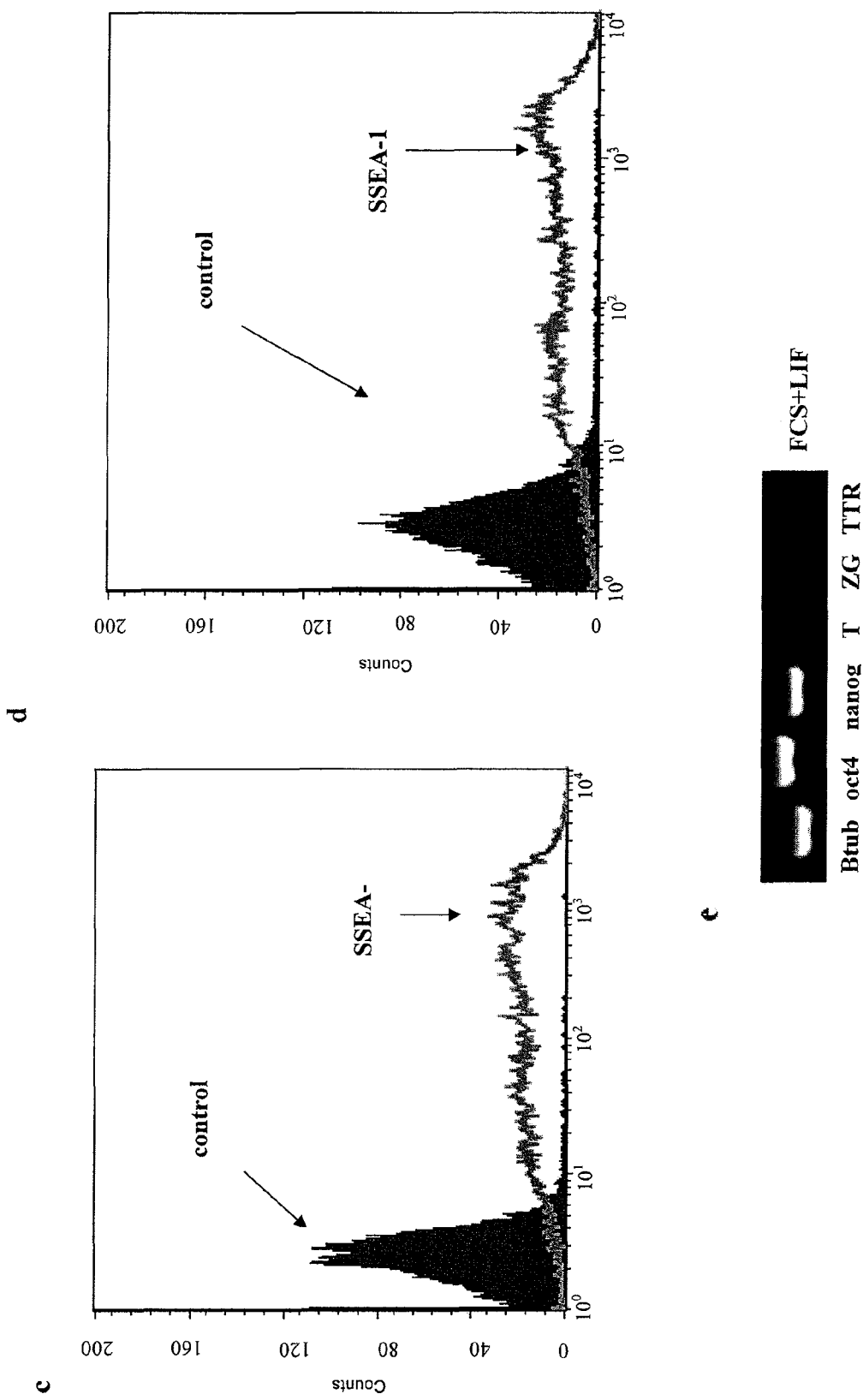

The properties of these cells were investigated in a series of studies, the results of which are shown in FIG. 22.

Panel A of FIG. 22 compares phase contrast microscopy images of day 5 cultures of M1 ES cells and wild type ES cells. These images clearly show the lack of adhesion in clone M1 ES cell suspensions compared to wild-type ES cells. Clone M1 ES cells (lacking E-cadherin activity) do not form the embryoid bodies observed in wild type cultures.

After 30 days in the absence of LIF, the cell suspensions were cultured in gelatin-treated plates in the presence of LIF for 2 passages and assessed for NANOG protein expression using fluorescent microscopy. Representative fluorescent microscopy images are shown in panel B of FIG. 22. Here it can be seen that that E-cadherin null ES cells (shown in the lower two images) maintain expression of nuclear NANOG. Wild-type cells did not exhibit any NANOG positive cells. These results further serve to illustrate that cells in which E-cadherin activity is inhibited (in this case by RNAi) express markers indicative of pluripotency.

Panel C of FIG. 22 shows the results of fluorescent flow cytometry undertaken to assess expression SSEA-1 in clone M1 cells cultured for 30 days in suspension in the absence of LIF in gelatin treated plates.

Panel D of FIG. 22 shows the results of fluorescent flow cytometry undertaken to assess expression of SSEA-1 by clone M1 cells cultured for 30 days in suspension in the absence of LIF and after 2 passages in the presence of LIF. The expression of SSEA-1 in these cells demonstrates that the majority of the cells are pluripotent (a finding that substantiates the result shown in FIGS. 22B and E).

Expression of pluripotent transcripts (Oct-4 and Nanog) and the differentiation-associated transcripts brachury (T), zeta-globin (zg) and transthyretin (TTR) by clone M1 after 30 days in suspension culture in the absence of LIF was investigated using RT-PCR analysis, and the results are shown in panel E of FIG. 22. These show that the cells expressed the pluripotent markers but not differentiation markers. This provides a further illustration of the fact that inhibition of E-cadherin allows biological cells to divide without undergoing differentiation.

18. Complete Inhibition of E-Cadherin is not Required for Undifferentiated Monolayer Culture of ES Cells in the Absence of LIF.

MESC20 ES cells were transfected with RNAi constructs as described in the experimental protocols to produce two separate clones, M1 (as described previously) and "clone 2" (cl2).

Figure 23:
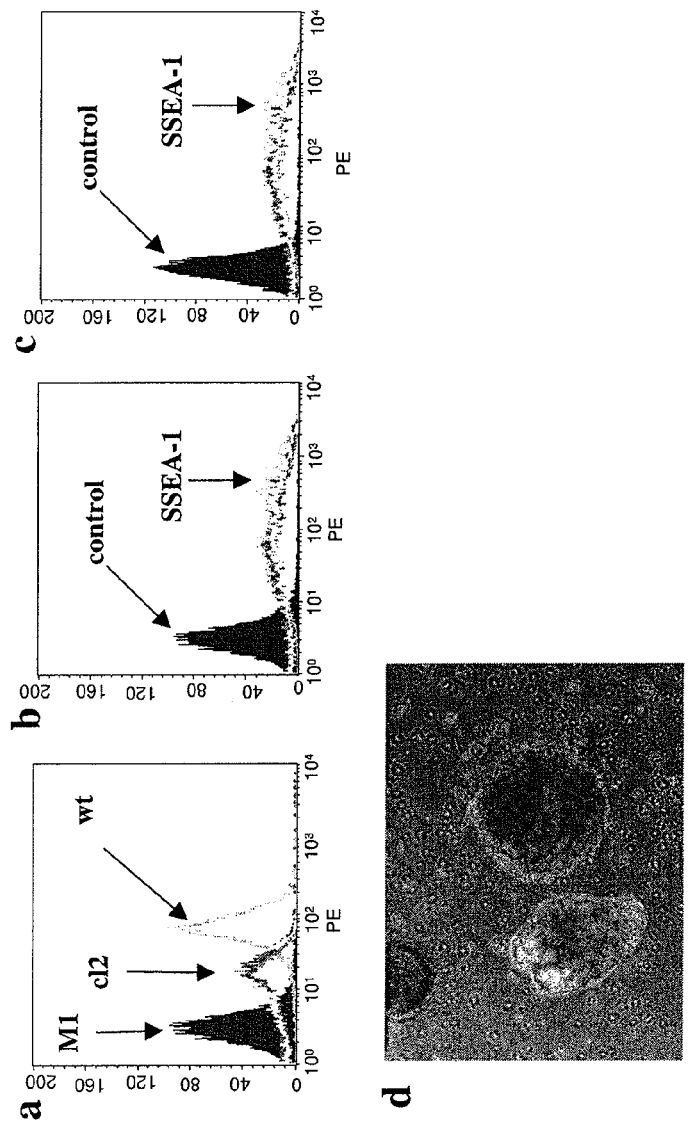
FIGS. 23A, B, C and D shows the results described in the study set out under heading 18 of the Experimental Results section.

Panel A of FIG. 23 illustrates E-cadherin expression by wild type ES cells (wt), M1 and clone 2, as determined using fluorescently labelled DECMA-1 antibody for fluorescent flow cytometry. It can be seen that (as shown previously) clone M1 exhibits little or no expression of E-cadherin (levels comparable to negative control), whereas wild type cells express E-cadherin protein. Clone 2 exhibits a level of E-cadherin expression that is intermediate between that of wt and M1 cells.

Panel B of FIG. 23 shows SSEA-1 expression (determined by fluorescent flow cytometry) of MESC20 clone 2 ES cells cultured for 5 passages in the presence of LIF. In contrast, panel C of FIG. 23 shows SSEA-1 expression (determined by fluorescent flow cytometry) in MESC20 clone 2 ES cells cultured for 5 passages in the absence of LIF. Comparison of panels B and C illustrates that expression of the primitive cell marker SSEA-1 was not decreased following removal of LIF from clone 2 ES cells, indicating that inhibition of E-cadherin activity represents a technique by which differentiation of cells in monolayer culture may be retarded (and cell numbers increased) even without the addition of LIF.

Panel D of FIG. 23 shows a phase contrast microscopy image illustrating the formation of three dimensional embryoid bodies following culture of clone 2 ES cells in suspension culture in the absence of LIF.

The results show that, although partial inhibition of E-cadherin activity is sufficient to retard differentiation of murine cells when grown in monolayer culture without LIF, it is not sufficient to retard differentiation of murine cells in suspension culture without LIF. Accordingly it will be appreciated that, in the event that it is wished to retard the differentiation of murine cells in suspension culture, it will be preferred that E-cadherin should be substantially totally inhibited. In the event that it is wished to retard the differentiation of murine cells in monolayer culture, this may be achieved using partial or total inhibition of E-cadherin activity. By the same token, it will be recognised that an inhibitor of E-cadherin activity that is only capable of partial inhibition of E-cadherin may still be used to retard the differentiation of murine cells in accordance with the present invention, but that the cells differentiation of which is to be retarded should be grown in monolayer culture.

Monolayer cultures of murine cells grown in the absence of LIF and with only partial inhibition of E-cadherin may exhibit some level of differentiation. As a result, it may generally be preferred that total (or substantially total) inhibition of E-cadherin activity be used in such cultures of cells in order to most effectively retard differentiation.

It should be noted that the results described in FIG. 23 were derived in investigations using murine cells. Accordingly, the information gained from these studies may be most applicable to the culture of murine cells. Further investigations of the effects of total or partial inhibition of E-cadherin activity in cultured human cells are described elsewhere in the specification.

19. Inhibition of E-Cadherin Activity in Human HES4 ES Cells Retards Differentiation of the Cells and Results in Increased Numbers of Undifferentiated ES Cell Colonies.

Human ES cell line HES4 was cultured in the presence of either control antibody (cAb) or SHE78.7 an E-cadherin neutralising antibody that serves to inhibit E-cadherin activity. 10 µl/ml of media of a stock 0.5 mg/ml solution of the relevant antibody was added to serum replacement medium containing FGF-2. Cells were grown on a fibroblast feeder layer for 2 days and assessed for colony morphology (phase contrast), actin cytoskeleton arrangement (phalloidin labelling) and expression of E-cadherin and OCT-4 proteins by immunofluorescent microscopy. Location of OCT-4 labelling was compared with that of DAPI staining, which shows cell nuclei. The results of these assessments are shown in panel A of FIG. 24.

Images from phase contrast microscopy show that addition of SHE78.7 causes loss of cell-cell contact. Incidences of cell to cell adhesion were reduced among cells treated with the inhibitor of E-cadherin activity compared to those treated with control antibody which exhibited normal levels of cell to cell adhesion in forming a monolayer.

The images obtained using phalloidin staining illustrate alteration of the actin cytoskeleton in cells treated with the inhibitor of E-cadherin activity, and it can be seen that these cells also exhibit decreased E-cadherin staining. However, expression of the pluripotency-associated marker OCT-4 is not decreased in human cells cultured in the presence of an inhibitor of E-cadherin activity (as shown by labelling of OCT-4).

HES4 colonies cultured in the presence of E-cadherin neutralising antibody or control antibody were passaged mechanically, and at passage 2 the number of undifferentiated colonies was assessed (after removal of nAb for 2 days). The results of this assessment are shown in panel B of FIG. 24. These results clearly illustrate that cells treated with a neutralising antibody inhibitor of E-cadherin activity exhibited higher numbers of undifferentiated colonies than did cells treated with a control antibody.

Figure 24:
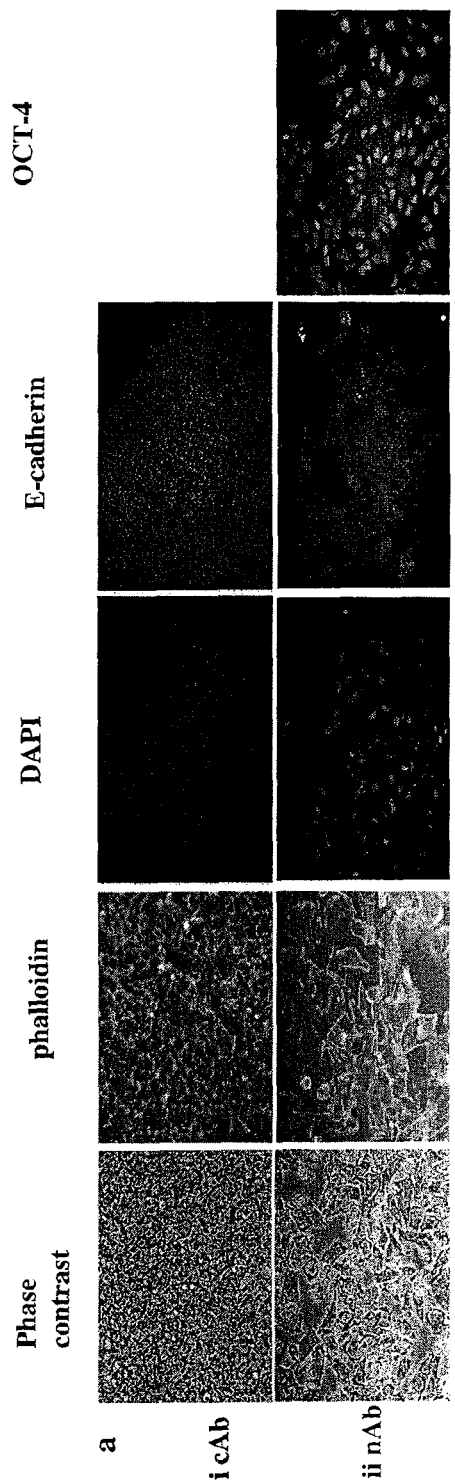
FIGS. 24A, B, C and D shows the results described in the study set out under heading 19 of the Experimental Results section.
Figure 24:
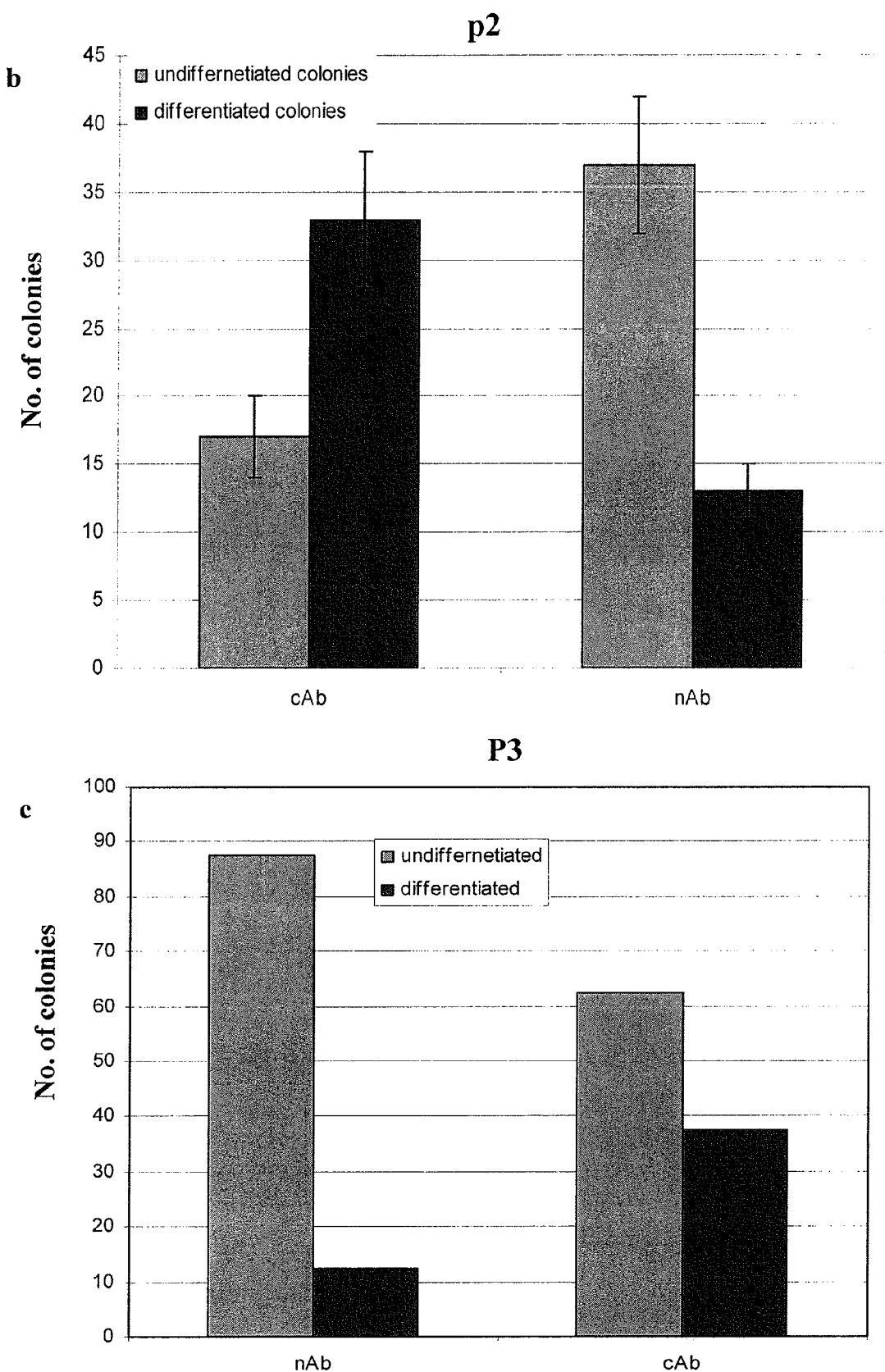
Figure 24:
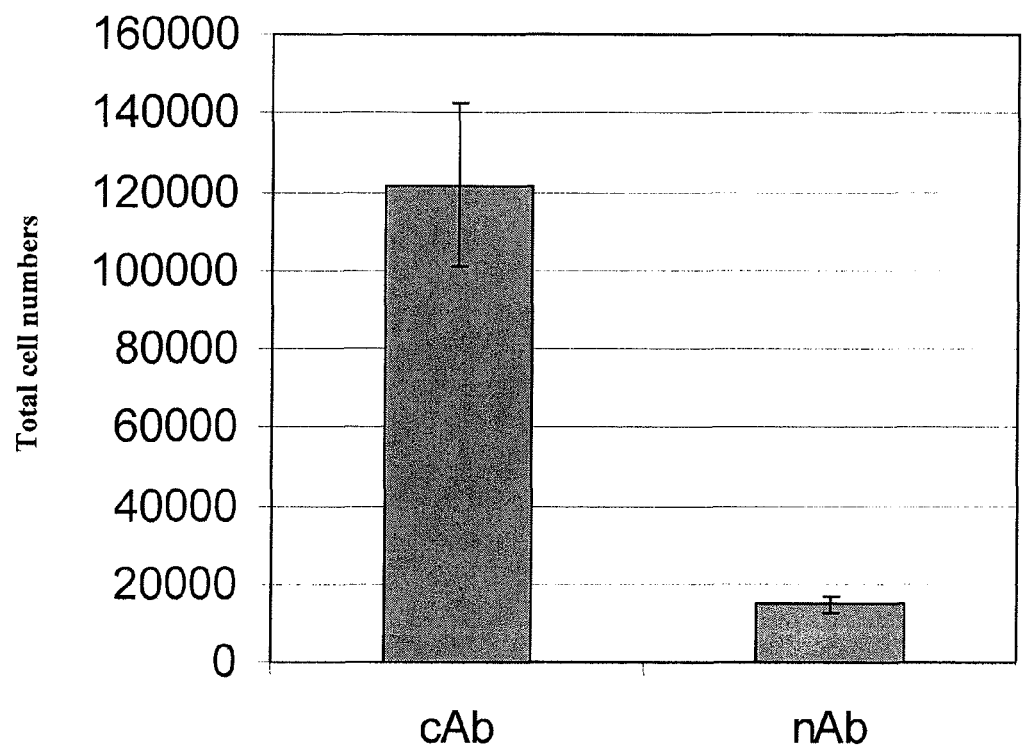

The number of undifferentiated colonies was also assessed at passage 3 (after removal of nAb for 2 days), and these results are shown in panel C of FIG. 24. It can be seen that, among cells treated with the inhibitor of E-cadherin activity SHE78.7, almost 90% of colonies exhibited an undifferentiated phenotype colonies compared to only approximately 60% of colonies among cells treated with control antibody.

HES4 cells cultured in the presence of control antibody or neutralising antibody (10 µl/ml of media of a stock 0.5 mg/ml solution) were assessed for cell numbers over 5 passages. The results are shown in panel D of FIG. 24, and illustrate that cell proliferation is decreased among cells treated with neutralising antibody compared to cells treated with control antibody.

20. Removal of Inhibitors of E-Cadherin Activity, Such as Neutralising Antibody SHE78.7, from HES4 ES Cells for 7 Days Restores Cell-Cell Contact.

The results reported above indicated that inhibition of E-cadherin activity was able to reduce E-cadherin expression, and also to reduce the incidence of cell to cell contacts between cultured cells. The following study was undertaken to investigate whether cells cultured in this manner were able restore normal cell to cell contact on cessation of E-cadherin inhibition.

Human ES cells HES4 were cultured in the presence of either control antibody (cAb) or E-cadherin neutralising antibody SHE78.7 (10 µl/ml of media of a stock 0.5 mg/ml solution) on a fibroblast feeder layer in serum replacement medium containing FGF-2 for 2 days, and then nAb removed for 7 days. Cells were then assessed for colony morphology (by phase contrast microscopy), actin cytoskeleton arrangement (by phalloidin labelling) and expression of OCT-4 protein (immunolabeling combined with a DAPI counterstain to show cell nuclei).

Figure 25:
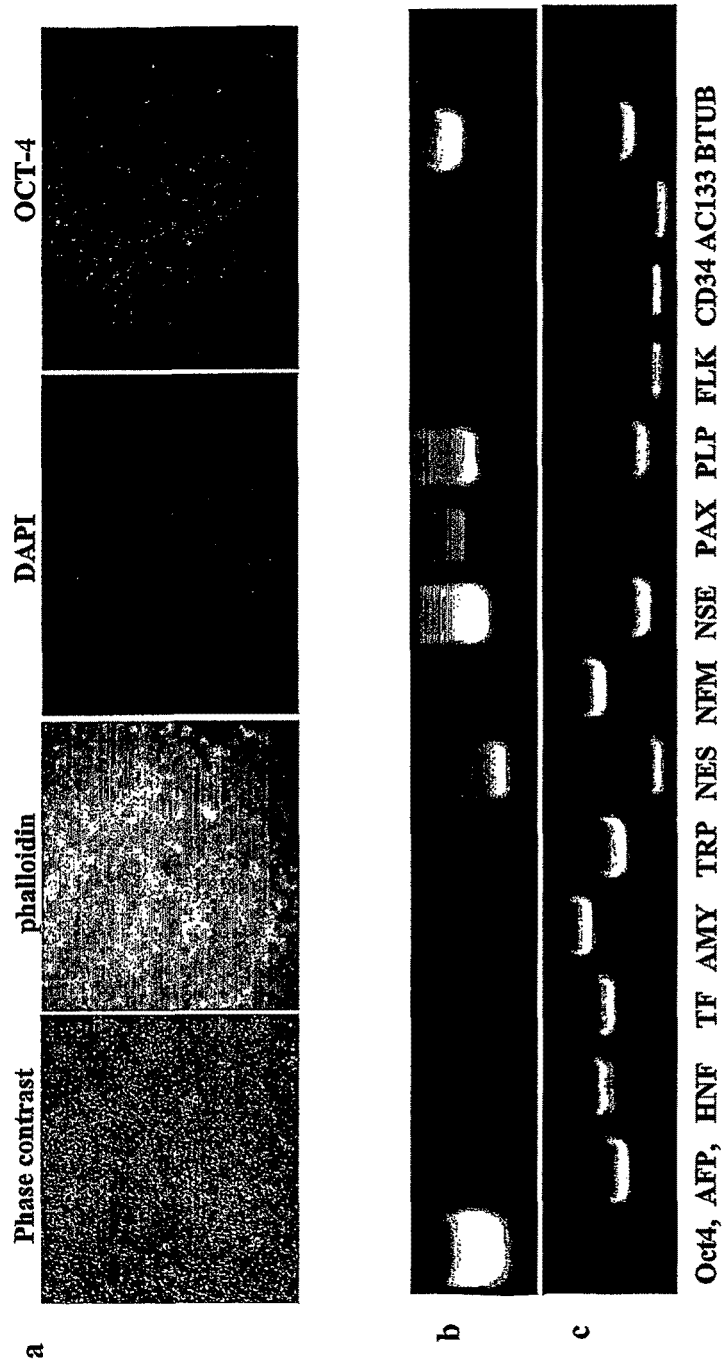
FIGS. 25A, B and C shows the results described in the study set out under heading 20 of the Experimental Results section.

The results of this assessment are shown in panel A of FIG. 25. Here it can be seen that removal of the inhibitor of E-cadherin activity SHE78.7 restores cell-cell contact and cortical actin cytoskeleton arrangement so that these resemble cells treated with a control antibody (for example, compared with "icAb" cells shown in panel A of FIG. 24). It can also be seen that, even after cessation of E-cadherin inhibition, the majority of the population of cells treated in this manner maintain expression of OCT-4 protein.

HES4 ES cell colonies treated as described in the preceding paragraph were assessed for expression of transcripts associated with pluripotency (Oct4) and further markers as described in Ward et al, 2006 and in the Methods. The expression profile observed (shown in panel B of FIG. 25) is consistent with that that has previously been observed in undifferentiated HES4 ES cells (for example in an expression profile described by Ward et al., 2006).

HES4 ES cell colonies described as described in the preceding passages were allowed to overgrow in the culture plates (i.e. without passaging) for 20 days to induce differentiation of the cells. Expression of various markers of differentiation was then investigated. The results of this investigation are shown in panel C of FIG. 25. Markers of differentiation expressed following differentiation of the cells included markers representative of all three germ layers (endoderm—HNF, TF, AMY; mesoderm—FLK, CD34, AC133; ectoderm—NES, NFM, NSE, PAX and PLP) and extra-embryonic visceral endoderm (AFP). This clearly illustrates that inhibition of E-cadherin activity does not prevent subsequent differentiation of cells once inhibition is ceased.

21. Inhibition of E-Cadherin Activity (Such as by the Neutralising Antibody SHE78.7) Allows the Culture of hES in the Absence of FGF-2.

HES4 and H1 human ES cell lines were cultured in the presence of a minimal fibroblast feeder layer (approximately 1000 cells/dish) in the absence of FGF-2 in serum replacement medium in the presence of either the E-cadherin neutralising antibody SHE78.7 or control antibody (0.5 µl/ml of media of a stock 0.5 mg/ml solution). The inventors believe that this concentration of SHE78.7 in culture medium is sufficient to partly inhibit E-cadherin activity in cells grown in the medium.

Figure 26:
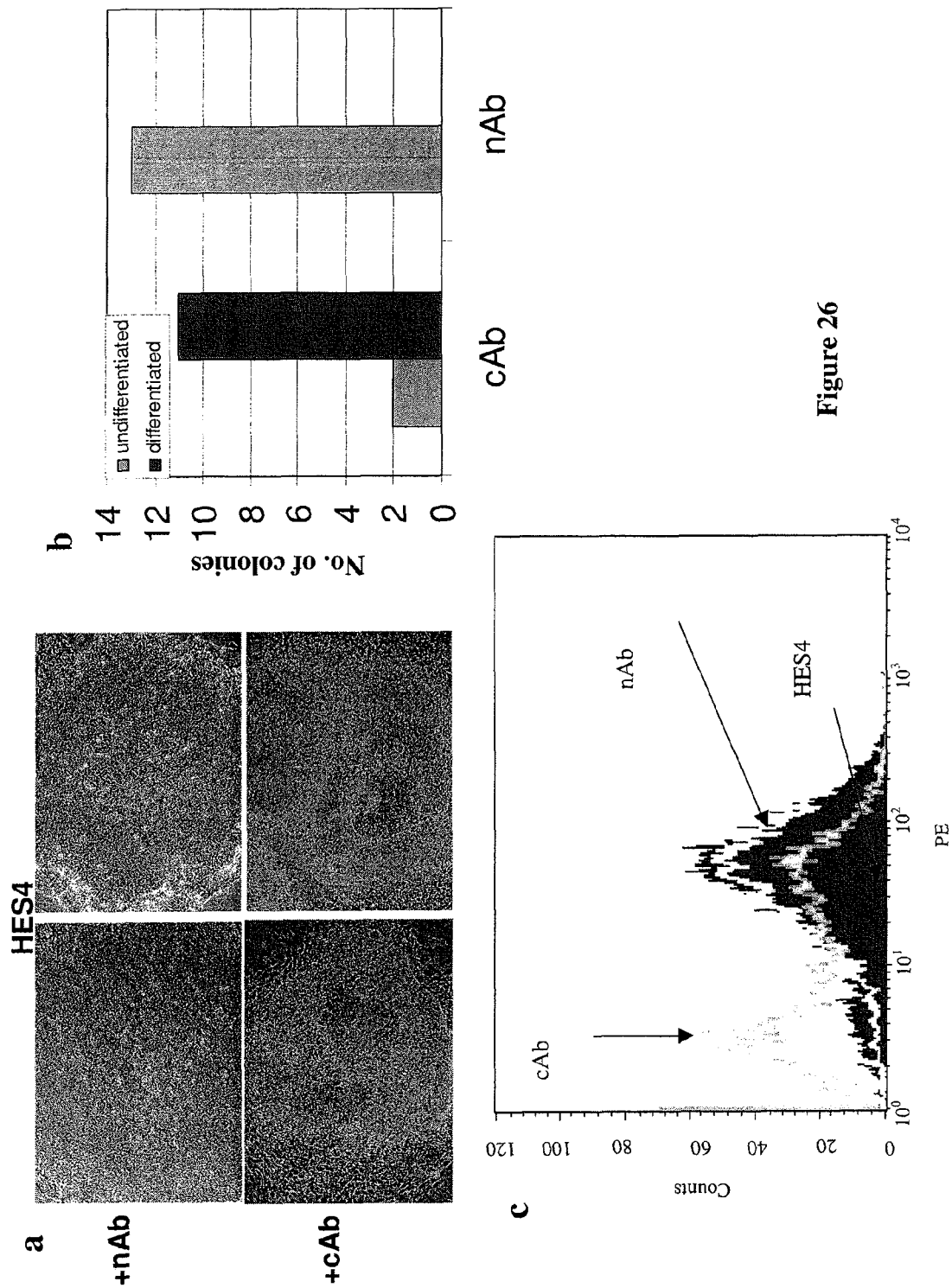
FIGS. 26A, B, C, D, E and F shows the results described in the study set out under heading 21 of the Experimental Results section.
Figure 26:
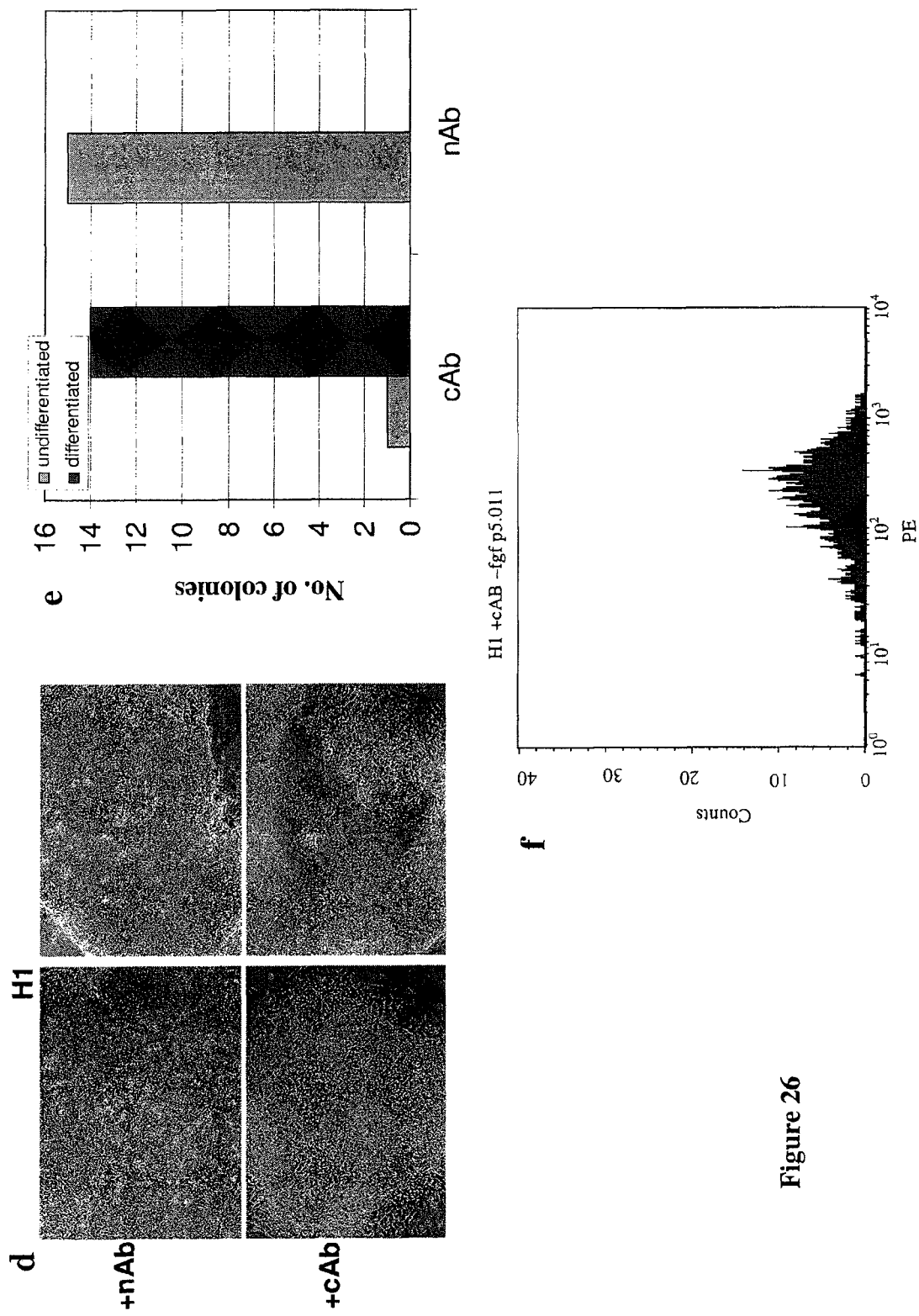

Panel A of FIG. 26 shows phase contrast microscopy images of HES4 ES cells cultured in control antibody (cAb) or E-cadherin neutralising antibody SHE78.7 (nAb) after 2 passages in the absence of FGF-2. Analysis of colony morphology shows that cells grown in the presence of the inhibitor of E-cadherin activity retain normal colony morphology (indicating that the cells had not undergone differentiation), whereas cells cultured using control antibody have morphologies indicating that they have undergone differentiation.

Panel B of FIG. 26 compares the number of undifferentiated and differentiated HES4 colonies among populations of cells treated with E-cadherin neutralising antibody or with control antibody as described above. It is very surprising to note that all colonies exhibited of cells grown in the presence of the inhibitor of E-cadherin activity SHE78.7, and in the absence of FGF-2, exhibit undifferentiated morphology.

Panel C of FIG. 26 shows the results of fluorescent flow cytometry analysis of cell surface expression of the pluripotent marker Tra-1-60 on HES4 ES cells. Expression of Tra-1-60 after 3 passages was compared between:
1. HES4 ES cells treated with control antibody in the absence of FGF-2 (labelled cAb in Panel C);
2. HES4 ES cells treated with E-cadherin neutralising antibody in the absence of FGF-2 (labelled nAb in Panel C); and
3. HES4 ES cells cultured under normal prior art conditions on a fibroblast feeder layer containing FGF-2 (labelled HES4 in Panel C).

The results illustrate that cells cultured in the presence of an inhibitor of E-cadherin activity (nAb cells) exhibited the highest expression of Tra-1-60, even when compared to HES4 cells cultured under normal prior art conditions.

Panel D of FIG. 26 shows phase contrast microscopy images of H1 ES cells cultured in control antibody (cAb) or E-cadherin neutralising antibody SHE78.7 (nAb) after 2 passages in the absence of FGF-2. As above, cells grown in the presence of an inhibitor of E-cadherin activity (nAb) exhibited normal colony morphology indicating that they had not undergone differentiation, whereas the morphology of cAb treated cells indicated that they were differentiated.

Panel E of FIG. 26 compares the number of undifferentiated and differentiated H1 colonies in cAb or nAb treated cells as shown in panel D above. This clearly shows that all nAb colonies exhibited undifferentiated morphology in the absence of FGF-2, whereas the majority of cAb treated colonies were differentiated.

Panel F shows the results of fluorescence flow cytometry analysis of surface expression of the pluripotent marker Tra-1-60 was on nAb treated HES4 ES cells (all cAb treated cells had died) after 5 passages in the absence of FGF-2. It can be seen that >99% of the nAb treated cells exhibited Tra-1-60 expression.

Taken together, these results shown in FIG. 26 illustrate that treatment of hES cells with an inhibitor of E-cadherin activity (such as the E-cadherin neutralising antibody SHE78.7) allows successful culture of the cells, and their maintenance in an undifferentiated state, in the absence of FGF-2.

The inventors believe that the concentration of SHE78.7 utilised in this study is sufficient to bring about partial (as opposed to complete) inhibition of E-cadherin activity (indicated by the fact that cells treated in this manner still exhibit cell-cell contact, indicative of retention of some E-cadherin activity). The partial inhibition of E-cadherin activity achieved by this concentration is sufficient to retard differentiation of treated cells, as compared to differentiation occurring in control treated populations. The partial inhibition of E-cadherin activity in this manner confers advantages in that human cells (such as stem cells) cultured in this way are able to retain normal cell to cell contacts, while still being subject to retarded differentiation. Accordingly the partial inhibition of E-cadherin activity represents a preferred mode by which differentiation of human cells in monolayer culture may be retarded, in particular when using a mechanical passage technique.

Not only is colony morphology maintained in populations in which E-cadherin activity is inhibited, but so is the cell surface pluripotent marker Tra-1-60. The results reported confirms the utility of this method in two independent hES cell lines; H1 and HES4.

22. Culture of hES Cells in E-Cadherin Neutralising Antibody SHE78.7 Allows their Prolonged Culture in the Absence of FGF-2.

HES4 and H1 human ES cells were cultured in medium containing E-cadherin neutralising antibody SHE78.7 ("nAb") (0.5 µl/ml of media of a stock 0.5 mg/ml solution) in the presence of minimal fibroblast feeder layer in the absence of FGF-2 in serum replacement medium for 10 passages (approximately 90 days).

Figure 27:
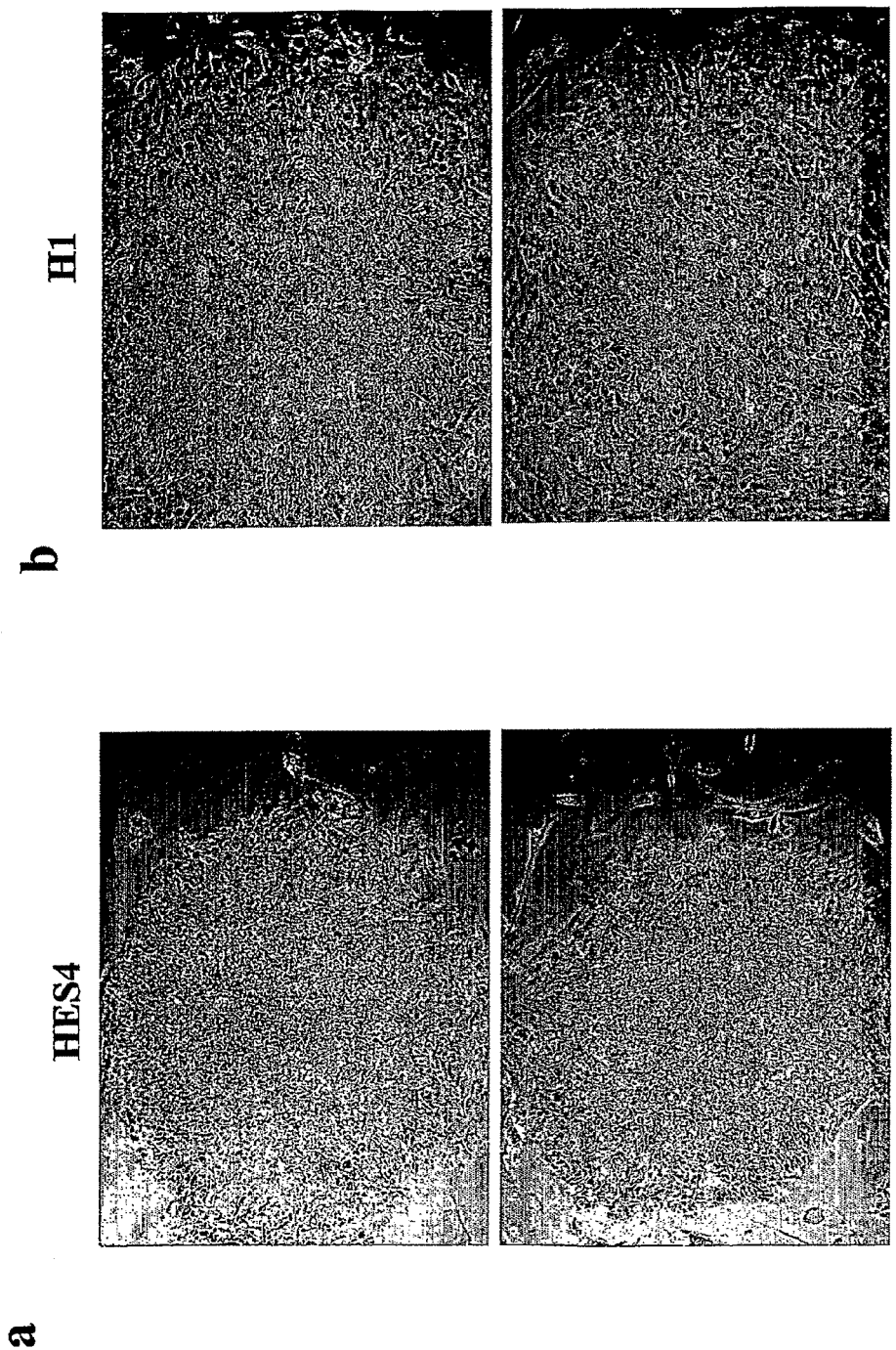
FIGS. 27A and B shows the results described in the study set out under heading 22 of the Experimental Results section.

Plate A of FIG. 27 shows phase contrast microscopy images of HES4 ES cells cultured in E-cadherin neutralising antibody SHE78.7 (nAb) after 10 passages in the absence of FGF-2 (2 days after transfer). It can be seen that all nAb-treated cells exhibited normal colony morphology (×100 magnification).

Plate B of FIG. 27 shows phase contrast microscopy images of H1 ES cells cultured in E-cadherin neutralising antibody SHE78.7 (nAb) after 10 passages in the absence of FGF-2 (2 days after transfer). It can be seen that all nAb-treated cells exhibited normal colony morphology (×100 magnification).

23. Culture of HES4 hES Cells in E-Cadherin Neutralising Antibody SHE78.7 Allows their Prolonged Culture in the Absence of FGF-2.

Figure 28:
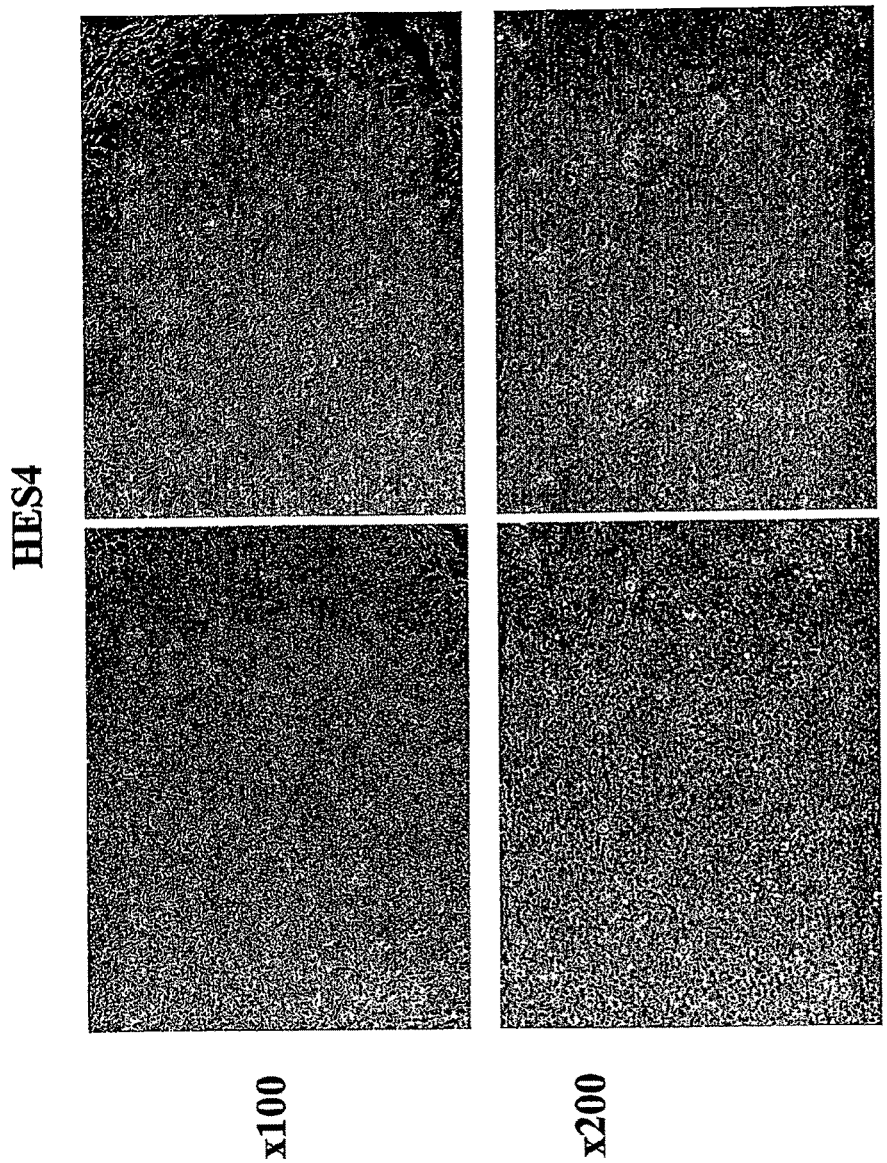
FIG. 28 shows the results described in the study set out under heading 23 of the Experimental Results section.

HES4 ES cells were cultured in nAb (0.5 µl/ml of media of a stock 0.5 mg/ml solution) in the presence of minimal fibroblast feeder layer in the absence of FGF-2 in serum replacement medium for 10 passages (approximately 90 days). FIG. 28 sets out phase contrast microscopy images showing colony morphology at ×100 and ×200 magnification. It can be seen that the cells cultured in the presence of an inhibitor of E-cadherin activity exhibit normal colony morphology.

24. Culture of H1 ES Cells in E-Cadherin Neutralising Antibody SHE78.7 Allows their Prolonged Culture in the Absence of FGF-2.

Figure 29:
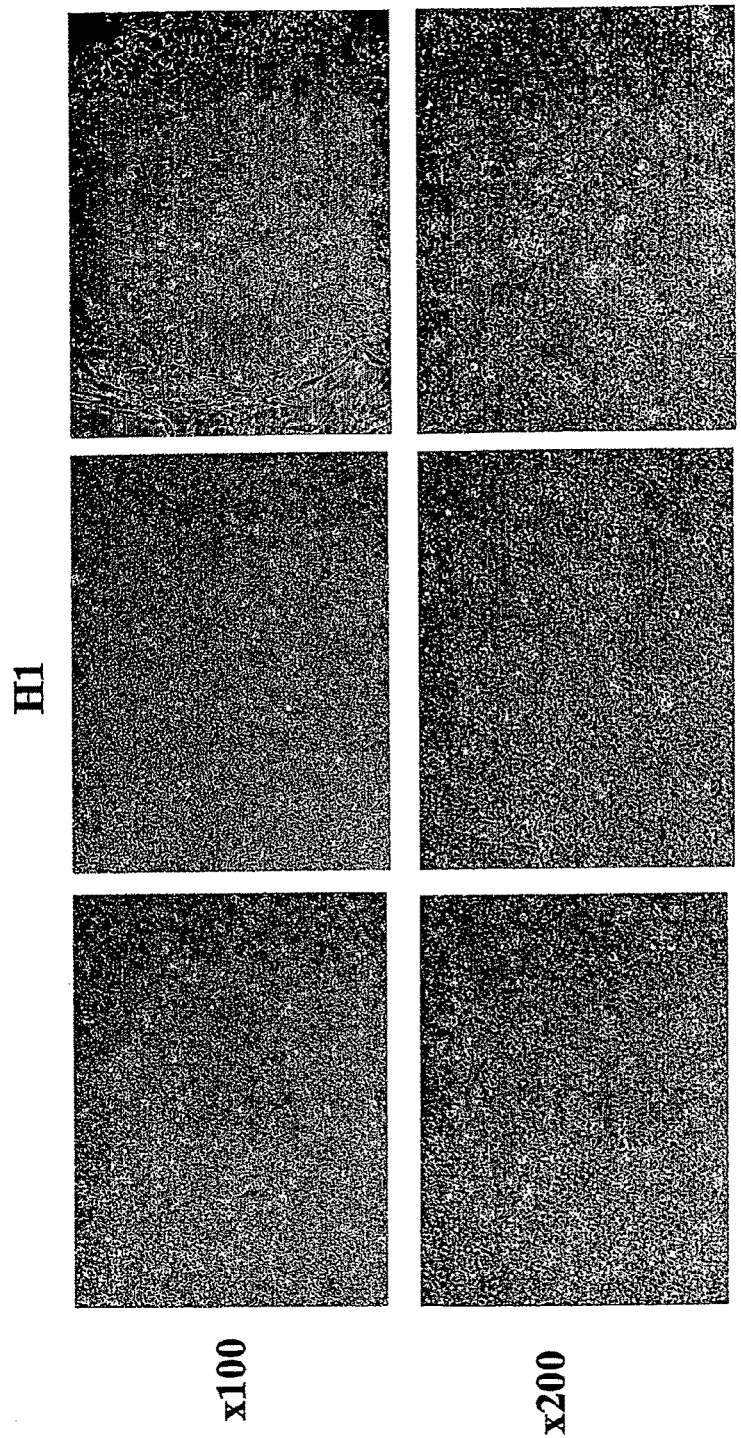
FIG. 29 shows the results described in the study set out under heading 24 of the Experimental Results section.

H1 ES cells were cultured in nAb (0.5 µl/ml of media of a stock 0.5 mg/ml solution) in the presence of minimal fibroblast feeder layer in the absence of FGF-2 in serum replacement medium for 10 passages (approximately 90 days). FIG. 29 sets out phase contrast microscopy images showing colony morphology at ×100 and ×200 magnification. As before, it can be seen that the cells exhibit normal colony morphology.

Taken as a whole, the results shown in FIGS. 27 to 29 illustrate that inhibition of E-cadherin activity (such as with the E-cadherin neutralising antibody SHE78.7) allows human stem cells (such as H1 and HES4 hES cells) to be maintained in culture, without significant differentiation, for prolonged periods in the absence of FGF-2 in synthetic serum using minimal feeder layers. Cells maintained in culture in this manner retain their pluripotent nature.

25. HES4 ES Cells Cultured for 10 Passages in E-Cadherin Neutralising Antibody Exhibit Normal Transcript Expression and are Able to Differentiate to Produce all Three Germ Layers.

HES4 ES cell colonies were cultured in nAb SHE78.7 (0.5 µl/ml of media of a stock 0.5 mg/ml solution) in the presence of a minimal fibroblast feeder layer in the absence of FGF-2 in serum replacement medium for 10 passages (approximately 90 days) and assessed for expression of transcripts associated with pluripotency (Oct4) and various lineage markers (as described in Ward et al., 2006). The results of this assessment are shown in panel A of FIG. 30. The transcript profile expression is consistent with that observed for undifferentiated HES4 ES cells (as reported in Ward et al, 2006).

HES4 ES cell colonies described in the preceding paragraph were allowed to overgrow in the culture plates (i.e. by culture without passaging) in normal ES cell culture medium (i.e. +FGF-2) for 20 days in the absence of nAb to induce differentiation of the cells. The cells were then assessed for expression of transcripts associated with pluripotency (Oct4) and various lineage markers (as described in Ward et al., 2006). The results of this assessment are shown in panel B of FIG. 30. Note that markers of differentiation expressed following differentiation of the cells included all three germ layers (endoderm—as shown by markers HNF, TF, AMY; mesoderm—as shown by markers FLK, CD34, AC133; ectoderm—as shown by markers NES, NFM, NSE, PAX and PLP) and extra-embryonic visceral endoderm (AFP).

26. H1 ES Cells Cultured for 10 Passages in E-Cadherin Neutralising Antibody Exhibit Normal Transcript Expression and Differentiate to all Three Germ Layers.

H1 ES cell colonies were cultured in nAb SHE78.7 (0.5 µl/ml of media of a stock 0.5 mg/ml solution) in the presence of a minimal fibroblast feeder layer in the absence of FGF-2 in serum replacement medium for 10 passages (approximately 90 days). The cells were then assessed for expression of transcripts associated with pluripotency (Oct4) and for various lineage markers (as described in Ward et al., 2006). The results of this assessment are shown in panel A of FIG. 31. This demonstrates that the transcript profile expression is consistent with that observed for undifferentiated H1 ES cells (as reported in Ward et al., 2006).

H1 ES cell colonies grown as described in the preceding paragraph were allowed to overgrow in the culture plates (i.e. grown without passaging) in normal ES cell culture medium (i.e. +FGF-2) for 20 days in the absence of nAb to induce differentiation of the cells. The cells were then assessed for expression of transcripts associated with pluripotency (Oct4) and various lineage markers as described in Ward et al., 2006. The results of this assessment are shown in panel B of FIG. 31, and illustrate that markers of differentiation expressed following differentiation of the cells included all three germ layers (endoderm—TF, AMY; mesoderm—FLK, CD34, AC133; ectoderm—NES, NFM, NSE, PAX and PLP) and extra-embryonic visceral endoderm (AFP).

Figure 30:
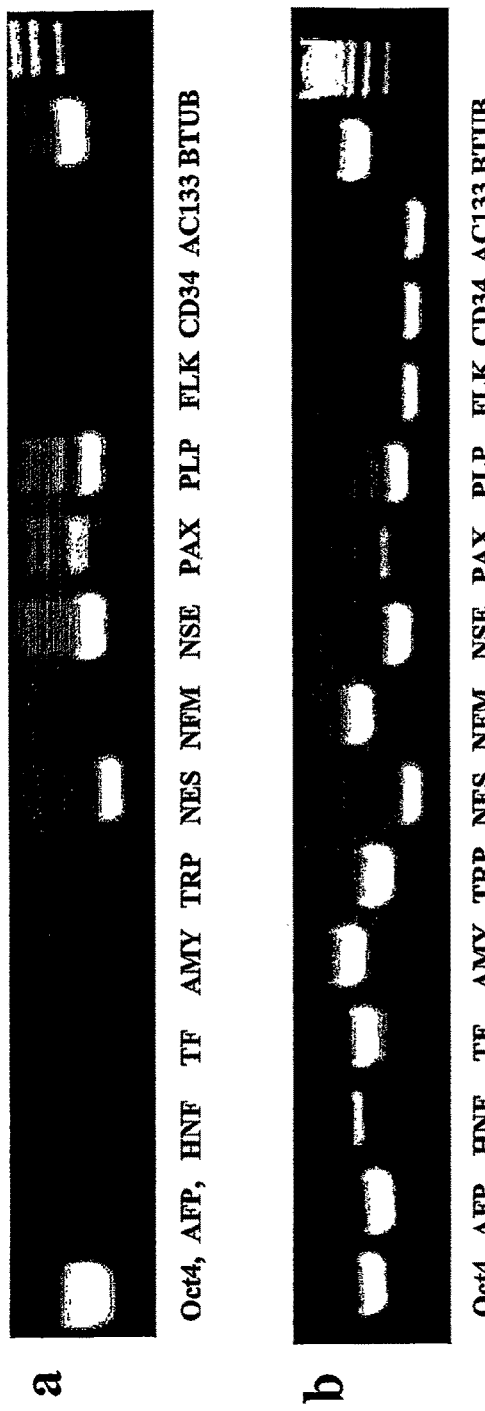
FIG. 30 shows the results described in the study set out under heading 25 of the Experimental Results section.
Figure 31:
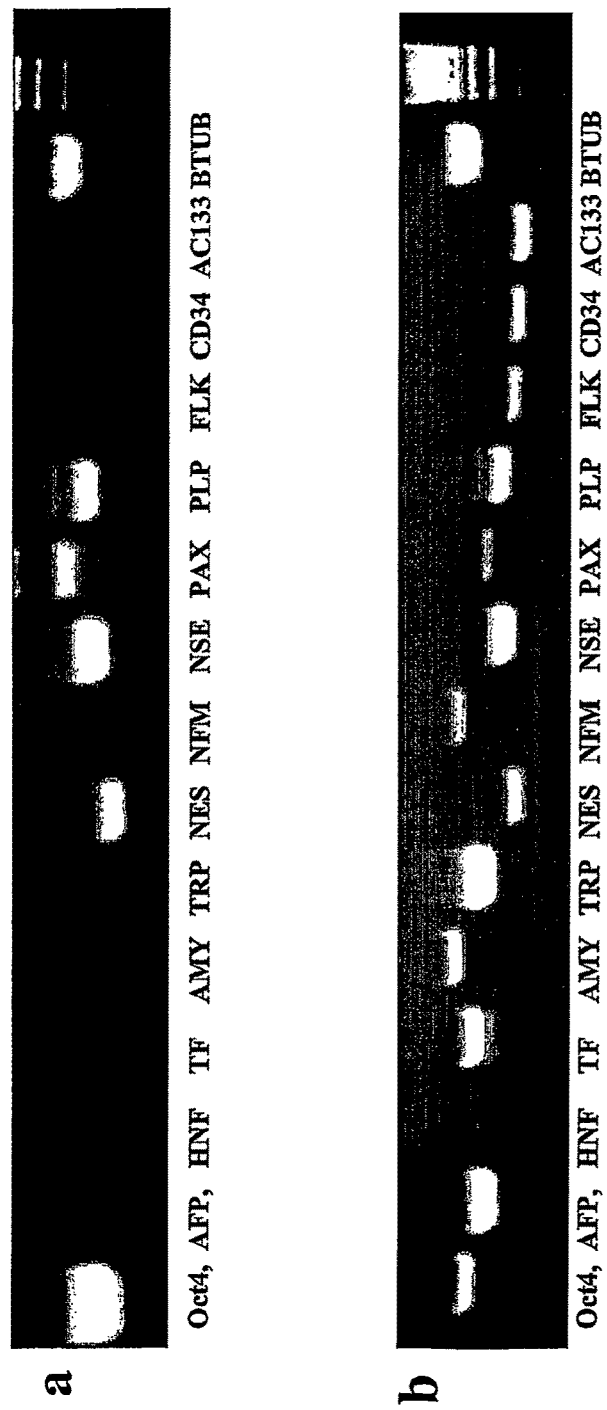
FIG. 31 shows the results described in the study set out under heading 26 of the Experimental Results section.

The results set out in FIGS. 30-31 show that human stem cells (such as H1 and HES4 human embryonic stem cells) can be cultured for prolonged periods in the absence of FGF-2 in synthetic serum in minimal feeders when E-cadherin activity is inhibited (for example by treatment with E-cadherin neutralising antibody SHE78.7). Cells cultured in this manner exhibit transcript expression associated with hES cells cultured under normal conditions known in the prior art (conditions that utilise components such as FGF-2). When inhibition of E-cadherin activity is ceased (for example on removal of nAb) differentiation of the cells may proceed as normal, and is able to give rise to cells of the three germ layers. This clearly shows that, on reversal of inhibition of E-cadherin activity, the retardation of differentiation ends, and normal differentiation (for example to achieve therapeutically useful cell types) can be achieved.

27. Human Stem Cells (HES4 and H1 ES Cells) Treated with an Inhibitor of E-Cadherin Activity (Neutralising Antibody SHE78.7) Maintain Undifferentiated Colony Morphology after Prolonged Passage in the Absence of FGF-2.

Figure 32:
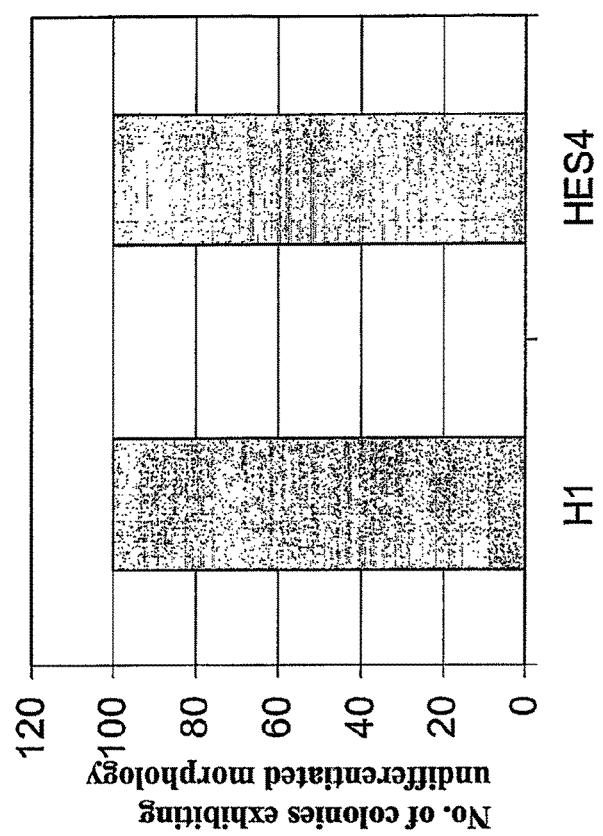
FIG. 32 shows the results described in the study set out under heading 27 of the Experimental Results section.

H1 and HES4 ES cells were cultured in nAb (0.5 µl/ml of media of a stock 0.5 mg/ml solution) in the presence of a minimal fibroblast feeder layer in the absence of FGF-2 in serum replacement medium for 15 passages (approximately 130 days) and assessed for colony morphology by phase contrast microscopy. All colonies exhibited characteristic undifferentiated morphology, as shown in the results set out in FIG. 32. These results clearly indicate that differentiation of human stem cells in culture can be inhibited by inhibition of E-cadherin activity.

28. Prolonged Culture of Wild Type D3 ES Cells in the Absence of LIF Selects for E-Cadherin Negative/SSEA-1 Positive Cells.

D3 ES cells were cultured in gelatin-treated 6-well plates in the presence of LIF and assessed for cell surface E-cadherin or SSEA-1 expression by fluorescent flow cytometry. The results of this assessment are shown in panel A of FIG. 33, in which it can be seen that cells at the outset expressed high levels of both cell surface E-cadherin and SSEA-1.

D3 ES cells were then cultured for 12 passages without LIF by carefully sub-culturing the cells according to the cell number present. For example, where low cell numbers were observed the entire population of cells was transferred to a fresh 6-well plate (such a transfer was not counted as a passage since all of the cells were transferred). After approximately 30 days (12 passages) a sudden expansion of cells was observed and these cells appeared to lack any cell-cell contacts. The cells were assessed at passage 12 for cell surface E-cadherin or SSEA-1 expression by fluorescent flow cytometry. The results of this assessment are shown in panel B of FIG. 33, in which it can be seen that the majority of the cell population lacked E-cadherin but expressed SSEA-1, demonstrating an undifferentiated phenotype.

In both fluorescent flow cytometry experiments cell fluorescence was analysed using a Becton Dickinson FACScaliber. Viable cells were gated using forward and side scatter and the data represent cells from this population.

Figure 33:
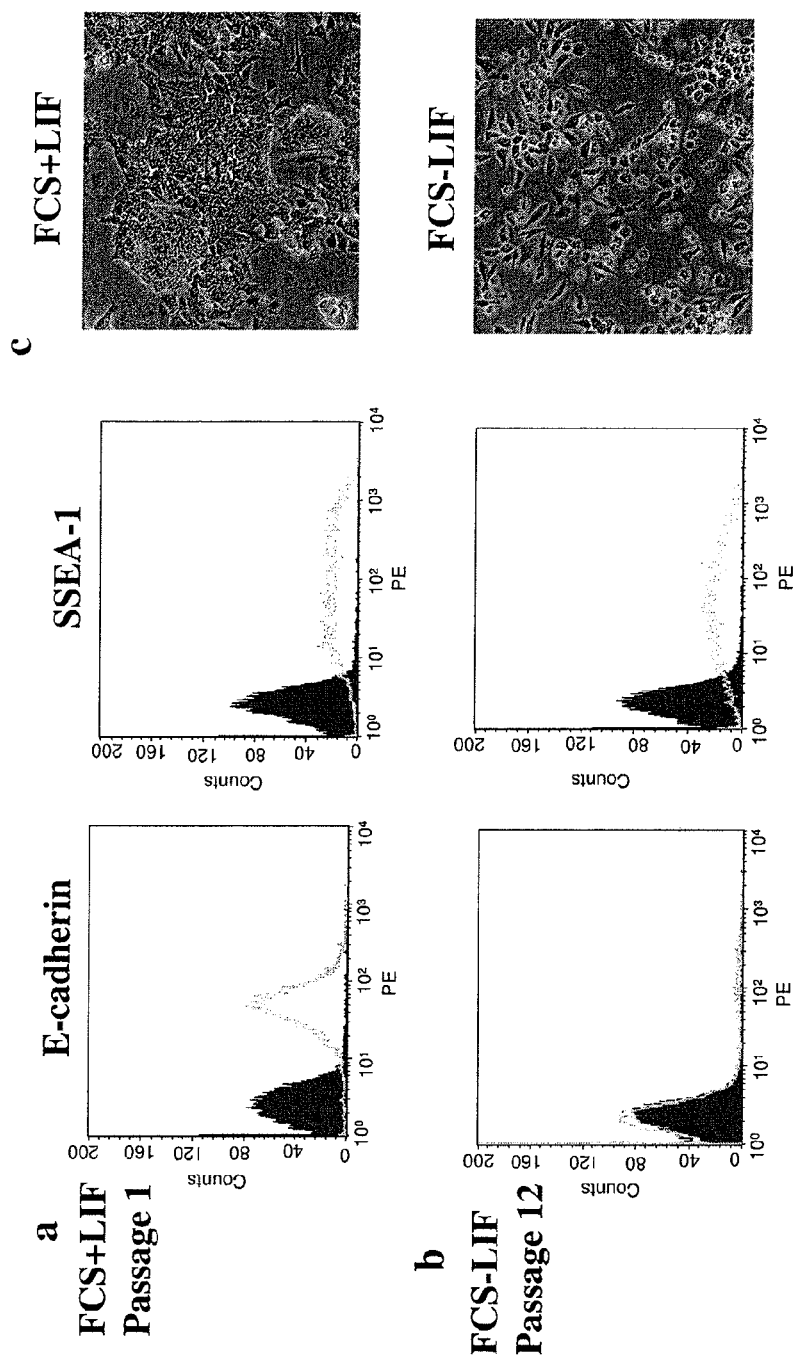
FIGS. 33A, B and C shows the results described in the study set out under heading 28 of the Experimental Results section.

Panel C of FIG. 33 shows phase contrast image of D3 cells cultured in the presence (FCS+LIF) or absence (FCS−LIF) of LIF for 12 passages. Note that the FCS−LIF cells lacked cell-cell contacts, similar to the phenotype observed for E-cadherin null ES cells.

Without wishing to be bound by any hypothesis, the inventors believe that these data indicate that wild type ES cells may naturally down-regulate E-cadherin in response to withdrawal of LIF, thus allowing them to divide in its absence and increase cell division compared to E-cadherin positive cells. Alternatively, it may be that the E-cadherin negative cells identified at passage 12 in FCS−LIF are derived from a small number of E-cadherin negative cells present at the outset that were subsequently expanded. Irrespective of the mechanism, it demonstrates that lack of E-cadherin asserts a distinct advantage to the growth of the cells in the absence of LIF.

Experimental Protocols

1. Karyotype Analysis

Cell numbers required for this method range from $5 \times 10^6$-$10^7$, and at the minimum, should be 50% confluent, ideally 70% confluent.

1. Add colcemid at 0.02-μg/ml in tissue culture medium to the cells.
2. Incubate for 2 hours at 37° C./7.5% $CO_2$.
3. Trypsinise the treated cells and collect in 15-ml centrifuge tubes in PBS.
4. Pellet cells by centrifugation.
5. Remove the supernatant and disrupt cell pellet.
6. Using a plastic pasteur pipette, add 1 ml of KCl (0.56% w/v) drop by drop, and then an excess up to 6 ml. Invert the tube several times to ensure thorough mixing.
7. Leave for 10-min for cells to swell.
8. Pellet by centrifugation.
9. Remove the supernatant and disrupt the pellet.
10. Add ice-cold fixative (3:1 absolute methanol:glacial acetic acid) 1 drop at a time and mix thoroughly to prevent cell clumping.
11. Add the fixative to give a final volume of 6-ml, and leave for 5 min at room temperature.
12. Pellet the cells by centrifugation.
13. Repeat steps 9-12 a further 3 times, leaving a final volume of 1-ml of cells in fixative.

Spread cells onto a slide. Prepare 4-5 spreads per specimen and stain overnight with Giemsa Human ES Cell Culture in Normal Medium HES4 hES cells (Reubinoff et al., 2000 *Nature Biotechnology* 18, 399-404) and H1 hES cells (Thomson et al, 1998 *Science* 282, 1145-1147) were cultured in tissue organ culture dishes (BD Falcon, Bedford Mass., USA) coated with 0.1% gelatin and $1 \times 10^5$ irradiated 129 mouse embryonic fibroblast feeder cells per dish. Cells were grown in DMEM+F12 mix media supplemented with 20% serum replacement (synthetic serum; Invitrogen Corp.), L-glutamine (1 mM), 2-mercaptoethanol (50 μM), NEAA (100×, 1:100 dilution) and bFGF (FGF-2; 0.2 μg/ml in 0.1% BSA) (all Invitrogen), as described by Thomson et al (Thomson et al., 1998) and incubated at 37° C./5% $CO_2$. The media was changed daily. Cells were passaged after 7-10 days by gently cutting and teasing the morphologically undifferentiated cells using a yellow pipette tip and transferring colony pieces to a fresh culture dish.

Human ES Cell Culture in the Presence of E-Cadherin Neutralising Antibody SHE78.7

HES4 hES cells and H1 hES cells were cultured in tissue organ culture dishes (BD Falcon, Bedford Mass., USA) coated with 0.1% gelatin and $1 \times 10^3$ irradiated 129 mouse embryonic fibroblast feeder cells per dish. Cells were grown in DMEM+F12 mix media supplemented with 20% serum replacement (synthetic serum; Invitrogen Corp.), L-glutamine (1 mM), 2-mercaptoethanol (50 μM) and NEAA (100×, 1:100 dilution) and bFGF (FGF-2; 0.2 μg/ml in 0.1% BSA) (all Invitrogen) as described by Thomson et al (Thomson et al., 1998) and incubated at 37° C./5% $CO_2$ in the presence of a control antibody (Mouse $IgG_{2a}$; Invitrogen Corp) or E-cadherin neutralising antibody SHE78.7 (Invitrogen) (10 μl/ml of media of a stock 0.5 mg/ml solution). The media was changed daily. Cells were passaged after 7-10 days by gently cutting and teasing the morphologically undifferentiated cells using a yellow pipette tip and transferring undifferentiated colony pieces to a fresh culture dish.

Human ES Cell Culture in the Presence of E-Cadherin Neutralising Antibody SHE78.7 in the Absence of FGF-2

HES4 hES cells and H1 hES cells were cultured in tissue organ culture dishes (BD Falcon, Bedford Mass., USA) coated with 0.1% gelatin and $1 \times 10^3$ irradiated 129 mouse embryonic fibroblast feeder cells per dish. Cells were grown in DMEM+F12 mix media supplemented with 20% serum replacement (synthetic serum; Invitrogen Corp.), L-glutamine (1 mM), 2-mercaptoethanol (50 μM) and NEAA (100×, 1:100 dilution) (all Invitrogen) and incubated at 37° C./5% $CO_2$ in the presence of a control antibody (Mouse $IgG_{2a}$; Invitrogen Corp) or E-cadherin neutralising antibody SHE78.7 (0.5 μl/ml of media of a stock 0.5 mg/ml solution). The media was changed daily. Cells were passaged after 7-10 days by gently cutting and teasing the morphologically undifferentiated cells using a yellow pipette tip and transferring undifferentiated colony pieces to a fresh culture dish. Some spontaneous differentiation of the cells was observed in the early passage cultures, which is to be expected due to the stress of the altered culture conditions.

Differentiation of hES Cells

Control and neutralising antibodies were removed from the cultures and the cells differentiated by overgrowth of the cells in DMEM+F12 mix media supplemented with L-glutamine (1 mM), 2-mercaptoethanol (50 μM), NEAA (100×, 1:100 dilution), and bFGF (0.2 μg/ml in 0.1% BSA) (all Invitrogen) without removal of the feeder layer.

Mouse ES Cell Culture

MESC20 (and E-cadherin RNAi cell lines derived from this parental line), D3, OCT4-GFP (E14TG2a parental cell line) and E-cadherin null ES cells were cultured on gelatin-treated plates in Knockout DMEM supplemented with 10% foetal bovine serum, 2 mM L-glutamine, non-essential amino acids (100×, 1:100 dilution), 50 μM 2-mercaptoethanol (all Invitrogen Corporation, Paisley, UK) and 1000 units/ml leukemia inhibitory factor (ESGRO; Chemicon Int., Middx., UK) (FCS+LIF) at 37° C./5% $CO_2$. The media was replenished every 24 h and cells passaged before confluence. Alternatively, foetal bovine serum was replaced with serum replacement at the same concentration (synthetic serum; Invitrogen Corporation). Gelatin-treated plates were prepared as described previously (Ward et al., 2003). Cells were also cultured in the medium as described above but in the absence of LIF (culture conditions and cultured cells referred to elsewhere in the specification "FCS–LIF" or "–LIF").

Antibody Induced Loss of Cell-Cell E-Cadherin Contacts in Mouse ES Cells

E-cadherin mediated cell to cell contacts were abrogated by culture of D3 or MESC20 ES cells in 5.8 μg/ml IgG component of rat-anti E-cadherin DECMA-1 ascites solution (Sigma, Dorset, UK) for various times as described elsewhere. Rat-anti Tenascin Ab was used as a control in all experiments at the same concentrations as above (Sigma).

Suspension Culture of mES Cells in the Presence of Inhibiting Antibody.

MESC20 ES cells were cultured in suspension by plating $10^6$ cells in 10 mls of medium lacking LIF in a plastic bacteriological Petri dish and the media changed every day. Cells were treated with either control antibody (cAb) or the E-cadherin inhibitory antibody DECMA-1 (nAb) at a concentration of 16 μg total IgG component. Cell suspensions were agitated every 24 h by pipetting up and down several times in a 10 ml pipette. Cells were passaged when required (usually every 2 days for nAb treated cells ES cells) by transfer of 2.5 mls of cell suspension into 7.5 mls of fresh medium.

Suspension Culture of E-Cadherin Null or E-Cadherin RNAi ES Cells

E-cadherin null or RNAi E-cadherin ES cells were cultured in suspension by plating $10^6$ cells in 10 mls of medium lacking LIF in a plastic bacteriological Petri dish and the media changed every day. Cell suspensions were agitated every 24 h by pipetting up and down several times in a 10 ml pipette. Cells were passaged when required (usually every 2 days for E-cadherin RNAi ES cells) by transfer of 2.5 mls of cell suspension into 7.5 mls of fresh medium.

Forced Expression of E-Cadherin cDNA in E-Cad−/− ES Cells

E-cadherin null ES cells were cultured as described above, trypsinised and washed twice in PBS. Cells were electroporated using an Amaxa Biosystems NucleofectorII and ES cell electroporation kit (Amaxa Biosystems, Germany) as described in the manufacturer's instructions. Briefly, $2 \times 10^6$ E-cadherin null ES cells were suspended in Amaxa ES cell solution and either pCMVα or pCMVα-E-cadherin vectors (2 μg total plasmid) and electroporated using program A-30 on the Amaxa NucleofectorII. Cells were plated out in a single well of a gelatinized 6-well plate in ES cell medium lacking LIF for 3 days (without overgrowth of the cells) and assessed for transcript expression by RT-PCR.

Isolation of Mouse ES Cells Exhibiting E-Cadherin Repression Using Hairpin Loop RNAi.

MESC20 mouse ES cells were cultured as described above, trypsinised and washed twice in PBS. Cells were electroporated as described in the manufacturer's instructions using an Amaxa Biosystems NucleofectorII and ES cell electroporation kit (Amaxa Biosystems, Germany). Briefly, $2 \times 10^6$ E-cadherin null ES cells were suspended in Amaxa ES cell solution containing a mixture of E-cadherin RNAi vectors (see FIG. 14 (part 2)) (2 μg total plasmid) and electroporated using program A-30 on the Amaxa NucleofectorII. Cells were plated out in a single well of a gelatinized 6-well plate in ES cell medium for 2 days and G418 added to the medium (350 μg/ml) for 10 days. Surviving colonies were isolated and transferred to a single well of a gelatin-treated 96-well plate in ES cell medium. Cell numbers were increased by transfer of the entire population to an individual well of a 24-well and then 6-well plates. Clones (designated M1, 2, 5 and 7, as described elsewhere in the specification) were isolated using this method. Alternatively, MESC20 ES cells were transfected with the E-cadherin RNAi vectors as described above and cells lacking E-cadherin isolated by removal of LIF from the medium for 10 days. Clone MM was isolated in this way.

Immunofluorescent Imaging of ES Cells

Human ES cells were cultured on Nunc plastic slide flask chambers (Nalge, Nunc International, Rochester, N.Y., USA) coated with feeder layers (of the type described previously) and grown in the stated media for 2-7 days. Mouse ES cells were cultured on gelatin-treated tissue culture grade 6-well plates. Cells were rinsed in PBS and fixed in 4% paraformaldehyde for 15 min, followed by two washes with PBS. Cells were blocked for 30 min in filtered 1% goat serum, 0.1% Triton-X-100 in PBS for prevention of non-specific binding. Primary antibodies used were as follows: NANOG (Chemicon, rabbit anti-mouse), OCT-4 (Santa Cruz; mouse IgG$_{2b}$), E-cadherin (SHE78.7, Invitrogen Corp. for human or mouse IgG$_{2a}$, Santa Cruz for mouse). Actin cytoskeleton was detected using phalloidin-Texas Red Conjugate (1:1000 dilution; Sigma). Primary antibodies were diluted in blocking buffer (all 1:100) and incubated for 2 h at room temperature. Cells were then washed 4×5 min in PBS prior to secondary antibody labelling. Secondary antibodies that recognised the primary antibody to be detected, and were conjugated with Alexa Fluor 488 or 546 (Molecular Probes, OR, USA), were diluted in blocking buffer (1:500 dilution) and incubated with the cells for 1 h at room temperature. Final washes in PBS 2×5 min, 1×15 min and 2×5 min were performed before mounting samples in DAPI Vector shield (Vector, Peterborough, UK). The cells were viewed on an Olympus BX51 fluorescence microscope and/or a Zeiss Laser Scanning Confocal Microscope. Images were overlaid using Adobe Photoshop version 6.0.

Fluorescent Flow Cytometry Analysis of ES Cells

Human or mouse ES cells were trypsinised, washed once in 900 μl of PBS, and resuspended in 100 μl of 0.2% BSA in PBS (FACS buffer) containing a primary antibody from the group listed below. Cells were then incubated in this solution for 1 h on ice. Primary antibodies used were as follows: SSEA-1 (Santa Cruz; mouse IgM), Tra-1-60 (phycoerythrin conjugated anti-Tra-1-60; Santa Cruz), E-cadherin (DECMA-1). After incubation, cells were washed once in 900-μl of PBS, resuspended in 100 μl of FACS buffer containing a phycoerythrin-conjugated secondary antibody that recognised the primary antibody (all 1:100 dilution; Santa Cruz) and incubated for 30 min on ice. The cells were washed once in 900 μl of PBS and fixed in 400 μl of 1% formaldehyde. Cell fluorescence was analysed using a Becton Dickinson FACScaliber. Viable cells were gated using forward and side scatter and the data represent cells from this population.

RT-PCR

Total RNA was extracted from cells using RNAzol B according to the manufacturer's instructions (Biogenesis, Dorset, UK), treated with DNase (Promega, WI, USA) and phenol/chloroform extracted. Synthesis of cDNA from mRNA transcripts was performed using the following method: RNA (10 μg), dNTP (250 μM), oligo(dT) (5.0 μg total), were combined with reverse transcriptase (40 U) in a total volume of 200 μl and incubated at 42° C. for 1 hour to produce cDNA. RT-PCR was performed using 1 μl of the cDNA solution and 35 or 45 cycles. Samples were run on 2% agarose gels containing 400 ng/ml ethidium bromide and visualised using an Epi Chemi II Darkroom and Sensicam imager with Labworks 4 software (UVP, CA, USA).

Primers used were as follows (read 5' to 3'; all 60° C. annealing):

β-tubulin (β-Tub): forward primer (Sequence ID No. 32): GGA ACA TAG CCG TAA ACT GC, and reverse primer (Sequence ID No. 33): TCA CTG TGC CTG AAC TTA CC, giving a product of 317 bp;

Oct-4 (OCT): forward primer (Sequence ID No. 34): AGA AGG AGC TAG AAC AGT TTG C; and reverse primer (Sequence ID No. 35): CGG TTA CAG AAC CAT ACT CG, giving a product of 415 bp;

alpha-foetal protein (AFP): forward primer (Sequence ID No. 36): CCA TGT ACA TGA GCA CTG TTG; and reverse primer (Sequence ID No. 37): CTC CAA TAA CTC CTG GTA TCC, giving a product of 338 bp;

hepatocyte nuclear factor (HNF): forward primer (Sequence ID No. 38): GAG TTT ACA GGC TTG TGG CA; and reverse primer (Sequence ID No. 39): GAG GGC AAT TCC TGA GGA TT, giving a product of 390 bp;

nestin (NES): forward primer (Sequence ID No. 40): GCC CTG ACC ACT CCA GTT TA; and reverse primer (Sequence ID No. 41): GGA GTC CTG GAT TTC CTT CC, giving a product of 199 bp;

neurofilament middle chain (NFM): forward primer (Sequence ID No. 42): GAG CGC AAA GAC TAC CTG AAG A; and reverse primer (Sequence ID No. 43): CAG CGA TTT CTA TAT CCA GAG CC, 430 bp;

neuron-specific enolase (NSE): forward primer (Sequence ID No. 44): CCC ACT GAT CCT TCC CGA TAC AT; and reverse primer (Sequence ID No. 45): CCG ATC TGG TTG ACC TTG AGC A, giving a product of 254 bp;

Pax-6 (PAX): forward primer (Sequence ID No. 46): AAC AGA CAC AGC CCT CAC AAA CA; and reverse primer (Sequence ID No. 47): CGG GAA CTT GAA CTG GAA CTG AC, giving a product of 275 bp;

proteolipid protein (PLP): forward primer (Sequence ID No. 48): CCA TGC CTT CCA GTA TGT CAT C; and reverse primer (Sequence ID No. 49): GTG GTC CAG GTG TTG AAG TAA ATG T, giving products of 354 bp (plp) and 249 bp (dm-20);

amylase (AMY): forward primer (Sequence ID No. 50): GCT GGG CTC AGT ATT CCC CAA ATA C; and reverse primer (Sequence ID No. 51): GAC GAC AAT CTC TGA CCT GAG TAG C, giving a product of 490 bp;

α1-antitrypsin (TRP): forward primer (Sequence ID No. 52): AGA CCC TTT GAA GTC AAG GAC ACC G; and reverse primer (Sequence ID No. 53): CCA TTG CTG AAG ACC TTA GTG ATG C, giving a product of 360 bp;

Flk-1 (Flk): forward primer (Sequence ID No. 54): GGT ATT GGC AGT TGG AGG AA; and reverse primer (Sequence ID No. 55): ACA TTT GCC GCT TGG ATA AC, giving a product of 203 bp;

CD34 (CD34): forward primer (Sequence ID No. 56): TGA AGC CTA GCC TGT CAC CT; and reverse primer (Sequence ID No. 57): CGC ACA GCT GGA GGT CTT AT, giving a product of 200 bp;

AC133 (AC1): forward primer (Sequence ID No. 60): CAG TCT GAC CAG CGT GAA AA; and reverse primer (Sequence ID No. 61): GGC CAT CCA AAT CTG TCC TA, giving a product of 199 bp;

Transferrin (Tf): forward primer (Sequence ID No. 62): CTG ACC TCA CCT GGG ACA AT; and reverse primer (Sequence ID No. 63): R CCA TCA AGG CAC AGC, giving a product of 367 bp;

Transthyretin (TTR): forward primer (Sequence ID No. 64): GGT ATT TGT GTC TGA AGC TGG; and reverse primer (Sequence ID No. 64): GGT TGC TGA CGA CAG CCG TGG giving a product of 392 bp.

fibroblast growth factor-5 (FGF-5): forward primer (Sequence ID No. 66): GGC AGA AGT AGC GCG ACG TT; and reverse primer (Sequence ID No. 67): TCC GGT TGC TCG GAC TGC TT, giving products of 537 and ~515 bp.

zeta-globin (ZG): forward primer (Sequence ID No. 68): GATGAAGAATGAGAGAGC; and reverse primer (Sequence ID No. 69): AGTCAGGATAGAAGACAGG, giving a product of 406 bp.

Neurofilament-68 (NF68): forward primer (Sequence ID No. 70): CCA GGA AGA GCA GAC AGA GGT; and reverse primer (Sequence ID No. 71): GTT GGG AAT AGG GCT CAA TCT, giving a product of 302 bp.

Brachyury (T): forward primer (Sequence ID No. 72): CAT TAC ACA CCA CTG ACG; and reverse primer (Sequence ID No. 73): GAT ATA GGA CCC TAC CTA GC, giving a product of 472 bp.

α-fetoprotein (AFP): forward primer (Sequence ID No. 74): GAA GAA TTG CAG AAA CAC ATC G; and reverse primer (Sequence ID No. 75): AGCCAAAAGGCTCA-CACC, giving a product of 699 bp.

Isolation of E-Cadherin Negative/SSEA-1 Positive Cells from Wild-Type ES Cells Cultured in the Absence of LIF.

D3 ES cells were cultured on gelatin-treated plates in Knockout DMEM supplemented with 10% foetal bovine serum, 2 mM L-glutamine, non-essential amino acids (100×, 1:100 dilution), 50CM 2-mercaptoethanol (all Invitrogen Corporation, Paisley, UK) and 1000 units/ml leukemia inhibitory factor prior to the experiment (ESGRO; Chemicon Int., Middx., UK) (FCS+LIF) at 37° C./5% $CO_2$. The media was replenished every 24 h and cells passaged before confluence. Gelatin-treated plates were prepared as described previously (Ward et al., 2003). To select for E-cadherin negative ES cells, LIF was removed from the culture medium and the cells carefully expanded over approximately 30 days. It should be noted that significant differentiation and apoptosis was observed in the early passages (passage 3-9), with the cells being transferred in their entirety to fresh 6-well plates on several occasions to encourage cell growth (such a transfer was not counted as a passage since all of the cells were transferred). All passages were carried out prior to confluence by transferring one third of the cell population to a fresh gelatin-treated 6-well plate. After approximately 30 days (passage 12) a sudden increase in cell number was observed and the cells assessed for cell surface E-cadherin and SSEA-1 to confirm loss of the former but presence of the latter.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of retarding the differentiation of pluripotent cells into cells of the three primary germ layers, comprising the steps of:
   providing at least one pluripotent cell; and
   culturing the at least one pluripotent cell in vitro with at least one inhibitor of E-cadherin activity.

2. The method according to claim 1, wherein the at least one pluripotent cell is an embryonic stem cell.

3. The method according to claim 1, wherein the at least one pluripotent cell is cultured in vitro in a medium lacking LIF or in a medium lacking FGF-2.

4. The method according to claim 1, wherein said at least one inhibitor of E-cadherin activity is selected from the group consisting of: an inhibitor comprising the CAD-HAV domain; an inhibitor comprising a soluble fragment incorporating the Trp156 residue of E-cadherin; slug; snail; SIP1; E2A; and Twist.

5. The method according to any claim 1, wherein said at least one inhibitor of E-cadherin activity comprises an E-cadherin neutralising antibody.

6. The method according to claim 5, wherein said at least one E-cadherin neutralizing antibody is selected from the group consisting of: DECMA-1; and SHE78.7.

7. The method according claim 1, wherein said at least one inhibitor of Ecadherin activity is selected from the group consisting of: an antisense oligonucleotide specific to E-cadherin mRNA; an RNAi molecule specific to E-cadherin mRNA; a ribozyme specific to E-cadherin mRNA; and a molecule that causes methylation of the E-cadherin promoter.

8. A method of maintaining pluripotent cells in culture, comprising the steps of:
   providing at least one pluripotent cell; and
   contacting the at least one pluripotent cell with at least one inhibitor of E-cadherin activity and at least one factor that maintain pluripotency.

9. The method according to claim 8, wherein the at least one pluripoent cell is a stem or progenitor cell.

10. The method according to claim 8, wherein said at least one inhibitor of E-cadherin activity is selected from the group consisting of: an inhibitor comprising the CAD-HAV domain; an inhibitor comprising a soluble fragment incorporating the Trp156 residue of E-cadherin; slug; snail; SIP1; E2A; and Twist.

11. The method according to any claim 8, wherein said at least one inhibitor of Ecadherin activity comprises an E-cadherin neutralising antibody.

12. The method according to claim 11, wherein said E-cadherin neutralizing antibody is selected from the group consisting of: DECMA-1; and SHE78.7.

13. The method according claim 8, wherein said at least one inhibitor of Ecadherin activity is selected from the group consisting of: an antisense oligonucleotide specific to E-cadherin mRNA; an RNAi molecule specific to E-cadherin mRNA; a ribozyme specific to Ecadherin mRNA; and a molecule that causes methylation of the E-cadherin promoter.

14. A method of retarding the differentiation of pluripotent cells into cells of the three primary germs layers, comprising the step of:
   providing a culture medium and at least one inhibitor of E-cadherin activity in a concentration sufficient to retard differentiation of at least one pluripotent cell into at least one cell of the three primary germ layers, wherein the culture medium is a liquid culture medium; and culturing at least one pluripotent cell in the culture medium.

15. The method according to claim 14, wherein the at least one inhibitor of E-cadherin activity is selected from the group consisting of: an inhibitor comprising the CAD-HAV domain; an inhibitor comprising the Trp156 residue of E-cadherin; slug; snail; SIP1; E2A; and Twist.

16. The method according to any claim 14, wherein said at least one inhibitor of E-cadherin activity comprises an E-cadherin neutralising antibody.

17. The method according to claim 16, wherein said E-cadherin neutralizing antibody is selected from the group consisting of: DECMA-1; and SHE78.7.

18. The method according claim 14, wherein said least one inhibitor of E-cadherin activity is selected from the group consisting of: an antisense oligonucleotide specific to E-cadherin mRNA; an RNAi molecule specific to E-cadherin mRNA; a ribozyme specific to E-cadherin mRNA; and a molecule that causes methylation of the E-cadherin promoter.

19. A method of preparing a pluripotent cell for therapeutic use, comprising the steps of:
   i) providing at least one pluripotent biological cell;
   ii) culturing the at least one pluripotent cell in vitro in the presence of at least one inhibitor of E-cadherin activity wherein the inhibitor of E-cadherin retards the differentiation of the plurioptent cell; and
   iii) adapting the at least one pluripotent cell for therapeutic use by differentiating the pluripotent cell into a progenitor cell.

20. The method according to claim 14, wherein the at least one pluripotent cell is an embryonic stem cell or an induced pluripotent cell.

21. The method of claim 8, wherein the at least one at least one factor that maintains pluripotency is a minimal fibroblast feeder layer.

* * * * *

SEQUENCE LISTING

```
<160> NUMBER OF SEQ ID NOS: 75

<210> SEQ ID NO 1
<211> LENGTH: 4828
<212> TYPE: DNA
<213> ORGANISM: Homo sapiens

<400> SEQUENCE: 1
agtggcgtcg gaactgcaaa gcacctgtga gcttgcggaa gtcagttcag actccagccc      60
gctccagccc ggcccgaccc gaccgcaccc ggcgcctgcc ctcgctcggc gtcccggcc     120 agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaagga cagcctattt ttccctcgac acccgattca aagtgggcac     360
agatggtgtg attacagtca aaaggcctct acggtttcat aacccacaga tccatttctt     420
```

```
ggtctacgcc tgggactcca cctacagaaa gttttccacc aaagtcacgc tgaatacagt    480
ggggcaccac caccgccccc cgccccatca ggcctccgtt tctggaatcc aagcagaatt    540
gctcacattt cccaactcct ctcctggcct cagaagacag aagagagact gggttattcc    600
tcccatcagc tgcccagaaa atgaaaaagg cccatttcct aaaaacctgg ttcagatcaa    660
atccaacaaa gacaaagaag gcaaggtttt ctacagcatc actggccaag gagctgacac    720
accccctgtt ggtgtcttta ttattgaaag agaaacagga tggctgaagg tgacagagcc    780
tctggataga gaacgcattg ccacatacac tctcttctct cacgctgtgt catccaacgg    840
gaatgcagtt gaggatccaa tggagatttt gatcacggta accgatcaga atgcaacaa     900 gcccgaattc acccaggagg tctttaaggg gtctgtcatg gaaggtgctc ttccaggaac    960
ctctgtgatg gaggtcacag ccacagacgc ggacgatgat gtgaacacct acaatgccgc   1020
catcgcttac accatcctca gccaagatcc tgagctccct gacaaaaata tgttcaccat   1080
taacaggaac acaggagtca tcagtgtggt caccactggg ctggaccgag agagtttccc   1140
tacgtatacc ctggtggttc aagctgctga ccttcaaggt gaggggttaa gcacaacagc   1200
aacagctgtg atcacagtca ctgacaccaa cgataatcct ccgatcttca atccccaccac  1260 gtacaagggt caggtgcctg agaacgaggc taacgtcgta atcaccacac tgaaagtgac   1320
tgatgctgat gccccaata cccagcgtg ggaggctgta tacaccatat tgaatgatga     1380
tggtggacaa tttgtcgtca ccacaaatcc agtgaacaac gatggcattt tgaaaacagc   1440
aaagggcttg gattttgagg ccaagcagca gtacattcta cacgtagcag tgacgaatgt   1500 ggtaccttt gaggtctctc tcaccacctc cacagccacc gtcaccgtgg atgtgctgga   1560
tgtgaatgaa gcccccatct ttgtgcctcc tgaaaagaga gtggaagtgt ccgaggactt   1620
tggcgtgggc caggaaatca catcctacac tgcccaggag ccagacacat ttatggaaca   1680
gaaaataaca tatcggattt ggagagacac tgccaactgg ctggagatta atccggacac   1740
tggtgccatt tccactcggg ctgagctgga cagggaggat tttgagcacg tgaagaacag   1800
cacgtacaca gccctaatca tagctacaga caatggttct ccagttgcta ctggaacagg   1860
gacacttctg ctgatcctgt ctgatgtgaa tgacaacgcc cccataccag aacctcgaac   1920
tatattcttc tgtgagagga atccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgcc ggcgtctgta ggaaggcaca   2220
gcctgtcgaa gcaggattgc aaattcctgc cattctgggg attcttggag gaattcttgc   2280
tttgctaatt ctgattctgc tgctcttgct gttttcttcgg aggagagcgg tggtcaaaga   2340
gcccttactg cccccagagg atgacacccg ggacaacgtt tattactatg atgaagaagg   2400
aggcggagaa gaggaccagg actttgactt gagccagctg cacaggggcc tggacgctcg   2460
gcctgaagtg actcgtaacg acgttgcacc aaccctcatg agtgtccccc ggtatcttcc   2520 ccgcctgcc aatcccgatg aaattggaaa ttttattgat gaaaatctga agcggctga     2580 tactgacccc acagccccgc cttatgattc tctgctcgtg tttgactatg aaggaagcgg   2640
ttccgaagct gctagtctga gctccctgaa ctcctcagag tcagacaaag accaggacta   2700
tgactacttg aacgaatggg gcaatcgctt caagaagctg gctgacatgt acggaggcgg   2760
cgaggacgac tagggggactc gagagaggcg ggccccagac ccatgtgctg ggaaatgcag   2820
```

```
aaatcacgtt gctggtggtt tttcagctcc cttcccttga gatgagtttc tggggaaaaa      2880
aaagagactg gttagtgatg cagttagtat agctttatac tctctccact ttatagctct      2940
aataagtttg tgttagaaaa gtttcgactt atttcttaaa gctttttttt ttttcccatc      3000
actctttaca tggtggtgat gtccaaagaa tacccaaatt ttaatattcc agaagaacaa      3060
ctttagcatc agaaggttca cccagcacct tgcagatttt cttaaggaat tttgtctcac      3120
ttttaaaaag aaggggagaa gtcagctact ctagttctgt tgttttgtgt atataatttt      3180
ttaaaaaaaa tttgtgtgct tctgctcatt actacactgg tgtgtccctc tgccttttt       3240 tttttttta agacagggtc tcattctatc ggccaggctg gagtgcagtg gtgcaatcac       3300
agctcactgc agccttgtcc tcccaggctc aagctatcct tgcacctcag cctcccaagt      3360
agctgggacc acaggcatgc accactacgc atgactaatt ttttaaatat ttgagacggg      3420
gtctccctgt gttacccagg ctggtctcaa actcctgggc tcaagtgatc ctcccatctt      3480
ggcctcccag agtattggga ttacagacat gagccactgc acctgcccag ctccccaact      3540
ccctgccatt ttttaagaga cagtttcgct ccatcgccca ggcctgggat gcagtgatgt      3600
gatcatagct cactgtaacc tcaaactctg ggctcaagc agttctccca ccagcctcct      3660
ttttattttt ttgtacagat ggggtcttgc tatgttgccc aagctggtct taaactcctg      3720
gcctcaagca atccttctgc cttggccccc caaagtgctg ggattgtggg catgagctgc      3780
tgtgcccagc ctccatgttt taatatcaac tctcactcct gaattcagtt gctttgccca      3840
agataggagt tctctgatgc agaaattatt gggctctttt agggtaagaa gtttgtgtct      3900
ttgtctggcc acatcttgac taggtattgt ctactctgaa gacctttaat ggcttccctc      3960
tttcatctcc tgagtatgta acttgcaatg ggcagctatc cagtgacttg ttctgagtaa      4020
gtgtgttcat taatgtttat ttagctctga agcaagagtg atatactcca ggacttagaa      4080
tagtgcctaa agtgctgcag ccaaagacag agcggaacta tgaaaagtgg gcttggagat      4140
ggcaggagag cttgtcattg agcctggcaa tttagcaaac tgatgctgag gatgattgag      4200
gtgggtctac ctcatctctg aaaattctgg aaggaatgga ggagtctcaa catgtgtttc      4260
tgacacaaga tccgtggttt gtactcaaag cccagaatcc ccaagtgcct gcttttgatg      4320
atgtctacag aaaatgctgg ctgagctgaa cacatttgcc caattccagg tgtgcacaga      4380
aaaccgagaa tattcaaaat tccaaatttt ttcttaggag caagaagaaa atgtggccct      4440 aaaggggggtt agttgagggg taggggtag tgaggatctt gatttggatc tcttttatt      4500 taaatgtgaa tttcaacttt tgacaatcaa agaaaagact tttgttgaaa tagctttact      4560
gtttctcaag tgtttggag aaaaaaatca accctgcaat cacttttttgg aattgtcttg      4620 attttcggc agttcaagct atatcgaata tagttctgtg tagagaatgt cactgtagtt      4680
ttgagtgtat acatgtgtgg gtgctgataa ttgtgtatttt tctttggggg tggaaaagga      4740
aaacaattca agctgagaaa agtattctca aagatgcatt tttataaatt ttattaaaca      4800
attttgttaa accataaaaa aaaaaaaa                                         4828
```

<210> SEQ ID NO 2
<211> LENGTH: 882
<212> TYPE: PRT
<213> ORGANISM: Homo sapiens

<400> SEQUENCE: 2

```
Met Gly Pro Trp Ser Arg Ser Leu Ser Ala Leu Leu Leu Leu Leu Gln
1               5                   10                  15
```

```
Val Ser Ser Trp Leu Cys Gln Glu Pro Glu Pro Cys His Pro Gly Phe
             20                  25                  30

Asp Ala Glu Ser Tyr Thr Phe Thr Val Pro Arg Arg His Leu Glu Arg
             35                  40                  45

Gly Arg Val Leu Gly Arg Val Asn Phe Glu Asp Cys Thr Gly Arg Gln
 50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
             85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
            115                 120                 125

Gln Ala Ser Val Ser Gly Ile Gln Ala Glu Leu Leu Thr Phe Pro Asn
130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
            165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
            210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
            245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
            290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
            325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
            370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
            405                 410                 415

Asn Asp Asp Gly Gly Gln Phe Val Val Thr Thr Asn Pro Val Asn Asn
            420                 425                 430
```

```
Asp Gly Ile Leu Lys Thr Ala Lys Gly Leu Asp Phe Glu Ala Lys Gln
        435                 440                 445
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
        595                 600                 605
Pro Gln Val Ile Asn Ile Ile Asp Ala Asp Leu Pro Pro Asn Thr Ser
    610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
                645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
        675                 680                 685
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
                725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Gly Glu Glu Asp Gln Asp Phe Asp
        755                 760                 765
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
        835                 840                 845
Asn Ser Ser Glu Ser Asp Lys Asp Gln Asp Tyr Asp Tyr Leu Asn Glu
```

Trp Gly Asn Arg Phe Lys Lys Leu Ala Asp Met Tyr Gly Gly Gly Glu
865                 870                 875                 880

Asp Asp

<210> SEQ ID NO 3
<211> LENGTH: 3314
<212> TYPE: DNA
<213> ORGANISM: Mus musculus

<400> SEQUENCE: 3

| | | | | | |
|---|---|---|---|---|---|
| agccgcggcg | cactactgag | ttcccaagaa | cttctgctag | actcctgccc | ggcctaaccc | 60 |
| ggccctgccc | gaccgcaccc | gagctcagtg | tttgctcggc | gtctgccggg | tccgccatgg | 120 |
| gagcccggtg | ccgcagcttt | tccgcgctcc | tgctcctgct | gcaggtctcc | tcatggcttt | 180 |
| gccaggagct | ggagcctgag | tcctgcagtc | ccggcttcag | ttccgaggtc | tacaccttcc | 240 |
| cggtgccgga | gaggcacctg | agagaggcc | atgtcctggg | cagagtgaga | tttgaaggat | 300 |
| gcaccggccg | gccaaggaca | gccttctttt | cggaagactc | ccgattcaaa | gtggcgacag | 360 |
| acggcaccat | cacagtgaag | cggcatctaa | agctccacaa | gctggagacc | agtttcctcg | 420 |
| tccgcgcccg | ggactccagt | catagggagc | tgtctaccaa | agtgacgctg | aagtccatgg | 480 |
| ggcaccacca | tcaccggcac | caccaccgcg | accctgcctc | tgaatccaac | ccagagctgc | 540 |
| tcatgtttcc | cagcgtgtac | ccaggtctca | gaagacagaa | acgagactgg | gtcatccctc | 600 |
| ccatcagctg | ccccgaaaat | gaaaagggtg | aattcccaaa | gaacctggtt | cagatcaaat | 660 |
| ccaacaggga | caaagaaaca | aaggttttct | acagcatcac | cggccaagga | gctgacaaac | 720 |
| cccccgttgg | cgttttcatc | attgagaggg | agacaggctg | gctgaaagtg | acacagcctc | 780 |
| tggatagaga | agccattgcc | aagtacatcc | tctattctca | tgccgtgtca | tcaaatgggg | 840 |
| aagcggtgga | ggatcccatg | agatagtga | tcacagtgac | agatcagaat | gacaacaggc | 900 |
| cagagtttac | ccaggaggtg | tttgagggat | ccgttgcaga | aggcgctgtt | ccaggaacct | 960 |
| ccgtgatgaa | ggtctcagcc | accgatgcag | acgatgacgt | caacacctac | aacgctgcca | 1020 |
| tcgcctacac | catcgtcagc | caggatcctg | agctgcctca | caaaacatg | ttcactgtca | 1080 |
| atagggacac | cggggtcatc | agtgtgctca | cctctgggct | ggaccgagag | agttacccta | 1140 |
| catacactct | ggtggttcag | gctgctgacc | ttcaaggcga | aggcttgagc | acaacagcca | 1200 |
| aggctgtgat | cactgtcaag | gatattaatg | acaacgctcc | tgtcttcaac | ccgagcacgt | 1260 |
| atcagggtca | agtgcctgag | aatgaggtca | atgcccggat | cgccacactc | aaagtgaccg | 1320 |
| atgatgatgc | ccccaacact | ccggcgtgga | agctgtgta | caccgtagtc | aacgatcctg | 1380 |
| accagcagtt | cgttgtcgtc | acagacccca | cgaccaatga | tggcattttg | aaaacagcca | 1440 |
| agggcttgga | ttttgaggcc | aagcagcaat | acatccttca | tgtgagagtg | gagaacgagg | 1500 |
| aacccttga | ggggtctctt | gtcccttcca | cagccactgt | cactgtggac | gtggtagacg | 1560 |
| tgaatgaagc | ccccatcttt | atgcctgcgg | agaggagagt | cgaagtgccc | gaagactttg | 1620 |
| gtgtgggtca | ggaaatcaca | tcttatatccg | ctcgagagcc | ggacacgttc | atggatcaga | 1680 |
| agatcacgta | tcggatttgg | agggacactg | ccaactggct | ggagattaac | ccagagactg | 1740 |
| gtgccatttt | cacgcgcgct | gagatggaca | gagaagacgc | tgagcatgtg | aagaacagca | 1800 |
| catatgtagc | tctcatcatc | gccacagatg | atggttcacc | cattgccact | ggcacgggca | 1860 |
| ctcttctcct | ggtcctgtta | gacgtcaatg | ataacgctcc | catcccagaa | cctcgaaaca | 1920 |

```
tgcagttctg ccagaggaac ccacagcctc atatcatcac catcttggat ccagaccttc    1980
cccccaacac gtcccccttt actgctgagc taacccatgg ggccagcgtc aactggacca    2040
ttgagtataa tgacgcagct caagaatctc tcattttgca accaagaaag gacttagaga    2100
ttggcgaata caaatccat ctcaagctcg cggataacca gaacaaagac caggtgacca     2160
cgttggacgt ccatgtgtgt gactgtgaag ggacggtcaa caactgcatg aaggcgggaa    2220
tcgtggcagc aggattgcaa gttcctgcca tcctcggaat ccttggaggg atcctcgccc    2280
tgctgattct gatcctgctg ctcctactgt ttctacggag gagaacggtg gtcaaagagc    2340
ccctgctgcc accagatgat gatacccggg acaatgtgta ttactatgat gaagaaggag    2400
gtggagaaga agaccaggac tttgatttga gccagctgca caggggcctg gatgcccgac    2460
cggaagtgac tcgaaatgat gtggctccca ccctcatgag cgtgcccccag tatcgtcccc   2520 gtcctgccaa tcctgatgaa attggaaact tcatcgatga aaacctgaag gcagccgaca    2580
gcgaccccac ggcacccccct tacgactctc tgttggtgtt cgattacgag ggcagtggtt   2640
ctgaagccgc tagcctgagc tcactgaact cctctgagtc ggatcaggac caggactacg    2700
attatctgaa cgagtggggc aaccgattca gaagctggc ggacatgtac ggcggtggcg     2760
aggacgacta ggggactagc aagtctcccc cgtgtggcac catgggagat gcagaataat    2820
tatatcagtg gtctttcagc tccttccctg agtgtgtaga agagagactg atctgagaag    2880
tgtgcagatt gcatagtggt ctcattctcc ttactggact gtctgtgtta ggatggtttt    2940
cactgattgt tgaaatcttt tttatttt tatttttaca gtgctgagat ataaactgtg      3000 ccttttttg tttgtttgtt tctgttttg ttcttttgag cagaacaaaa aaagggacc        3060 actatgcatg ctgcacacgt ctcagattct taggtacaca cctgattctt aggtgcatgc    3120
catagtggga tatgttgctt tgatcagaac ctgcagggag gttttcgggc accacttaag    3180
tttcttggcg tttctttcaa accgttctct aagatgcatt tttatgaatt ttattaaaga    3240
gttttgttaa aaaaaaaaaa aaaaaaaaaa aaaaaaaaaa aaaaaaaaaa aaaaaaaaaa    3300
aaaaaaaaaa aaaa                                                       3314
```

<210> SEQ ID NO 4
<211> LENGTH: 884
<212> TYPE: PRT
<213> ORGANISM: Mus musculus

<400> SEQUENCE: 4

```
Met Gly Ala Arg Cys Arg Ser Phe Ser Ala Leu Leu Leu Leu Leu Gln
1               5                   10                  15

Val Ser Ser Trp Leu Cys Gln Glu Leu Glu Pro Glu Ser Cys Ser Pro
            20                  25                  30

Gly Phe Ser Ser Glu Val Tyr Thr Phe Pro Val Pro Glu Arg His Leu
        35                  40                  45

Glu Arg Gly His Val Leu Gly Arg Val Arg Phe Glu Gly Cys Thr Gly
    50                  55                  60

Arg Pro Arg Thr Ala Phe Phe Ser Glu Asp Ser Arg Phe Lys Val Ala
65                  70                  75                  80

Thr Asp Gly Thr Ile Thr Val Lys Arg His Leu Lys Leu His Lys Leu
                85                  90                  95

Glu Thr Ser Phe Leu Val Arg Ala Arg Asp Ser Ser His Arg Glu Leu
            100                 105                 110

Ser Thr Lys Val Thr Leu Lys Ser Met Gly His His His Arg His
        115                 120                 125
```

His His Arg Asp Pro Ala Ser Glu Ser Asn Pro Glu Leu Leu Met Phe
130                 135                 140

Pro Ser Val Tyr Pro Gly Leu Arg Arg Gln Lys Arg Asp Trp Val Ile
145                 150                 155                 160

Pro Pro Ile Ser Cys Pro Glu Asn Glu Lys Gly Glu Phe Pro Lys Asn
                165                 170                 175

Leu Val Gln Ile Lys Ser Asn Arg Asp Lys Glu Thr Lys Val Phe Tyr
            180                 185                 190

Ser Ile Thr Gly Gln Gly Ala Asp Lys Pro Pro Val Gly Val Phe Ile
        195                 200                 205

Ile Glu Arg Glu Thr Gly Trp Leu Lys Val Thr Gln Pro Leu Asp Arg
    210                 215                 220

Glu Ala Ile Ala Lys Tyr Ile Leu Tyr Ser His Ala Val Ser Ser Asn
225                 230                 235                 240

Gly Glu Ala Val Glu Asp Pro Met Glu Ile Val Ile Thr Val Thr Asp
                245                 250                 255

Gln Asn Asp Asn Arg Pro Glu Phe Thr Gln Pro Val Phe Glu Gly Phe
            260                 265                 270

Val Ala Glu Gly Ala Val Pro Gly Thr Ser Val Met Lys Val Ser Ala
        275                 280                 285

Thr Asp Ala Asp Asp Asp Val Asn Thr Tyr Asn Ala Ala Ile Ala Tyr
    290                 295                 300

Thr Ile Val Ser Gln Asp Pro Glu Leu Pro His Lys Asn Met Phe Thr
305                 310                 315                 320

Val Asn Arg Asp Thr Gly Val Ile Ser Val Leu Thr Ser Gly Leu Asp
                325                 330                 335

Arg Glu Ser Tyr Pro Thr Tyr Thr Leu Val Val Gln Ala Ala Asp Leu
            340                 345                 350

Gln Gly Glu Gly Leu Ser Thr Thr Ala Lys Ala Val Ile Thr Val Lys
        355                 360                 365

Asp Ile Asn Asp Asn Ala Pro Val Phe Asn Pro Ser Thr Tyr Gln Gly
    370                 375                 380

Gln Val Pro Glu Asn Glu Val Asn Ala Arg Ile Ala Thr Leu Lys Val
385                 390                 395                 400

Thr Asp Asp Asp Ala Pro Asn Thr Pro Ala Trp Lys Ala Val Tyr Thr
                405                 410                 415

Val Val Asn Asp Pro Asp Gln Gln Phe Val Val Thr Asp Pro Thr Thr
            420                 425                 430

Thr Asn Asp Gly Ile Leu Lys Thr Ala Lys Gly Leu Asp Phe Glu Ala
        435                 440                 445

Lys Gln Gln Tyr Ile Leu His Val Arg Val Glu Asn Glu Glu Pro Phe
    450                 455                 460

Glu Gly Ser Leu Val Pro Ser Thr Ala Thr Val Thr Val Asp Val Val
465                 470                 475                 480

Asp Val Asn Glu Ala Pro Ile Phe Met Pro Ala Glu Arg Arg Val Glu
                485                 490                 495

Val Pro Glu Asp Phe Gly Val Gly Gln Glu Ile Thr Ser Tyr Thr Ala
            500                 505                 510

Arg Glu Pro Asp Thr Phe Met Asp Gln Lys Ile Thr Tyr Arg Ile Trp
        515                 520                 525

Arg Asp Thr Ala Asn Trp Leu Glu Ile Asn Pro Glu Thr Gly Ala Ile
    530                 535                 540

Phe Thr Arg Ala Glu Met Asp Arg Glu Asp Ala His Val Lys Asn
545                 550                 555                 560

Ser Thr Tyr Val Ala Leu Ile Ile Ala Thr Asp Asp Gly Ser Pro Ile
                565                 570                 575

Ala Thr Gly Thr Gly Thr Leu Leu Leu Val Leu Leu Asp Val Asn Asp
            580                 585                 590

Asn Ala Pro Ile Pro Glu Pro Arg Asn Met Gln Phe Cys Gln Arg Asn
        595                 600                 605

Pro Gln Pro His Ile Ile Thr Ile Leu Asp Pro Asp Leu Pro Pro Asn
    610                 615                 620

Thr Ser Pro Phe Thr Ala Glu Leu Thr His Gly Ala Ser Val Asn Trp
625                 630                 635                 640

Thr Ile Glu Tyr Asn Asp Ala Ala Gln Glu Ser Leu Ile Leu Gln Pro
                645                 650                 655

Arg Lys Asp Leu Glu Ile Gly Glu Tyr Lys Ile His Leu Lys Leu Ala
            660                 665                 670

Asp Asn Gln Asn Lys Asp Gln Val Thr Thr Leu Asp Val His Val Cys
        675                 680                 685

Asp Cys Glu Gly Thr Val Asn Asn Cys Met Lys Ala Gly Ile Val Ala
    690                 695                 700

Ala Gly Leu Gln Val Pro Ala Ile Leu Gly Ile Leu Gly Gly Ile Leu
705                 710                 715                 720

Ala Leu Leu Ile Leu Ile Leu Leu Leu Leu Phe Leu Arg Arg Arg
                725                 730                 735

Thr Val Val Lys Glu Pro Leu Leu Pro Pro Asp Asp Asp Thr Arg Asp
            740                 745                 750

Asn Val Tyr Tyr Tyr Asp Glu Glu Gly Gly Gly Glu Glu Asp Gln Asp
        755                 760                 765

Phe Asp Leu Ser Gln Leu His Arg Gly Leu Asp Ala Arg Pro Glu Val
    770                 775                 780

Thr Arg Asn Asp Val Ala Pro Thr Leu Met Ser Val Pro Gln Tyr Arg
785                 790                 795                 800

Pro Arg Pro Ala Asn Pro Asp Glu Ile Gly Asn Phe Ile Asp Glu Asn
                805                 810                 815

Leu Lys Ala Ala Asp Ser Asp Pro Thr Ala Pro Pro Tyr Asp Ser Leu
            820                 825                 830

Leu Val Phe Asp Tyr Glu Gly Ser Gly Ser Glu Ala Ala Ser Leu Ser
        835                 840                 845

Ser Leu Asn Ser Ser Glu Ser Asp Gln Asp Gln Asp Tyr Asp Tyr Leu
    850                 855                 860

Asn Glu Trp Gly Asn Arg Phe Lys Lys Leu Ala Asp Met Tyr Gly Gly
865                 870                 875                 880

Gly Glu Asp Asp

<210> SEQ ID NO 5
<211> LENGTH: 4396
<212> TYPE: DNA
<213> ORGANISM: Rattus sp.

<400> SEQUENCE: 5
ctggtgtggg agccgcggcg cactactgag ttctcaagaa cttctgctag acttcagccc      60
ggcctaaccc ggctctgccc gaccgcaccc gagctcagtg tttgctcggc gtttgcccgg     120
ccagccatgg gagcccggtg ccgcagcttc tccgcgctcc tgctcctgct gcaggtctcc     180

-continued

```
tcgtggcttt gtcagcagcc ggagtcggag tctgactcct gccgtcccgg cttcagttcc     240
gaggtctaca ccttcctggt gccggagagg cacctggaga gaggccacat cctgggcaga     300
gtgaaatttg aaggatgcac cggccgtcca aggacagcct tcttttctga agactcccga     360
ttcaaagtgt ctacagatgg cgtcatcaca gtcaaacggc atctaaagct tcacaagctg     420
gagaccagtt ttctcgtcca tgcctgggac tccagttaca ggaagctttc taccaaagtg     480
acactgaagt ccctgggcca ccaccaccac cggcatcacc acagagaccc tgtctctgaa     540
tccaacccag agctgctcac gtttcccagc tttcaccagg gtctgagaag acagaaacga     600
gactgggtca tccctcccat caactgcccg aaaatcaaa agggcgaatt ccccagcga      660 ctggttcaga tcaaatccaa cagggacaaa gagacaacgg ttttctacag catcaccggc     720
ccaggagctg acaaaccccc tgttggcgtt ttcatcattg agagggagac aggctggctg     780
aaagtgacgc agcctctgga cagagaagcc attgacaagt accttctcta ctctcatgct     840
gtgtcatcaa tggggaagc cgtggaggat cccatggaga tagtggtcac agtcacagat      900
cagaatgaca acaggccaga gtttatccag gaggtctttg agggatctgt tgcagaaggc     960
gctcttccag gaacctccgt gatgcaggtc tcagccactg atgcagacga tgacataaac    1020
acctacaatc tgccatcgc ctacaccatc ctcagccaag atcctgagct gcctcacaaa     1080
aacatgttca ctgtcaaccg ggacactggg gtcatcagtg tggtcacctc cggactggac    1140
cgagagagtt ccctacata tactctggtg gttcaggctg ccgaccttca aggcgaaggc    1200
ctaagcacaa cagcaaaagc tgtgatcact gtcaaggata ttaatgacaa cgctcccatc    1260
ttcaacccaa gcacgtacca gggtcaagtg cttgagaatg aggtcggtgc cgtattgcc     1320 acactcaagg tgactgatga tgatgccccc aacactccag cgtggaatgc tgtgtacacc    1380
gtagtcaatg atcctgatca tcagttcact gtcatcacag accccaagac caacgagggc    1440
attctgaaaa cagccaaggg cttggatttt gaggccaagc agcagtacat tctgcacgtg    1500
acagtggaaa atgaggagcc ctttgagggg tctcttgtcc cttccacagc cactgtcacc    1560
gtggatgtgg tagacgtgaa tgaagccccc attttttgtgc ctgcggagaa gagagtcgag    1620
gtgcctgagg actttggtgt gggtctggag atcgcatctt acactgcgcg agagccagac    1680
acattcatgg aacagaagat cacgtatcgg atttggaggg acactgccaa ttggctggag    1740
attaacccag agactggggt catttccact cgggctgaga tggacagaga agattcggag    1800
catgtgaaga acagcacgta tacagctctc atcattgcca cagatgatgg ttcacccatt    1860
gccactggca cagggactct tctcctggtc ctgtcagacg tcaacgacaa tgctcccatc    1920
ccagaacctc gaaatatgca gttctgccag agaaacccga agccccatgt catcaccatc    1980
ttggatccag accttccccc aaacacatcc cccttcactg cagagctcac ccatggggcc    2040
agcgtcaact ggaccattga gtacaatgac gcagaacaag aatctctcat tttgcaacca    2100
agaaaggact tagagattgg cgaatacaaa atcaatctca gctctcgga taaccagaat    2160 aaagaccagg tgaccacgtt ggaggtccac gtgtgtgact gtgaagggac cgtcaacaac    2220
tgcatgaagg cgatctccct ggaagcagga ttacaagttc ccgccatcct tggaatcctg    2280
ggagggatcc tggcccctcct gattctgatc ctcctgctcc tactgttct acggaggaga    2340 acggtggtca aagagccctt gctgccacca gatgacgata cccgggacaa tgtgtattac    2400
tatgatgaag agggaggtgg agaagaagac caggactttg atttgagcca gctgcacagg    2460
ggccttgatg ccagaccgga agtgattcga atgatgtgg ctcccaccct catgagcatg    2520
ccccagtatc gtccccgtcc agccaatcct gatgaaatcg ggaacttcat cgatgaaaac    2580
```

```
ctgaaggcag cggacagtga ccccacagcg ccccccttacg actctctgtt ggtgtttgac    2640
tatgagggga gtggttctga agctgcctcc ctgagctcgc tgaactcctc tgagtcagat    2700
caggaccagg actacgatta tctgaacgaa tggggcaacc ggttcaagaa gctggccgat    2760
atgtatggtg gcggcgaaga agactagaga gtcgttcctg tgtggcacca tgggagatgc    2820
agaatcatga tgtcagtggt ctttcagctc cttccctgac tttgtagaag agagactgat    2880
ctgagaagta tgcagattgc atactggtcc cactctacct accagtctgt ctgtgttagg    2940
agggttttca ctggttgttg gaatcttttt ctaaaatgtt tttgttttta cagtgctgtg    3000
atgtgatgaa ctgtaccctc ttttttgtttt tgttttgagc tatgttctgc tccggacaca    3060
cagcccccaa gcccttcacc cctcactaat ttttttacat tgtatacttt cactcaatta    3120
ccatgtttat gttctgtatt ctaatagcca ctaagttcct gaattctgtt gcctggccca    3180
ggtgctattc tgtgacacag tagtgcctgg gccctttat ggtaagagac aggtttcttg    3240
gtgtgggtgc aactgagctg atagtgtat gtttcaaaca cctttcctgt gttctctccc    3300
cacctccaga gtgtctttac ttattcagct gtgtgtttgg ggcagaacaa aaaaataatg    3360
ggaccactat gcaagctgcg aagattctaa ggtgcacacc tgattcttag gcagatgcca    3420
tagtgagata tgttgctttg gttctctatc caatgctgtg accgggacct gcagcgaggt    3480
tttcggacac cgtggtttct tgcgtttctt tcaaaccagc agtaaaaaat ggttttttct    3540
gagagagact ggagtgccac caccaaagat agaggagaga agccaagctt ggggacagca    3600
agcatgccag tgaacctgac cactgtcatg agtcatgtgg gtggccacat gtccgtgaac    3660
ctggccagtt ggcacactga tggtgagggt acaaggaggc tagacctcgt cccacaaaat    3720
ttctggaaga attagggttg tctcagccaa tgtttcctag ctggaatcct gtccatgtat    3780
gtgttcctga agcccaggaa atacacccct ctagtgcctg cttttgatgg tagttataga    3840
aaagaccggc tgatttggac ctgagttgcc caatcttaag tacaaataga aaactgagac    3900
tatgctgggt gtgttggtgc acgcctttaa tcccggcact cgggaggcag agacagtctc    3960
agatctctct gagttcaagg tcagcctggt atagtaagtg aattccagga cagccagggc    4020
tacacagaaa ctctgtcttg gaaaaccaaa aagaaaact gagaatatta gagattgtgc    4080
attttctcag aaagcaggaa gaaaacacca ctctgatggg aaaagggagg caaggccctt    4140 gagactttc attgaaattg ctgtactcac ataattttgg aagcaaatga tgactgcaat    4200
caactgtgag aactgttggt ttctctgtag tttaattgtc taatgttgat agcgtgccct    4260
ttgtatgtag tttgagtgta tatgtgtgtg ggtgctgata attttgtatt ttgtggggag    4320
tggaaaaggc aagcaatcgg aactgttctc taagatgcat tttttatgaat tttattaaag    4380 agttttgtta aactgt                                                    4396
```

<210> SEQ ID NO 6
<211> LENGTH: 886
<212> TYPE: PRT
<213> ORGANISM: Rattus sp.

<400> SEQUENCE: 6

Met Gly Ala Arg Cys Arg Ser Phe Ser Ala Leu Leu Leu Leu Gln
1               5                   10                  15

Val Ser Ser Trp Leu Cys Gln Gln Pro Glu Ser Glu Ser Asp Ser Cys
                20                  25                  30

Arg Pro Gly Phe Ser Ser Glu Val Tyr Thr Phe Leu Val Pro Glu Arg
            35                  40                  45

```
His Leu Glu Arg Gly His Ile Leu Gly Arg Val Lys Phe Glu Gly Cys
     50                  55                  60

Thr Gly Arg Pro Arg Thr Ala Phe Phe Ser Glu Asp Ser Arg Phe Lys
 65                  70                  75                  80

Val Ser Thr Asp Gly Val Ile Thr Val Lys Arg His Leu Lys Leu His
                 85                  90                  95

Lys Leu Glu Thr Ser Phe Leu Val His Ala Trp Asp Ser Ser Tyr Arg
            100                 105                 110

Lys Leu Ser Thr Lys Val Thr Leu Lys Ser Leu Gly His His His His
            115                 120                 125

Arg His His His Arg Asp Pro Val Ser Glu Ser Asn Pro Glu Leu Leu
130                 135                 140

Thr Phe Pro Ser Phe His Gln Gly Leu Arg Arg Gln Lys Arg Asp Trp
145                 150                 155                 160

Val Ile Pro Pro Ile Asn Cys Pro Glu Asn Gln Lys Gly Glu Phe Pro
                165                 170                 175

Gln Arg Leu Val Gln Ile Lys Ser Asn Arg Asp Lys Glu Thr Thr Val
                180                 185                 190

Phe Tyr Ser Ile Thr Gly Pro Gly Ala Asp Lys Pro Pro Val Gly Val
            195                 200                 205

Phe Ile Ile Glu Arg Glu Thr Gly Trp Leu Lys Val Thr Gln Pro Leu
210                 215                 220

Asp Arg Glu Ala Ile Asp Lys Tyr Leu Leu Tyr Ser His Ala Val Ser
225                 230                 235                 240

Ser Asn Gly Glu Ala Val Glu Asp Pro Met Glu Ile Val Val Thr Val
                245                 250                 255

Thr Asp Gln Asn Asp Asn Arg Pro Glu Phe Ile Gln Glu Val Phe Glu
            260                 265                 270

Gly Ser Val Ala Glu Gly Ala Leu Pro Gly Thr Ser Val Met Gln Val
            275                 280                 285

Ser Ala Thr Asp Ala Asp Asp Ile Asn Thr Tyr Asn Ala Ala Ile
290                 295                 300

Ala Tyr Thr Ile Leu Ser Gln Asp Pro Glu Leu Pro His Lys Asn Met
305                 310                 315                 320

Phe Thr Val Asn Arg Asp Thr Gly Val Ile Ser Val Val Thr Ser Gly
                325                 330                 335

Leu Asp Arg Glu Ser Tyr Pro Thr Tyr Thr Leu Val Val Gln Ala Ala
            340                 345                 350

Asp Leu Gln Gly Glu Gly Leu Ser Thr Thr Ala Lys Ala Val Ile Thr
            355                 360                 365

Val Lys Asp Ile Asn Asp Asn Ala Pro Ile Phe Asn Pro Ser Thr Tyr
370                 375                 380

Gln Gly Gln Val Leu Glu Asn Glu Val Gly Ala Arg Ile Ala Thr Leu
385                 390                 395                 400

Lys Val Thr Asp Asp Ala Pro Asn Thr Pro Ala Trp Asn Ala Val
                405                 410                 415

Tyr Thr Val Val Asn Asp Pro Asp His Gln Phe Thr Val Ile Thr Asp
                420                 425                 430

Pro Lys Thr Asn Glu Gly Ile Leu Lys Thr Ala Lys Gly Leu Asp Phe
            435                 440                 445

Glu Ala Lys Gln Gln Tyr Ile Leu His Val Thr Val Glu Asn Glu Glu
450                 455                 460
```

```
Pro Phe Glu Gly Ser Leu Val Pro Ser Thr Ala Thr Val Thr Val Asp
465                 470                 475                 480

Val Val Asp Val Asn Glu Ala Pro Ile Phe Val Pro Ala Glu Lys Arg
                485                 490                 495

Val Glu Val Pro Glu Asp Phe Gly Val Gly Leu Glu Ile Ala Ser Tyr
            500                 505                 510

Thr Ala Arg Glu Pro Asp Thr Phe Met Glu Gln Lys Ile Thr Tyr Arg
            515                 520                 525

Ile Trp Arg Asp Thr Ala Asn Trp Leu Glu Ile Asn Pro Glu Thr Gly
        530                 535                 540

Val Ile Ser Thr Arg Ala Glu Met Asp Arg Glu Asp Ser Glu His Val
545                 550                 555                 560

Lys Asn Ser Thr Tyr Thr Ala Leu Ile Ile Ala Thr Asp Asp Gly Ser
                565                 570                 575

Pro Ile Ala Thr Gly Thr Gly Thr Leu Leu Leu Val Leu Ser Asp Val
                580                 585                 590

Asn Asp Asn Ala Pro Ile Pro Glu Pro Arg Asn Met Gln Phe Cys Gln
            595                 600                 605

Arg Asn Pro Lys Pro His Val Ile Thr Ile Leu Asp Pro Asp Leu Pro
        610                 615                 620

Pro Asn Thr Ser Pro Phe Thr Ala Glu Leu Thr His Gly Ala Ser Val
625                 630                 635                 640

Asn Trp Thr Ile Glu Tyr Asn Asp Ala Glu Gln Glu Ser Leu Ile Leu
                645                 650                 655

Gln Pro Arg Lys Asp Leu Glu Ile Gly Glu Tyr Lys Ile Asn Leu Lys
            660                 665                 670

Leu Ser Asp Asn Gln Asn Lys Asp Gln Val Thr Thr Leu Glu Val His
        675                 680                 685

Val Cys Asp Cys Glu Gly Thr Val Asn Asn Cys Met Lys Ala Ile Ser
        690                 695                 700

Leu Glu Ala Gly Leu Gln Val Pro Ala Ile Leu Gly Ile Leu Gly Gly
705                 710                 715                 720

Ile Leu Ala Leu Leu Ile Leu Ile Leu Leu Leu Leu Phe Leu Arg
                725                 730                 735

Arg Arg Thr Val Val Lys Glu Pro Leu Leu Pro Pro Asp Asp Asp Thr
            740                 745                 750

Arg Asp Asn Val Tyr Tyr Tyr Asp Glu Glu Gly Gly Gly Glu Glu Asp
            755                 760                 765

Gln Asp Phe Asp Leu Ser Gln Leu His Arg Gly Leu Asp Ala Arg Pro
            770                 775                 780

Glu Val Ile Arg Asn Asp Val Ala Pro Thr Leu Met Ser Met Pro Gln
785                 790                 795                 800

Tyr Arg Pro Arg Pro Ala Asn Pro Asp Glu Ile Gly Asn Phe Ile Asp
                805                 810                 815

Glu Asn Leu Lys Ala Ala Asp Ser Asp Pro Thr Ala Pro Pro Tyr Asp
            820                 825                 830

Ser Leu Leu Val Phe Asp Tyr Glu Gly Ser Gly Ser Glu Ala Ala Ser
            835                 840                 845

Leu Ser Ser Leu Asn Ser Ser Glu Ser Asp Gln Asp Gln Asp Tyr Asp
            850                 855                 860

Tyr Leu Asn Glu Trp Gly Asn Arg Phe Lys Lys Leu Ala Asp Met Tyr
865                 870                 875                 880

Gly Gly Gly Glu Glu Asp
```

885

<210> SEQ ID NO 7
<211> LENGTH: 2898
<212> TYPE: DNA
<213> ORGANISM: Canis sp.

<400> SEQUENCE: 7

| | | | | | |
|---|---|---|---|---|---|
| atggccttgt | ttgggatcaa | ggctgcccgc | ttccatgtgg | aggggtgcag | ccgcagccaa | 60 |
| tcagcggcgc | gggggcggg | gcctcgcggc | tcacctggcg | gccggacgcg | gccccgctca | 120 |
| gtggcgtcgg | gcgctgcggg | cacctgtgat | tcgcggaagt | cctgccgcct | cgcgccgcct | 180 |
| cgcgccgcct | cgcgccgcct | cgcgcccggc | tctcgacccc | cgcccgccat | gggccctcgg | 240 |
| tacggcggcg | ccccgcgct | cctgctcccg | ctgctgctgc | tgctgcaggt | ctcatcgggg | 300 |
| ctctgccaag | agccggagcc | ctgccgccct | ggctttggcg | ctgacagcta | cacgttcacc | 360 |
| gtgccccggc | gacacttgga | gagaggccgt | gtcctgggca | gggtgagttt | tgaaggatgc | 420 |
| accggtctac | ctaggacagc | ctatgtttct | gatgacaccc | gattcaaagt | gggcacagat | 480 |
| ggtgtgatta | cagtcaagcg | gcctctacaa | cttcataaac | cagagataag | ttttcttgtc | 540 |
| catgcctggg | actccagccg | caggaagctc | tccaccagag | ttaggctgaa | ggcagcgacg | 600 |
| caccaccacc | accaccatca | tgatgctccc | tctaaaaccc | agacagaggt | gctcacattt | 660 |
| cccagttccc | agcatggact | cagaagacag | aagagagact | gggttatccc | tcctatcagc | 720 |
| tgcccggaaa | acgagaaagg | cccatttcct | aaaaacctgg | ttcagatcaa | gtctaacagg | 780 |
| gacaaagaaa | tcaaggtttt | ctacagcatc | actggccaag | gagctgacgc | acctcctgtt | 840 |
| ggtgtgttta | ttattgaaag | agaaacagga | tggctgaagg | tgactgagcc | tctggataga | 900 |
| gaacaaattg | ctaagtacat | tctctactct | catgccgtat | cttctaatgg | gaatgcggtt | 960 |
| gaagacccaa | tggagatcgt | gatcacggtg | acagatcaga | atgacaacaa | gcccgagttc | 1020 |
| acccaggcag | tcttccaagg | atctgtcacg | gaaggtgccc | ttccaggcac | ctctgtgatg | 1080 |
| caggtgacag | ccacagatgc | ggatgatgat | gtgaatacct | acaacgctgc | catcgcttac | 1140 |
| agcatcctca | cacaagaccc | cctcctgcct | agcagcatga | tgttcactat | caacaaggac | 1200 |
| acaggagtca | tcagcgtgct | caccactggg | ctggaccgag | agggtgtccc | catgtacacc | 1260 |
| ttggtggttc | aggctgctga | cctgcaaggc | gaaggcttaa | ctacaactgc | aacagctgtg | 1320 |
| atcacagtca | ctgacatcaa | tgataacccc | cccatcttca | acccaaccac | gtaccaggga | 1380 |
| cgggtgcctg | agaacaaggc | taacgtcgaa | atcgctgtac | tcaaagtgac | ggatgctgat | 1440 |
| gtccccgata | ccccggcctg | gagggctgtg | tacaccatat | tgaacaataa | caatgatcaa | 1500 |
| tttgttgtca | ccacagaccc | agtaactaac | gacggcattt | tgaaaacaac | taagggcttg | 1560 |
| gattttgagg | acaagcagca | gtatgtcttg | tacgtgactg | tggtgaacgt | gaccccgttt | 1620 |
| gaggtcatcc | tctccacctc | cacagccact | gtcactgtgg | acgtggaaga | tgtgaatgaa | 1680 |
| gcccccatct | tcatcccttg | cccaaaggta | gtgtcaatcc | tgaagacttt | ggtgtgggc | 1740 |
| caggaaatca | catcctacac | cgccgaggat | ccagatacat | atatggaaca | gaggataacg | 1800 |
| tatcggattt | ggagggatgc | tgccggttgg | ctggaggtta | tccagaatc | tggtgccatt | 1860 |
| ttcactcggg | ctgagctgga | cagagaggat | tttgagcacg | tgaagaatag | cacgtatgaa | 1920 |
| gccctcatta | tagccattga | caacggttct | ccagttgcta | ctggaacggg | aactcttcta | 1980 |
| ctggtcctct | ctgatgtgaa | tgacaatggc | cccattccag | aacctcgaaa | tatggacttc | 2040 |
| tgccagaaaa | acccacagcc | tcatgtcatc | aacatcattg | atccagatct | tcccccaac | 2100 |

```
acatctccct tcacagcaga actaacacac ggcgcaagtg tcaactggac catcgagtac   2160
aatgacccag gtgggaattg gactcgtgaa tctctaattt tgaagccaaa gaaaacttta   2220
gagttgggtg actacaaaat aaatctcaag ctcacagata accagaacaa ggaccaggtg   2280
accaccctag atgtgtttgt gtgcgactgc gaaggtgtcg tcaacagctg caagaggacg   2340
gcgccttacg ccgaagcagg cttgcaggtt cctgccatct tgggcattct cggaggaatc   2400
ctcgctctac taatcctgat tctgctgctt ctgctatttg ttcggaggag aagggtggtc   2460
aaagagccct tacttccccc agaagatgac acccgggaca atgtttatta ctatgatgaa   2520
gaaggaggtg gagaggagga tcaggacttt gacttgagcc agttgcacag ggcctggat    2580 gctcggcctg aagtgactcg caatgatgtg gccccaaccc tcctgagtgt gccccagtat   2640
cggccccgcc ctgccaatcc tgatgaaatt ggaaactta ttgatgaaaa cctgaaggca    2700
gcggacactg accctactgc tcctccttat gactctctgc tcgtgtttga ctatgaagga   2760
agcggttctg aagctgctag tctgagctcc ttgaactcct cagagtcaga ccaagaccag   2820
gactatgact acctgaatga atggggcaat cgcttcaaga agctggcgga catgtatgga   2880
ggtggcgagg acgactag                                                 2898
```

<210> SEQ ID NO 8
<211> LENGTH: 174
<212> TYPE: PRT
<213> ORGANISM: Canis sp.

<400> SEQUENCE: 8

```
Met Gly Pro Arg Tyr Gly Gly Ala Pro Ala Leu Leu Pro Leu Leu
1               5                   10                  15

Leu Leu Leu Gln Val Ser Ser Gly Leu Cys Gln Glu Pro Glu Pro Cys
                20                  25                  30

Arg Pro Gly Phe Gly Ala Asp Ser Tyr Thr Phe Thr Val Pro Arg Arg
            35                  40                  45

His Leu Glu Arg Gly Arg Val Leu Gly Arg Val Ser Phe Glu Gly Cys
        50                  55                  60

Thr Gly Leu Pro Arg Thr Ala Tyr Val Ser Asp Asp Thr Arg Phe Lys
65                  70                  75                  80

Val Gly Thr Asp Gly Val Ile Thr Val Lys Arg Pro Leu Gln Leu His
                85                  90                  95

Lys Pro Glu Ile Ser Phe Leu Val His Ala Trp Asp Ser Ser Arg Arg
            100                 105                 110

Lys Leu Ser Thr Arg Val Arg Leu Lys Ala Ala Thr His His His
        115                 120                 125

His His His Asp Ala Pro Ser Lys Thr Gln Thr Glu Val Leu Thr Phe
    130                 135                 140

Pro Ser Ser Gln His Gly Leu Arg Arg Gln Lys Arg Asp Trp Val Ile
145                 150                 155                 160

Pro Pro Ile Ser Cys Pro Glu Asn Glu Lys Gly Pro Phe Pro
                165                 170
```

<210> SEQ ID NO 9
<211> LENGTH: 2649
<212> TYPE: DNA
<213> ORGANISM: Bos sp.

<400> SEQUENCE: 9

```
atgggccctt ggagccgcag cctctctgcg ctctgctgct gctgcaggtg taatccgtgg   60
```

```
ctctgccggg agccggagcc ctgcattcct ggctttggtg ctgagagtta cacgttcacc      120
gtgccccggc ggaacttgga gagagggcga gtcctaggca gagtgagttt tgaaggatgt      180
gctggcctac caaggacagt ctatgtttct gatgacaccc gattcaaagt gcacacagat      240
ggcgtgctta cagtcagacg acctgtacac cttcatcgtc cagagctaag ttttcttgtc      300
catgcctggg actccaccca caggaagctc tccaccaaag tgacactgga ggtatcagcg      360
caccaccacc accaccacag tcatcatgac tctccctctg gaacccagac agaagtgctc      420
acatttcctg gcccccacca tggtctcagg agacagaaga gagactgggt tattcctcct      480
atcagctgcc cagaaaatga gaaaggccca tttcctaagt cgctggtcca gatcaaatct      540
aacaaggaga agaaaccca agttttctac agcatcactg gccaacgagc tgatacaccc      600
cctgtcggtg ttttattat tgaaagagaa acaggatggt taaaagtgac acagcctctg      660
gatagagaac agattgccaa gtacattctc ttctctcatg ccgtgtcttc aaatggacaa      720
gccattgaag agcctatgga gattgtgatc accgtgaccg accagaatga caacaagccc      780
cagttcaccc aggaggtctt caaggcgtct gccctggaag gcgctcttcc aggaacctct      840
gtgatgcagg tcacggccac agatatagat gacgaggtga acacctacac cgctgccatc      900
ggttacacaa tcccagccca agatcccatg ctgccgcaca acaaaatgtt caccatcaac      960
aaggaaacag gcgtcatcag tgtgctcacc accgggctgg accgtgagag ttttccccaca     1020 tacaccctga tggtccaagc agcagacctt aacggcgaag gcttgagcac aactgcaacg     1080
gccgtgatca cagtcttgga caccaatgat aatgctccca gattcaaccc aaccacgtac     1140
gtggggtcgg tgcctgagaa cgaggctaat gtggccatca ccacactcac agtgactgat     1200
gccgacgacc ccaacacccc ggcatgggag gctgtttaca cagtattaaa tgataacgag     1260
aagcaattta tcgtcgtcac agacccagtc accaatgaag gcactctgaa aacagctaag     1320
ggcttggatt ttgaggccaa gcagcagtac atcctgtacg tggcagtgac aaatgtggcc     1380 cccttgaag tcactctccc cacttccaca gccaccgtca ctgtggatgt gatagatgtg     1440
aatgaagccc ccatctttgt gcctcctcaa aagagagtgg aagtgcccga ggactttggc     1500
gtgggcctgg agatcacatc ctatactgcc cgggagccag acacatttat ggaacagaag     1560
atcacgtatc ggatttggag ggacactgcc aactggctgg agattaatcc agaaacgggt     1620
gccatttcca ctcgggctga gttggacaga gaggatgtcg atcatgtgaa gaacagcacg     1680
tacacggccc tcattatagc cactgacaat ggttctccac ctgccactgg gacaggcacc     1740
ctgctcttgt tcctcgatga tgtgaatgac aatggccccg taccagaacc ccggaccatg     1800
gacttctgcc agaggaatcc tgagcctcat atcatcaaca tcaatgatcc tgatctccct     1860
ccgaacacct ccccctttac agcagaactg acacatgggg cgagtgtcaa ttggaccatt     1920
gagtacaatg accaagaacg tgagtctctg attttgaagc caaagaaaac cttagagctg     1980
ggtgaccaca aaatcaatct caagctcata gacaaccaga caaagaccaa ggtgaccaca     2040
cttgatgtgc acgtgtgtga ctgtgatggg atcgtcagca actgcaggaa ggcacggcct     2100
gctgaagcag gattgcaagt tcccgccatc ctggggatcc ttggaggcat ccttgctttt     2160
ctgatcctta ttttgctgct tctgctactt gttcggagga agggtggt caaagagccc     2220 ttactgcccc cagaagatga caccccggac aatgtgtatt actatgatga agaaggaggt     2280
ggagaagaag atcaggactt tgacttgagc cagttacata ggggcctgga tgctcggcct     2340
gaagtgactc gcaatgacgt ggcaccaacc ctcatgagtg tgcccagta ccgacccgc      2400
```

-continued

```
cctgccaatc ctgatgaaat tggaaacttt attgatgaaa acctgaaggc agctgatagt    2460
gaccccactg ccccacccta tgactctctg ctggtgtttg attatgaagg aagtggttcc    2520
gaagctgcta ctctgagctc cctgaactcc tcagagtcag accaagacca ggactatgac    2580
tacctgaatg aatggggcaa tcgcttcaag aagctggcgg acatgtatgg aggcggcgag    2640
gacgactag                                                             2649
```

<210> SEQ ID NO 10
<211> LENGTH: 882
<212> TYPE: PRT
<213> ORGANISM: Bos sp.

<400> SEQUENCE: 10

```
Met Gly Pro Trp Ser Arg Ser Leu Ser Ala Leu Cys Cys Cys Cys Arg
1               5                   10                  15

Cys Asn Pro Trp Leu Cys Arg Glu Pro Glu Pro Cys Ile Pro Gly Phe
            20                  25                  30

Gly Ala Glu Ser Tyr Thr Phe Thr Val Pro Arg Arg Asn Leu Glu Arg
        35                  40                  45

Gly Arg Val Leu Gly Arg Val Ser Phe Glu Gly Cys Ala Gly Leu Pro
    50                  55                  60

Arg Thr Val Tyr Val Ser Asp Asp Thr Arg Phe Lys Val His Thr Asp
65                  70                  75                  80

Gly Val Leu Thr Val Arg Arg Pro Val His Leu His Arg Pro Glu Leu
                85                  90                  95

Ser Phe Leu Val His Ala Trp Asp Ser Thr His Arg Lys Leu Ser Thr
            100                 105                 110

Lys Val Thr Leu Glu Val Ser Ala His His His His His Ser His
        115                 120                 125

His Asp Ser Pro Ser Gly Thr Gln Thr Glu Val Leu Thr Phe Pro Gly
    130                 135                 140

Pro His His Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Ser Leu Val
                165                 170                 175

Gln Ile Lys Ser Asn Lys Glu Lys Glu Thr Gln Val Phe Tyr Ser Ile
            180                 185                 190

Thr Gly Gln Arg Ala Asp Thr Pro Pro Val Gly Val Phe Ile Ile Glu
        195                 200                 205

Arg Glu Thr Gly Trp Leu Lys Val Thr Gln Pro Leu Asp Arg Glu Gln
    210                 215                 220

Ile Ala Lys Tyr Ile Leu Phe Ser His Ala Val Ser Ser Asn Gly Gln
225                 230                 235                 240

Ala Ile Glu Glu Pro Met Glu Ile Val Ile Thr Val Thr Asp Gln Asn
                245                 250                 255

Asp Asn Lys Pro Gln Phe Thr Gln Glu Val Phe Lys Ala Ser Ala Leu
            260                 265                 270

Glu Gly Ala Leu Pro Gly Thr Ser Val Met Gln Val Thr Ala Thr Asp
        275                 280                 285

Ile Asp Asp Glu Val Asn Thr Tyr Thr Ala Ala Ile Gly Tyr Thr Ile
    290                 295                 300

Pro Ala Gln Asp Pro Met Leu Pro His Asn Lys Met Phe Thr Ile Asn
305                 310                 315                 320

Lys Glu Thr Gly Val Ile Ser Val Leu Thr Thr Gly Leu Asp Arg Glu
```

```
                325                 330                 335
Ser Phe Pro Thr Tyr Thr Leu Met Val Gln Ala Ala Asp Leu Asn Gly
                340                 345                 350
Glu Gly Leu Ser Thr Thr Ala Thr Ala Val Ile Thr Val Leu Asp Thr
                355                 360                 365
Asn Asp Asn Ala Pro Arg Phe Asn Pro Thr Thr Tyr Val Gly Ser Val
    370                 375                 380
Pro Glu Asn Glu Ala Asn Val Ala Ile Thr Thr Leu Thr Val Thr Asp
385                 390                 395                 400
Ala Asp Asp Pro Asn Thr Pro Ala Trp Glu Ala Val Tyr Thr Val Leu
                405                 410                 415
Asn Asp Asn Glu Lys Gln Phe Ile Val Val Thr Asp Pro Val Thr Asn
                420                 425                 430
Glu Gly Thr Leu Lys Thr Ala Lys Gly Leu Asp Phe Glu Ala Lys Gln
                435                 440                 445
Gln Tyr Ile Leu Tyr Val Ala Val Thr Asn Val Ala Pro Phe Glu Val
                450                 455                 460
Thr Leu Pro Thr Ser Thr Ala Thr Val Thr Val Asp Val Ile Asp Val
465                 470                 475                 480
Asn Glu Ala Pro Ile Phe Val Pro Pro Gln Lys Arg Val Glu Val Pro
                485                 490                 495
Glu Asp Phe Gly Val Gly Leu Glu Ile Thr Ser Tyr Thr Ala Arg Glu
                500                 505                 510
Pro Asp Thr Phe Met Glu Gln Lys Ile Thr Tyr Arg Ile Trp Arg Asp
                515                 520                 525
Thr Ala Asn Trp Leu Glu Ile Asn Pro Glu Thr Gly Ala Ile Ser Thr
                530                 535                 540
Arg Ala Glu Leu Asp Arg Glu Asp Val Asp His Val Lys Asn Ser Thr
545                 550                 555                 560
Tyr Thr Ala Leu Ile Ile Ala Thr Asp Asn Gly Ser Pro Pro Ala Thr
                565                 570                 575
Gly Thr Gly Thr Leu Leu Leu Phe Leu Asp Asp Val Asn Asp Asn Gly
                580                 585                 590
Pro Val Pro Glu Pro Arg Thr Met Asp Phe Cys Gln Arg Asn Pro Glu
                595                 600                 605
Pro His Ile Ile Asn Ile Asn Asp Pro Asp Leu Pro Pro Asn Thr Ser
                610                 615                 620
Pro Phe Thr Ala Glu Leu Thr His Gly Ala Ser Val Asn Trp Thr Ile
625                 630                 635                 640
Glu Tyr Asn Asp Gln Glu Arg Glu Ser Leu Ile Leu Lys Pro Lys Lys
                645                 650                 655
Thr Leu Glu Leu Gly Asp His Lys Ile Asn Leu Lys Leu Ile Asp Asn
                660                 665                 670
Gln Asn Lys Asp Gln Val Thr Thr Leu Asp Val His Val Cys Asp Cys
                675                 680                 685
Asp Gly Ile Val Ser Asn Cys Arg Lys Ala Arg Pro Ala Glu Ala Gly
                690                 695                 700
Leu Gln Val Pro Ala Ile Leu Gly Ile Leu Gly Gly Ile Leu Ala Phe
705                 710                 715                 720
Leu Ile Leu Ile Leu Leu Leu Leu Leu Val Arg Arg Arg Val
                725                 730                 735
Val Lys Glu Pro Leu Leu Pro Pro Glu Asp Asp Thr Arg Asp Asn Val
                740                 745                 750
```

```
Tyr Tyr Tyr Asp Glu Glu Gly Gly Glu Glu Asp Gln Asp Phe Asp
        755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Gln Tyr Arg Pro Arg
785                 790                 795                 800

Pro Ala Asn Pro Asp Glu Ile Gly Asn Phe Ile Asp Glu Asn Leu Lys
                805                 810                 815

Ala Ala Asp Ser Asp Pro Thr Ala Pro Pro Tyr Asp Ser Leu Leu Val
                820                 825                 830

Phe Asp Tyr Glu Gly Ser Gly Ser Glu Ala Ala Thr Leu Ser Ser Leu
                835                 840                 845

Asn Ser Ser Glu Ser Asp Gln Asp Gln Asp Tyr Asp Tyr Leu Asn Glu
                850                 855                 860

Trp Gly Asn Arg Phe Lys Lys Leu Ala Asp Met Tyr Gly Gly Gly Glu
865                 870                 875                 880

Asp Asp

<210> SEQ ID NO 11
<211> LENGTH: 3
<212> TYPE: PRT
<213> ORGANISM: Homo sapiens

<400> SEQUENCE: 11

His Ala Val
1

<210> SEQ ID NO 12
<211> LENGTH: 268
<212> TYPE: PRT
<213> ORGANISM: Homo sapiens

<400> SEQUENCE: 12

Met Pro Arg Ser Phe Leu Val Lys Lys His Phe Asn Ala Ser Lys Lys
1               5                   10                  15

Pro Asn Tyr Ser Glu Leu Asp Thr His Thr Val Ile Ile Ser Pro Tyr
                20                  25                  30

Leu Tyr Glu Ser Tyr Ser Met Pro Val Ile Pro Gln Pro Glu Ile Leu
            35                  40                  45

Ser Ser Gly Ala Tyr Ser Pro Ile Thr Val Trp Thr Thr Ala Ala Pro
        50                  55                  60

Phe His Ala Gln Leu Pro Asn Gly Leu Ser Pro Leu Ser Gly Tyr Ser
65                  70                  75                  80

Ser Ser Leu Gly Arg Val Ser Pro Pro Pro Ser Asp Thr Ser Ser
                85                  90                  95

Lys Asp His Ser Gly Ser Glu Ser Pro Ile Ser Asp Glu Glu Glu Arg
            100                 105                 110

Leu Gln Ser Lys Leu Ser Asp Pro His Ala Ile Glu Ala Glu Lys Phe
        115                 120                 125

Gln Cys Asn Leu Cys Asn Lys Thr Tyr Ser Thr Phe Ser Gly Leu Ala
    130                 135                 140

Lys His Lys Gln Leu His Cys Asp Ala Gln Ser Arg Lys Ser Phe Ser
145                 150                 155                 160

Cys Lys Tyr Cys Asp Lys Glu Tyr Val Ser Leu Gly Ala Leu Lys Met
                165                 170                 175
```

His Ile Arg Thr His Thr Leu Pro Cys Val Cys Lys Ile Cys Gly Lys
            180                 185                 190

Ala Phe Ser Arg Pro Trp Leu Leu Gln Gly His Ile Arg Thr His Thr
        195                 200                 205

Gly Glu Lys Pro Phe Ser Cys Pro His Cys Asn Arg Ala Phe Ala Asp
    210                 215                 220

Arg Ser Asn Leu Arg Ala His Leu Gln Thr His Ser Asp Val Lys Lys
225                 230                 235                 240

Tyr Gln Cys Lys Asn Cys Ser Lys Thr Phe Ser Arg Met Ser Leu Leu
                245                 250                 255

His Lys His Glu Glu Ser Gly Cys Cys Val Ala His
            260                 265

<210> SEQ ID NO 13
<211> LENGTH: 269
<212> TYPE: PRT
<213> ORGANISM: Mus musculus

<400> SEQUENCE: 13

Met Pro Arg Ser Phe Leu Val Lys Lys His Phe Asn Ala Ser Lys Lys
1               5                   10                  15

Pro Asn Tyr Ser Glu Leu Asp Thr His Thr Val Ile Ile Ser Pro Tyr
            20                  25                  30

Leu Tyr Glu Ser Tyr Pro Ile Pro Val Ile Pro Lys Pro Glu Ile Leu
        35                  40                  45

Thr Ser Gly Ala Tyr Ser Pro Ile Thr Val Trp Thr Ser Ser Ala Ala
    50                  55                  60

Pro Leu His Ser Pro Leu Pro Ser Gly Leu Ser Pro Leu Thr Gly Tyr
65                  70                  75                  80

Ser Ser Ser Leu Gly Arg Val Ser Pro Pro Ser Ser Asp Thr Ser
                85                  90                  95

Ser Lys Asp His Ser Gly Ser Glu Ser Pro Ile Ser Asp Glu Glu Glu
            100                 105                 110

Arg Leu Gln Pro Lys Leu Ser Asp Pro His Ala Ile Glu Ala Glu Lys
        115                 120                 125

Phe Gln Cys Asn Leu Cys Asn Lys Thr Tyr Ser Thr Phe Ser Gly Leu
    130                 135                 140

Ala Lys His Lys Gln Leu His Cys Asp Ala Gln Ser Arg Lys Ser Phe
145                 150                 155                 160

Ser Cys Lys Tyr Cys Asp Lys Glu Tyr Val Ser Leu Gly Ala Leu Lys
                165                 170                 175

Met His Ile Arg Thr His Thr Leu Pro Cys Val Cys Lys Ile Cys Gly
            180                 185                 190

Lys Ala Phe Ser Arg Pro Trp Leu Leu Gln Gly His Ile Arg Thr His
        195                 200                 205

Thr Gly Glu Lys Pro Phe Ser Cys Pro His Cys Asn Arg Ala Phe Ala
    210                 215                 220

Asp Arg Ser Asn Leu Arg Ala His Leu Gln Thr His Ser Asp Val Lys
225                 230                 235                 240

Lys Tyr Gln Cys Lys Asn Cys Ser Lys Thr Phe Ser Arg Met Ser Leu
                245                 250                 255

Leu His Lys His Glu Glu Ser Gly Cys Cys Val Ala His
            260                 265

<210> SEQ ID NO 14

```
<211> LENGTH: 264
<212> TYPE: PRT
<213> ORGANISM: Homo sapiens

<400> SEQUENCE: 14

Met Pro Arg Ser Phe Leu Val Arg Lys Pro Ser Asp Pro Asn Arg Lys
1               5                   10                  15

Pro Asn Tyr Ser Glu Leu Gln Asp Ser Asn Pro Glu Phe Thr Phe Gln
            20                  25                  30

Gln Pro Tyr Asp Gln Ala His Leu Leu Ala Ala Ile Pro Pro Pro Glu
        35                  40                  45

Ile Leu Asn Pro Thr Ala Ser Leu Pro Met Leu Ile Trp Asp Ser Val
50                  55                  60

Leu Ala Pro Gln Ala Gln Pro Ile Ala Trp Ala Ser Leu Arg Leu Gln
65                  70                  75                  80

Glu Ser Pro Arg Val Ala Glu Leu Thr Ser Leu Ser Asp Glu Asp Ser
                85                  90                  95

Gly Lys Gly Ser Gln Pro Pro Ser Pro Ser Pro Ala Pro Ser Ser
            100                 105                 110

Phe Ser Ser Thr Ser Val Ser Ser Leu Glu Ala Glu Ala Tyr Ala Ala
        115                 120                 125

Phe Pro Gly Leu Gly Gln Val Pro Lys Gln Leu Ala Gln Leu Ser Glu
130                 135                 140

Ala Lys Asp Leu Gln Ala Arg Lys Ala Phe Asn Cys Lys Tyr Cys Asn
145                 150                 155                 160

Lys Glu Tyr Leu Ser Leu Gly Ala Leu Lys Met His Ile Arg Ser His
                165                 170                 175

Thr Leu Pro Cys Val Cys Gly Thr Cys Gly Lys Ala Phe Ser Arg Pro
            180                 185                 190

Trp Leu Leu Gln Gly His Val Arg Thr His Thr Gly Glu Lys Pro Phe
        195                 200                 205

Ser Cys Pro His Cys Ser Arg Ala Phe Ala Asp Arg Ser Asn Leu Arg
210                 215                 220

Ala His Leu Gln Thr His Ser Asp Val Lys Lys Tyr Gln Cys Gln Ala
225                 230                 235                 240

Cys Ala Arg Thr Phe Ser Arg Met Ser Leu Leu His Lys His Gln Glu
                245                 250                 255

Ser Gly Cys Ser Gly Cys Pro Arg
            260

<210> SEQ ID NO 15
<211> LENGTH: 264
<212> TYPE: PRT
<213> ORGANISM: Mus musculus

<400> SEQUENCE: 15

Met Pro Arg Ser Phe Leu Val Arg Lys Pro Ser Asp Pro Arg Arg Lys
1               5                   10                  15

Pro Asn Tyr Ser Glu Leu Gln Asp Ala Cys Val Glu Phe Thr Phe Gln
            20                  25                  30

Gln Pro Tyr Asp Gln Ala His Leu Leu Ala Ala Ile Pro Pro Pro Glu
        35                  40                  45

Val Leu Asn Pro Ala Ala Ser Leu Pro Thr Leu Ile Trp Asp Ser Leu
50                  55                  60

Leu Val Pro Gln Val Arg Pro Val Ala Trp Ala Thr Leu Pro Leu Arg
65                  70                  75                  80
```

```
Glu Ser Pro Lys Ala Val Glu Leu Thr Ser Leu Ser Asp Glu Asp Ser
                85                  90                  95

Gly Lys Ser Ser Gln Pro Pro Ser Pro Pro Ser Ala Pro Ser Ser
                100                 105                 110

Phe Ser Ser Thr Ser Ala Ser Ser Leu Glu Ala Glu Ala Phe Ile Ala
                115                 120                 125

Phe Pro Gly Leu Gly Gln Leu Pro Lys Gln Leu Ala Arg Leu Ser Val
            130                 135                 140

Ala Lys Asp Pro Gln Ser Arg Lys Ile Phe Asn Cys Lys Tyr Cys Asn
145                 150                 155                 160

Lys Glu Tyr Leu Ser Leu Gly Ala Leu Lys Met His Ile Arg Ser His
                165                 170                 175

Thr Leu Pro Cys Val Cys Thr Thr Cys Gly Lys Ala Phe Ser Arg Pro
                180                 185                 190

Trp Leu Leu Gln Gly His Val Arg Thr His Thr Gly Glu Lys Pro Phe
                195                 200                 205

Ser Cys Ser His Cys Asn Arg Ala Phe Ala Asp Arg Ser Asn Leu Arg
                210                 215                 220

Ala His Leu Gln Thr His Ser Asp Val Lys Arg Tyr Gln Cys Gln Ala
225                 230                 235                 240

Cys Ala Arg Thr Phe Ser Arg Met Ser Leu Leu His Lys His Gln Glu
                245                 250                 255

Ser Gly Cys Ser Gly Gly Pro Arg
                260

<210> SEQ ID NO 16
<211> LENGTH: 1214
<212> TYPE: PRT
<213> ORGANISM: Homo sapiens

<400> SEQUENCE: 16

Met Lys Gln Pro Ile Met Ala Asp Gly Pro Arg Cys Lys Arg Arg Lys
1               5                   10                  15

Gln Ala Asn Pro Arg Arg Lys Asn Val Val Asn Tyr Asp Asn Val Val
                20                  25                  30

Asp Thr Gly Ser Glu Thr Asp Glu Glu Asp Lys Leu His Ile Ala Glu
            35                  40                  45

Asp Asp Gly Ile Ala Asn Pro Leu Asp Gln Glu Thr Ser Pro Ala Ser
        50                  55                  60

Val Pro Asn His Glu Ser Ser Pro His Val Ser Gln Ala Leu Leu Pro
65                  70                  75                  80

Arg Glu Glu Glu Asp Glu Ile Arg Glu Gly Gly Val Glu His Pro
                85                  90                  95

Trp His Asn Asn Glu Ile Leu Gln Ala Ser Val Asp Gly Pro Glu Glu
                100                 105                 110

Met Lys Glu Asp Tyr Asp Thr Met Gly Pro Glu Ala Thr Ile Gln Thr
            115                 120                 125

Ala Ile Asn Asn Gly Thr Val Lys Asn Ala Asn Cys Thr Ser Asp Phe
130                 135                 140

Glu Glu Tyr Phe Ala Lys Arg Lys Leu Glu Arg Asp Gly His Ala
145                 150                 155                 160

Val Ser Ile Glu Glu Tyr Leu Gln Arg Ser Asp Thr Ala Ile Ile Tyr
                165                 170                 175

Pro Glu Ala Pro Glu Glu Leu Ser Arg Leu Gly Thr Pro Glu Ala Asn
```

```
                    180                 185                 190
Gly Gln Glu Glu Asn Asp Leu Pro Pro Gly Thr Pro Asp Ala Phe Ala
            195                 200                 205
Gln Leu Leu Thr Cys Pro Tyr Cys Asp Arg Gly Tyr Lys Arg Leu Thr
            210                 215                 220
Ser Leu Lys Glu His Ile Lys Tyr Arg His Glu Lys Asn Glu Glu Asn
225                 230                 235                 240
Phe Ser Cys Pro Leu Cys Ser Tyr Thr Phe Ala Tyr Arg Thr Gln Leu
                245                 250                 255
Glu Arg His Met Val Thr His Lys Pro Gly Thr Asp Gln His Gln Met
            260                 265                 270
Leu Thr Gln Gly Ala Gly Asn Arg Lys Phe Lys Cys Thr Glu Cys Gly
            275                 280                 285
Lys Ala Phe Lys Tyr Lys His His Leu Lys Glu His Leu Arg Ile His
            290                 295                 300
Ser Gly Glu Lys Pro Tyr Glu Cys Pro Asn Cys Lys Lys Arg Phe Ser
305                 310                 315                 320
His Ser Gly Ser Tyr Ser Ser His Ile Ser Ser Lys Lys Cys Ile Gly
                325                 330                 335
Leu Ile Ser Val Asn Gly Arg Met Arg Asn Asn Ile Lys Thr Gly Ser
            340                 345                 350
Ser Pro Asn Ser Val Ser Ser Pro Thr Asn Ser Ala Ile Thr Gln
            355                 360                 365
Leu Arg Asn Lys Leu Glu Asn Gly Lys Pro Leu Ser Met Ser Glu Gln
            370                 375                 380
Thr Gly Leu Leu Lys Ile Lys Thr Glu Pro Leu Asp Phe Asn Asp Tyr
385                 390                 395                 400
Lys Val Leu Met Ala Thr His Gly Phe Ser Gly Thr Ser Pro Phe Met
                405                 410                 415
Asn Gly Gly Leu Gly Ala Thr Ser Pro Leu Gly Val His Pro Ser Ala
            420                 425                 430
Gln Ser Pro Met Gln His Leu Gly Val Gly Met Glu Ala Pro Leu Leu
            435                 440                 445
Gly Phe Pro Thr Met Asn Ser Asn Leu Ser Glu Val Gln Lys Val Leu
            450                 455                 460
Gln Ile Val Asp Asn Thr Val Ser Arg Gln Lys Met Asp Cys Lys Ala
465                 470                 475                 480
Glu Glu Ile Ser Lys Leu Lys Gly Tyr His Met Lys Asp Pro Cys Ser
                485                 490                 495
Gln Pro Glu Glu Gln Gly Val Thr Ser Pro Asn Ile Pro Pro Val Gly
            500                 505                 510
Leu Pro Val Val Ser His Asn Gly Ala Thr Lys Ser Ile Ile Asp Tyr
            515                 520                 525
Thr Leu Glu Lys Val Asn Glu Ala Lys Ala Cys Leu Gln Ser Leu Thr
            530                 535                 540
Thr Asp Ser Arg Arg Gln Ile Ser Asn Ile Lys Lys Glu Lys Leu Arg
545                 550                 555                 560
Thr Leu Ile Asp Leu Val Thr Asp Asp Lys Met Ile Glu Asn His Asn
                565                 570                 575
Ile Ser Thr Pro Phe Ser Cys Gln Phe Cys Lys Glu Ser Phe Pro Gly
                580                 585                 590
Pro Ile Pro Leu His Gln His Glu Arg Tyr Leu Cys Lys Met Asn Glu
            595                 600                 605
```

```
Glu Ile Lys Ala Val Leu Gln Pro His Glu Asn Ile Val Pro Asn Lys
    610                 615                 620

Ala Gly Val Phe Val Asp Asn Lys Ala Leu Leu Ser Ser Val Leu
625                 630                 635                 640

Ser Glu Lys Gly Met Thr Ser Pro Ile Asn Pro Tyr Lys Asp His Met
                645                 650                 655

Ser Val Leu Lys Ala Tyr Tyr Ala Met Asn Met Glu Pro Asn Ser Asp
            660                 665                 670

Glu Leu Leu Lys Ile Ser Ile Ala Val Gly Leu Pro Gln Glu Phe Val
        675                 680                 685

Lys Glu Trp Phe Glu Gln Arg Lys Val Tyr Gln Tyr Ser Asn Ser Arg
    690                 695                 700

Ser Pro Ser Leu Glu Arg Ser Ser Lys Pro Leu Ala Pro Asn Ser Asn
705                 710                 715                 720

Pro Pro Thr Lys Asp Ser Leu Leu Pro Arg Ser Pro Val Lys Pro Met
                725                 730                 735

Asp Ser Ile Thr Ser Pro Ser Ile Ala Glu Leu His Asn Ser Val Thr
            740                 745                 750

Asn Cys Asp Pro Pro Leu Arg Leu Thr Lys Pro Ser His Phe Thr Asn
        755                 760                 765

Ile Lys Pro Val Glu Lys Leu Asp His Ser Arg Ser Asn Thr Pro Ser
770                 775                 780

Pro Leu Asn Leu Ser Ser Thr Ser Ser Lys Asn Ser His Ser Ser Ser
785                 790                 795                 800

Tyr Thr Pro Asn Ser Phe Ser Ser Glu Glu Leu Gln Ala Glu Pro Leu
                805                 810                 815

Asp Leu Ser Leu Pro Lys Gln Met Lys Glu Pro Lys Ser Ile Ile Ala
            820                 825                 830

Thr Lys Asn Lys Thr Lys Ala Ser Ser Ile Ser Leu Asp His Asn Ser
        835                 840                 845

Val Ser Ser Ser Glu Asn Ser Asp Glu Pro Leu Asn Leu Thr Phe
850                 855                 860

Ile Lys Lys Glu Phe Ser Asn Ser Asn Asn Leu Asp Asn Lys Ser Thr
865                 870                 875                 880

Asn Pro Val Phe Ser Met Asn Pro Phe Ser Ala Lys Pro Leu Tyr Thr
                885                 890                 895

Ala Leu Pro Pro Gln Ser Ala Phe Pro Pro Ala Thr Phe Met Pro Pro
            900                 905                 910

Val Gln Thr Ser Ile Pro Gly Leu Arg Pro Tyr Pro Gly Leu Asp Gln
        915                 920                 925

Met Ser Phe Leu Pro His Met Ala Tyr Thr Tyr Pro Thr Gly Ala Ala
    930                 935                 940

Thr Phe Ala Asp Met Gln Gln Arg Arg Lys Tyr Gln Arg Lys Gln Gly
945                 950                 955                 960

Phe Gln Gly Glu Leu Leu Asp Gly Ala Gln Asp Tyr Met Ser Gly Leu
                965                 970                 975

Asp Asp Met Thr Asp Ser Asp Ser Cys Leu Ser Arg Lys Lys Ile Lys
            980                 985                 990

Lys Thr Glu Ser Gly Met Tyr Ala Cys Asp Leu Cys Asp Lys Thr Phe
        995                 1000                1005

Gln Lys Ser Ser Ser Leu Leu Arg His Lys Tyr Glu His Thr Gly
    1010                1015                1020
```

```
Lys Arg Pro His Gln Cys Gln Ile Cys Lys Lys Ala Phe Lys His
    1025                1030                1035

Lys His His Leu Ile Glu His Ser Arg Leu His Ser Gly Glu Lys
    1040                1045                1050

Pro Tyr Gln Cys Asp Lys Cys Gly Lys Arg Phe Ser His Ser Gly
    1055                1060                1065

Ser Tyr Ser Gln His Met Asn His Arg Tyr Ser Tyr Cys Lys Arg
    1070                1075                1080

Glu Ala Glu Glu Arg Glu Ala Ala Glu Arg Glu Ala Arg Glu Lys
    1085                1090                1095

Gly His Leu Glu Pro Thr Glu Leu Leu Met Asn Arg Ala Tyr Leu
    1100                1105                1110

Gln Ser Ile Thr Pro Gln Gly Tyr Ser Asp Ser Glu Glu Arg Glu
    1115                1120                1125

Ser Met Pro Arg Asp Gly Glu Ser Glu Lys Glu His Glu Lys Glu
    1130                1135                1140

Gly Glu Asp Gly Tyr Gly Lys Leu Gly Arg Gln Asp Gly Asp Glu
    1145                1150                1155

Glu Phe Glu Glu Glu Glu Glu Ser Glu Asn Lys Ser Met Asp
    1160                1165                1170

Thr Asp Pro Glu Thr Ile Arg Asp Glu Glu Thr Gly Asp His
    1175                1180                1185

Ser Met Asp Asp Ser Ser Glu Asp Gly Lys Met Glu Thr Lys Ser
    1190                1195                1200

Asp His Glu Glu Asp Asn Met Glu Asp Gly Met
    1205                1210

<210> SEQ ID NO 17
<211> LENGTH: 1215
<212> TYPE: PRT
<213> ORGANISM: Mus musculus

<400> SEQUENCE: 17

Met Lys Gln Pro Ile Met Ala Asp Gly Pro Arg Cys Lys Arg Lys
1               5                   10                  15

Gln Ala Asn Pro Arg Arg Lys Asn Val Val Asn Tyr Asp Asn Val
                20                  25                  30

Asp Ala Gly Ser Glu Thr Asp Glu Glu Asp Lys Leu His Ile Ala Glu
                35                  40                  45

Asp Asp Ser Leu Ala Asn Pro Leu Asp Gln Asp Thr Ser Pro Ala Ser
    50                  55                  60

Met Pro Asn His Glu Ser Ser Pro His Met Ser Gln Gly Leu Leu Pro
65                  70                  75                  80

Arg Glu Glu Glu Glu Glu Leu Arg Glu Ser Val Val Glu His Ser
                85                  90                  95

Trp His Ser Gly Glu Ile Leu Gln Ala Ser Val Ala Gly Pro Glu Glu
                100                 105                 110

Met Lys Glu Asp Tyr Asp Ala Met Gly Pro Glu Ala Thr Ile Gln Thr
                115                 120                 125

Thr Ile Asn Asn Gly Thr Val Lys Asn Ala Asn Cys Thr Ser Asp Phe
                130                 135                 140

Glu Glu Tyr Phe Ala Lys Arg Lys Leu Glu Glu Arg Asp Gly His Ala
145                 150                 155                 160

Val Ser Ile Glu Glu Tyr Leu Gln Arg Ser Asp Thr Ala Ile Ile Tyr
                165                 170                 175
```

-continued

```
Pro Glu Ala Pro Glu Leu Ser Arg Leu Gly Thr Pro Glu Ala Asn
            180                 185                 190
Gly Gln Glu Glu Asn Asp Leu Pro Gly Thr Pro Asp Ala Phe Ala
        195                 200                 205
Gln Leu Leu Thr Cys Pro Tyr Cys Asp Arg Gly Tyr Lys Arg Leu Thr
    210                 215                 220
Ser Leu Lys Glu His Ile Lys Tyr Arg His Glu Lys Asn Glu Asn
225                 230                 235                 240
Phe Ser Cys Pro Leu Cys Ser Tyr Thr Phe Ala Tyr Arg Thr Gln Leu
                245                 250                 255
Glu Arg His Met Val Thr His Lys Pro Gly Thr Asp Gln His Gln Met
            260                 265                 270
Leu Thr Gln Gly Ala Gly Asn Arg Lys Phe Lys Cys Thr Glu Cys Gly
        275                 280                 285
Lys Ala Phe Lys Tyr Lys His His Leu Lys Glu His Leu Arg Ile His
    290                 295                 300
Ser Gly Glu Lys Pro Tyr Glu Cys Pro Asn Cys Lys Lys Arg Phe Ser
305                 310                 315                 320
His Ser Gly Ser Tyr Ser Ser His Ile Ser Ser Lys Lys Cys Ile Gly
                325                 330                 335
Leu Ile Ser Val Asn Gly Arg Met Arg Asn Asn Ile Lys Thr Gly Ser
            340                 345                 350
Ser Pro Asn Ser Val Ser Ser Pro Thr Asn Ser Ala Ile Thr Gln
        355                 360                 365
Leu Arg Asn Lys Leu Glu Asn Gly Lys Pro Leu Ser Met Ser Glu Gln
    370                 375                 380
Thr Gly Leu Leu Lys Ile Lys Thr Glu Pro Leu Asp Phe Asn Asp Tyr
385                 390                 395                 400
Lys Val Leu Met Ala Thr His Gly Phe Ser Gly Ser Ser Pro Phe Met
                405                 410                 415
Asn Gly Gly Leu Gly Ala Thr Ser Pro Leu Gly Val His Pro Ser Ala
            420                 425                 430
Gln Ser Pro Met Gln His Leu Gly Val Gly Met Glu Ala Pro Leu Leu
        435                 440                 445
Gly Phe Pro Thr Met Asn Ser Asn Leu Ser Glu Val Gln Lys Val Leu
    450                 455                 460
Gln Ile Val Asp Asn Thr Val Ser Arg Gln Lys Met Asp Cys Lys Thr
465                 470                 475                 480
Glu Asp Ile Ser Lys Leu Lys Gly Tyr His Met Lys Asp Pro Cys Ser
                485                 490                 495
Gln Pro Glu Glu Gln Gly Val Thr Ser Pro Asn Ile Pro Pro Val Gly
            500                 505                 510
Leu Pro Val Val Ser His Asn Gly Ala Thr Lys Ser Ile Ile Asp Tyr
        515                 520                 525
Thr Leu Glu Lys Val Asn Glu Ala Lys Ala Cys Leu Gln Ser Leu Thr
    530                 535                 540
Thr Asp Ser Arg Arg Gln Ile Ser Asn Ile Lys Lys Glu Lys Leu Arg
545                 550                 555                 560
Thr Leu Ile Asp Leu Val Thr Asp Asp Lys Met Ile Glu Asn His Ser
                565                 570                 575
Ile Ser Thr Pro Phe Ser Cys Gln Phe Cys Lys Glu Ser Phe Pro Gly
            580                 585                 590
```

Pro Ile Pro Leu His Gln His Glu Arg Tyr Leu Cys Lys Met Asn Glu
            595                 600                 605

Glu Ile Lys Ala Val Leu Gln Pro His Glu Asn Ile Val Pro Asn Lys
610                 615                 620

Ala Gly Val Phe Val Asp Asn Lys Ala Leu Leu Leu Ser Ser Val Leu
625                 630                 635                 640

Ser Glu Lys Gly Leu Thr Ser Pro Ile Asn Pro Tyr Lys Asp His Met
                645                 650                 655

Ser Val Leu Lys Ala Tyr Tyr Ala Met Asn Met Glu Pro Asn Ser Asp
            660                 665                 670

Glu Leu Leu Lys Ile Ser Ile Ala Val Gly Leu Pro Gln Glu Phe Val
            675                 680                 685

Lys Glu Trp Phe Glu Gln Arg Lys Val Tyr Gln Tyr Ser Asn Ser Arg
690                 695                 700

Ser Pro Ser Leu Glu Arg Thr Ser Lys Pro Leu Ala Pro Asn Ser Asn
705                 710                 715                 720

Pro Thr Thr Lys Asp Ser Leu Leu Pro Arg Ser Pro Val Lys Pro Met
                725                 730                 735

Asp Ser Ile Thr Ser Pro Ser Ile Ala Glu Leu His Asn Ser Val Thr
            740                 745                 750

Ser Cys Asp Pro Pro Leu Arg Leu Thr Lys Ser Ser His Phe Thr Asn
            755                 760                 765

Ile Lys Ala Val Asp Lys Leu Asp His Ser Arg Ser Asn Thr Pro Ser
770                 775                 780

Pro Leu Asn Leu Ser Ser Thr Ser Ser Lys Asn Ser His Ser Ser Ser
785                 790                 795                 800

Tyr Thr Pro Asn Ser Phe Ser Ser Glu Glu Leu Gln Ala Glu Pro Leu
                805                 810                 815

Asp Leu Ser Leu Pro Lys Gln Met Arg Glu Pro Lys Gly Ile Ile Ala
            820                 825                 830

Thr Lys Asn Lys Thr Lys Ala Thr Ser Ile Asn Leu Asp His Asn Ser
            835                 840                 845

Val Ser Ser Ser Glu Asn Ser Asp Glu Pro Leu Asn Leu Thr Phe
850                 855                 860

Ile Lys Lys Glu Phe Ser Asn Ser Asn Asn Leu Asp Asn Lys Ser Asn
865                 870                 875                 880

Asn Pro Val Phe Gly Met Asn Pro Phe Ser Ala Lys Pro Leu Tyr Thr
                885                 890                 895

Pro Leu Pro Pro Gln Ser Ala Phe Pro Pro Ala Thr Phe Met Pro Pro
            900                 905                 910

Val Gln Thr Ser Ile Pro Gly Leu Arg Pro Tyr Pro Gly Leu Asp Gln
            915                 920                 925

Met Ser Phe Leu Pro His Met Ala Tyr Thr Tyr Pro Thr Gly Ala Ala
            930                 935                 940

Thr Phe Ala Asp Met Gln Gln Arg Arg Lys Tyr Gln Arg Lys Gln Gly
945                 950                 955                 960

Phe Gln Gly Asp Leu Leu Asp Gly Ala Gln Asp Tyr Met Ser Gly Leu
                965                 970                 975

Asp Asp Met Thr Asp Ser Asp Ser Cys Leu Ser Arg Lys Lys Ile Lys
            980                 985                 990

Lys Thr Glu Ser Gly Met Tyr Ala Cys Asp Leu Cys Asp Lys Thr Phe
            995                 1000                1005

Gln Lys Ser Ser Ser Leu Leu Arg His Lys Tyr Glu His Thr Gly

```
                    1010                1015                1020

Lys  Arg  Pro  His  Gln  Cys  Gln  Ile  Cys  Lys  Lys  Ala  Phe  Lys  His
               1025                1030                1035

Lys  His  His  Leu  Ile  Glu  His  Ser  Arg  Leu  His  Ser  Gly  Glu  Lys
          1040                1045                1050

Pro  Tyr  Gln  Cys  Asp  Lys  Cys  Gly  Lys  Arg  Phe  Ser  His  Ser  Gly
     1055                1060                1065

Ser  Tyr  Ser  Gln  His  Met  Asn  His  Arg  Tyr  Ser  Tyr  Cys  Lys  Arg
1070                1075                1080

Glu  Ala  Glu  Glu  Arg  Glu  Ala  Ala  Glu  Arg  Glu  Ala  Arg  Glu  Lys
               1085                1090                1095

Gly  His  Leu  Gly  Pro  Thr  Glu  Leu  Leu  Met  Asn  Arg  Ala  Tyr  Leu
          1100                1105                1110

Gln  Ser  Ile  Thr  Pro  Gln  Gly  Tyr  Ser  Asp  Ser  Glu  Glu  Arg  Glu
     1115                1120                1125

Ser  Met  Pro  Arg  Asp  Gly  Glu  Ser  Glu  Lys  Glu  His  Glu  Lys  Glu
1130                1135                1140

Gly  Glu  Glu  Gly  Tyr  Gly  Lys  Leu  Arg  Arg  Arg  Asp  Gly  Asp  Glu
               1145                1150                1155

Glu  Glu  Glu  Glu  Glu  Glu  Glu  Ser  Glu  Asn  Lys  Ser  Met  Asp
          1160                1165                1170

Thr  Asp  Pro  Glu  Thr  Ile  Arg  Asp  Glu  Glu  Thr  Gly  Asp  His
     1175                1180                1185

Ser  Met  Asp  Asp  Ser  Ser  Glu  Asp  Gly  Lys  Met  Glu  Thr  Lys  Ser
1190                1195                1200

Asp  His  Glu  Glu  Asp  Asn  Met  Glu  Asp  Gly  Met  Gly
               1205                1210                1215

<210> SEQ ID NO 18
<211> LENGTH: 654
<212> TYPE: PRT
<213> ORGANISM: Homo sapiens

<400> SEQUENCE: 18

Met  Asn  Gln  Pro  Gln  Arg  Met  Ala  Pro  Val  Gly  Thr  Asp  Lys  Glu  Leu
1                   5                   10                  15

Ser  Asp  Leu  Leu  Asp  Phe  Ser  Met  Met  Phe  Pro  Leu  Pro  Val  Thr  Asn
               20                  25                  30

Gly  Lys  Gly  Arg  Pro  Ala  Ser  Leu  Ala  Gly  Ala  Gln  Phe  Gly  Gly  Ser
          35                  40                  45

Gly  Leu  Glu  Asp  Arg  Pro  Ser  Ser  Gly  Ser  Trp  Gly  Ser  Gly  Asp  Gln
     50                  55                  60

Ser  Ser  Ser  Ser  Phe  Asp  Pro  Ser  Arg  Thr  Phe  Ser  Glu  Gly  Thr  His
65                  70                  75                  80

Phe  Thr  Glu  Ser  His  Ser  Ser  Leu  Ser  Ser  Thr  Phe  Leu  Gly  Pro
               85                  90                  95

Gly  Leu  Gly  Gly  Lys  Ser  Gly  Glu  Arg  Gly  Ala  Tyr  Ala  Ser  Phe  Gly
          100                 105                 110

Arg  Asp  Ala  Gly  Val  Gly  Gly  Leu  Thr  Gln  Ala  Gly  Phe  Leu  Ser  Gly
     115                 120                 125

Glu  Leu  Ala  Leu  Asn  Ser  Pro  Gly  Pro  Leu  Ser  Pro  Ser  Gly  Met  Lys
130                 135                 140

Gly  Thr  Ser  Gln  Tyr  Tyr  Pro  Ser  Tyr  Ser  Gly  Ser  Ser  Arg  Arg  Arg
145                 150                 155                 160
```

```
Ala Ala Asp Gly Ser Leu Asp Thr Gln Pro Lys Lys Val Arg Lys Val
            165                 170                 175

Pro Pro Gly Leu Pro Ser Ser Val Tyr Pro Pro Ser Ser Gly Glu Asp
        180                 185                 190

Tyr Gly Arg Asp Ala Thr Ala Tyr Pro Ser Ala Lys Thr Pro Ser Ser
    195                 200                 205

Thr Tyr Pro Ala Pro Phe Tyr Val Ala Asp Gly Ser Leu His Pro Ser
        210                 215                 220

Ala Glu Leu Trp Ser Pro Gly Gln Ala Gly Phe Gly Pro Met Leu
225                 230                 235                 240

Gly Gly Gly Ser Ser Pro Leu Pro Leu Pro Pro Gly Ser Gly Pro Val
                245                 250                 255

Gly Ser Ser Gly Ser Ser Ser Thr Phe Gly Gly Leu His Gln His Glu
            260                 265                 270

Arg Met Gly Tyr Gln Leu His Gly Ala Glu Val Asn Gly Gly Leu Pro
        275                 280                 285

Ser Ala Ser Ser Phe Ser Ser Ala Pro Gly Ala Thr Tyr Gly Gly Val
        290                 295                 300

Ser Ser His Thr Pro Pro Val Ser Gly Ala Asp Ser Leu Leu Gly Ser
305                 310                 315                 320

Arg Gly Thr Thr Ala Gly Ser Ser Gly Asp Ala Leu Gly Lys Ala Leu
                325                 330                 335

Ala Ser Ile Tyr Ser Pro Asp His Ser Ser Asn Asn Phe Ser Ser Ser
            340                 345                 350

Pro Ser Thr Pro Val Gly Ser Pro Gln Gly Leu Ala Gly Thr Ser Gln
            355                 360                 365

Trp Pro Arg Ala Gly Ala Pro Gly Ala Leu Ser Pro Ser Tyr Asp Gly
        370                 375                 380

Gly Leu His Gly Leu Gln Ser Lys Ile Glu Asp His Leu Asp Glu Ala
385                 390                 395                 400

Ile His Val Leu Arg Ser His Ala Val Gly Thr Ala Gly Asp Met His
                405                 410                 415

Thr Leu Leu Pro Gly His Gly Ala Leu Ala Ser Gly Phe Thr Gly Pro
                420                 425                 430

Met Ser Leu Gly Gly Arg His Ala Gly Leu Val Gly Gly Ser His Pro
        435                 440                 445

Glu Asp Gly Leu Ala Gly Ser Thr Ser Leu Met His Asn His Ala Ala
        450                 455                 460

Leu Pro Ser Gln Pro Gly Thr Leu Pro Asp Leu Ser Arg Pro Pro Asp
465                 470                 475                 480

Ser Tyr Ser Gly Leu Gly Arg Ala Gly Ala Thr Ala Ala Ala Ser Glu
                485                 490                 495

Ile Lys Arg Glu Glu Lys Glu Asp Glu Glu Asn Thr Ser Ala Ala Asp
            500                 505                 510

His Ser Glu Glu Glu Lys Lys Glu Leu Lys Ala Pro Arg Ala Arg Thr
        515                 520                 525

Ser Pro Asp Glu Asp Glu Asp Leu Leu Pro Pro Glu Gln Lys Ala
530                 535                 540

Glu Arg Glu Lys Glu Arg Val Ala Asn Asn Ala Arg Glu Arg Leu
545                 550                 555                 560

Arg Val Arg Asp Ile Asn Glu Ala Phe Lys Glu Leu Gly Arg Met Cys
                565                 570                 575

Gln Leu His Leu Asn Ser Glu Lys Pro Gln Thr Lys Leu Leu Ile Leu
```

|   |   |   |   |   |   |   |   |   |   |   |   |
|---|---|---|---|---|---|---|---|---|---|---|---|
|   |   | 580 |   |   |   | 585 |   |   |   | 590 |   |
| His | Gln | Ala | Val | Ser | Val | Ile | Leu | Asn | Leu | Glu | Gln |
|   |   |   | 595 |   |   |   | 600 |   |   |   | 605 |
| Gln | Val | Arg | Glu |   |   |   |   |   |   |   |   |

| Arg | Asn | Leu | Asn | Pro | Lys | Ala | Ala | Cys | Leu | Lys | Arg |
|---|---|---|---|---|---|---|---|---|---|---|---|
|   |   |   | 610 |   |   |   | 615 |   |   |   | 620 |
| Arg | Glu | Glu | Glu |   |   |   |   |   |   |   |   |

| Lys | Val | Ser | Gly | Val | Val | Gly | Asp | Pro | Gln | Met | Val |
|---|---|---|---|---|---|---|---|---|---|---|---|
| 625 |   |   |   | 630 |   |   |   | 635 |   |   |   |
| Leu | Ser | Ala | Pro |   |   |   |   |   |   |   | 640 |

| His | Pro | Gly | Leu | Ser | Glu | Ala | His | Asn | Pro | Ala | Gly |
|---|---|---|---|---|---|---|---|---|---|---|---|
|   |   |   | 645 |   |   |   | 650 |   |   |   |   |
| His | Met |   |   |   |   |   |   |   |   |   |   |

<210> SEQ ID NO 19
<211> LENGTH: 4396
<212> TYPE: DNA
<213> ORGANISM: Homo sapiens

<400> SEQUENCE: 19

| | | | | | |
|---|---|---|---|---|---|
| gcctgaggtg | cccgccctgg | ccccaggaga | atgaaccagc | cgcagaggat | ggcgcctgtg | 60 |
| ggcacagaca | aggagctcag | tgacctcctg | gacttcagca | tgatgttccc | gctgcctgtc | 120 |
| accaacggga | agggccggcc | cgcctccctg | gccggggcgc | agttcggagg | ttcaggtctt | 180 |
| gaggaccggc | ccagctcagg | ctcctggggc | agcggcgacc | agagcagctc | ctcctttgac | 240 |
| cccagccgga | ccttcagcga | gggcacccac | ttcactgagt | cgcacagcag | cctctcttca | 300 |
| tccacattcc | tgggaccggg | actcggaggc | aagagcggtg | agcggggcgc | ctatgcctcc | 360 |
| ttcgggagag | acgcaggcgt | gggcggcctg | actcaggctg | gcttcctgtc | aggcgagctg | 420 |
| gccctcaaca | gccccgggcc | cctgtcccct | tcgggcatga | aggggacctc | ccagtactac | 480 |
| ccctcctact | ccggcagctc | ccggcggaga | gcggcagacg | gcagcctaga | cacgcagccc | 540 |
| aagaaggtcc | ggaaggtccc | gccgggtctt | ccatcctcgg | tgtacccacc | cagctcaggt | 600 |
| gaggactacg | gcagggatgc | caccgcctac | ccgtccgcca | agaccccag | cagcacctat | 660 |
| cccgccccct | tctacgtggc | agatggcagc | ctgcaccct | cagccgagct | ctggagtccc | 720 |
| ccgggccagg | cgggcttcgg | gcccatgctg | ggtggggct | catccccgct | gcccctcccg | 780 |
| cccggtagcg | gcccggtggg | cagcagtgga | agcagcagca | cgtttggtgg | cctgcaccag | 840 |
| cacgagcgta | tgggctacca | gctgcatgga | gcagaggtga | acggtgggct | cccatctgca | 900 |
| tcctcctttct | cctcagcccc | cggagccacg | tacggcggcg | tctccagcca | cacgccgcct | 960 |
| gtcagcgggg | ccgacagcct | cctgggctcc | gagggacca | cagctggcag | ctccggggat | 1020 |
| gccctcggca | aagcactggc | ctcgatctac | tccccggatc | actcaagcaa | taacttctcg | 1080 |
| tccagcccctt | ctaccccccgt | gggctccccc | cagggcctgg | caggaacgtc | acagtggcct | 1140 |
| cgagcaggag | ccccggtgc | cttatcgccc | agctacgacg | ggggtctcca | cggcctgcag | 1200 |
| agtaagatag | aagaccacct | ggacgaggcc | atccacgtgc | tccgcagcca | cgccgtgggc | 1260 |
| acagccggcg | acatgcacac | gctgctgcct | ggccacgggg | cgctggcctc | aggtttcacc | 1320 |
| ggccccatgt | cgctgggtgg | gcggcacgca | ggcctggttg | gaggcagcca | ccccgaggac | 1380 |
| ggcctcgcag | gcagcaccag | cctcatgcac | aaccacgcgg | ccctccccag | ccagccaggc | 1440 |
| accctccctg | acctgtctcg | gcctcccgac | tcctacagtg | ggctagggcg | agcaggtgcc | 1500 |
| acggcggccg | ccagcgagat | caagcgggag | gagaaggagg | acgaggagaa | cacgtcagcg | 1560 |
| gctgaccact | cggaggagga | gaagaaggag | ctgaaggccc | ccggggcccg | gaccagccca | 1620 |
| gacgaggacac | aggacgacct | tctcccccca | gagcagaagg | ccgagcggga | gaaggagcgc | 1680 |
| cgggtggcca | ataacgcccg | ggagcggctg | cgggtccgtg | acatcaacga | ggcctttaag | 1740 |

```
gagctgggc gcatgtgcca actgcacctc aacagcgaga agccccagac caaactgctc    1800
atcctgcacc aggctgtctc ggtcatcctg aacttggagc agcaagtgcg agagcggaac    1860
ctgaatccca aagcagcctg tttgaaacgg cgagaagagg aaaaggtgtc aggtgtggtt    1920 ggagacccc agatggtgct ttcagctccc cacccaggcc tgagcgaagc ccacaacccc     1980
gccgggcaca tgtgaaaggt atgcctccgt gggacgagcc accgcttc agccctgtgc      2040 tctggcccca gaagccggac tcgagacccc gggcttcatc cacatccaca cctcacacac    2100
ctgttgtcag catcgagcca acaccaacct gacaaggttc ggagtgatgg gggcggccaa    2160
ggtgacactg ggtccaggag ctccctgggg ccctggccta ccactcactg gcctcgctcc    2220
ccctgtcccc gaatctcagc caccgtgtca ctctgtgacc tgtcccatgg atcctgaaac    2280
tgcatcttgg ccctgttgcc tgggctgaca ggagcatttt ttttttttcc agtaaacaaa    2340
acctgaaagc aagcaacaaa acatacactt tgtcagagaa gaaaaaaatg ccttaactat    2400
aaaaagcgga gaaatggaaa catatcactc aaggggatg ctgtggaaac ctggcttatt     2460
cttctaaagc caccagcaaa ttgtgcctaa gcgaaatatt ttttttaagg aaaataaaaa    2520
cattagttac aagatttttt ttttcttaag gtagatgaaa attagcaagg atgctgcctt    2580
tggtctctgg ttttttaag ctttttttgc atatgttttg taagcaacaa attttttgt      2640 ataaagtcc cgtgtctctc gctatttctg ctgctgttcc tagactgagc attgcatttc     2700
ttgatcaacc agatgattaa acgttgtatt aaaaagaccc cgtgtaaacc tgagccccc     2760 ccgtccccc ccccggaagc cactgcacac agacagacgg ggacaggcgg cgggtctttt    2820 gttttttga tgttgggggt tctcttggtt ttgtcatgtg gaaagtgatg cgtgggcgtt     2880
ccctgatgaa ggcaccttgg ggcttccctg ccgcatcctc tcccctcagg aaggggactg    2940
acctgggctt ggggaaggg acgtcagcaa ggtggctctg accctcccag gtgactctgc     3000
caagcagctg tggccccagc ggtacccta caacgccct ccccaggccc cctaagctg       3060 ctctcccttg gaacctgcac agctctctga aatgggcat tttgttggga ccagtgaccc     3120
ctggcatggg gaccacaccc tggagcccgg tgctggggac ctcctggaca ccctgtcctt    3180
cactccttgc cccagggacc caggctcatg ctctgaactc tggctgagag gagtctgctc    3240
aggagccagc acaggacacc ccccacccca ccccaccatg tccccattac accagagggc    3300
catcgtgacg tagacaggat gccagggggcc tgaccagcct ccccaatgct ggggagcatc   3360
cctggcctgg ggccacacct gctgccctcc ctctgtgtgg tccaagggca agagtggctg    3420 gagccgggg actgtgctgg tctgagcccc acgaaggcct tgggctgtgg ctccgaccct    3480
gctgcagaac cagcagggtg tccctcggg cccatctgtg tccatgtcc cagcacccag     3540 gcctctctcc aggtctcctt ttctggtctt ttgccatgag ggtaaccagc tcttcccagc    3600
tggctgggac tgtcttgggt ttaaaactgc aagtctccta ccctgggatc ccatccagtt    3660
ccacacgaac tagggcagtg gtcactgtgg cacccaggtg tgggcctggc tagctggggg    3720
ccttcatgtg ccttcatgc ccctccctgc attgaggcct tgtggacccc tgggctggct    3780
gtgttcatcc ccgctgcagg tcgggcgtct ccccccgtgc cactcctgag actccaccgt    3840 taccccagg agatcctgga ctgcctgact ccctcccca gactggcttg ggagcctggg     3900 cccatggta gatgcaaggg aaacctcaag gccagctcaa tgcctggtat ctgccccag     3960 tccaggccag gcggagggga ggggctgtcc ggctgcctct cccttctcgg tggcttcccc    4020
tgcgccctgg gagtttgatc tcttaaggga acttgcctct ccctcttgtt ttgctcctgc    4080
```

-continued

```
cctgcccta ggtctgggtg gcagtggccc catagcctct ggaactgtgc gttctgcata   4140
gaattcaaac gagattcacc cagcgcgagg aggaagaaac agcagttcct gggaaccaca   4200
attatggggg gtgggggtg tgatctgagt gcctcaagat ggttttcaaa aaatttttt    4260 taaagaaaat aattgtatac gtgtcaacac agctggctgg atgattggga ctttaaaacg   4320
accctctttc aggtggattc agagacctgt cctgtatata acagcactgt agcaataaac   4380
gtgacatttt ataaag                                                  4396
```

<210> SEQ ID NO 20
<211> LENGTH: 648
<212> TYPE: PRT
<213> ORGANISM: Mus musculus

<400> SEQUENCE: 20

```
Met Met Asn Gln Ser Gln Arg Met Ala Pro Val Gly Ser Asp Lys Glu
 1               5                  10                  15

Leu Ser Asp Leu Leu Asp Phe Ser Met Met Phe Pro Leu Pro Val Ala
            20                  25                  30

Asn Gly Lys Ser Arg Pro Ala Ser Leu Gly Gly Thr Gln Phe Ala Gly
        35                  40                  45

Ser Gly Leu Glu Asp Arg Pro Ser Ser Gly Ser Trp Gly Ser Ser Asp
    50                  55                  60

Gln Asn Ser Ser Phe Asp Pro Ser Arg Thr Tyr Ser Glu Gly Ala
65                  70                  75                  80

His Phe Ser Asp Ser His Ser Ser Leu Pro Pro Ser Thr Phe Leu Gly
                85                  90                  95

Ala Gly Leu Gly Gly Lys Gly Ser Glu Arg Asn Ala Tyr Ala Thr Phe
            100                 105                 110

Gly Arg Asp Thr Ser Val Gly Thr Leu Ser Gln Ala Gly Phe Leu Pro
        115                 120                 125

Gly Glu Leu Ser Leu Ser Ser Pro Gly Pro Leu Ser Pro Ser Gly Ile
    130                 135                 140

Lys Ser Ser Ser Gln Tyr Tyr Pro Ser Phe Pro Ser Asn Pro Arg Arg
145                 150                 155                 160

Arg Ala Ala Asp Gly Gly Leu Asp Thr Gln Pro Lys Lys Val Arg Lys
                165                 170                 175

Val Pro Pro Gly Leu Pro Ser Ser Val Tyr Pro Pro Ser Ser Gly Asp
            180                 185                 190

Ser Tyr Ser Arg Asp Ala Ala Ala Tyr Pro Ser Ala Lys Thr Pro Ser
        195                 200                 205

Ser Ala Tyr Pro Ser Pro Phe Tyr Val Ala Asp Gly Ser Leu His Pro
    210                 215                 220

Ser Ala Glu Leu Trp Ser Thr Pro Ser Gln Val Gly Phe Gly Pro Met
225                 230                 235                 240

Leu Gly Asp Gly Ser Ser Pro Leu Pro Leu Ala Pro Gly Ser Ser Ser
                245                 250                 255

Val Gly Ser Gly Thr Phe Gly Gly Leu Gln Gln Gln Asp Arg Met Gly
            260                 265                 270

Tyr Gln Leu His Gly Ser Glu Val Asn Gly Ser Leu Pro Ala Val Ser
        275                 280                 285

Ser Phe Ser Ala Ala Pro Gly Thr Tyr Ser Gly Thr Ser Gly His Thr
    290                 295                 300

Pro Pro Val Ser Gly Ala Ala Ala Glu Ser Leu Leu Gly Thr Arg Gly
305                 310                 315                 320
```

Thr Thr Ala Ser Ser Ser Gly Asp Ala Leu Gly Lys Ala Leu Ala Ser
              325                 330                 335

Ile Tyr Ser Pro Asp His Ser Ser Asn Asn Phe Ser Pro Ser Pro Ser
              340                 345                 350

Thr Pro Val Gly Ser Pro Gln Gly Leu Pro Gly Thr Ser Gln Trp Pro
              355                 360                 365

Arg Ala Gly Ala Pro Ser Ala Leu Ser Pro Asn Tyr Asp Ala Gly Leu
         370                 375                 380

His Gly Leu Ser Lys Met Glu Asp Arg Leu Asp Glu Ala Ile His Val
385                 390                 395                 400

Leu Arg Ser His Ala Val Gly Thr Ala Ser Asp Leu His Gly Leu Leu
              405                 410                 415

Pro Gly His Gly Ala Leu Thr Thr Ser Phe Thr Gly Pro Met Ser Leu
              420                 425                 430

Gly Gly Arg His Ala Gly Leu Val Gly Gly Ser His Pro Glu Glu Gly
              435                 440                 445

Leu Thr Ser Gly Ala Ser Leu Leu His Asn His Ala Ser Leu Pro Ser
         450                 455                 460

Gln Pro Ser Ser Leu Pro Asp Leu Ser Gln Arg Pro Pro Asp Ser Tyr
465                 470                 475                 480

Ser Gly Leu Gly Arg Ala Gly Thr Thr Ala Gly Ala Ser Glu Ile Lys
              485                 490                 495

Arg Glu Glu Lys Glu Asp Glu Glu Ile Ala Ser Val Ala Asp Ala Glu
              500                 505                 510

Glu Asp Lys Lys Asp Leu Lys Val Pro Arg Thr Arg Thr Ser Ser Thr
              515                 520                 525

Asp Glu Val Leu Ser Leu Glu Glu Lys Asp Leu Arg Asp Arg Glu Arg
         530                 535                 540

Arg Met Ala Asn Asn Ala Arg Glu Arg Val Arg Val Arg Asp Ile Asn
545                 550                 555                 560

Glu Ala Phe Arg Glu Leu Gly Arg Met Cys Gln Leu His Leu Lys Ser
              565                 570                 575

Asp Lys Ala Gln Thr Lys Leu Leu Ile Leu Gln Gln Ala Val Gln Val
              580                 585                 590

Ile Leu Gly Leu Glu Gln Gln Val Arg Glu Arg Asn Leu Asn Pro Lys
              595                 600                 605

Ala Ala Cys Leu Lys Arg Arg Glu Glu Glu Lys Val Ser Gly Val Val
         610                 615                 620

Gly Asp Pro Gln Leu Pro Leu Ser Ala Ala His Pro Gly Leu Gly Glu
625                 630                 635                 640

Ala His Asn Pro Ala Gly His Leu
              645

<210> SEQ ID NO 21
<211> LENGTH: 2898
<212> TYPE: DNA
<213> ORGANISM: Mus musculus

<400> SEQUENCE: 21
gcgccggcgg ctgcgggcgt agcgggccac cgcgggccac cgccgcgcgc cgccgcctct    60
gctacagtcc cttcccgcgg ggcctgctct gagagaagct cgagagagac caggcgacgc   120
gaacgcgagt ggggaggagg aaggacgcgc gaccccgagc cctgcgcgct cccgccgccc   180
acgcgcgacc ctcggggacg cgcccgccac ccttttgtcc ccggggtccc cgagggcggt   240

```
gggcagcagg gagccccggt gcacccggtg catgccccg cccagcaggg ctgtctctag      300
acctggggga cgcaccccag ttccaacacc tgctgtcctg ggtggatgat gaaccagtct      360
cagagaatgg cacccgtggg ctctgacaag gaactgagtg acctcctgga cttcagcatg      420
atgttcccgc tacctgtggc caatgggaag agccggcccg cctccctcgg gggaacccag      480
tttgcaggct caggactgga ggaccgaccc agctcaggct cctggggcag cagtgaccag      540
aacagttctt cctttgaccc tagccggaca tacagcgaag gtgcccactt cagtgactcc      600
cacagcagcc tgccgccttc cacgttccta ggagctgggc ttggaggcaa gggcagtgag      660
cggaatgcct atgccaccTt tgggagagac accagtgttg gcaccttgag tcaggctggc      720
ttcctgccag gtgagctgag cctcagcagt cccgggccac tgtccccatc gggcatcaag      780
agcagctccc agtattaccc ctcattcccc agcaaccctc gtcggagagc tgcagatggt      840
ggcctggata tcagccgaa gaaggtccgg aaggttccgc ctggtctccc ttcctcggtg      900
tatccgccca gctcaggtga cagctacagc agggatgctg cagcctaccc ctccgccaag      960
acccccagca gcgcttaccc ctcccccttc tacgtggcag atggcagcct gcacccatca     1020
gctgagctct ggagtacgcc tagccaggtg ggctttgggc ccatgctagg tgacggctct     1080
tcccctctgc cccttgcacc gggcagcagc tccgtgggca gtggtacctt tgggggcctc     1140
cagcagcagg atcgcatggg ctaccagctg catggatctg aggttaatgg ctcgctccca     1200
gctgtatcca gcttttcggc tgcccctggc acttacagtg ggacttccgg ccacacgccc     1260
cctgtgagtg gggccgcagc tgaaagcctc ctaggcaccc gagggactac agccagcagc     1320
tcaggggatg cccttgggaa ggcactggcc tcgatctact ccccggatca ctccagcaat     1380
aatttctcac ctagcccctc aacgcctgtg ggttcacccc agggcctgcc agggacatca     1440
cagtggcccc gggcaggagc gcccagtgcc ttatccccca actacgatgc aggtctccat     1500
ggcctgagca agatggagga ccgcttggac gaggccatcc atgtcctgcg aagccacgct     1560
gttggcaccg ctagcgatct ccatgggctt ttgcctggcc atggcgcact gaccacgagc     1620
ttcaccggcc ccatgtcact gggcgggcgg catgccggcc tggtcggggg aagccatcct     1680
gaggagggcc tcacaagtgg ggccagtctt ttgcataacc atgccagcct ccccagccag     1740
cccagttccc tccctgacct ctcacagaga cctcccgact cctatagtgg actcgggagg     1800
gcaggcacaa cagcgggtgc cagcgagatc aagcgggagg agaaagagga tgaggaaatc     1860
gcatcagtag ccgacgccga agaggacaag aaggacctga aggtcccacg cacgcgcacc     1920
agcagtacag atgaggtgct gtccctggag gagaaggacc tgagggaccg ggagaggcgt     1980
atggccaata cgctcgggag gcgggtgcgc gtgcgggaca ttaacgaggc cttccgggag     2040
ctgggccgca tgtgccagct gcacctcaag tcggataagg cgcagaccaa gctgctcatc     2100
ctgcagcagg cggtgcaggt catcctgggc ctggagcagc aggtgcgaga acgcaacctg     2160
aaccccaaag cagcctgctt gaagcggagg gaggaggaga aggtgtctgg cgtggtcggg     2220
gacccacagc tgcccctgtc agccgcccac ccgggcctgg gtgaggccca aacccagcc      2280 gggcacctgt gagccgtcac agcttcttcg ttggaccagg gaccaccata tctctgcccg     2340
gggtgcatca ggacggttct ggatgagaca ggtctccatc gaagcatgag cagagagagg     2400
gctctgggga cacttcaggg cctggggagg gtggcactga acagctccct gcttggcccc     2460
agtgaccaag cagaaaagtt ccttcctctc ggttaaccag aactggaaac aaagcagcat     2520
gctccctttt caaaaaggaa agaaagatgc cttaactatg taagacggaa gagtcggacc     2580
```

```
gtgccctggc agggcggcct gggactggct tctacttcag agccaccagc acatcgtgcc      2640
taagcatttt tcgttttttt aaaggagaat aaaggaacat tagttttcag attttttttt      2700
taaatgtaga caaaagttag caagaacgag gccttccgtg tctttttttt ttcccttagc      2760
ttttttttcc gtatgttttg taagcaacaa atttttgtat aaaagtctca tgtctgtttc      2820
tgtttctaga aaaaaaaaa aaaaaaaaa aaaaatatt taaaaaaaaa aaaaaaaaaa        2880
aaaaaaaaaa aaaaaaaa                                                    2898
```

<210> SEQ ID NO 22
<211> LENGTH: 76
<212> TYPE: DNA
<213> ORGANISM: Artificial
<220> FEATURE:
<223> OTHER INFORMATION: Human siRNA insert 1

<400> SEQUENCE: 22

```
ggatcccgta tttacgacct ttcttggcat tgatatccgt gccaagaaag gtcgtaaata      60
ttttttccaa aagctt                                                      76
```

<210> SEQ ID NO 23
<211> LENGTH: 76
<212> TYPE: DNA
<213> ORGANISM: Artificial
<220> FEATURE:
<223> OTHER INFORMATION: Human siRNA insert 2

<400> SEQUENCE: 23

```
ggatcccgtt tcttgagcca taaatgctct tgatatccgg agcatttatg gctcaagaaa      60
ttttttccaa aagctt                                                      76
```

<210> SEQ ID NO 24
<211> LENGTH: 76
<212> TYPE: DNA
<213> ORGANISM: Artificial
<220> FEATURE:
<223> OTHER INFORMATION: Human siRNA insert 3

<400> SEQUENCE: 24

```
ggatcccgtt agtgagtcag caaattgatt tgatatccga tcaatttgct gactcactaa      60
ttttttccaa aagctt                                                      76
```

<210> SEQ ID NO 25
<211> LENGTH: 76
<212> TYPE: DNA
<213> ORGANISM: Artificial
<220> FEATURE:
<223> OTHER INFORMATION: Human siRNA insert 4

<400> SEQUENCE: 25

```
ggatcccgtg tgagccatga gccactgagt tgatatccgc tcagtggctc atggctcaca      60
ttttttccaa aagctt                                                      76
```

<210> SEQ ID NO 26
<211> LENGTH: 76
<212> TYPE: DNA
<213> ORGANISM: Artificial
<220> FEATURE:
<223> OTHER INFORMATION: Human siRNA insert 5

<400> SEQUENCE: 26

```
ggatcccgca tagtcaacaa ccaggcaggt tgatatccgc ctgcctggtt gttgactatg      60
```

```
tttttttccaa aagctt                                                    76

<210> SEQ ID NO 27
<211> LENGTH: 76
<212> TYPE: DNA
<213> ORGANISM: Artificial
<220> FEATURE:
<223> OTHER INFORMATION: Murine siRNA insert 1

<400> SEQUENCE: 27
ggatcccgtt gttctggtta tccgcgagct tgatatccgg ctcgcggata accagaacaa     60 tttttttccaa aagctt                                                    76

<210> SEQ ID NO 28
<211> LENGTH: 76
<212> TYPE: DNA
<213> ORGANISM: Artificial
<220> FEATURE:
<223> OTHER INFORMATION: Murine siRNA insert 2

<400> SEQUENCE: 28
ggatcccgtc tgtgacgaca acgaactgct tgatatccgg cagttcgttg tcgtcacaga     60 tttttttccaa aagctt                                                    76

<210> SEQ ID NO 29
<211> LENGTH: 76
<212> TYPE: DNA
<213> ORGANISM: Artificial
<220> FEATURE:
<223> OTHER INFORMATION: Murine siRNA insert 3

<400> SEQUENCE: 29
ggatcccgta gatgccgctt cactgtgatt tgatatccga tcacagtgaa gcggcatcta     60 tttttttccaa aagctt                                                    76

<210> SEQ ID NO 30
<211> LENGTH: 4828
<212> TYPE: DNA
<213> ORGANISM: Homo sapiens

<400> SEQUENCE: 30
agtggcgtcg gaactgcaaa gcacctgtga gcttgcggaa gtcagttcag actccagccc     60
gctccagccc ggcccgaccc gaccgcaccc ggcgcctgcc ctcgctcggc gtccccggcc    120
agccatgggc ccttggagcc gcagcctctc ggcgctgctg ctgctgctgc aggtctcctc    180
ttggctctgc caggagccgg agccctgcca ccctggcttt gacgccgaga gctacacgtt    240
cacggtgccc cggcgccacc tggagagagg ccgcgtcctg ggcagagtga attttgaaga    300
ttgcaccggt cgacaaagga cagcctattt ttccctcgac acccgattca agtgggcac     360 agatggtgtg attacagtca aaaggcctct acgtttcat aacccacaga tccatttctt     420
ggtctacgcc tgggactcca cctacagaaa gttttccacc aaagtcacgc tgaatacagt    480
ggggcaccac caccgccccc cgccccatca ggcctccgtt tctggaatcc aagcagaatt    540
gctcacattt cccaactcct ctcctggcct cagaagacag aagagagact gggttattcc    600
tcccatcagc tgcccagaaa tgaaaaagg cccatttcct aaaaacctgg ttcagatcaa    660
atccaacaaa gacaaagaag gcaaggtttt ctacagcatc actggccaag agctgacac    720 acccctgtt ggtgtcttta ttattgaaag agaaacagga tggctgaagg tgacagagcc    780
```

```
tctggataga gaacgcattg ccacatacac tctcttctct cacgctgtgt catccaacgg    840
gaatgcagtt gaggatccaa tggagatttt gatcacggta accgatcaga atgacaacaa    900
gcccgaattc acccaggagg tctttaaggg gtctgtcatg gaaggtgctc ttccaggaac    960
ctctgtgatg gaggtcacag ccacagacgc ggacgatgat gtgaacacct acaatgccgc   1020
catcgcttac accatcctca gccaagatcc tgagctccct gacaaaaata tgttcaccat   1080
taacaggaac acaggagtca tcagtgtggt caccactggg ctggaccgag agagtttccc   1140
tacgtatacc ctggtggttc aagctgctga ccttcaaggt gaggggttaa gcacaacagc   1200
aacagctgtg atcacagtca ctgacaccaa cgataatcct ccgatcttca atcccaccac   1260
gtacaagggt caggtgcctg agaacgaggc taacgtcgta atcaccacac tgaaagtgac   1320
tgatgctgat gcccccaata ccccagcgtg ggaggctgta tacaccatat gaatgatga    1380
tggtggacaa tttgtcgtca ccacaaatcc agtgaacaac gatggcattt tgaaaacagc   1440
aaagggcttg gattttgagg ccaagcagca gtacattcta cacgtagcag tgacgaatgt   1500
ggtacctttt gaggtctctc tcaccacctc cacagccacc gtcaccgtgg atgtgctgga   1560
tgtgaatgaa gcccccatct ttgtgcctcc tgaaaagaga gtggaagtgt ccgaggactt   1620
tggcgtgggc caggaaatca catcctacac tgcccaggag ccagacacat ttatggaaca   1680
gaaaataaca tatcggattt ggagagacac tgccaactgg ctggagatta atccggacac   1740
tggtgccatt tccactcggg ctgagctgga cagggaggat tttgagcacg tgaagaacag   1800
cacgtacaca gccctaatca tagctacaga caatggttct ccagttgcta ctggaacagg   1860
gacacttctg ctgatcctgt ctgatgtgaa tgacaacgcc cccatccag aacctcgaac    1920
tatattcttc tgtgagagga tccaaagcc tcaggtcata aacatcattg atgcagacct   1980
tcctcccaat acatctccct tcacagcaga actaacacac ggggcgagtg ccaactggac   2040
cattcagtac aacgacccaa cccaagaatc tatcattttg aagccaaaga tggccttaga   2100
ggtgggtgac tacaaaatca atctcaagct catggataac cagaataaag accaagtgac   2160
caccttagag gtcagcgtgt gtgactgtga aggggccgcc ggcgtctgta ggaaggcaca   2220
gcctgtcgaa gcaggattgc aaattcctgc cattctgggg attcttggag gaattcttgc   2280
tttgctaatt ctgattctgc tgctcttgct gtttcttcgg aggagagcgg tggtcaaaga   2340
gcccttactg cccccagagg atgacacccg ggacaacgtt tattactatg atgaagaagg   2400
aggcggagaa gaggaccagg actttgactt gagccagctg cacaggggcc tggacgctcg   2460
gcctgaagtg actcgtaacg acgttgcacc aaccctcatg agtgtccccc ggtatcttcc   2520
ccgccctgcc aatcccgatg aaattggaaa ttttattgat gaaaatctga agcggctga   2580
tactgacccc acagcccgc cttatgattc tctgctcgtg tttgactatg aaggaagcgg   2640
ttccgaagct gctagtctga gctccctgaa ctcctcagag tcagacaaag accaggacta   2700
tgactacttg aacgaatggg gcaatcgctt caagaagctg gctgacatgt acggaggcgg   2760
cgaggacgac tagggggactc gagagaggcg ggccccagac ccatgtgctg ggaaatgcag   2820
aaatcacgtt gctggtggtt tttcagctcc cttcccttga gatgagtttc tggggaaaaa   2880
aaagagactg gttagtgatg cagttagtat agctttatac tctctccact ttatagctct   2940
aataagtttg tgttagaaaa gtttcgactt atttcttaaa gcttttttt ttttcccatc   3000
actctttaca tggtggtgat gtccaaaaga tacccaaatt ttaatattcc agaagaacaa   3060
ctttagcatc agaaggttca cccagcacct tgcagatttt cttaaggaat tttgtctcac   3120
tttaaaaag aaggggagaa gtcagctact ctagttctgt tgttttgtgt atataatttt   3180
```

| | |
|---|---|
| ttaaaaaaaa tttgtgtgct tctgctcatt actacactgg tgtgtccctc tgccttttt | 3240 |
| ttttttttta agacagggtc tcattctatc ggccaggctg gagtgcagtg gtgcaatcac | 3300 |
| agctcactgc agccttgtcc tcccaggctc aagctatcct tgcacctcag cctcccaagt | 3360 |
| agctgggacc acaggcatgc accactacgc atgactaatt ttttaaatat ttgagacggg | 3420 |
| gtctccctgt gttacccagg ctggtctcaa actcctgggc tcaagtgatc ctcccatctt | 3480 |
| ggcctcccag agtattggga ttacagacat gagccactgc acctgccag ctcccccaact | 3540 |
| ccctgccatt ttttaagaga cagtttcgct ccatcgccca ggcctgggat gcagtgatgt | 3600 |
| gatcatagct cactgtaacc tcaaactctg gggctcaagc agttctccca ccagcctcct | 3660 |
| ttttattttt ttgtacagat ggggtcttgc tatgttgccc aagctggtct aaaactcctg | 3720 |
| gcctcaagca atccttctgc cttggccccc aaagtgctg ggattgtggg catgagctgc | 3780 |
| tgtgcccagc ctccatgttt aatatcaac tctcactcct gaattcagtt gctttgccca | 3840 |
| agataggagt tctctgatgc agaaattatt gggctctttt agggtaagaa gtttgtgtct | 3900 |
| ttgtctggcc acatcttgac taggtattgt ctactctgaa gaccttttaat ggcttccctc | 3960 |
| tttcatctcc tgagtatgta acttgcaatg ggcagctatc cagtgacttg ttctgagtaa | 4020 |
| gtgtgttcat taatgtttat ttagctctga agcaagagtg atatactcca ggacttagaa | 4080 |
| tagtgcctaa agtgctgcag ccaaagacag agcggaacta tgaaaagtgg gcttggagat | 4140 |
| ggcaggagag cttgtcattg agcctggcaa tttagcaaac tgatgctgag gatgattgag | 4200 |
| gtgggtctac ctcatctctg aaaattctgg aaggaatgga ggagtctcaa catgtgtttc | 4260 |
| tgacacaaga tccgtggttt gtactcaaag cccagaatcc ccaagtgcct gcttttgatg | 4320 |
| atgtctacag aaaatgctgg ctgagctgaa cacatttgcc caattccagg tgtgcacaga | 4380 |
| aaaccgagaa tattcaaaat tccaaatttt ttcttaggag caagaagaaa atgtggccct | 4440 |
| aaaggggtt agttgagggg taggggtag tgaggatctt gatttggatc tcttttatt | 4500 |
| taaatgtgaa tttcaacttt tgacaatcaa agaaaagact tttgttgaaa tagctttact | 4560 |
| gtttctcaag tgttttggag aaaaaaatca accctgcaat cacttttttgg aattgtcttg | 4620 |
| attttcggc agttcaagct atatcgaata tagttctgtg tagagaatgt cactgtagtt | 4680 |
| ttgagtgtat acatgtgtgg gtgctgataa ttgtgtattt tctttggggg tggaaaagga | 4740 |
| aaacaattca agctgagaaa agtattctca agatgcatt tttataaatt ttattaaaca | 4800 |
| attttgttaa accataaaa aaaaaaaa | 4828 |

<210> SEQ ID NO 31
<211> LENGTH: 3314
<212> TYPE: DNA
<213> ORGANISM: Mus musculus

<400> SEQUENCE: 31

| | |
|---|---|
| agccgcggcg cactactgag ttcccaagaa cttctgctag actcctgccc ggcctaaccc | 60 |
| ggccctgccc gaccgcaccc gagctcagtg tttgctcggc gtctgccggg tccgccatgg | 120 |
| gagcccggtg ccgcagcttt tccgcgctcc tgctcctgct gcaggtctcc tcatggcttt | 180 |
| gccaggagct ggagcctgag tcctgcagtc ccggcttcag ttccgaggtc tacaccttcc | 240 |
| cggtgccgga gaggcacctg agagaggcc atgtcctggg cagagtgaga tttgaaggat | 300 |
| gcaccggccg gccaaggaca gccttctttt cggaagactc ccgattcaaa gtggcgacag | 360 |
| acggcaccat cacagtgaag cggcatctaa agctccacaa gctggagacc agtttcctcg | 420 |

```
tccgcgcccg ggactccagt catagggagc tgtctaccaa agtgacgctg aagtccatgg      480
ggcaccacca tcaccggcac caccaccgcg accctgcctc tgaatccaac ccagagctgc      540
tcatgtttcc cagcgtgtac ccaggtctca gaagacagaa acgagactgg gtcatccctc      600
ccatcagctg ccccgaaaat gaaaagggtg aattcccaaa gaacctggtt cagatcaaat      660
ccaacaggga caaagaaaca aaggttttct acagcatcac cggccaagga gctgacaaac      720
cccccgttgg cgttttcatc attgagaggg agacaggctg gctgaaagtg acacagcctc      780
tggatagaga agccattgcc aagtacatcc tctattctca tgccgtgtca tcaaatgggg      840
aagcggtgga ggatcccatg gagatagtga tcacagtgac agatcagaat gacaacaggc      900
cagagtttac ccaggaggtg tttgagggat ccgttgcaga aggcgctgtt ccaggaacct      960
ccgtgatgaa ggtctcagcc accgatgcag acgatgacgt caacacctac aacgctgcca     1020
tcgcctacac catcgtcagc caggatcctg agctgcctca caaaacatg ttcactgtca      1080 atagggacac cggggtcatc agtgtgctca cctctgggct ggaccgagag agttacccta     1140
catacactct ggtggttcag gctgctgacc ttcaaggcga aggcttgagc acaacagcca     1200
aggctgtgat cactgtcaag gatattaatg acaacgctcc tgtcttcaac ccgagcacgt     1260
atcagggtca agtgcctgag aatgaggtca atgcccggat cgccacactc aaagtgaccg     1320
atgatgatgc ccccaacact ccggcgtgga agctgtgta caccgtagtc aacgatcctg      1380
accagcagtt cgttgtcgtc acagaccccca cgaccaatga tggcattttg aaaacagcca     1440
agggcttgga tttgaggcc aagcagcaat acatccttca tgtgagagtg gagaacgagg      1500 aacccttga ggggtctctt gtccttccaa cagccactgt cactgtggac gtggtagacg       1560
tgaatgaagc ccccatctctt atgcctgcgg agaggagagt cgaagtgccc gaagactttg    1620
gtgtgggtca ggaaatcaca tcttataccg ctcgagagcc ggacacgttc atggatcaga     1680
agatcacgta tcggatttgg agggacactg ccaactggct ggagattaac ccagagactg     1740
gtgccatttt cacgcgcgct gagatggaca gagaagacgc tgagcatgtg aagaacagca     1800
catatgtagc tctcatcatc gccacagatg atggttcacc cattgccact ggcacgggca     1860
ctcttctcct ggtcctgtta gacgtcaatg ataacgctcc catcccagaa cctcgaaaca     1920
tgcagttctg ccagaggaac ccacagcctc atatcatcac catcttggat ccagaccttc     1980
cccccaacac gtccccccttt actgctgagc taacccatgg ggccagcgtc aactggacca     2040
ttgagtataa tgacgcagct caagaatctc tcattttgca accaagaaag gacttagaga     2100
ttggcgaata caaatccat ctcaagctcg cggataacca gaacaaagac caggtgacca      2160
cgttggacgt ccatgtgtgt gactgtgaag ggacggtcaa caactgcatg aaggcgggaa     2220
tcgtggcagc aggattgcaa gttcctgcca tcctcggaat ccttggaggg atcctcgccc     2280
tgctgattct gatcctgctg ctcctactgt ttctacggag gagaacggtg gtcaaagagc     2340
ccctgctgcc accagatgat gatacccggg acaatgtgta ttactatgat gaagaaggag     2400
gtggagaaga agaccaggac tttgatttga gccagctgca cagggggcctg gatgcccgac     2460 cggaagtgac tcgaaatgat gtggctccca ccctcatgag cgtgccccag tatcgtcccc     2520
gtcctgccaa tcctgatgaa attggaaact tcatcgatga aaacctgaag gcagccgaca     2580
gcgaccccac ggcaccccct tacgactctc tgttggtgtt cgattacgag ggcagtggtt     2640
ctgaagccgc tagcctgagc tcactgaact cctctgagtc ggatcaggac caggactacg     2700
attatctgaa cgagtggggc aaccgattca agaagctggc ggacatgtac ggcggtggcg     2760
aggacgacta ggggactagc aagtctcccc cgtgtggcac catgggagat gcagaataat     2820
```

```
tatatcagtg gtctttcagc tccttccctg agtgtgtaga agagagactg atctgagaag    2880
tgtgcagatt gcatagtggt ctcattctcc ttactggact gtctgtgtta ggatggtttt    2940
cactgattgt tgaaatcttt ttttatttt tatttttaca gtgctgagat ataaactgtg     3000 ccttttttg tttgtttgtt tctgtttttg ttcttttgag cagaacaaaa aaaagggacc     3060
actatgcatg ctgcacacgt ctcagattct taggtacaca cctgattctt aggtgcatgc    3120
catagtggga tatgttgctt tgatcagaac ctgcagggag gttttcgggc accacttaag    3180
tttcttggcg tttctttcaa accgttctct aagatgcatt tttatgaatt ttattaaaga    3240
gttttgttaa aaaaaaaaaa aaaaaaaaaa aaaaaaaaaa aaaaaaaaaa aaaaaaaaaa    3300
aaaaaaaaaa aaaa                                                      3314
```

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
ggaacatagc cgtaaactgc                                                  20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
tcactgtgcc tgaacttacc                                                  20

<210> SEQ ID NO 34
<211> LENGTH: 22
<212> TYPE: DNA
<213> ORGANISM: Artificial
<220> FEATURE:
<223> OTHER INFORMATION: Primer

<400> SEQUENCE: 34
agaaggagct agaacagttt gc                                               22

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
cggttacaga accatactcg                                                  20

<210> SEQ ID NO 36
<211> LENGTH: 21
<212> TYPE: DNA
<213> ORGANISM: Artificial
<220> FEATURE:
<223> OTHER INFORMATION: Primer

<400> SEQUENCE: 36
ccatgtacat gagcactgtt g                                                21

<210> SEQ ID NO 37
<211> LENGTH: 21
<212> TYPE: DNA
<213> ORGANISM: Artificial
<220> FEATURE:
<223> OTHER INFORMATION: Primer

<400> SEQUENCE: 37
ctccaataac tcctggtatc c                                              21

<210> SEQ ID NO 38
<211> LENGTH: 20
<212> TYPE: DNA
<213> ORGANISM: Artificial
<220> FEATURE:
<223> OTHER INFORMATION: Primer

<400> SEQUENCE: 38
gagtttacag gcttgtggca                                                20

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
gagggcaatt cctgaggatt                                                20

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
gccctgacca ctccagttta                                                20

<210> SEQ ID NO 41
<211> LENGTH: 20
<212> TYPE: DNA
<213> ORGANISM: Artificial
<220> FEATURE:
<223> OTHER INFORMATION: Primer

<400> SEQUENCE: 41
ggagtcctgg atttccttcc                                                20

<210> SEQ ID NO 42
<211> LENGTH: 22
<212> TYPE: DNA
<213> ORGANISM: Artificial
<220> FEATURE:
<223> OTHER INFORMATION: Primer

<400> SEQUENCE: 42
gagcgcaaag actacctgaa ga                                             22

<210> SEQ ID NO 43
<211> LENGTH: 23
<212> TYPE: DNA
<213> ORGANISM: Artificial
<220> FEATURE:
<223> OTHER INFORMATION: Primer

```
<400> SEQUENCE: 43
cagcgatttc tatatccaga gcc                                         23

<210> SEQ ID NO 44
<211> LENGTH: 23
<212> TYPE: DNA
<213> ORGANISM: Artificial
<220> FEATURE:
<223> OTHER INFORMATION: Primer

<400> SEQUENCE: 44
cccactgatc cttcccgata cat                                         23

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
ccgatctggt tgaccttgag ca                                          22

<210> SEQ ID NO 46
<211> LENGTH: 23
<212> TYPE: DNA
<213> ORGANISM: Artificial
<220> FEATURE:
<223> OTHER INFORMATION: Primer

<400> SEQUENCE: 46
aacagacaca gccctcacaa aca                                         23

<210> SEQ ID NO 47
<211> LENGTH: 23
<212> TYPE: DNA
<213> ORGANISM: Artificial
<220> FEATURE:
<223> OTHER INFORMATION: Primer

<400> SEQUENCE: 47
cgggaacttg aactggaact gac                                         23

<210> SEQ ID NO 48
<211> LENGTH: 22
<212> TYPE: DNA
<213> ORGANISM: Artificial
<220> FEATURE:
<223> OTHER INFORMATION: Primer

<400> SEQUENCE: 48
ccatgccttc cagtatgtca tc                                          22

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
gtggtccagg tgttgaagta aatgt                                       25

<210> SEQ ID NO 50
```

```
<211> LENGTH: 25
<212> TYPE: DNA
<213> ORGANISM: Artificial
<220> FEATURE:
<223> OTHER INFORMATION: Primer

<400> SEQUENCE: 50
gctgggctca gtattcccca aatac                                    25

<210> SEQ ID NO 51
<211> LENGTH: 25
<212> TYPE: DNA
<213> ORGANISM: Artificial
<220> FEATURE:
<223> OTHER INFORMATION: Primer

<400> SEQUENCE: 51
gacgacaatc tctgacctga gtagc                                    25

<210> SEQ ID NO 52
<211> LENGTH: 25
<212> TYPE: DNA
<213> ORGANISM: Artificial
<220> FEATURE:
<223> OTHER INFORMATION: Primer

<400> SEQUENCE: 52
agaccctttg aagtcaagga caccg                                    25

<210> SEQ ID NO 53
<211> LENGTH: 25
<212> TYPE: DNA
<213> ORGANISM: Artificial
<220> FEATURE:
<223> OTHER INFORMATION: Primer

<400> SEQUENCE: 53
ccattgctga agaccttagt gatgc                                    25

<210> SEQ ID NO 54
<211> LENGTH: 20
<212> TYPE: DNA
<213> ORGANISM: Artificial
<220> FEATURE:
<223> OTHER INFORMATION: Primer

<400> SEQUENCE: 54
ggtattggca gttggaggaa                                          20

<210> SEQ ID NO 55
<211> LENGTH: 20
<212> TYPE: DNA
<213> ORGANISM: Artificial
<220> FEATURE:
<223> OTHER INFORMATION: Primer

<400> SEQUENCE: 55
acatttgccg cttggataac                                          20

<210> SEQ ID NO 56
<211> LENGTH: 20
<212> TYPE: DNA
<213> ORGANISM: Artificial
<220> FEATURE:
<223> OTHER INFORMATION: Primer

<400> SEQUENCE: 56
```

```
tgaagcctag cctgtcacct                                              20

<210> SEQ ID NO 57
<211> LENGTH: 20
<212> TYPE: DNA
<213> ORGANISM: Artificial
<220> FEATURE:
<223> OTHER INFORMATION: Primer

<400> SEQUENCE: 57
cgcacagctg gaggtcttat                                              20

<210> SEQ ID NO 58
<211> LENGTH: 91
<212> TYPE: DNA
<213> ORGANISM: Canis sp.

<400> SEQUENCE: 58
ccgcccgccg caggtgcagc cgcagccaat cagcggcgcg ggggggcgggg cctcgcggct    60 cacctggcgg ccggacgcgg ccccgctcag t                                 91

<210> SEQ ID NO 59
<211> LENGTH: 613
<212> TYPE: DNA
<213> ORGANISM: Canis sp.

<400> SEQUENCE: 59
agtggcgtcg ggcgctgcgg gcacctgtga ttcgcggaag tcctgccgcc tcgcgccgcc    60
tcgcgcccgg ctctcgaccc ccgcccgcca tgggccctcg gtacggcggc gccccgcgc    120 tcctgctccc gctgctgctg ctgctgcagg tctcatcggg gctctgccaa gagccggagc   180
cctgccgccc tggctttggc gctgacagct acacgttcac cgtgccccgg cgacacttgg   240
agagaggccg tgtcctgggc agggtgagtt ttgaaggatg caccggtcta cctaggacag   300
cctatgtttc tgatgacacc cgattcaaag tgggcacaga tggtgtgatt acagtcaagc   360
ggcctctaca acttcataaa ccagagataa gttttcttgt ccatgcctgg gactccagcc   420
gcaggaagct ctccaccaga gttaggctga aggcagcgac gcaccaccac caccaccatc   480
atgatgctcc ctctaaaacc cagacagagg tgctcacatt tcccagttcc cagcatggac   540
tcagaagaca gaagagagac tgggttatcc ctcctatcag ctgcccggaa aacgagaaag   600
gcccatttcc taa                                                    613

<210> SEQ ID NO 60
<211> LENGTH: 20
<212> TYPE: DNA
<213> ORGANISM: Artificial
<220> FEATURE:
<223> OTHER INFORMATION: Primer

<400> SEQUENCE: 60
cagtctgacc agcgtgaaaa                                              20

<210> SEQ ID NO 61
<211> LENGTH: 20
<212> TYPE: DNA
<213> ORGANISM: Artificial
<220> FEATURE:
<223> OTHER INFORMATION: Primer

<400> SEQUENCE: 61
```
ggccatccaa atctgtccta					20

<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62
ctgacctcac ctgggacaat					20

<210> SEQ ID NO 63
<211> LENGTH: 15
<212> TYPE: DNA
<213> ORGANISM: Artificial
<220> FEATURE:
<223> OTHER INFORMATION: Primer

<400> SEQUENCE: 63
ccatcaaggc acagc					15

<210> SEQ ID NO 64
<211> LENGTH: 21
<212> TYPE: DNA
<213> ORGANISM: Artificial
<220> FEATURE:
<223> OTHER INFORMATION: Primer

<400> SEQUENCE: 64
ggtatttgtg tctgaagctg g					21

<210> SEQ ID NO 65
<211> LENGTH: 21
<212> TYPE: DNA
<213> ORGANISM: Artificial
<220> FEATURE:
<223> OTHER INFORMATION: Primer

<400> SEQUENCE: 65
ggttgctgac gacagccgtg g					21

<210> SEQ ID NO 66
<211> LENGTH: 20
<212> TYPE: DNA
<213> ORGANISM: Artificial
<220> FEATURE:
<223> OTHER INFORMATION: Primer

<400> SEQUENCE: 66
ggcagaagta gcgcgacgtt					20

<210> SEQ ID NO 67
<211> LENGTH: 20
<212> TYPE: DNA
<213> ORGANISM: Artificial
<220> FEATURE:
<223> OTHER INFORMATION: Primer

<400> SEQUENCE: 67
tccggttgct cggactgctt					20

<210> SEQ ID NO 68
<211> LENGTH: 18
<212> TYPE: DNA
<213> ORGANISM: Artificial

```
<220> FEATURE:
<223> OTHER INFORMATION: Primer

<400> SEQUENCE: 68
gatgaagaat gagagagc                                                    18

<210> SEQ ID NO 69
<211> LENGTH: 19
<212> TYPE: DNA
<213> ORGANISM: Artificial
<220> FEATURE:
<223> OTHER INFORMATION: Primer

<400> SEQUENCE: 69
agtcaggata gaagacagg                                                   19

<210> SEQ ID NO 70
<211> LENGTH: 21
<212> TYPE: DNA
<213> ORGANISM: Artificial
<220> FEATURE:
<223> OTHER INFORMATION: Primer

<400> SEQUENCE: 70
ccaggaagag cagacagagg t                                                21

<210> SEQ ID NO 71
<211> LENGTH: 21
<212> TYPE: DNA
<213> ORGANISM: Artificial
<220> FEATURE:
<223> OTHER INFORMATION: Primer

<400> SEQUENCE: 71
gttgggaata gggctcaatc t                                                21

<210> SEQ ID NO 72
<211> LENGTH: 18
<212> TYPE: DNA
<213> ORGANISM: Artificial
<220> FEATURE:
<223> OTHER INFORMATION: Primer

<400> SEQUENCE: 72
cattacacac cactgacg                                                    18

<210> SEQ ID NO 73
<211> LENGTH: 20
<212> TYPE: DNA
<213> ORGANISM: Artificial
<220> FEATURE:
<223> OTHER INFORMATION: Primer

<400> SEQUENCE: 73
gatataggac cctacctagc                                                  20

<210> SEQ ID NO 74
<211> LENGTH: 22
<212> TYPE: DNA
<213> ORGANISM: Artificial
<220> FEATURE:
<223> OTHER INFORMATION: Primer

<400> SEQUENCE: 74
gaagaattgc agaaacacat cg                                               22
```

```
<210> SEQ ID NO 75
<211> LENGTH: 18
<212> TYPE: DNA
<213> ORGANISM: Artificial
<220> FEATURE:
<223> OTHER INFORMATION: Primer

<400> SEQUENCE: 75
agccaaaagg ctcacacc                                                   18
```